United States Patent
Ruvo et al.

(10) Patent No.: US 10,494,428 B2
(45) Date of Patent: Dec. 3, 2019

(54) ANTI-NODAL ANTIBODIES AND METHODS OF USING SAME

(71) Applicants: ANN AND ROBERT H. LURIE CHILDREN'S HOSPITAL OF CHICAGO, Chicago, IL (US); Menotti Ruvo, Caserta (IT); Annamaria Sandomenico, Naples (IT); Antonio Leonardi, Naples (IT); Luca Sanguigno, Naples (IT)

(72) Inventors: Menotti Ruvo, Caserta (IT); Annamaria Sandomenico, Naples (IT); Antonio Leonardi, Naples (IT); Luca Sanguigno, Naples (IT); Mary J. C. Hendrix, Lake Forest, IL (US); Elisabeth A. Seftor, Chicago, IL (US); Richard E. B. Seftor, Chicago, IL (US); Luigi Strizzi, Chicago, IL (US); Zhila Khalkhali-Ellis, Evanston, IL (US)

(73) Assignee: Ann & Robert H. Lurie Children's Hosp. of Chicago, Chicago, IL (US)

( * ) Notice: Subject to any disclaimer, the term of this patent is extended or adjusted under 35 U.S.C. 154(b) by 0 days.

(21) Appl. No.: 15/895,771

(22) Filed: Feb. 13, 2018

(65) Prior Publication Data
US 2018/0319875 A1    Nov. 8, 2018

Related U.S. Application Data

(63) Continuation of application No. 15/634,355, filed on Jun. 27, 2017, which is a continuation of application No. 14/877,617, filed on Oct. 7, 2015, now Pat. No. 9,688,750.

(60) Provisional application No. 62/060,974, filed on Oct. 7, 2014.

(51) Int. Cl.
| | |
|---|---|
| *A61K 39/395* | (2006.01) |
| *A61K 39/44* | (2006.01) |
| *C07K 16/22* | (2006.01) |
| *G01N 33/68* | (2006.01) |
| *G01N 33/53* | (2006.01) |
| *G01N 33/543* | (2006.01) |
| *G01N 33/50* | (2006.01) |
| *A61K 31/655* | (2006.01) |
| *C12N 15/113* | (2010.01) |
| *A61K 45/06* | (2006.01) |
| *A61K 39/00* | (2006.01) |

(52) U.S. Cl.
CPC ........... *C07K 16/22* (2013.01); *A61K 31/655* (2013.01); *A61K 39/3955* (2013.01); *A61K 39/39558* (2013.01); *A61K 39/44* (2013.01); *A61K 45/06* (2013.01); *C12N 15/1136* (2013.01); *G01N 33/50* (2013.01); *G01N 33/53* (2013.01); *G01N 33/543* (2013.01); *G01N 33/68* (2013.01); *G01N 33/6863* (2013.01); *A61K 2039/505* (2013.01); *C07K 2317/34* (2013.01); *C07K 2317/41* (2013.01); *C07K 2317/54* (2013.01); *C07K 2317/55* (2013.01); *C07K 2317/73* (2013.01); *C07K 2317/76* (2013.01); *C07K 2317/92* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 9,688,750 B2 | 6/2017 | Ruvo et al. | |
| 2003/0069408 A1* | 4/2003 | Ebner | C07K 14/47 536/23.5 |
| 2008/0242604 A1 | 10/2008 | Ebner et al. | |
| 2010/0273707 A1 | 10/2010 | Hendrix et al. | |
| 2013/0310577 A1 | 12/2010 | Knopf et al. | |

FOREIGN PATENT DOCUMENTS

| | | |
|---|---|---|
| WO | WO 2009/051220 | 4/2009 |
| WO | WO 2010/042562 | 4/2010 |
| WO | WO 2011/047146 | 4/2011 |
| WO | WO 2013/126810 | 8/2013 |
| WO | WO 2016/057683 | 4/2016 |

OTHER PUBLICATIONS

Calvanese et al., Biopolymers, 2010, vol. 93(11):1011-1021.*
Extended European Search Report for EP15849199.3, dated Feb. 15, 2018, 10 pages.
Adkins et al. Antibody blockade of the Cripto CFC domain suppresses tumor cell growth in vivo. J Clin Invest. 2003;112(4):575-87.
Ascierto et al. Phase II trial (BREAK-2) of the BRAF inhibitor dabrafenib (GSK2118436) in patients with metastatic melanoma. J Clin Oncol. 2013; 31(26):3205-3211.
Ascierto, Immunotherapies and novel combinations: the focus of advances in the treatment of melanoma. Cancer Immunol Immunother. 2015; 64(3):271-274.

(Continued)

*Primary Examiner* — Xiaozhen Xie

(74) *Attorney, Agent, or Firm* — Casimir Jones SC; David W. Staple

(57) ABSTRACT

The present invention relates to anti-Nodal antibodies and use of the anti-Nodal antibodies for diagnosing, preventing, and treating a Nodal-related disorder or disease.

20 Claims, 84 Drawing Sheets
Specification includes a Sequence Listing.

(56) References Cited

OTHER PUBLICATIONS

Aykul et al., Human Cerberus prevents nodal-receptor binding, inhibits nodal signaling, and suppresses nodal-mediated phenotypes. PLoS One. Jan. 20, 2015;10(1):e0114954.

Besser, Expression of nodal, lefty-a, and lefty-B in undifferentiated human embryonic stem cells requires activation of Smad2/3. J Biol Chem. Oct. 22, 2004;279(43):45076-84.

Bianco et al. Cripto-1 activates nodal- and ALK4-dependent and -independent signaling pathways in mammary epithelial Cells. Mol Cell Biol. Apr. 2002;22(8):2586-97.

Bittner et al., Molecular classification of cutaneous malignant melanoma by gene expression profiling. Nature. Aug. 3, 2000;406(6795):536-40.

Bodenstine et al., Internalization by multiple endocytic pathways and lysosomal processing impact maspin-based therapeutics. Mol Cancer Res. Oct. 2014;12(10):1480-91.

Bradford, Rapid and sensitive method for the quantitation of microgram quantities of protein utilizing the principle of protein-dye binding. Anal Biochem. May 7, 1976;72:248-54.

Calvanese et al., Conformational features and binding affinities to Cripto, ALK7 and ALK4 of Nodal synthetic fragments. J Pept Sci. Apr. 2015;21(4):283-93.

Calvanese et al., Essential dynamics analysis captures the concerted motion of the integrin-binding site in jerdostatin, an RTS disintegrin. Biopolymers. Mar. 2015;103(3):158-66.

Calvanese et al., Structural investigations on the Nodal-Cripto binding: a theoretical and experimental approach. Biopolymers. Nov. 2010;93(11):1011-21.

Carter, Techniques for conjugation of synthetic peptides to carrier molecules. Methods Mol Biol. 1994;36:155-91.

Chapman et al., Improved survival with vemurafenib in melanoma with BRAF V600E mutation. N Engl J Med. Jun. 30, 2011;364(26):2507-16.

Coit et al. Melanoma, version 4.2014. J Natl Compr Canc Netw. May 2014;12(5):621-9.

Costa et al., Epigenetically reprogramming metastatic tumor cells with an embryonic microenvironment. Epigenomics. Dec. 2009;1(2):387-98.

De Caestecker, The transforming growth factor-beta superfamily of receptors. Cytokine Growth Factor Rev. Feb. 2004;15(1):1-11.

De Luca et al., Normanno N. Expression and functional role of CRIPTO-1 in cutaneous melanoma. Br J Cancer. Sep. 27, 2011;105(7):1030-8.

Delyon et al., Experience in daily practice with ipilimumab for the treatment of patients with metastatic melanoma: an early increase in lymphocyte and eosinophil counts is associated with improved survival. Ann Oncol. 2013; 24(6):1697-1703.

Duan et al., Overexpression of Nodal induces a metastatic phenotype in pancreatic cancer cells via the Smad2/3 pathway. Oncotarget. Jan. 30, 2015;6(3):1490-506.

Eggermont et al., Re-evaluating the role of dacarbazine in metastatic melanoma: What have we learned in 30 years? Eur J Cancer. Aug. 2004;40(12):1825-36.

Endo et al., Multiple label-free detection of antigen-antibody reaction using localized surface plasmon resonance-based core-shell structured nanoparticle layer nanochip. Anal Chem. Sep. 15, 2006;78(18):6465-75.

Fields et al., Solid phase peptide synthesis utilizing 9 fluorenylmethoxycarbonyl amino acids. Int J Pept Protein Res. Mar. 1990;35(3):161-214.

Flaherty et al., Improved survival with MEK inhibition in BRAF-mutated melanoma. N Engl J Med. 2012; 367(2):107-114.

Foca et al., New anti-Nodal monoclonal antibodies targeting the Nodal pre-helix loop involved in Cripto-1 binding. Int J Mol Sci. Sep. 7, 2015;16(9):21342-62.

Fu et al., Nodal enhances the activity of FoxO3a and its synergistic interaction with Smads to regulate cyclin G2 transcription in ovarian cancer cells. Oncogene. Sep. 15, 2011;30(37):3953-66.

Gaddameedhi et al., Similar nucleotide excision repair capacity in melanocytes and melanoma cells. Cancer Res. Jun. 15, 2010;70(12):4922-30.

Gerschenson et al., Regulation of melanoma by the embryonic skin. Proc Natl Acad Sci U S A. Oct. 1986;83(19):7307-10.

Gogas et al., Chemotherapy for metastatic melanoma: time for a change? Cancer. Feb. 1, 2007;109(3):455-64.

Han et al., The opposite-direction modulation of CD4+CD25+ Tregs and T helper 1 cells in acute coronary syndromes. Clin Immunol. Jul. 2007;124(1):90-7. Epub May 23, 2007.

Hao et al., Advances in targeted therapy for unresectable melanoma: New drugs and combinations. Cancer Lett. Apr. 1, 2015;359(1):1-8.

Hardy et al., Regulation of the embryonic morphogen Nodal by Notch4 facilitates manifestation of the aggressive melanoma phenotype. Cancer Res. Dec. 15, 2010;70(24):10340-50.

Hardy et al., Targeting nodal in conjunction with dacarbazine induces synergistic anticancer effects in metastatic melanoma. Mol Cancer Res. Apr. 2015;13(4):670-80.

Hendrix et al., Vasculogenic mimicry and tumour-cell plasticity: lessons from melanoma. Nat Rev Cancer, 2003, 3:411-421.

Hodi et al., Improved Survival with Ipilimumab in Patients with Metastatic Melanoma N Engl J Med. Aug. 19, 2010;363(8):711-23.

Hodis et al., A landscape of driver mutations in melanoma. Cell. Jul. 20, 2012;150(2):251-63.

Huang et al., MED12 controls the response to multiple cancer drugs through regulation of TGF-beta receptor signaling. Cell. Nov. 21, 2012;151(5):937-50.

Iannaconne et al., Insertional mutation of a gene involved in growth regulation of the early mouse embryo. Dev Dyn. Jul. 1992;194(3):198-208.

Jamil et al., Neuroblastoma cells injected into experimental mature teratoma reveal a tropism for embryonic loose mesenchyme. Int J Oncol. Sep. 2013;43(3):831-8.

Johnsson et al., Immobilization of proteins to a carboxymethyldextran-modified gold surface for biospecific interaction analysis in surface plasmon resonance sensors. Anal Biochem. Nov. 1, 1991;198(2):268-77.

Karimkhani et al., A review of novel therapies for melanoma. Am J Clin Dermatol. Aug. 2014;15(4):323-37.

Khalkhali-Ellis et al., Divergence(s) in nodal signaling between aggressive melanoma and embryonic stem cells. Int J Cancer. Mar. 1, 2015;136(5):E242-51.

Kirsammer et al., Nodal signaling promotes a tumorigenic phenotype in human breast cancer. Semin Cancer Biol. Dec. 2014;29:40-50.

Kirschmann et al., Molecular pathways: vasculogenic mimicry in tumor cells: diagnostic and therapeutic implications. Clin Cancer Res. May 15, 2012;18(10):2726-32.

Klinac et al., Advances in personalized targeted treatment of metastatic melanoma and non-invasive tumor monitoring. Front Oncol. Mar. 19, 2013;3:54.

Kohler et al., Derivation of specific antibody-producing tissue culture and tumor lines by cell fusion. Eur J Immunol. Jul. 1976;6(7):511-9.

Kong et al., Increased expression of Nodal correlates with reduced patient survival in pancreatic cancer. Pancreatology. Mar.-Apr. 2015;15(2):156-61.

Kosaki et. al., Characterization and mutation analysis of human LEFTY A and LEFTY B, homologues of murine genes implicated in left-right axis development. Am J Hum Genet. Mar. 1999;64(3):712-21.

Kozlowski et al., A human melanoma line heterogeneous with respect to metastatic capacity in athymic nude mice. J Natl Cancer Inst. Apr. 1984;72(4):913-7.

Kwiatkowski et al., Engineering TGF-β superfamily ligands for clinical applications. Trends Pharmacol Sci. Dec. 2014;35(12):648-57.

Larkin et al., Combined Nivolumab and Ipilimumab or Monotherapy in Untreated Melanoma. N Engl J Med. Sep. 24, 2015;373(13):1270-1.

Lawrence et al., Reactivation of embryonic nodal signaling is associated with tumor progression and promotes the growth of prostate cancer cells. Prostate. Prostate. Aug. 1, 2011;71(11):1198-209.

(56) References Cited

OTHER PUBLICATIONS

Lee et al., Nodal promotes growth and invasion in human gliomas. Oncogene. May 27, 2010;29(21):3110-23.
Lee et al., The fate of human malignant melanoma cells transplanted into zebrafish embryos: assessment of migration and cell division in the absence of tumor formation. Dev Dyn. Aug. 2005;233(4):1560-70.
Lee et. al., Embryogenesis meets tumorigenesis. Nat Med. Aug. 2006;12(8):882-4.
Li et al., Phenotype switching in melanoma: implications for progression and therapy. Front Oncol. Feb. 13, 2015;5:31.
Lo et al., The melanoma revolution: from UV carcinogenesis to a new era in therapeutics. Science. Nov. 21, 2014;346(6212):945-9.
Long et al., Increased MAPK reactivation in early resistance to dabrafenib/trametinib combination therapy of BRAF-mutant metastatic melanoma. Nat Commun. Dec. 2, 2014;5:5694.
Malchenko et al., Cancer hallmarks in induced pluripotent cells: New insights. J Cell Physiol. Nov. 2010;225(2):390-3.
Maniotis et al., Vascular channel formation by human melanoma cells in vivo and in vitro: vasculogenic mimicry. Am J Pathol. Sep. 1999;155(3):739-52.
Mintz et al., Normal genetically mosaic mice produced from malignant teratocarcinoma cells. Proc Natl Acad Sci U S A. Sep. 1975;72(9):3585-9.
Murphy et al., Stem cells and targeted approaches to melanoma cure. Mol Aspects Med. Oct. 2014;39:33-49.
Pierce et al., Specificity of the control of tumor formation by the blastocyst. Cancer Res. Mar. 1982;42(3):1082-7.
Postovit et al., Human embryonic stem cell microenvironment suppresses the tumorigenic phenotype of aggressive cancer cells. Proc Natl Acad Sci U S A. Mar. 18, 2008;105(11):4329-34.
Postovit et al., Role of nodal signaling and the microenvironment underlying melanoma plasticity. Pigment Cell Melanoma Res. Jun. 2008;21(3):348-57.
Quail et al., Nodal promotes invasive phenotypes via a mitogen-activated protein kinase-dependent pathway. Oncogene. Jan. 23, 2014;33(4):461-73.
Quail et al.,Nodal signalling in embryogenesis and tumorigenesis. Int J Biochem Cell Biol. Apr. 2013;45(4):885-98.
Rebagliati et al., Cyclops encodes a nodal-related factor involved in midline signaling. Proc Natl Acad Sci U S A. Aug. 18, 1998;95(17):9932-7.
Reissmann et al., The orphan receptor ALK7 and the Activin receptor ALK4 mediate signaling by Nodal proteins during vertebrate development. Genes Dev. Aug. 1, 2001;15(15):2010-22.
Robert et al. Improved overall survival in melanoma with combined dabrafenib and trametinib. N Engl J Med. Jan. 1, 2015;372(1):30-9.
Roesch, Tumor heterogeneity and plasticity as elusive drivers for resistance to MAPK pathway inhibition in melanoma. Oncogene. Jun. 4, 2015;34(23):2951-7.
Schier et al., Nodal signaling in vertebrate development. Annu Rev Cell Dev Biol. 2003;19:589-621.
Schier, Nodal morphogens. Cold Spring Harb Perspect Biol. Nov. 2009;1(5):a003459.
Seftor et al., Expression of multiple molecular phenotypes by aggressive melanoma tumor cells: role in vasculogenic mimicry. Crit Rev Oncol Hematol. Oct. 2002;44(1):17-27.
Seftor et al., Melanoma tumor cell heterogeneity: a molecular approach to study subpopulations expressing the embryonic morphogen nodal. Semin Oncol. Apr. 2014;41(2):259-66.
Shen, Nodal signaling: developmental roles and regulation. Development. Mar. 2007;134(6):1023-34.
Smalley et al., Multiple signaling pathways must be targeted to overcome drug resistance in cell lines derived from melanoma metastases. Mol Cancer Ther. May 2006;5(5):1136-44.
Smith, Mesoderm-inducing factors and mesodermal patterning. Curr Opin Cell Biol. Dec. 1995;7(6):856-61.
Sondermann et al., The 3.2-A crystal structure of the human IgG1 Fc fragment-Fc gamma RIII complex. Nature. Jul. 20, 2000;406(6793):267-73.
Song et al., Overall survival in patients with metastatic melanoma. Curr Med Res Opin. May 2015;31(5):987-91.
Spagnolo et al., BRAF-mutant melanoma: treatment approaches, resistance mechanisms, and diagnostic strategies. Onco Targets Ther. Jan. 16, 2015;8:157-68.
Strizzi et al., Embryonic signaling in melanoma: potential for diagnosis and therapy. Lab Invest. Jun. 2011;91(6):819-24.
Strizzi et al., Development and cancer: at the crossroads of Nodal and Notch signaling. Cancer Res. Sep. 15, 2009;69(18):7131-4.
Strizzi et al., Effects of a novel Nodal-targeting monoclonal antibdoy in melanoma, Oncotarget, 2015, 6:34071-34086.
Strizzi et al., Nodal as a biomarker for melanoma progression and a new therapeutic target for clinical intervention. Expert Rev Dermatol. 2009;4(1):67-78.
Strizzi et al., Nodal expression and detection in cancer: Experience and challenges. Cancer Res. Apr. 15, 2012;72(8):1915-20.
Strizzi et al., Potential for the embryonic morphogen Nodal as a prognostic and predictive biomarker in breast cancer. Breast Cancer Res. May 11, 2012;14(3):R75.
Strizzi et al., The significance of a Cripto-1 positive subpopulation of human melanoma cells exhibiting stem cell-like characteristics. Cell Cycle. May 1, 2013;12(9):1450-6.
Sullivan et al., Resistance to BRAF-targeted therapy in melanoma. EurJ Cancer. Apr. 2013;49(6):1297-304.
Topalian et al., Safety, activity, and immune correlates of anti-PD-1 antibody in cancer. N Engl J Med. Jun. 28, 2012;366(26):2443-54.
Topczewska et al., Embryonic and tumorigenic pathways converge via Nodal signaling: role in melanoma aggressiveness. Nat Med. Aug. 2006;12(8):925-3.
Toyama et al., Nodal induces ectopic goosecoid and lim1 expression and axis duplication in zebrafish. Development. Feb. 1995;121(2):383-91.
Vallier et al., Nodal inhibits differentiation of human embryonic stem cells along the neuroectodermal default pathway. Dev Biol. Nov. 15, 2004;275(2):403-21.
Whitman, Nodal signaling in early vertebrate embryos: themes and variations. Dev Cell. Nov. 2001;1(5):605-17.
Wilson et al., Improved method for pepsinolysis of mouse IgG(1) molecules to F(ab')(2) fragments. J Immunol Methods. Feb. 1, 2002;260(1-2):29-36.
Yamaguchi et al., Proteolytic fragmentation with high specificity of mouse immunoglobulin G. Mapping of proteolytic cleavage sites in the hinge region.J Immunol Methods. Apr. 26, 1995;181(2):259-67.
Yan et al., Preparation of Nodal Antibody and Development of its ELISA kit. Chongqing University of Technology: Natural Science. 2012; 26(9):31-36. Abstract Only, 1 page.
Yu et al., Expression of the embryonic morphogen Nodal in cutaneous melanocytic lesions. Mod Pathol. Sep. 2010;23(9):1209-14.
Zhou et al., Nodal is a novel TGF-beta-like gene expressed in the mouse node during gastrulation. Nature. Feb. 11, 1993;361(6412):543-7.
International Search Report and Written Opinion for PCT/US2015/054515, dated Mar. 18, 2016, 20 pages.

* cited by examiner

FIG. 2

$\overset{43}{\text{Ac-CPNPVG}}\overset{49\ 50}{\text{EE}}\overset{52}{\text{FHPTNHAYIQSLLKRYQPH}}\text{-NH2}$ Ac-CPNPVG EE FHPTNHAYIQSLLKRYQPH -NH2

Pre-helix loop          Helix H3

Amino acid sequence of *h*Nodal [43-69]

(SEQ ID NO: 15)

FIG. 4

| mAbs 100 nM | binding to rhNodal |
|---|---|
| 1B4 | No |
| 9B9 | No |
| 2D12 | No |
| 10B12 | No |
| 3D1 | YES |
| 5F10 | YES |

FIG. 9

| | PEPTIDE NUMBER | PEPTIDE NAME | SEQUENCE | |
|---|---|---|---|---|
| SEQ ID NO:15 | WT(1) | 43-69 | CPNPVGEEFHPTNHAYIQSLLKRYQPH | A |
| SEQ ID NO:16 | 2 | 43-69 EE-AA | CPNPVGAAFHPTNHAYIQSLLKRYQPH | |
| SEQ ID NO:17 | 14 | 44-67 | PNPVGEEFHPTNHAYIQSLLKRYQ | |
| SEQ ID NO:18 | 14C | 43-67 | CPNPVGEEFHPTNHAYIQSLLKRYQ | |
| SEQ ID NO:19 | 15 | 44-67 EE-AA | PNPVGAAFHPTNHAYIQSLLKRYQ | |
| SEQ ID NO:20 | 16 | 44-67 PV-AA | PNAAGEEFHPTNHAYIQSLLKRYQ | |
| SEQ ID NO:21 | 17 | 44-67 Y-A | PNPVGEEFHPTNHAAIQSLLKRYQ | |
| SEQ ID NO:22 | CH | CH [43-56] | CPNPVGEEFHPTNH | |
| SEQ ID NO:23 | HQ | HQ [52-60] | HPTNHAYIQ | |
| SEQ ID NO:24 | AH | AH [56-69] | AYIQSLLKRYQPH | |

1. Coupling of anti-Nodal 3D1 (capture Ab) to fluorescently dyed magnetic beads by carbodiimide chemistry

2. Incubation with serum/plasma samples and wash of unbound

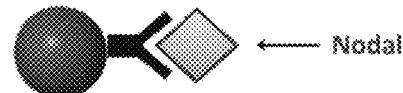

3. Incubation with a biotinylated anti-Nodal (detection Ab)

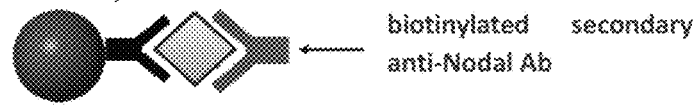

biotinylated secondary anti-Nodal Ab

4. Detection with streptavidin conjugated with a phycoerytrin (PE) fluorescent reporter

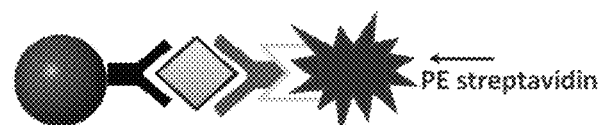

PE streptavidin

5. By using a Bio-Plex reader, a red (635 nm) laser excites the bead fluorescent dye allowing its qualitative identification. A green (532 nm) laser excites PE for the accurate and sensitive analyte quantification.

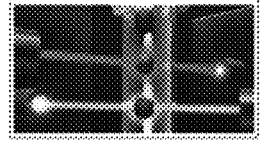

The secondary anti-Nodal Antibody has been already identified. This approach is being tested in the laboratories in Naples. The approach should allow the selective detection of Nodal at pg/mL levels.

Pre-DTIC Tx

Post-DTIC Tx

IgG control

Cy3-Nodal (Green)
CD133 (Red)

(SEQ ID NO: 32)

SEQUENCE LISTING

<160> NUMBER OF SEQ ID NOS: 33

<210> SEQ ID NO 1
<211> LENGTH: 110
<212> TYPE: PRT
<213> ORGANISM: Artificial Sequence
<220> FEATURE:
<223> OTHER INFORMATION: Synthetic

<400> SEQUENCE: 1

Asp Ile Lys Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro His
                85                  90                  95

Val Arg Cys Trp Asp Gln Ala Gly Thr Glu Thr Glu Ala Trp
            100                 105                 110

<210> SEQ ID NO 2
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (120)..(120)
<223> OTHER INFORMATION: Xaa can be any naturally occurring amino acid

<400> SEQUENCE: 2

Val Lys Leu Val Glu Ser Gly Gly Gly Leu Val Lys Pro Gly Gly Ser
1               5                   10                  15

Leu Lys Leu Ser Cys Ala Ala Ser Gly Phe Thr Phe Ser Ser Tyr Ala
            20                  25                  30

Met Ser Trp Val Arg Gln Thr Pro Glu Lys Arg Leu Glu Trp Val Ala
        35                  40                  45

Ser Ile Ser Ser Gly Gly Cys Thr Tyr Tyr Pro Asp Ser Val Lys Gly
50                  55                  60

Arg Phe Thr Ile Ser Arg Asp Asn Ala Arg Asn Ile Leu Tyr Leu Gln
65                  70                  75                  80

Met Ser Ser Leu Arg Ser Glu Asp Thr Ala Met Tyr Tyr Cys Ala Arg
                85                  90                  95

Gly Ser Met Ile Thr Ala Asp Gly Asn Ser Leu Leu Cys Tyr Gly
            100                 105                 110

Leu Leu Gly Ser Arg Asn Leu Xaa His Arg
        115                 120

<210> SEQ ID NO 3
<211> LENGTH: 111
<212> TYPE: PRT
<213> ORGANISM: Artificial Sequence
<220> FEATURE:
<223> OTHER INFORMATION: Synthetic

<400> SEQUENCE: 3

Val Lys Leu Val Glu Ser Gly Gly Leu Val Gln Pro Gly Gly Ser
1               5                   10                  15

Met Lys Leu Ser Cys Val Ala Ser Gly Phe Thr Phe Arg Asn Tyr Trp
            20                  25                  30

Met Ser Trp Val Arg Gln Ser Pro Glu Lys Gly Leu Glu Trp Val Ala
        35                  40                  45

Glu Ile Arg Leu Lys Ser Asp Asn Tyr Ala Ala Arg Tyr Ala Glu Ser
50                  55                  60

Val Lys Gly Lys Phe Thr Ile Ser Arg Asp Asp Ser Lys Ser Arg Leu
65                  70                  75                  80

Tyr Leu Gln Met Asn Ser Leu Arg Ala Glu Asp Thr Gly Ile Tyr Tyr
                85                  90                  95

Cys Thr Gly Ile Arg Arg Phe Ala Tyr Trp Gly Gln Gly Thr Leu
            100                 105                 110

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Asn Ile His Asn Tyr Leu Ala
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Leu Leu Val Tyr Asn Ala Lys Thr Leu Ala Asp
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Gln His Phe Trp Ser Thr Pro His Val Arg Cys Trp Asp Gln Ala
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Phe Thr Phe Ser Ser Tyr Ala Met Ser
1               5

<210> SEQ ID NO 8
<211> LENGTH: 13
<212> TYPE: PRT

```
<213> ORGANISM: Artificial Sequence
<220> FEATURE:
<223> OTHER INFORMATION: Synthetic

<400> SEQUENCE: 8

Trp Val Ala Ser Ile Ser Ser Gly Gly Cys Thr Tyr Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Ala Arg Gly Ser Met Ile Thr Ala Asp Gly Asn
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Phe Thr Phe Arg Asn Tyr Trp Met Ser
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic

<400> SEQUENCE: 11

Trp Val Ala Glu Ile Arg Leu Lys Ser Asp Asn Tyr Ala Ala Arg Tyr
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gly Ile Arg Arg Phe Ala Tyr
1               5

<210> SEQ ID NO 13
<211> LENGTH: 26
<212> TYPE: PRT
<213> ORGANISM: Artificial Sequence
<220> FEATURE:
<223> OTHER INFORMATION: Synthetic

<400> SEQUENCE: 13

Pro Asn Pro Val Gly Glu Glu Phe His Pro Thr Asn His Ala Tyr Ile
1               5                   10                  15

Gln Ser Leu Leu Lys Arg Tyr Gln Pro His
            20                  25

<210> SEQ ID NO 14
```

```
<211> LENGTH: 26
<212> TYPE: PRT
<213> ORGANISM: Artificial Sequence
<220> FEATURE:
<223> OTHER INFORMATION: Synthetic

<400> SEQUENCE: 14

Pro Asn Pro Val Gly Ala Ala Phe His Pro Thr Asn His Ala Tyr Ile
1               5                   10                  15

Gln Ser Leu Leu Lys Arg Tyr Gln Pro His
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic

<400> SEQUENCE: 15

Cys Pro Asn Pro Val Gly Glu Glu Phe His Pro Thr Asn His Ala Tyr
1               5                   10                  15

Ile Gln Ser Leu Leu Lys Arg Tyr Gln Pro His
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic

<400> SEQUENCE: 16

Cys Pro Asn Pro Val Gly Ala Ala Phe His Pro Thr Asn His Ala Tyr
1               5                   10                  15

Ile Gln Ser Leu Leu Lys Arg Tyr Gln Pro His
            20                  25

<210> SEQ ID NO 17
<211> LENGTH: 24
<212> TYPE: PRT
<213> ORGANISM: Artificial Sequence
<220> FEATURE:
<223> OTHER INFORMATION: Synthetic

<400> SEQUENCE: 17

Pro Asn Pro Val Gly Glu Glu Phe His Pro Thr Asn His Ala Tyr Ile
1               5                   10                  15

Gln Ser Leu Leu Lys Arg Tyr Gln
            20

<210> SEQ ID NO 18
<211> LENGTH: 25
<212> TYPE: PRT
<213> ORGANISM: Artificial Sequence
<220> FEATURE:
<223> OTHER INFORMATION: Synthetic

<400> SEQUENCE: 18

Cys Pro Asn Pro Val Gly Glu Glu Phe His Pro Thr Asn His Ala Tyr
1               5                   10                  15

Ile Gln Ser Leu Leu Lys Arg Tyr Gln
            20                  25
```

```
<210> SEQ ID NO 19
<211> LENGTH: 24
<212> TYPE: PRT
<213> ORGANISM: Artificial Sequence
<220> FEATURE:
<223> OTHER INFORMATION: Synthetic

<400> SEQUENCE: 19

Pro Asn Pro Val Gly Ala Ala Phe His Pro Thr Asn His Ala Tyr Ile
1               5                   10                  15

Gln Ser Leu Leu Lys Arg Tyr Gln
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic

<400> SEQUENCE: 20

Pro Asn Ala Ala Gly Glu Glu Phe His Pro Thr Asn His Ala Tyr Ile
1               5                   10                  15

Gln Ser Leu Leu Lys Arg Tyr Gln
            20

<210> SEQ ID NO 21
<211> LENGTH: 24
<212> TYPE: PRT
<213> ORGANISM: Artificial Sequence
<220> FEATURE:
<223> OTHER INFORMATION: Synthetic

<400> SEQUENCE: 21

Pro Asn Pro Val Gly Glu Glu Phe His Pro Thr Asn His Ala Ala Ile
1               5                   10                  15

Gln Ser Leu Leu Lys Arg Tyr Gln
            20

<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Cys Pro Asn Pro Val Gly Glu Glu Phe His Pro Thr Asn His
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

His Pro Thr Asn His Ala Tyr Ile Gln
1               5

<210> SEQ ID NO 24
<211> LENGTH: 13
<212> TYPE: PRT
<213> ORGANISM: Artificial Sequence
<220> FEATURE:
```

<223> OTHER INFORMATION: Synthetic

<400> SEQUENCE: 24

Ala Tyr Ile Gln Ser Leu Leu Lys Arg Tyr Gln Pro His
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic

<400> SEQUENCE: 25

Pro Asn Pro Val Gly Glu Glu Phe His Pro Thr Asn His
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Ala Tyr Ile Gln Ser Leu Leu Lys Arg Tyr Gln
1               5                   10

<210> SEQ ID NO 27
<211> LENGTH: 38
<212> TYPE: PRT
<213> ORGANISM: Artificial Sequence
<220> FEATURE:
<223> OTHER INFORMATION: Synthetic

<400> SEQUENCE: 27

His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
                20                  25                  30

Gln Tyr Asn Ala Tyr Arg
            35

<210> SEQ ID NO 28
<211> LENGTH: 37
<212> TYPE: PRT
<213> ORGANISM: Artificial Sequence
<220> FEATURE:
<223> OTHER INFORMATION: Synthetic

<400> SEQUENCE: 28

Cys Glu Gly Glu Cys Pro Asn Pro Val Gly Glu Glu Phe His Pro Thr
1               5                   10                  15

Asn His Ala Tyr Ile Gln Ser Leu Leu Lys Arg Tyr Gln Pro His Arg
                20                  25                  30

Val Pro Ser Thr Cys
            35

<210> SEQ ID NO 29
<211> LENGTH: 35
<212> TYPE: PRT
<213> ORGANISM: Artificial Sequence
<220> FEATURE:
<223> OTHER INFORMATION: Synthetic -continued

<400> SEQUENCE: 29

Cys Ala Pro Val Lys Thr Lys Pro Leu Ser Met Leu Tyr Val Asp Asn
1               5                   10                  15

Gly Arg Val Leu Leu Asp His His Lys Asp Met Ile Val Glu Glu Cys
            20                  25                  30

Gly Cys Leu
        35

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Cys Glu Phe Pro Leu Arg Ser His Leu Glu Pro Thr Asn His
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Cys Asp Phe Pro Leu Arg Ser His Leu Glu Pro Thr Asn His
1               5                   10

<210> SEQ ID NO 32
<211> LENGTH: 110
<212> TYPE: PRT
<213> ORGANISM: Artificial Sequence
<220> FEATURE:
<223> OTHER INFORMATION: Synthetic

<400> SEQUENCE: 32

His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
            20                  25                  30

Gln Tyr Asn Ala Tyr Arg Cys Glu Gly Glu Cys Pro Asn Pro Val Gly
        35                  40                  45

Glu Glu Phe His Pro Thr Asn His Ala Tyr Ile Gln Ser Leu Leu Lys
    50                  55                  60

Arg Tyr Gln Pro His Arg Val Pro Ser Thr Cys Cys Ala Pro Val Lys
65                  70                  75                  80

Thr Lys Pro Leu Ser Met Leu Tyr Val Asp Asn Gly Arg Val Leu Leu
                85                  90                  95

Asp His His Lys Asp Met Ile Val Glu Glu Cys Gly Cys Leu
            100                 105                 110

<210> SEQ ID NO 33
<211> LENGTH: 22
<212> TYPE: PRT
<213> ORGANISM: Mus musclus

-continued

```
<400> SEQUENCE: 33

Cys Lys Pro Cys Ile Cys Thr Val Pro Glu Val Ser Ser Val Phe Ile
1               5                   10                  15

Phe Pro Pro Lys Pro Lys
                20
```

ANTI-NODAL ANTIBODIES AND METHODS OF USING SAME

CROSS-REFERENCE TO RELATED APPLICATION

The present application is a continuation of U.S. patent application Ser. No. 15/634,355, filed Jun. 27, 2017, which is a continuation of U.S. patent application Ser. No. 14/877,617, filed Oct. 7, 2015, now U.S. Pat. No. 9,688,750, which claims priority to U.S. Provisional Patent Application Ser. No. 62/060,974 filed Oct. 7, 2014, each of which are hereby incorporated by reference in its entirety.

FIELD OF THE INVENTION

The present invention relates to anti-Nodal antibodies and use of the anti-Nodal antibodies for diagnosing, preventing and treating a Nodal-related disorder or disease.

BACKGROUND OF THE INVENTION

Aggressive tumor cells share a number of characteristics with embryonic progenitors. During vertebrate development, multipotent precursor cells are gradually specified to particular fates through the autocrine or paracrine delivery of signaling molecules, and during cancer progression, malignant cells similarly release and receive cues that promote tumor growth and metastasis. Aggressive tumor cells, such as melanoma cells, display stem cell-like plasticity as demonstrated by their molecular signature that signifies a dedifferentiated, multipotent plastic phenotype (capable of responding to microenvironmental factors as well as influencing other cells via epigenetic mechanisms) (Bittner et al., 2000, Nature 406:536-540; Hendrix et al., 2003, Nat. Rev. Cancer 3:411-421). Furthermore, aggressive melanoma cells are capable of vasculogenic mimicry, i.e. they are able to form vasculogenic-like networks while simultaneously expressing genes associated with an endothelial cell type. (Seftor et. al., 2002, Crit. Rev. Oncology Hematol. 44:17-27; Maniotis et. al 1999 Am. J. Pathol. 155:739-752; Kirschmann et. al., 2012, Clin. Cancer Res. 18:2726-2732).

Previous studies capitalized on the similarities between cancer and stem cells by examining the ability of embryonic microenvironments to modulate tumor cell behavior (Pierce et al., 1982, Cancer Res. 42:1082-1087; Gerschenson et al., 1986, Proc. Natl. Acad. Sci. U.S.A 83:7307-7310; Lee et al., 2005, Dev. Dyn. 233:1560-1570; Mintz et al., 1975, Proc. Natl. Acad. Sci. U.S. A 72:3585-3589). For example, Pierce and colleagues reported that neural stage mouse embryos regulate neuroblastoma cells, and that embryonic skin inhibits melanoma growth (Pierce et al., 1982, Cancer Res. 42:1082-1087; Gerschenson et al., 1986, Proc. Natl. Acad. Sci. U.S. A 83:7307-7310). Although studies have focused on the role of embryonic signals in the regulation of tumor cells, few have utilized embryonic models as a tool to discover molecular mechanisms by which cancer cells modulate their microenvironment and the resulting reciprocal interactions.

One of the major factors contributing to the plasticity of stem cells is Nodal. Nodal is a highly conserved morphogen belonging to the transforming growth factor beta (TGFβ) super family (Schier et al., 2003, Annu. Rev. Cell Dev. Biol. 19:589-621). By acting as an organizing signal before gastrulation, Nodal initiates embryonic axis formation, and previous studies demonstrated that the ectopic expression of Nodal induces mesendodermal fates in ectopic positions (Whitman, 2001, Dev. Cell 1:605-617; Schier, 2003, Annu. Rev. Cell Dev. Biol. 19:589-621; Iannaccone et al., 1992, Dev. Dyn. 194:198-208; Smith, 1995, Curr. Opin. Cell Biol. 7:856-861; Zhou et al., 1993, Nature 361:543-547; Rebagliati et al., 1998, Proc. Natl. Acad. Sci. U.S.A 95:9932-9937; Toyama et al., 1995, Development 121:383-391).

Activation of Nodal includes binding to the co-receptor Cripto-1 and subsequent phosphorylation of the type I and type II activin-like kinase receptors (ALK). In turn, SMAD2 and SMAD3 are activated (Lee et. al., 2006, Nature Medicine 12:882-884). Furthermore, human embryonic stem cells express Nodal and secrete endogenous inhibitors of Nodal such as Lefty A/B (Besser, D., 2004, J. Biol. Chem. 279:45076-45084). Lefty A and Lefty B, human homologs to murine Lefty 2 and Lefty 1, respectively, are separated by approximately 50 kb on chromosome q42 and are 96% identical to each other (Kosaki et. al., 1999, Am. J. Hum. Genet. 64:712-21). Lefty A and Lefty B are members of the TGFβ superfamily, and are considered amongst the most powerful inhibitors of Nodal.

Nodal is reactivated and aberrantly upregulated in many different forms of aggressive cancer; however, Lefty is silenced—allowing Nodal to signal in an unregulated manner (Postovit et. al., 2008, Proc. Natl. Acad. Sci. U.S.A. 105:4329-4334.

SUMMARY OF THE INVENTION

The present invention relates to anti-Nodal antibodies and methods of using the same (e.g., use of the anti-Nodal antibodies for diagnosing, preventing and treating a Nodal-related disorder or disease).

Accordingly, in one embodiment, the invention provides antibodies that bind to Nodal. In a preferred embodiment, the anti-Nodal antibodies are monoclonal antibodies. In another embodiment, the antibodies, or fragments thereof, specifically bind to an epitope of human Nodal in the pre-helix loop region. In one embodiment, the antibodies inhibit Nodal activity and/or signaling. In another embodiment, the antibodies bind to human Nodal (hNodal). In another embodiment, the antibodies bind to a Nodal with a $K_D$ of <10 nM. In another embodiment, the antibodies bind to a Nodal with a $K_D$ of <5 nM. In another embodiment, the antibodies bind to full length Nodal. In another embodiment, the antibodies inhibit Nodal binding to Cripto-1. In another embodiment, the antibodies inhibit Nodal binding to the Cripto-1 co-receptor complex. In another embodiment, the antibodies inhibit Nodal binding to the Alk4/7/ActRIIB receptor complex. In another embodiment, the antibodies inhibits signaling downstream of Nodal and/or the Nodal/Cripto-1 complex. In another embodiment, the antibodies downregulate Nodal expression. In another embodiment, the antibodies downregulate markers of proliferation.

In a further embodiment, a monoclonal antibody that binds to Nodal is provided, wherein the antibody comprises: (a) an HVR-H1 comprising the amino acid sequence of SEQ ID NO:10; (b) an HVR-H2 comprising the amino acid sequence of SEQ ID NO:11; (c) an HVR-H3 comprising the amino acid sequence of SEQ ID NO:12; (d) an HVR-L1 comprising the amino acid sequence of SEQ ID NO:4; (e) an HVR-L2 comprising the amino acid sequence of SEQ ID NO:5; and/or (f) an HVR-L3 comprising the amino acid sequence of SEQ ID NO:6. In one embodiment, the antibody further comprises at least one human framework region. In one embodiment, the human framework region comprises a human VH Acceptor 2 framework. In another embodiment, human framework region comprises a human VL kappa subgroup I consensus framework.

In another embodiment, a monoclonal antibody that binds to Nodal is provided, wherein the antibody comprises a heavy chain variable domain having at least 70%, at least 75%, at least 80%, at least 85%, at least 90%, or at least 95% sequence identity to the amino acid sequence of SEQ ID NO:3. In one embodiment, the monoclonal antibody has a light chain variable domain having at least 70%, at least 75%, at least 80%, at least 85%, at least 90%, or at least 95% sequence identity to the amino acid sequence of SEQ ID NO:1. In one embodiment, the monoclonal antibody has a heavy chain variable domain comprising the amino acid sequence of SEQ ID NO:3, and a light chain variable domain comprising the amino acid sequence of SEQ ID NO:1. In one embodiment, the antibody further comprises at least one human framework region. In one embodiment, the human framework region comprises a human VH Acceptor 2 framework. In another embodiment, human framework region comprises a human VL kappa subgroup I consensus framework.

In a further embodiment, a monoclonal antibody that binds to Nodal is provided, wherein the antibody comprises: (a) an HVR-H1 comprising the amino acid sequence of SEQ ID NO:7; (b) an HVR-H2 comprising the amino acid sequence of SEQ ID NO:8; (c) an HVR-H3 comprising the amino acid sequence of SEQ ID NO:9; (d) an HVR-L1 comprising the amino acid sequence of SEQ ID NO:4; (e) an HVR-L2 comprising the amino acid sequence of SEQ ID NO:5; and (f) an HVR-L3 comprising the amino acid sequence of SEQ ID NO:6. In one embodiment, the antibody further comprises at least one human framework region. In one embodiment, the human framework region comprises a human VH Acceptor 2 framework. In another embodiment, human framework region comprises a human VL kappa subgroup I consensus framework.

In another embodiment, monoclonal antibodies that bind to Nodal are provided, wherein the antibodies comprise a heavy chain variable domain having at least 70%, at least 75%, at least 80%, at least 85%, at least 90%, or at least 95% sequence identity to the amino acid sequence of SEQ ID NO:2. In one embodiment, the monoclonal antibodies comprise a light chain variable domain having at least 70%, at least 75%, at least 80%, at least 85%, at least 90%, or at least 95% sequence identity to the amino acid sequence of SEQ ID NO:1. In one embodiment, the antibody further comprises at least one human framework region. In one embodiment, the human framework region comprises a human VH Acceptor 2 framework. In another embodiment, human framework region comprises a human VL kappa subgroup I consensus framework.

In another embodiment, a monoclonal antibody that binds to Nodal is provided, wherein the antibody comprises an HVR-H1 comprising the amino acid sequence of SEQ ID NO:10; an HVR-L1 comprising the amino acid sequence of SEQ ID NO:4; an HVR-L2 comprising the amino acid sequence of SEQ ID NO:5; and an HVR-L3 comprising the amino acid sequence of SEQ ID NO:6. In one embodiment, the antibody further comprises at least one human framework region. In one embodiment, the human framework region comprises a human VH Acceptor 2 framework. In another embodiment, human framework region comprises a human VL kappa subgroup I consensus framework.

In another embodiment, a monoclonal antibody that binds to Nodal is provided, wherein the antibody comprises an HVR-H1 comprising the amino acid sequence of SEQ ID NO:7; an HVR-L1 comprising the amino acid sequence of SEQ ID NO:4; an HVR-L2 comprising the amino acid sequence of SEQ ID NO:5; and an HVR-L3 comprising the amino acid sequence of SEQ ID NO:6. In one embodiment, the antibody further comprises at least one human framework region. In one embodiment, the human framework region comprises a human VH Acceptor 2 framework. In another embodiment, human framework region comprises a human VL kappa subgroup I consensus framework.

The invention also provides an isolated antibody that binds to an epitope in SEQ ID NO:13. In another embodiment, an isolated antibody is provided that binds to the Nodal pre-helix loop region.

In one embodiment, the anti-Nodal antibody is an antibody fragment selected from a Fab, Fab'-SH, Fv, scFv, or (Fab')$_2$ fragment. In one embodiment, the antibody is an antigen-binding antibody fragment. In another embodiment, the antibody is a single chain Fv. In another embodiment, the antibody is a human, humanized, or chimeric antibody.

In an additional embodiment, the invention also provides that any one of the above embodiments is used individually (e.g., is present in a composition or in a diagnostic kit individually). In another embodiment, any of the above embodiments is used in combination with any other one of the embodiments.

The invention also provides a method of inhibiting Nodal activity using an anti-Nodal antibody of the invention. In one embodiment, the invention provides a method of inhibiting Nodal activity comprising exposing a cell that expresses Nodal to an antibody according to any of the above embodiments. In one embodiment the invention provides a method of treating a disorder associated with increased expression or activity of Nodal, the method comprising administering to a subject (e.g., a subject in need thereof) an effective amount of an anti-Nodal antibody of the invention. In one embodiment, the disorder is cancer. In one embodiment, the antibody is administered with at least one or more therapeutic agents—in a combinatorial or sequential manner. The invention is not limited to any particular agent. Indeed, a variety of agents may be administered with an antibody of the invention including, but not limited to, a chemotherapeutic agent or agents described herein. In one embodiment, the therapeutic agent is Lefty protein (e.g., recombinant Lefty protein). In one embodiment, an antibody of the invention and a therapeutic agent or agents are separately administered to the subject. In another embodiment, an antibody of the invention and the therapeutic agent are co-administered.

The invention also provides a method of inhibiting tumor cell growth, the method comprising administering to a subject (e.g., a subject in need thereof (e.g., a subject with cancer) an effective amount of an anti-Nodal antibody of the invention. In another embodiment, the invention provides a method of inhibiting cancer metastasis, the method comprising administering to a subject in need thereof an effective amount of an anti-Nodal antibody of the invention. The invention is not limited to any particular type of tumor or metastatic cancer or other Nodal-driven disease. Indeed, as described herein, a variety of cancers, neoplasms, tumors, and metastatic forms of the same may be treated including, but not limited to, those described herein. In one embodiment, the cancer is breast cancer. In another embodiment, the cancer is melanoma. In another embodiment, the cancer is prostate cancer.

The invention also provides isolated nucleic acid encoding a polypeptide comprising the amino acid sequence of the VH chain region of a monoclonal antibody that specifically binds Nodal. In one embodiment, the antibody specifically binds to an epitope in SEQ ID NO:13 and inhibits Nodal activity. In another embodiment, the VH chain region comprises CDR-H1 of SEQ ID NO:10, CDR-H2 of SEQ ID NO:11, and CDR-H3 of SEQ ID NO:12. In another embodiment, the VH chain region comprises SEQ ID NO:3. In another embodiment, the invention provides an isolated cell comprising a nucleic acid of any one of the above embodiments. The invention also provides a method for producing a polypeptide comprising the amino acid sequence of the VH chain region of a monoclonal antibody that specifically binds to Nodal comprising culturing the isolated cell comprising a nucleic acid of any one of the above embodiments under conditions appropriate for production of the polypeptide and isolating the polypeptide produced.

The invention also provides isolated nucleic acid encoding a polypeptide comprising the amino acid sequence of the VH chain region of a monoclonal antibody that specifically binds Nodal. In one embodiment, the antibody specifically binds to an epitope in SEQ ID NO:13 and inhibits Nodal activity. In another embodiment, the VH chain region comprises CDR-H1 of SEQ ID NO:7, CDR-H2 of SEQ ID NO:8, and CDR-H3 of SEQ ID NO:9. In another embodiment, the VH chain region comprises SEQ ID NO:2. In another embodiment, the invention provides an isolated cell comprising a nucleic acid of any one of the above embodiments. The invention also provides a method for producing a polypeptide comprising the amino acid sequence of the VH chain region of a monoclonal antibody that specifically binds to Nodal comprising culturing the isolated cell comprising a nucleic acid of any one of the above embodiments under conditions appropriate for production of the polypeptide and isolating the polypeptide produced.

The invention also provides isolated nucleic acid encoding a polypeptide comprising the amino acid sequence of the VL chain region of a monoclonal antibody that specifically binds to Nodal. In one embodiment, the antibody specifically binds to an epitope in SEQ ID NO:13 and inhibits Nodal activity. In another embodiment, the VL chain region comprises CDR-L1 of SEQ ID NO:4, CDR-L2 of SEQ ID NO:5, and CDR-L3 of SEQ ID NO:6. In another embodiment, the VL chain region comprises SEQ ID NO:1. In another embodiment, the invention provides an isolated cell comprising a nucleic acid of any one of the above embodiments. The invention also provides a method for producing a polypeptide comprising the amino acid sequence of the VL chain region of a monoclonal antibody that specifically binds to Nodal comprising culturing the isolated cell comprising a nucleic acid of any one of the above embodiments under conditions appropriate for production of the polypeptide and isolating the polypeptide produced.

The invention also provides isolated nucleic acid encoding a monoclonal antibody that specifically binds to Nodal, wherein the antibody specifically binds to an epitope in SEQ ID NO:13, and wherein the antibody inhibits Nodal activity. In one embodiment, the antibody comprises a VH chain region comprising CDR-H1 of SEQ ID NO:10, CDR-H2 of SEQ ID NO:11, and CDR-H3 of SEQ ID NO:12, and a VL chain region comprising CDR-L1 of SEQ ID NO:4, CDR-L2 of SEQ ID NO:5, and CDR-L3 of SEQ ID NO:6. In one embodiment, the VH chain region comprises SEQ ID NO:3 and the VL chain region comprises SEQ ID NO:1. In one embodiment, the antibody is a humanized form of a monoclonal antibody comprising the VH chain region of SEQ ID NO:3 and the VL chain region of SEQ ID NO:1. In one embodiment, the antibody inhibits Nodal binding to Cripto-1. In another embodiment, the antibody inhibits Nodal binding to the Alk4/7/ActRIIB receptor complex.

The invention also provides isolated nucleic acid encoding a monoclonal antibody that specifically binds to Nodal, wherein the antibody specifically binds to an epitope in SEQ ID NO:13, and wherein the antibody inhibits Nodal activity. In one embodiment, the antibody comprises a VH chain region comprising CDR-H1 of SEQ ID NO:7, CDR-H2 of SEQ ID NO:8, and CDR-H3 of SEQ ID NO:9, and a VL chain region comprising CDR-L1 of SEQ ID NO:4, CDR-L2 of SEQ ID NO:5, and CDR-L3 of SEQ ID NO:6. In one embodiment, the VH chain region comprises SEQ ID NO:2 and the VL chain region comprises SEQ ID NO:1. In one embodiment, the antibody is a humanized form of a monoclonal antibody comprising the VH chain region of SEQ ID NO:2 and the VL chain region of SEQ ID NO:1. In one embodiment, the antibody inhibits Nodal binding to Cripto-1. In another embodiment, the antibody inhibits Nodal binding to the Alk4/7/ActRIIB receptor complex The invention also provides isolated nucleic acid encoding a monoclonal antibody that specifically binds to Nodal, wherein the antibody specifically binds to an epitope in SEQ ID NO:13, and wherein the antibody inhibits Nodal activity. In one embodiment, the antibody comprises the VL chain region comprises CDR-L1 of SEQ ID NO:4, CDR-L2 of SEQ ID NO:5, and CDR-L3 of SEQ ID NO:6. In one embodiment, the VL chain region comprises SEQ ID NO:1. In one embodiment, the antibody is a humanized form of a monoclonal antibody comprising the VH chain region of SEQ ID NO:3 and the VL chain region of SEQ ID NO:1. In one embodiment, the antibody inhibits Nodal binding to Cripto-1. In another embodiment, the antibody inhibits Nodal binding to the Alk4/7/ActRIIB receptor complex.

The invention also provides isolated nucleic acid encoding a monoclonal antibody that specifically binds to Nodal, wherein the antibody specifically binds to an epitope in SEQ ID NO:13, and wherein the antibody inhibits Nodal activity. In one embodiment, the antibody comprises the VL chain region comprises CDR-L1 of SEQ ID NO:4, CDR-L2 of SEQ ID NO:5, and CDR-L3 of SEQ ID NO:6. In one embodiment, the VL chain region comprises SEQ ID NO:1. In one embodiment, the antibody is a humanized form of a monoclonal antibody comprising the VH chain region of SEQ ID NO:2 and the VL chain region of SEQ ID NO:1. In one embodiment, the antibody inhibits Nodal binding to Cripto-1. In another embodiment, the antibody inhibits Nodal binding to the Alk4/7/ActRIIB receptor complex The invention also provides monoclonal antibodies that bind to Nodal pre-helix loop region. In one embodiment, the antibodies inhibit Nodal activity and/or signaling. In one embodiment, antibodies reduces Nodal expression in metastatic cells (e.g., metastatic melanoma cells). In one embodiment, antibodies reduce phosphorylation of Smad2 and/or MAPK (e.g., in melanoma cells). In one embodiment, antibodies reduce lung colonization of metastatic cells (e.g., metastatic melanoma cells). In one embodiment, antibodies decrease melanoma cell viability and/or induce melanoma cell death in vitro. In one embodiment, antibodies inhibit tumor (e.g., breast cancer tumor) growth in vivo. In one embodiment, antibodies reduce breast cancer tumor volume compared to a control.

The invention also provides a method for diagnosing a cancer in a subject, comprising contacting a sample (e.g., a biological sample described herein) from the subject with an antibody or fragment thereof of the invention which binds to Nodal under conditions sufficient to bind Nodal, and wherein an increase in Nodal as compared to a normal noncancerous control is indicative of a cancer. The invention is not limited by the type of cancer detected. Indeed, any cancer described herein may be detected (e.g., including, but not limited to, glioblastoma, neuroblastoma, melanoma, breast cancer, pancreatic cancer, ovarian cancer, bladder cancer, colon cancer, prostate cancer, and leukemia). In a preferred embodiment, the cancer expresses Nodal protein. The antibodies or fragments thereof described herein may be used in the diagnostic methods of the invention. Any type of biological sample from a subject/patient may be tested for Nodal expression including, but not limited to, tissue, blood, feces, plasma, bodily fluid, serum, saliva, lung effusion, sputum, urine, and intestinal scraping. In one embodiment, the binding of an antibody to Nodal is detected by a label. The invention is not limited by the type of label. A variety of labels may be used including, but not limited to, an enzymatic label, a fluorescent label, a chemiluminescent label, a radioactive label, and a dye label. Nodal may be detected using any immunoassay known in the art including, but not limited to, an enzyme linked immunosorbent assay or radioimmunoassay or variations thereof. Nodal may be also detected using any label-free technology where the antibody is used to capture the protein. Label-free technologies include SPR, Bio-Layer Interferometry (BLI), Long Period Gratings (LPG), etc

BRIEF DESCRIPTION OF THE FIGURES

FIG. 2 depicts the amino acid sequence of human Nodal protein from amino acids 43-69 (SEQ ID NO: 15).

FIG. 4 shows the results of screening mAbs for selection of those binding full length Nodal.

The epitope recognized by 3D1 is underlined. Residues E49 and E50 involved in the binding to Cripto-1-1 are numbered.

Figure 43:
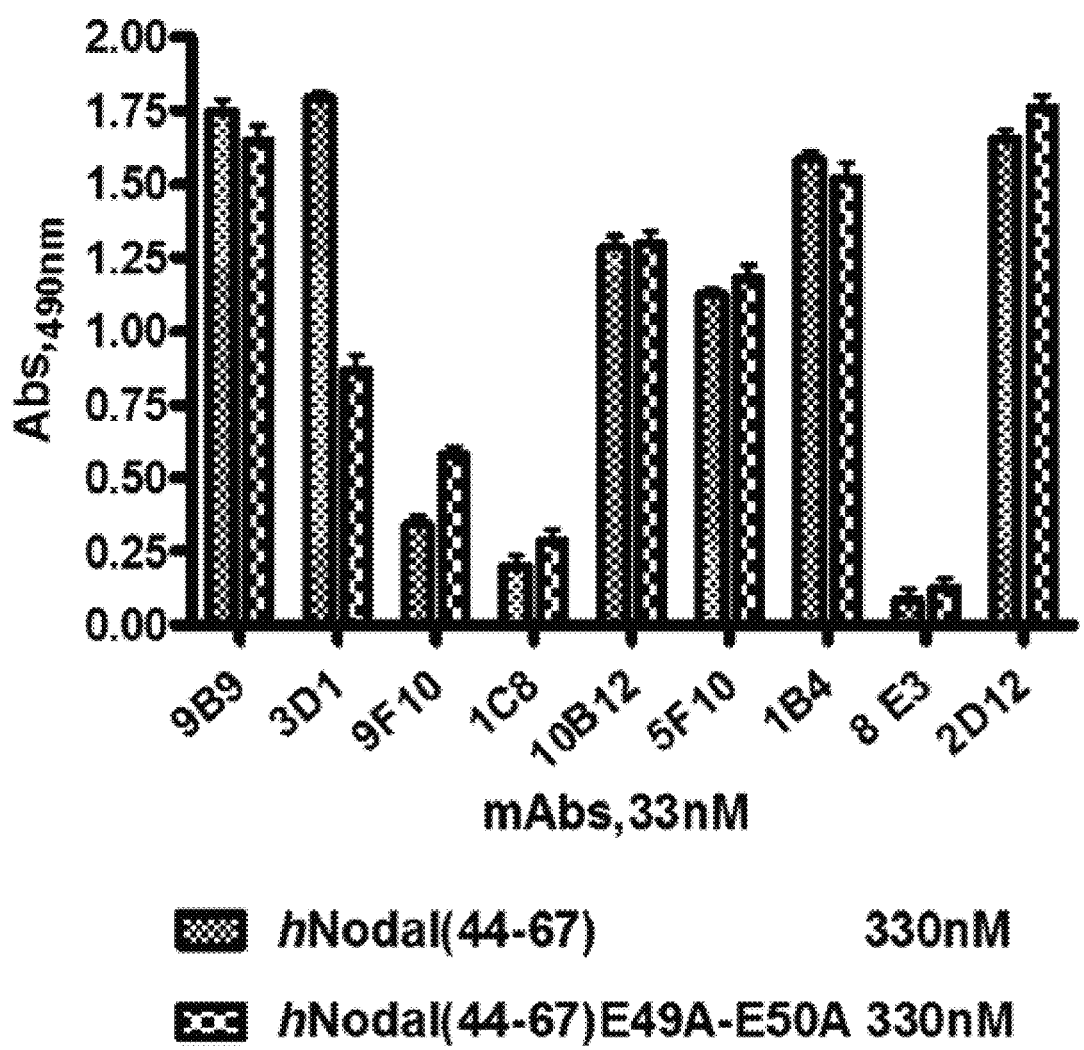

FIG. 43 shows results of an ELISA-based screening assay of hybridoma supernatants. hNodal(44-67) and hNodal(44-67)E49A-E50A were coated at 1.0 µg/mL (330 nM). Hybridoma supernatants were tested at 5.0 µg/mL total protein.

Figure 44:
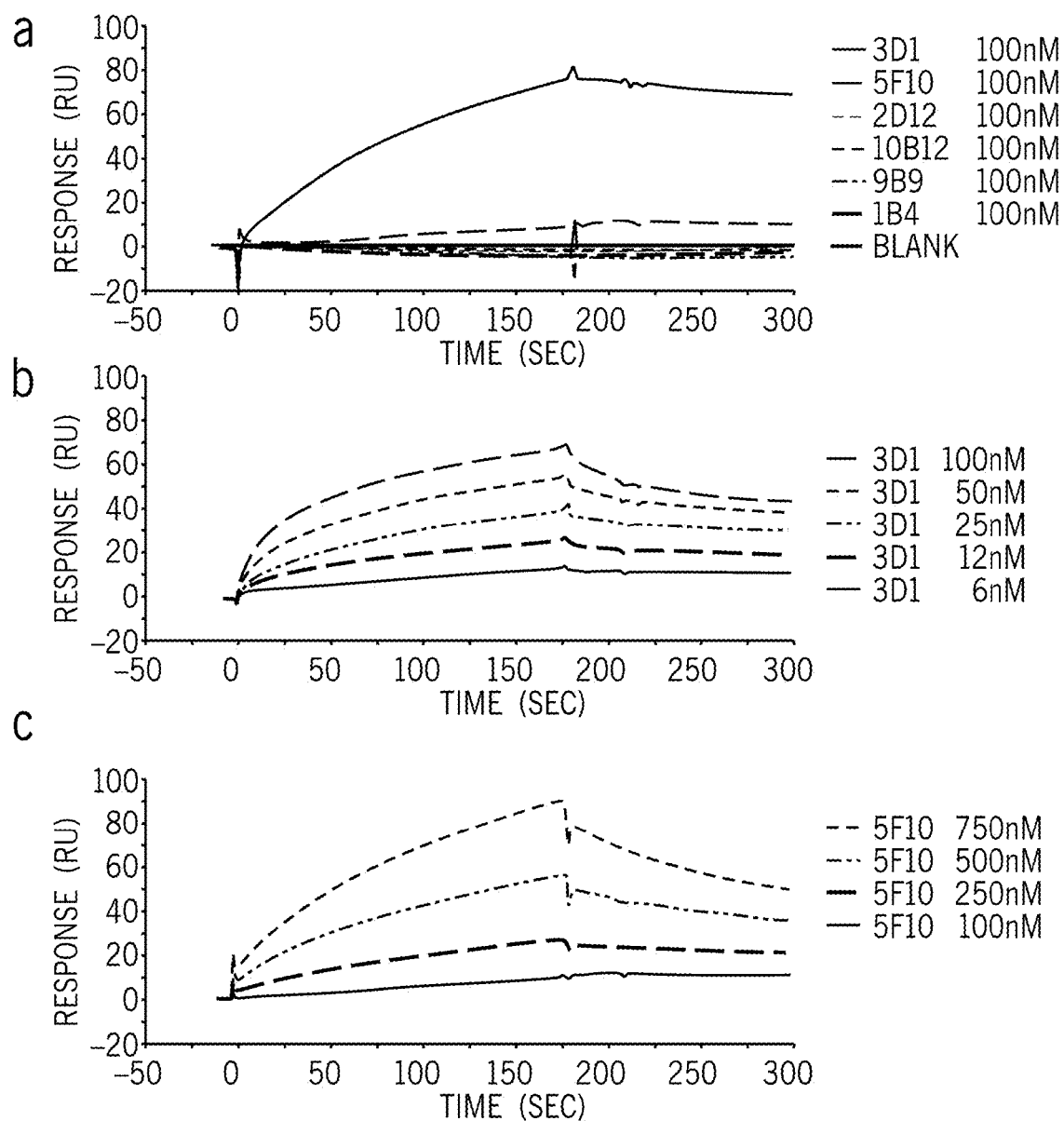

FIG. 44 shows (a) Screening of anti-Nodal monoclonal antibodies; Overlay plot of SPR sensorgrams showing the interaction between 3D1 and 5F10 mAbs with rhNodal immobilized on a CM5 sensor chip. The interaction was monitored at concentrations of mAb ranging between 6 and 100 nM for 3D1 (b) and 100 and 750 nM for 5F10 (c) obtaining dose-dependent binding curves.

Figure 45:
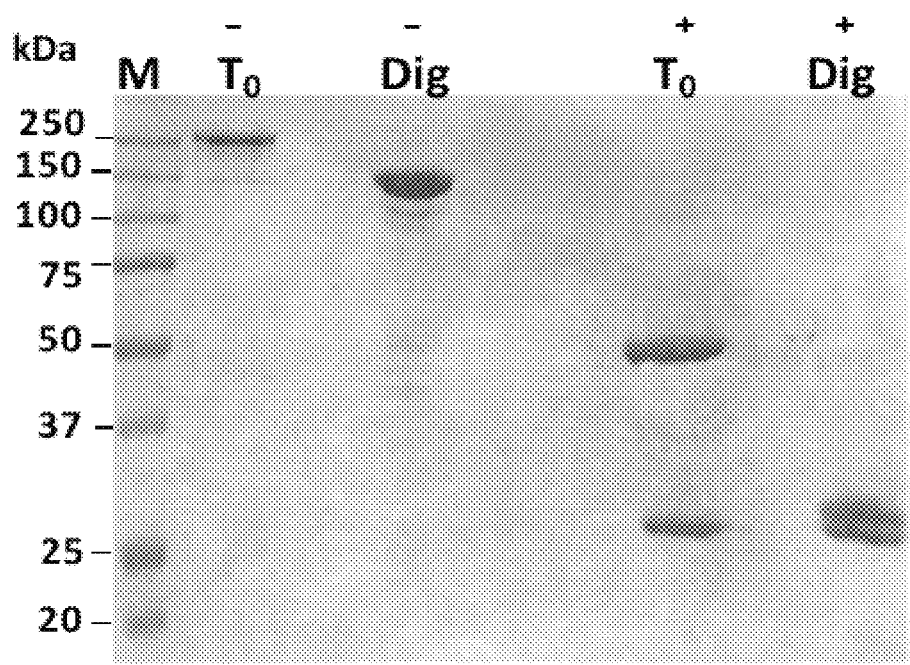

FIG. 45 shows 12% SDS-PAGE analysis under non reducing (−) and reducing (+) conditions of products obtained following digestion of the 3D1 mAb with Pepsin; T0: 3D1 antibody; Dig: proteolytic digest of 3D1 after 6 h.

Figure 46:
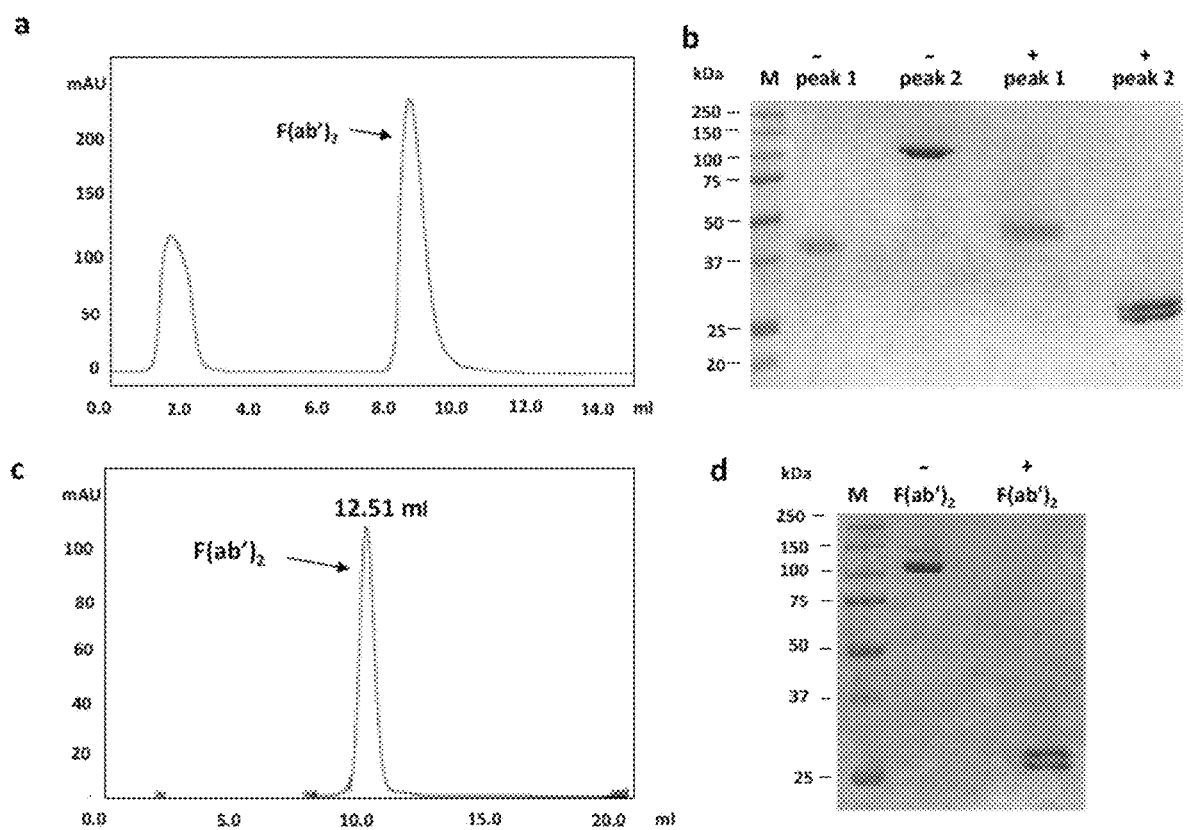

FIG. 46 shows (a) Chromatogram of Protein G affinity purification and (b) SDS-PAGE analysis of products obtained by pepsin digestion; (c) SEC profile with the retention volume and (d) SDS-PAGE analysis of F(ab')2 obtained by pepsin digestion.

Figure 47:
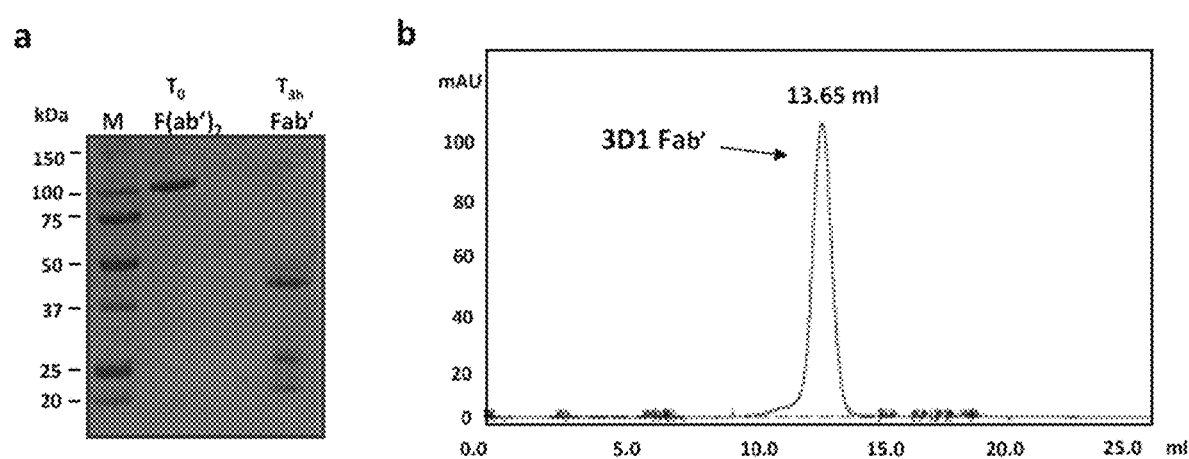

FIG. 47 shows (a) 12% SDS-PAGE analysis under non reducing conditions of the F(ab')2 and F(ab')2 reduced to Fab'; (b) SE-chromatographic profile of the Fab'.

Figure 48A:
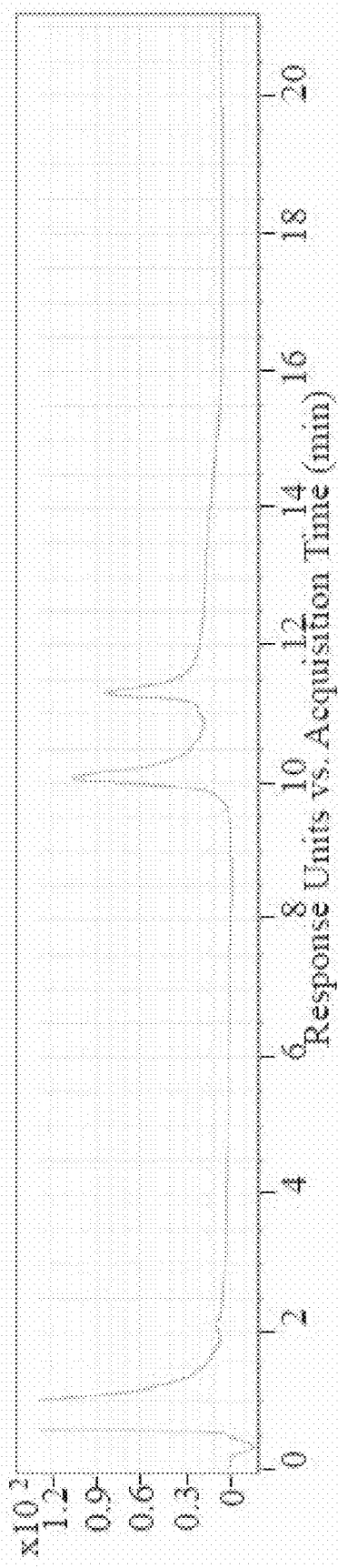
Figure 48B:
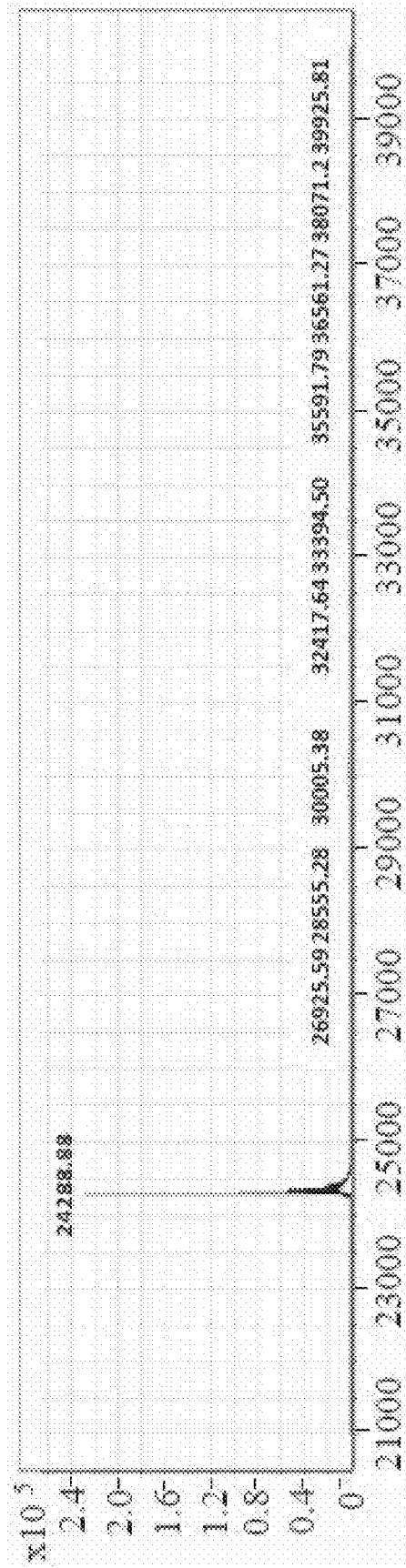
Figure 48C:
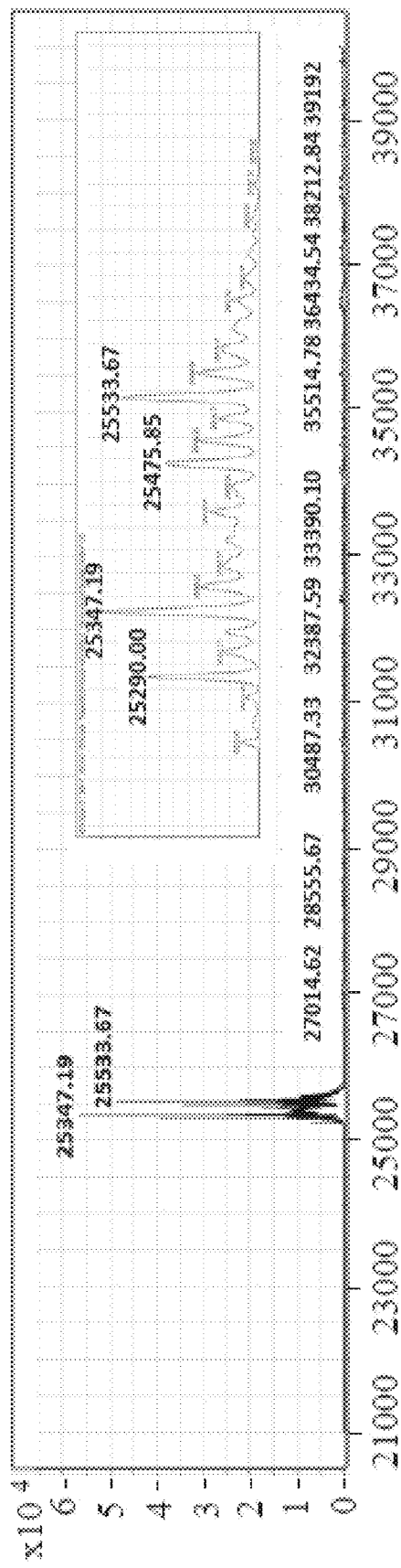
Figure 48D:
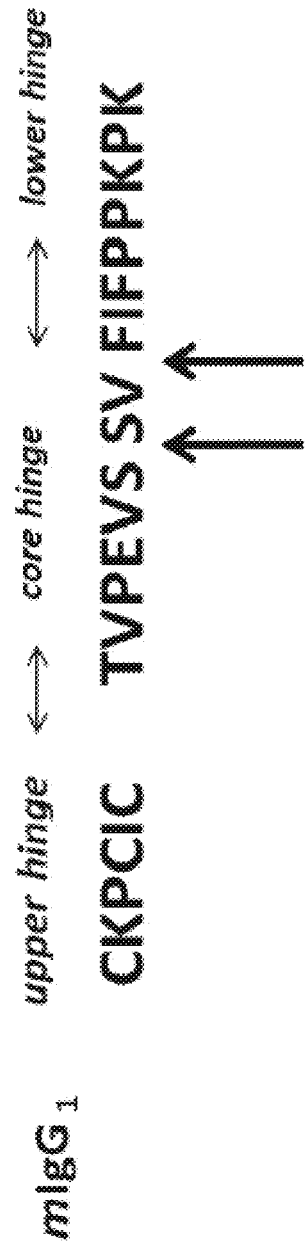

FIGS. 48A-D show LC-MS analysis of the reduced and alkylated 3D1-Fab': Chromatographic profile (FIG. 48A) of the two separated chains: the Light Chain (LC) eluted at 10.07 min and the 3D1-Fab' Heavy Chain (HC), eluted at 11.31 min. Deconvolution of mass spectra obtained for both peaks are also reported. LC exhibited a single and homogeneous product (FIG. 48B), whereas HC showed multiple products deriving from pepsin unspecific cleavage on the hinge region (FIG. 48C). Schematic representation of the supposed cleavage sites on the mouse IgG1 heavy chain (SEQ ID NO: 33) (FIG. 48D).

Figure 49:
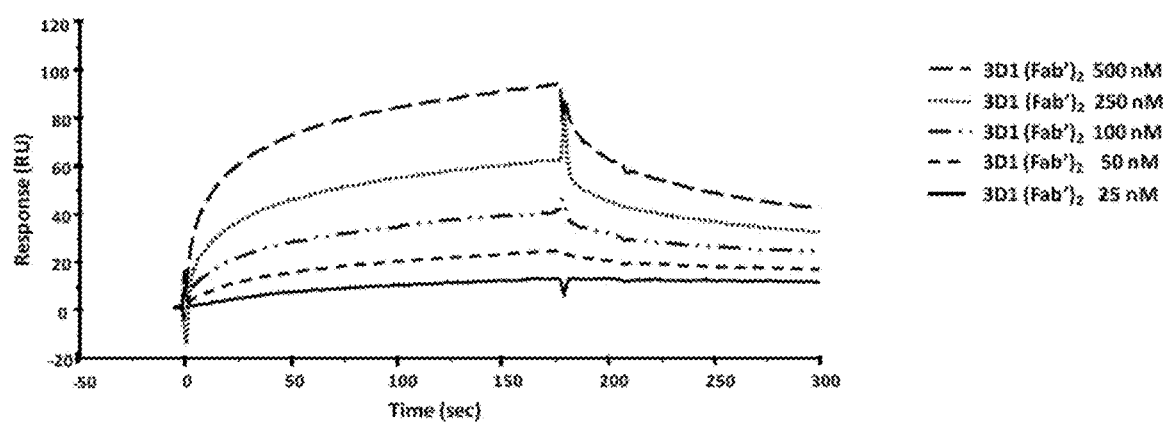
Figure 49:
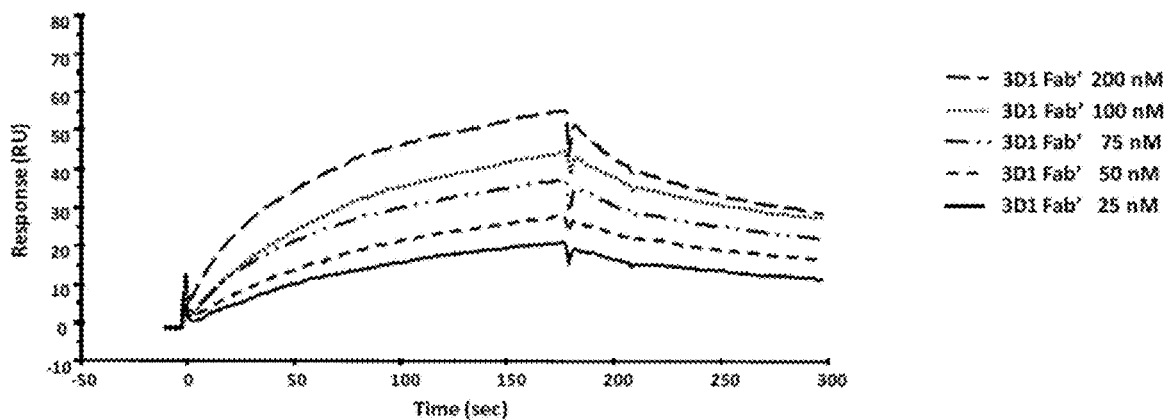

FIG. 49 shows an overlay plot of SPR sensorgrams showing the binding of the 3D1 F(ab')2 (a) and Fab' (b) to rhNodal immobilized on a CH5 sensor chip. The interaction was monitored at concentrations of F(ab')2 ranging between 25 and 500 nM, and of Fab' ranging between 25 and 200 nM, obtaining dose-dependent binding curves.

Figure 50:
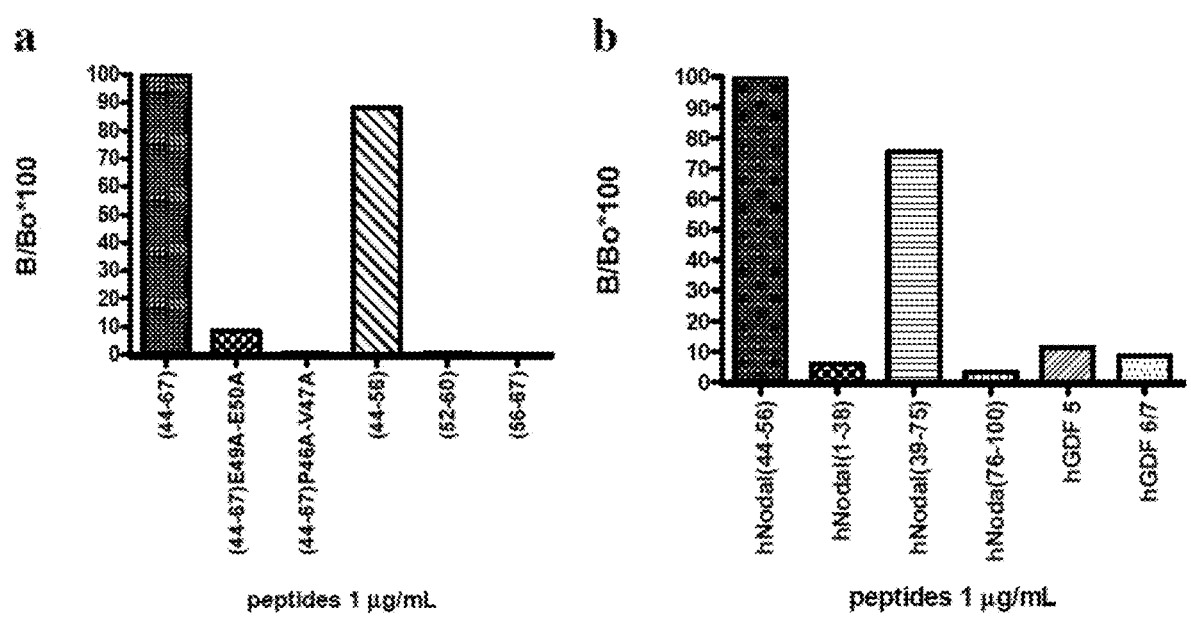

FIG. 50 shows characterization of the 3D1 binding properties. (a) Mapping of 3D1 mAb epitope; peptides were coated at 1.0 µg/mL; (b) Bar graph showing the specificity of the 3D1 for the central region of human Nodal; peptides were coated at 1.0 µg/mL. Absorbance value of each peptide (B) was normalized to the (44-67) peptide, assumed as 100% of signal ($B_0$). The signal was expressed as % of relative absorbance measured at 490 nm and calculated as $B/B_0 \times 100$.

Figure 51:
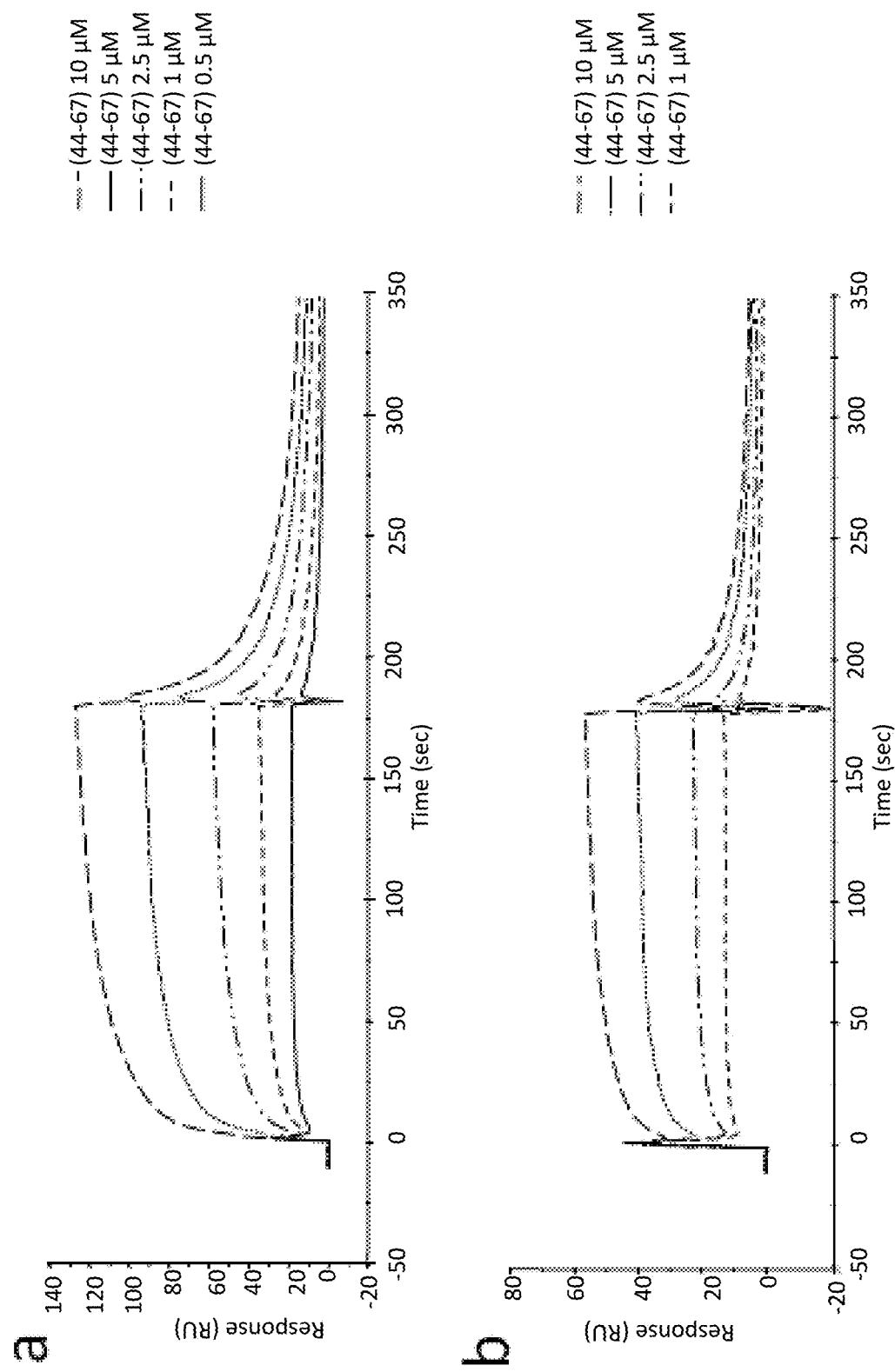

FIG. 51 shows overlay plots of SPR sensorgrams showing the binding of hNodal(44-67) with both 3D1 mAb (a) and its Fab' fragment (b) immobilized on a CH5 sensor chip. The interaction was monitored at concentrations of peptide ranging between 0.5 and 10 µM for the binding of hNodal(44-67) to 3D1 and between 1 and 10 µM for the binding to the Fab' fragment.

Figure 52:
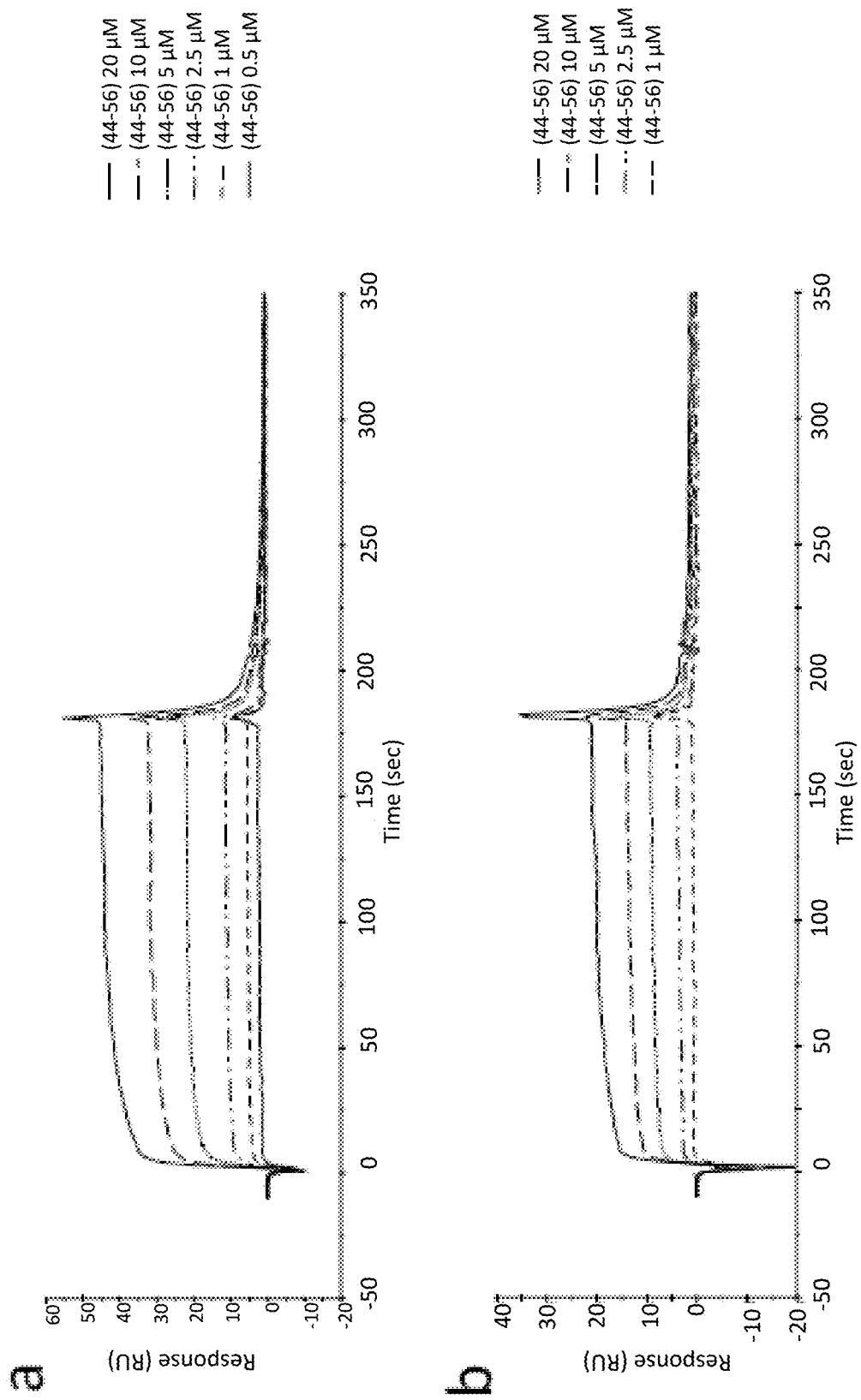

FIG. 52 shows overlay plots of SPR sensorgrams showing the binding of hNodal(44-56) with both the 3D1 mAb (a) and its Fab' fragment (b) immobilized on a CH5 sensor chip. The interaction was monitored at concentrations of peptide ranging between 0.5 and 20 µM for 3D1 and between 1 and 20 µM for the Fab' fragment, obtaining dose-dependent binding curves.

Figure 53:
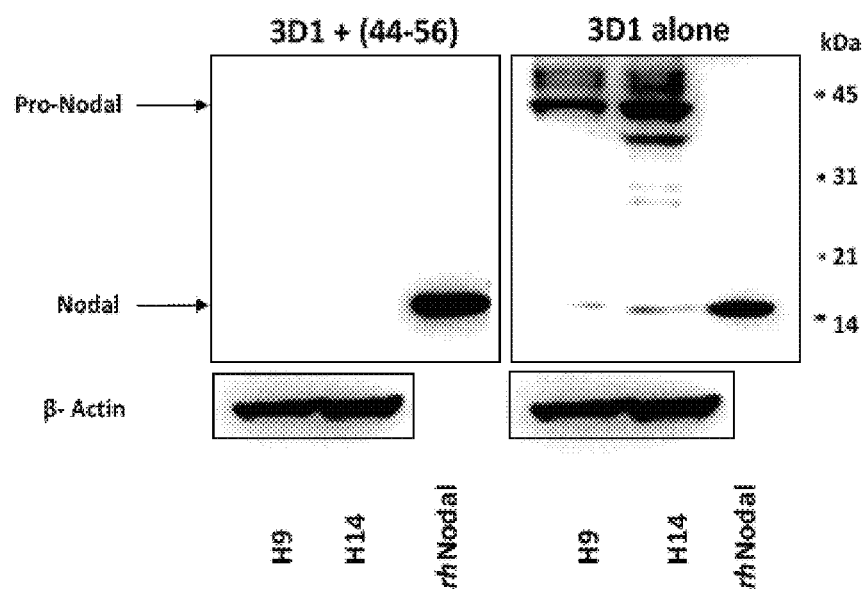

FIG. 53 shows a competition assay between endogenous Nodal in human embryonic stem cells lysates and the Nodal peptide corresponding to the 3D1 epitope. 3D1 was used at 4 µg/mL and hNodal(44-56) at 10 µg/mL.

FIGS. 54A-D show (a) Western blot analysis of melanoma cell lysates resolved by 15% SDS-PAGE under reducing conditions. As positive control HEK-293 cells and 100 ng of rhNodal were loaded. 3D1 antibody was used at 2.0 µg/mL. Detection was achieved using GAM-HRP antibody and ECL as substrate. Cytofluorimetric staining of Nodal in human melanoma cell lines LCP (b), A375 (c) and WM266 (d) using 3D1. Data were collected after cell fixation and permeabilization. An unrelated IgG1 isotype antibody was used as negative control.

Figure 55:
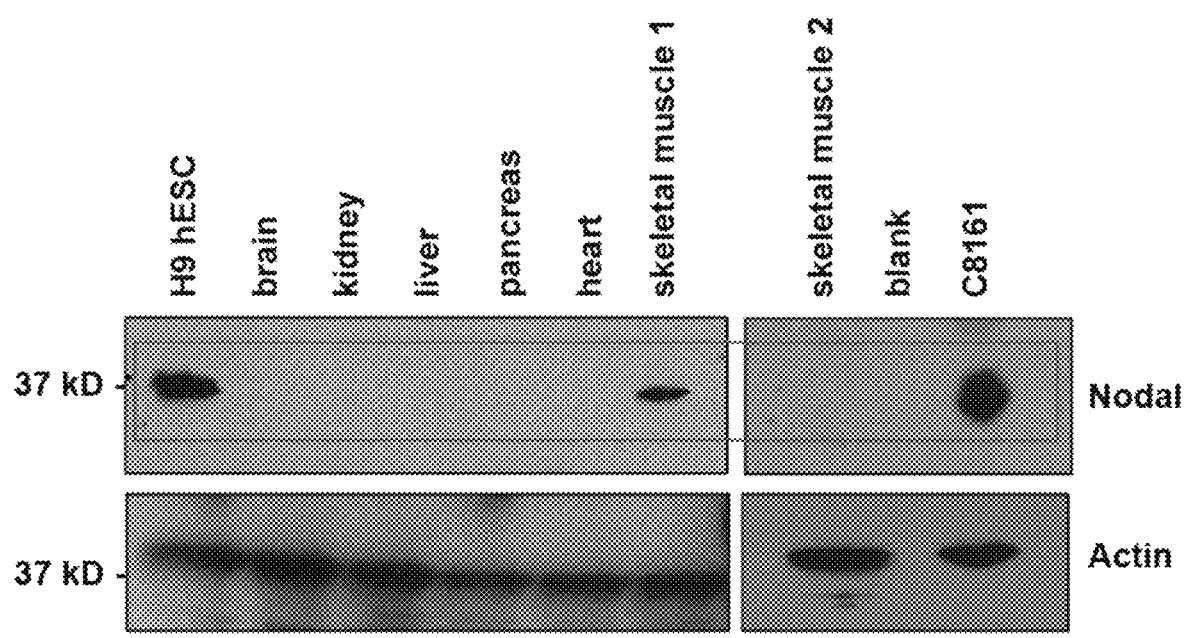

FIG. 55 shows Nodal expression in normal human tissue lysates. Commercially available Western blot grade normal human tissue lysates were analyzed for Nodal expression. Lysates from H9 hESCs were used as positive control for Nodal in the first lane. Nodal is not detected in lysates from normal human brain, kidney, liver, pancreas and heart. Low expression was detected in normal skeletal muscle sample 1, but no expression was detected in normal skeletal muscle sample 2. Nodal is highly expressed in C8161 human metastatic melanoma cells.

Figure 56:
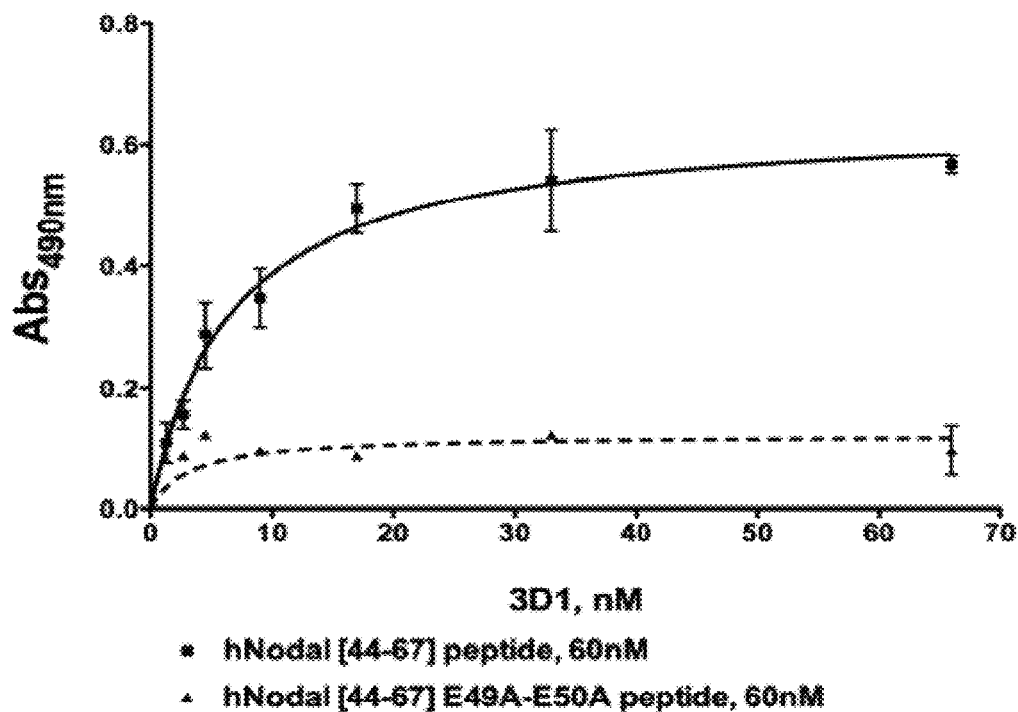
Figure 56:
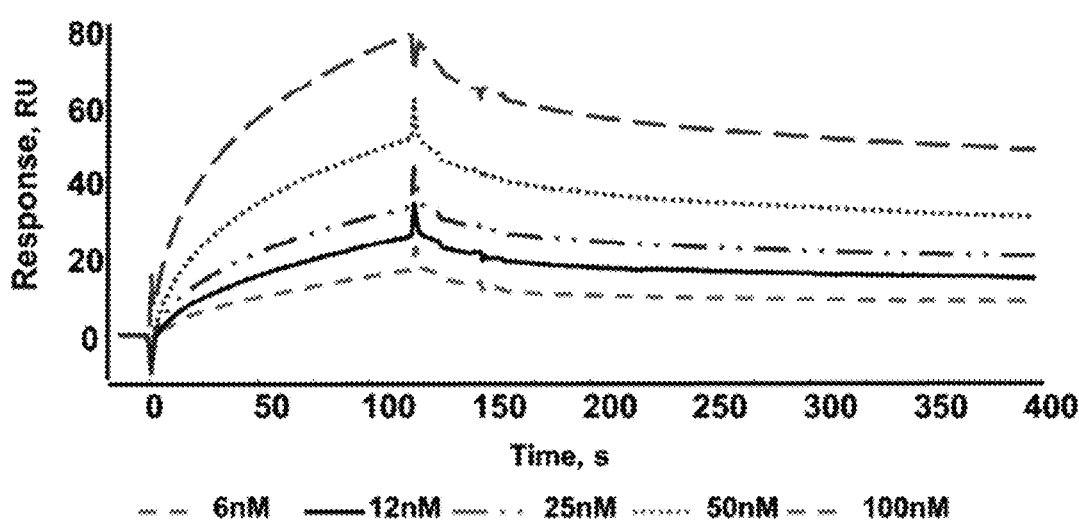
Figure 56:
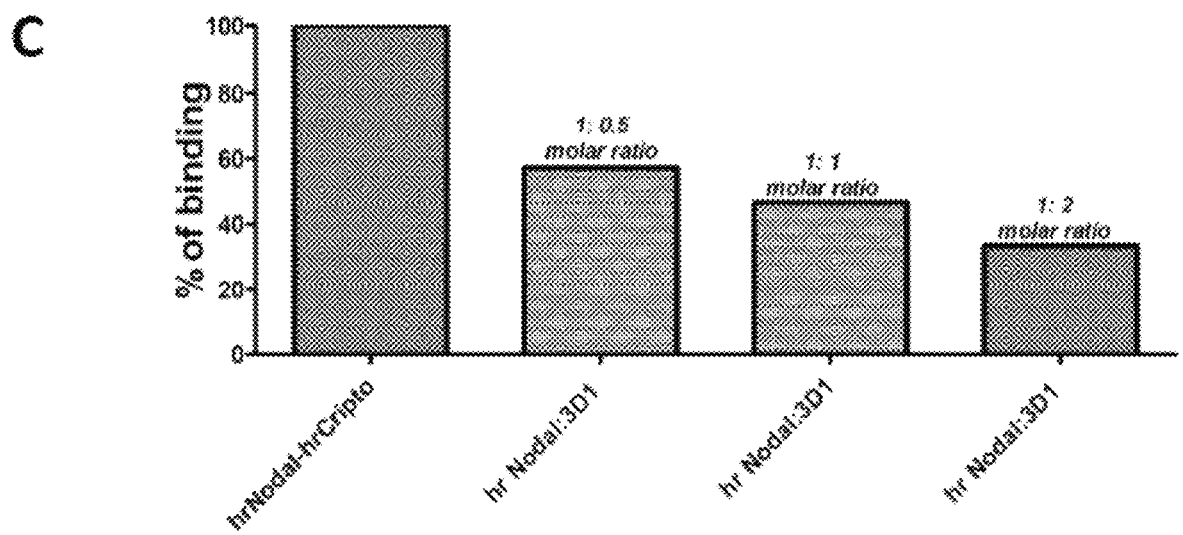

FIG. 56 shows characteristics of anti-Nodal 3D1 mAb. A) ELISA-based binding assay of 3D1 mAb to coated hNodall44-671 and hNodall44-671E49A-E50A. Peptides were coated at 0.18 µg/mL (60 nM). mAb 3D1 was tested at increasing concentrations between 1.0 and 67 nM. B) Overlay plot of SPR sensorgrams showing the interaction between 3D1 mAb and rhNodal immobilized on a CH5 sensor chip. The interaction was monitored at concentrations of mAb ranging between 6.0 and 100 nM, obtaining dose-dependent binding curves. rhNodal was immobilized on a Biacore CH5 sensor chip and 3D1 mAb solutions at increasing concentrations were injected over the chip. C) Inhibition of the rhNodal/rhCripto-1 complex by SPR concentration-dependent competition assay. A plot of % binding versus increasing antibody concentrations is reported. rhNodal was used at the fixed concentration of 5.0 nM whereas 3D1 was used at 1:0.5, 1; 1 and 1:2 molar ratio.

Figure 57A:
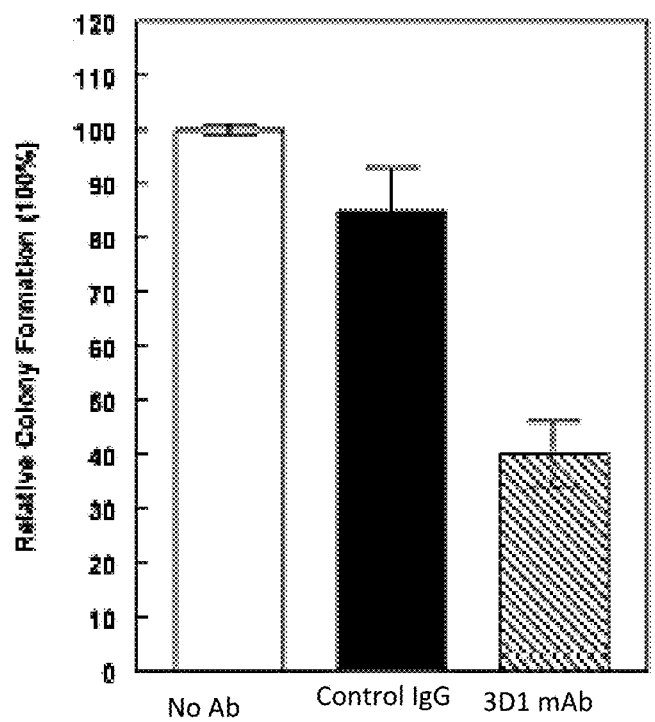
Figure 57B:
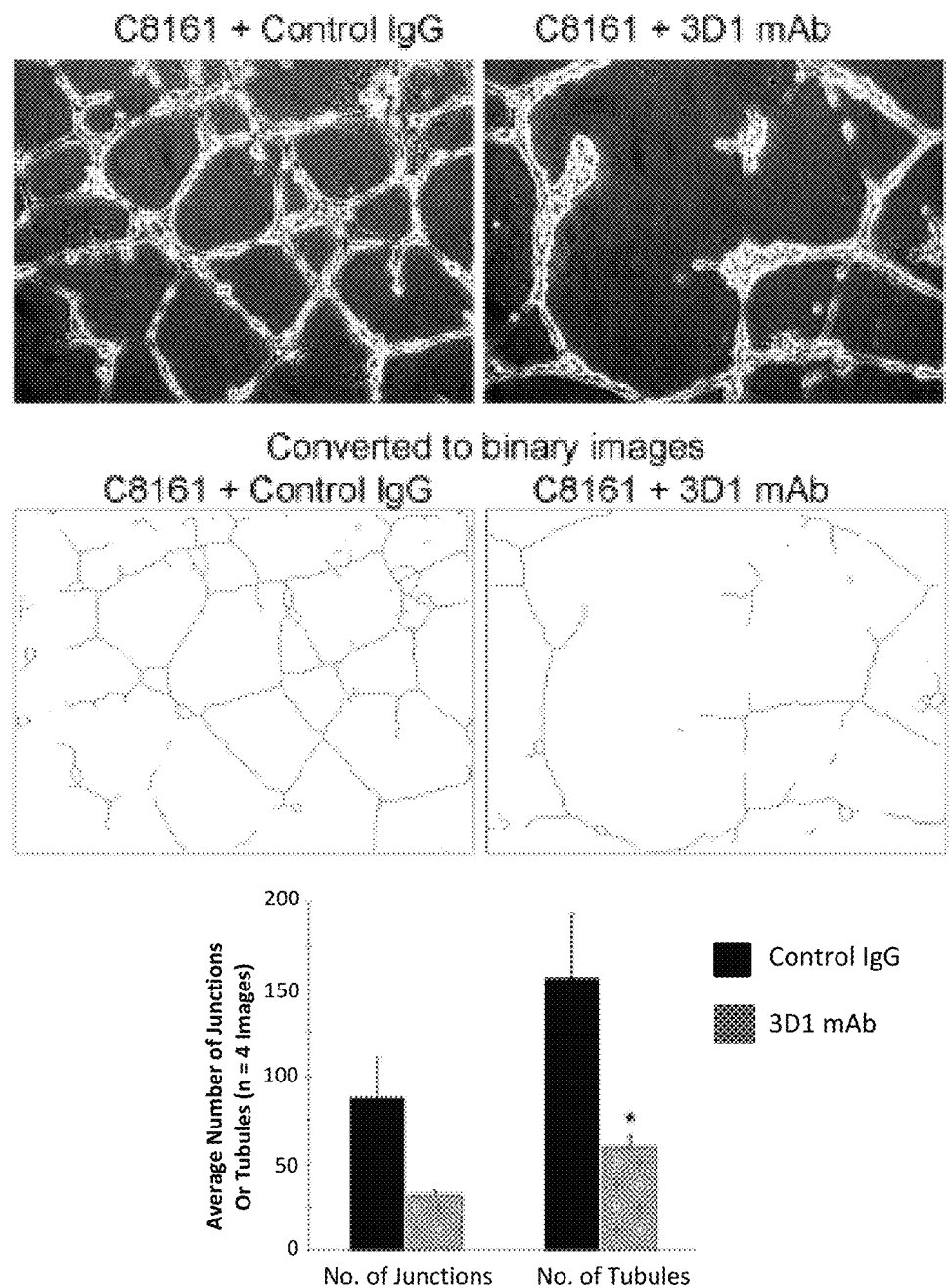

FIGS. 57A-B show in vitro effects of anti-Nodal 3D1 mAb. Results from anchorage independent growth assays (A) show a significant reduction in anchorage independent growth of C8161 cells treated with 3D1 mAb compared to control cells. B) Results from vasculogenic network formation assay show a significant reduction in the ability to form junctions and tubules in C8161 cells treated with 3D1 mAb compared to control cells. (*$P<0.05$). Histograms represent mean values +/−SEM.

Figure 58:
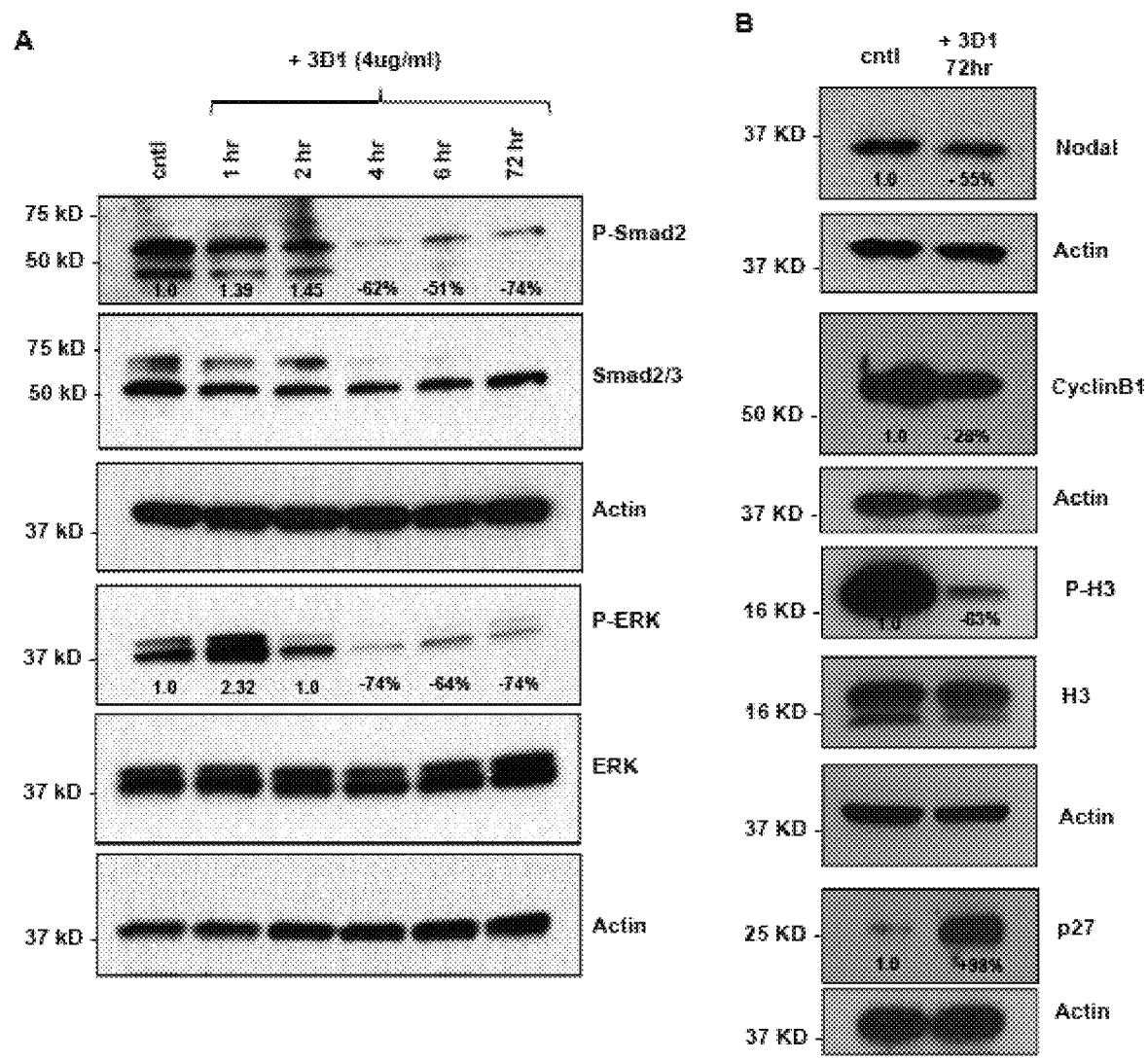

FIG. 58 shows effects of anti-Nodal 3D1 antibody on cell signaling and cell cycle related molecules. A) Levels of P-Smad2 and P-ERK1/2 are reduced within 4 hr of 3D1 mAb treatment (4 µg/ml) in C8161 human melanoma cells compared to IgG treated control. B) After 72 hr of 3D1 mAb treatment there is a reduction of Nodal, Cyclin B1 and P-H3 with a concomitant increase in p27 in C8161 cells compared to IgG treated control.

Figure 59:
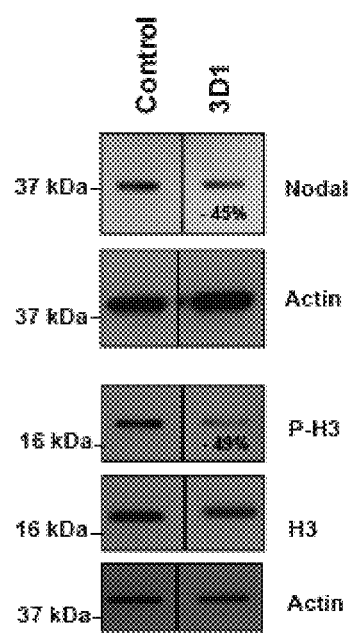

FIG. 59 shows effects of anti-Nodal 3D1 antibody on MDA-MB-231 breast cancer cells. Results from Western blot analysis show a 45% reduction in Nodal and a 49% reduction in the level of the proliferation/mitosis marker P-H3 in MDA-MB-231 breast cancer cells treated for 72 hrs (4 µg/ml) of 3D1 compared to the IgG control treated cells.

Figure 60:
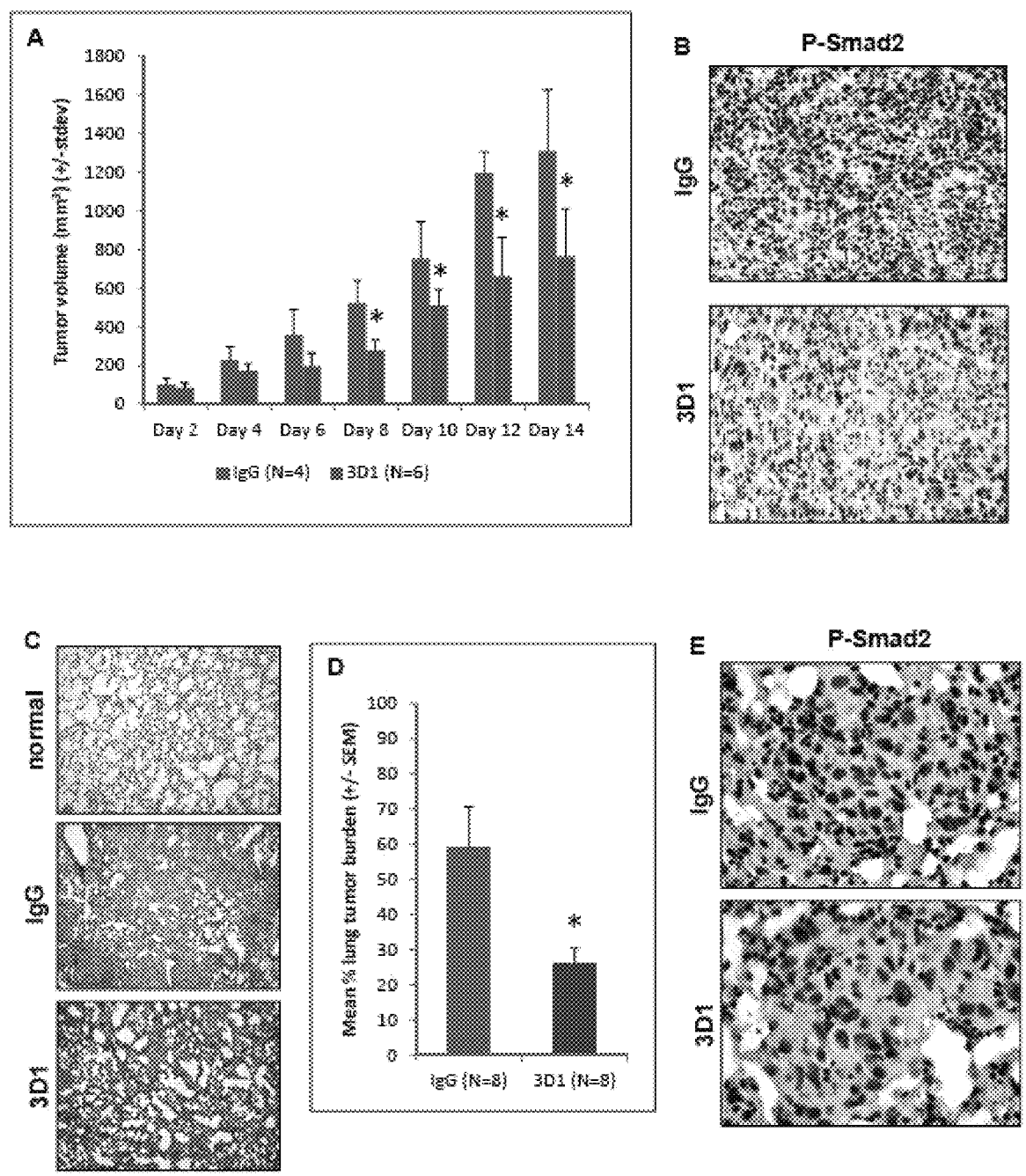

FIG. 60 shows in vivo effects of anti-Nodal 3D1 mAb on C8161 human melanoma cells. A) Reduced tumor volumes are observed in C8161 Nude mice orthotopic xenografts treated with direct tumor injections of 3D1 mAb versus control IgG. Histograms represent mean values +/−SD. Representative IHC staining in B) shows reduced nuclear expression (activation) of Smad2 in C8161 orthotopic xenograft Nude mouse treated with 3D1 mAb compared to IgG control (20× original magnification). The potential for lung colonization (shown microscopically with H&E staining) of C8161 cells (after systemic introduction) in Nude mice (C) (40× original magnification) is significantly reduced in animals treated with IP administration of 3D1 mAb vs IgG control (D). Histograms represent mean values +/−SEM. Representative IHC staining in E) shows reduced nuclear expression (activation) of P-Smad2 in C8161 lung colony of a 3D1 mAb treated Nude mouse versus IgG control (63× original magnification). (*P<0.05).

Figure 61:
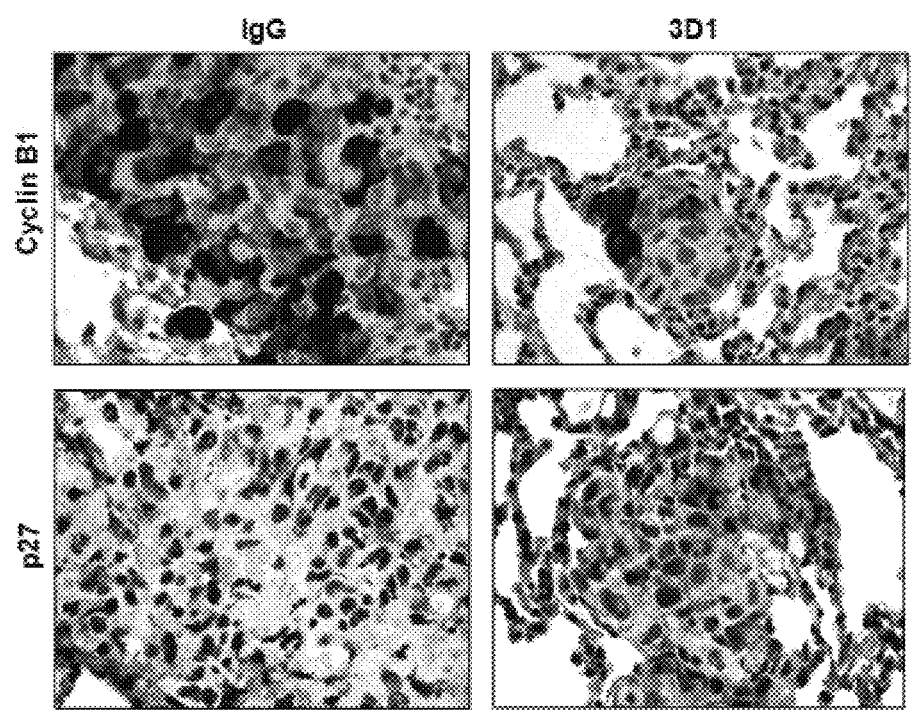

FIG. 61 shows representative IHC results showing expression of Cyclin B1 and p27 in C8161 lung colony in Nude mouse +/−3D1. Cyclin B1 expression is decreased in 3D1 treated tumors compared to IgG control. In contrast, p27 expression is increased in the 3D1 treated Nude mouse compared to control. (Original magnification 63× objective).

Figure 62:
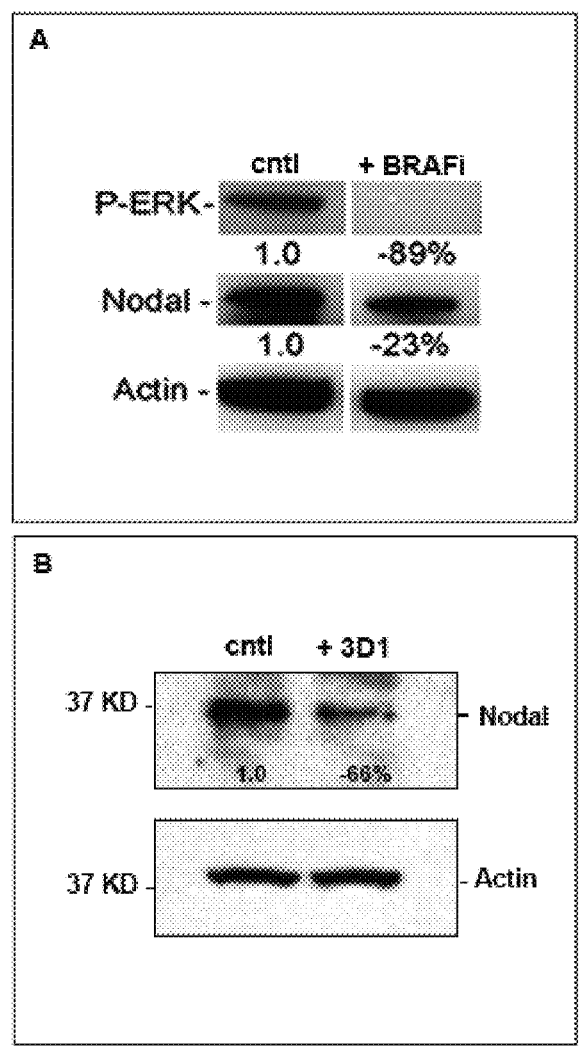

FIG. 62 shows effects of BRAFi (dabrafenib) or 3D1 in A375SM cells. A) After 72 hr, ERK1/2 activity (P-ERK1/2) is reduced in A375SM human melanoma cell line, which harbors the active BRAF mutation when treated with 10 nM of the BRAFi, dabrafenib compared to control, while Nodal is only minimally affected. In contrast, 72h 3D1 treatment of A375SM B) showed a more dramatic reduction in Nodal expression compared to control.

Figure 63:
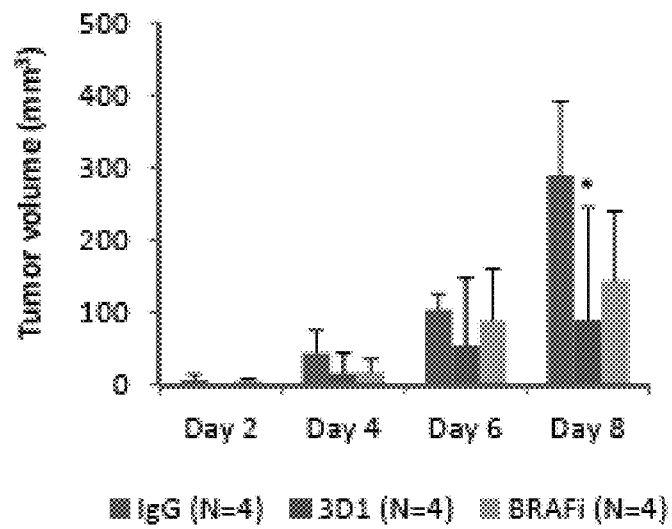
Figure 63:
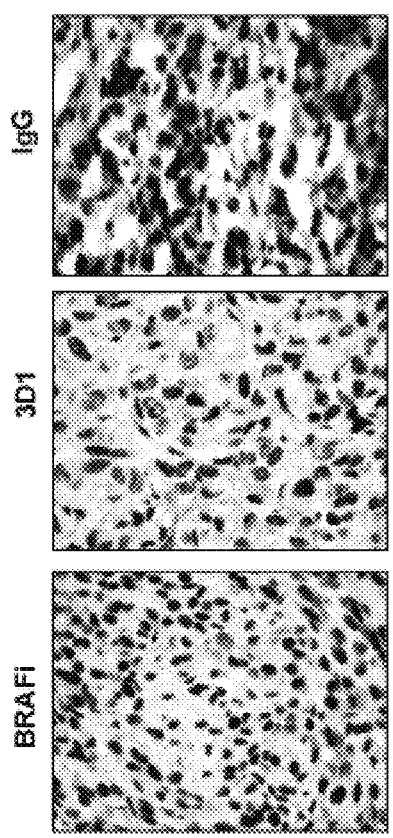

FIG. 63 shows in vivo effects of anti-Nodal 3D1 mAb on A375SM human melanoma cells. A) After 8 days, mean tumor volume of A375SM orthotopic Nude mice xenografts was significantly smaller in 3D1 mAb treated than in IgG control treated animals Tumor volumes in dabrafenib (BRAFi) treated animals also showed a trend towards reduced tumor volumes compared to control. Histograms represent mean values +/−SD. B) Representative IHC of P-Smad2 showing nuclear staining in A375SM orthotopic xenografts in Nude mice treated with control IgG, 3D1 mAb or BRAFi (*P<0.05).

Figure 64:
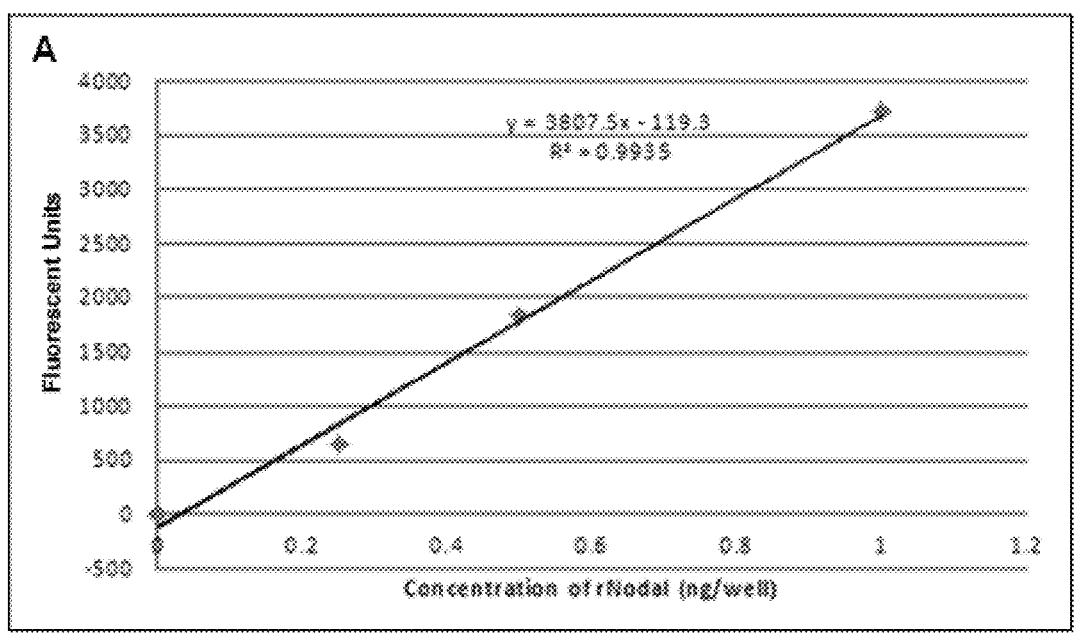
Figure 64:
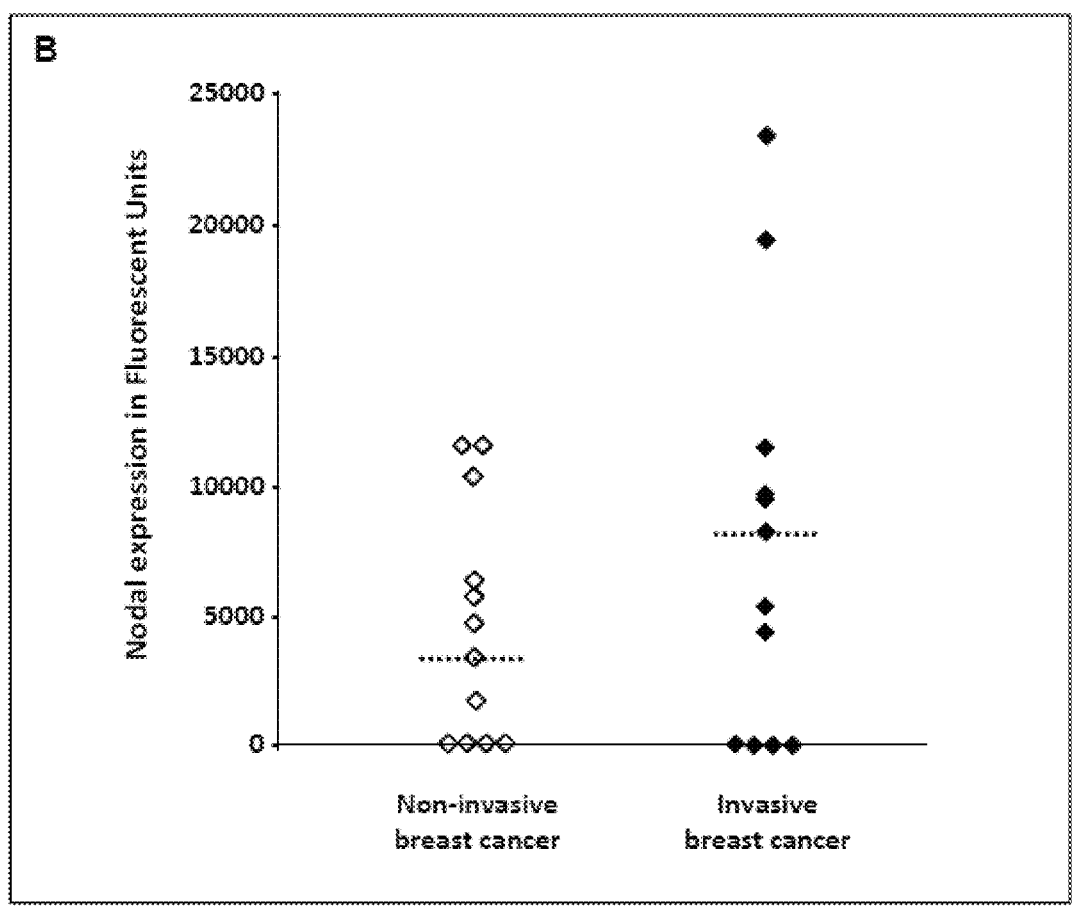

FIG. 64 shows a sandwich ELISA assay developed to detect Nodal in the serum of breast cancer patients. A) Illustrates a typical calibration curve using 3D1 mAb as the capture antibody for detecting recombinant Nodal; while B) depicts Nodal detected in patient's serum and with a trend for higher Nodal levels in the samples from patients with invasive compared to noninvasive breast cancer. (Dashed line=median level).

Figure 65:
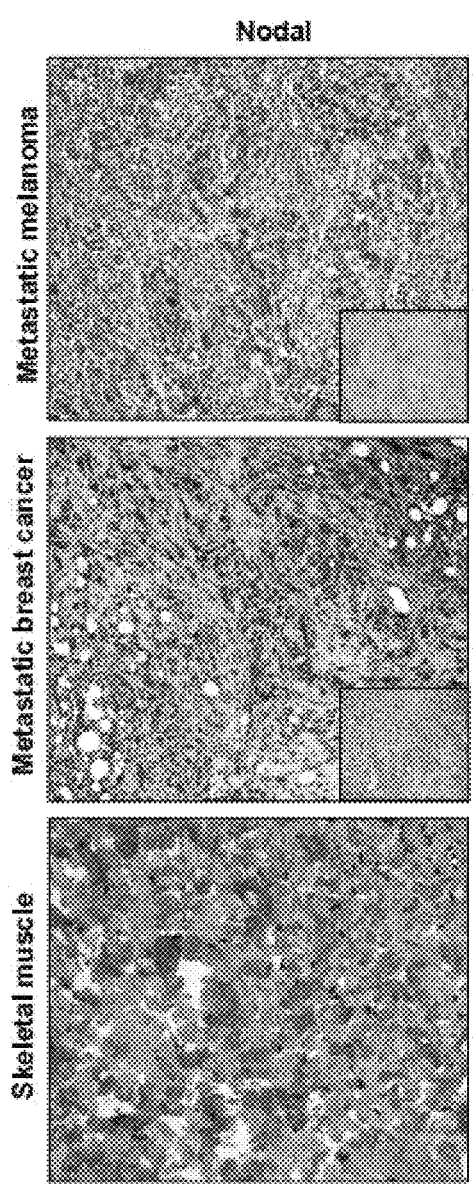

FIG. 65 shows Nodal expression in normal skeletal muscle—Immunohistochemistry analysis shows Nodal staining in metastatic melanoma and metastatic breast cancer tissue sections (insets=negative control with irrelevant isotype IgG). In contrast, no appreciable staining for Nodal was detected in a skeletal muscle tissue section.

DEFINITIONS

To facilitate an understanding of the invention, a number of terms are defined below.

As used herein, the term "antibody" is meant to include polyclonal antibodies, monoclonal antibodies (mAbs), chimeric antibodies, anti-idiotypic (anti-Id) antibodies and antibodies that can be labeled in soluble or bound form, as well as fragments, regions or derivatives thereof, provided by any known technique, such as, but not limited to, enzymatic or chemical cleavage, peptide synthesis or recombinant techniques. As described herein, anti-Nodal antibodies of the present invention bind Nodal (e.g., and inhibit Nodal activity). Thus, the term "antibody" refers to monoclonal antibodies (including full length monoclonal antibodies), polyclonal antibodies, and multispecific antibodies (e.g., antibodies specific for more than one target) as well as antibody fragments (e.g., that exhibit binding to the same target as full length antibody). Antibodies of the invention may be any type (e.g., IgG, IgE, IgM, IgD, IgA), class (e.g., IgG1, IgG2, IgG3, IgG4, IgA1 and IgA2) or subclass. Native antibodies, also referred to herein as "immunoglobulins" are heterotetrameric glycoproteins of about 150,000 Daltons (those of the G class), composed of two identical light (L) chains and two identical heavy (H) chains. Each heavy chain has a variable domain ($V_H$)) followed by a number of constant domains. Each light chain has a variable domain ($V_L$) and a constant domain.

As used herein, "anti-Nodal antibody" refers to an antibody which binds specifically to human Nodal (e.g., binds in a way that Nodal activity is inhibited). In one embodiment, an "anti-Nodal antibody" is an antibody that binds to human Nodal that allows detection, diagnosis, or predetermination of a disease or disorder associated with Nodal expression and/or activity, or that is used in a therapeutic composition of the invention (e.g., to treat and/or prevent Nodal-related disorder or disease).

As used herein, the term "neutralizable epitope" refers to a determinant portion of a protein, binding of which by an appropriate antibody will result in inhibition of a function of the protein. For example, a "neutralizable Nodal epitope" is a determinant portion fo the Nodal protein, the binding of which by an antibody inhibits Nodal interaction with Cripto-1 or the Cripto-1 coreceptor complex, or inhibits downstream signaling from Nodal or its complex with Cripto-1. In some embodiment herein, a neutralizable Nodal epitope is a polypeptide comprising the amino acid sequence of SEQ ID NO: 13, 15, or 17.

As used herein, the term "neutralizing antibody" refers to an antibody which is capable of specifically binding to a neutralizable epitope on a protein and substantially inhibiting or eliminating a biologically (e.g., complex formation, downstream signaling, etc.) activity of the protein.

The term "variable" as in "variable domain" (e.g., in the context of antibody variable domain) refers to structural features of the variable domain itself that differ extensively in sequence among all antibodies and the portions of the antibody that provide specificity for binding between the antibody and its specific target. These structural features within the variable domain are called hypervariable regions (HVRs) or complementarity determining regions (CDRs) and occur in both the light chain and heavy chain variable domains. There are three heavy chain HVRs or CDRs (HVRH1 or CDRH1 or H1, HVRH2 or CDRH2 or H2, and HVRH3 or CDRH3 or H3). Likewise, there are three light chain CDRs (HVRL1 or CDRL1 or L1, HVRL2 or CDRL2 or L2, and HVRL3 or CDRL3 or L3).

As used herein, the term "framework" refers to the residues of the variable region other than the CDR residues as defined herein. The FRs are more highly conserved portions of the variable domains. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat, et al. Sequences of Proteins of Immunological Interest, National Institutes of Health, Bethesda, Md., 1987). As used herein, numbering of immunoglobulin amino acid residues is done according to the immunoglobulin amino acid residue numbering system of Kabat, et al., unless otherwise indicated. The residues that make up these six CDRs have been characterized by Kabat as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference.

As used herein, the term "fully human framework" means a framework with an amino acid sequence found naturally in humans. Examples of fully human frameworks, include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970) J. Exp. Med. 132, 211-250, both of which are herein incorporated by reference). In certain embodiments, humanized antibodies of the present invention have fully human frameworks, or frameworks with one or more amino acids changed (e.g., to accommodate CDRs of the invention).

"Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. Humanized forms of non-human (e.g., murine) antibodies may be chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region (Fc), typically that of a human immunoglobulin template chosen. In one embodiment, humanized antibodies have one or more CDRs (one, two, three, four, five, six) which are altered with respect to the original antibody (e.g., affinity matured), which are also termed one or more CDRs "derived from" one or more CDRs from the original antibody.

The term "antibody fragment" refers to a portion of a full-length antibody, generally the target binding or variable region. Examples of antibody fragments include F(ab), F(ab'), F(ab')$_2$ and Fv fragments. The phrase "functional fragment or analog" of an antibody is a compound having qualitative biological activity in common with a full-length antibody. For example, a functional fragment or analog of an anti-Nodal antibody is one which can bind to Nodal in such a manner so as to prevent or substantially reduce the ability of Nodal to bind to its receptor (e.g., Cripto-1 or Alk4/7/ActRIIB receptor complex) and/or initiate signaling (e.g. through the Alk4/7/ActRIIB receptor complex).

As used herein, "functional fragment" with respect to antibodies, refers to Fv, F(ab) and F(ab')$_2$ fragments. An "Fv" fragment consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The term "diabodies" refers to small antibody fragments with two antigen-binding sites, which fragments comprise a heavy chain variable domain ($V_H$)) connected to a light chain variable domain ($V_L$) in the same polypeptide chain.

The F(ab) fragment contains the constant domain of the light chain and the first constant domain (CH1) of the heavy chain. F(ab') fragments differ from F(ab) fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, which the remainder of the chain(s) is identical with or homologous to corresponding sequences in antibodies derived from another species or belonging to another antibody class or subclass, as well as fragments of such antibodies, so long as they exhibit the desired biological activity. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well-known techniques. The parent monoclonal antibodies to be used in accordance with the present invention may be made by the hybridoma method first described by Kohler, et al., Nature 256:495 (1975), or may be made by recombinant methods.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495-497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES. A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, and any subclass thereof. A hybridoma producing a mAb of the present invention may be cultivated in vitro, in situ or in vivo.

Chimeric antibodies are molecules—different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273-3277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066-1074 (1986); Robinson et al., International Patent Publication #PCT/US86/02269 (published 7 May 1987); Liu et al., Proc. Natl. Acad. Sci. USA 84:3439-3443 (1987); Sun et al., Proc. Natl. Acad. Sci. USA 84:214-218 (1987); Better et al., Science 240:1041-1043 (1988); and Harlow and Lane Antibodies: a Laboratory Manual Cold Spring Harbor Laboratory (1988). These references are entirely incorporated herein by reference.

As used herein, the term "bispecific antibody" is refers to any immunoreactive agent having two different antigen-binding regions defined by different antibody sequences. The different targets may be epitopes on separate target species (e.g., Nodal and Cripto-1 or different epitopes in one target species (e.g., Nodal).

As used herein, the term "antibody-drug-conjugate" refers to an immunoreactive agent, such as an antibody or antigen binding fragment thereof, chemically linked to one or more chemical drug(s) that may optionally be therapeutic or cytotoxic agents. An antibody-drug-conjugate may include an antibody (or fragment), a cytotoxic or therapeutic drug, and a linker that enables attachment or conjugation of the drug to the antibody. An antibody-drug-conjugate may comprise 1 to 10 drugs conjugated to the antibody, including drug loaded species of 2, 3, 4, 5, 6, 7, 8, 9, 10, or any suitable ranges there between. Non-limiting examples of drugs that may be included in the antibody-drug-conjugates are mitotic inhibitors, antitumor antibiotics, immunomodulating agents, gene therapy vectors, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

As used herein, the term "patient" preferably refers to a human in need of treatment (e.g., to treat cancer, or a precancerous condition or lesion). However, the term "patient" can also refer to non-human animals, preferably mammals such as dogs, cats, horses, cows, pigs, sheep and non-human primates, among others, that are in need of treatment.

The term "group" refers to a group of patients as well as a sub-group of patients.

As used herein, the term "purified" or "to purify" refers to the removal of contaminants from a sample. For example, anti-Nodal antibodies may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial host cells and the polypeptides are purified by the removal of host cell proteins; the percentage of recombinant antigen-specific polypeptides is thereby increased in the sample.

As used herein, an "isolated" antibody or antibody fragment is one that has been identified and separated and/or recovered from a component of its natural environment. Contaminant components of its natural environment are materials that would interfere with diagnostic or therapeutic uses for the antibody or fragment thereof, and may include enzymes, hormones, and other proteinaceous or non-proteinaceous solutes. In certain embodiments, the isolated antibody is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, (3) to homogeneity by SDS-page under reducing or nonreducing conditions using Coomassie blue, or silver stain, or (4) using chromatography. An isolated antibody includes the antibody in situ within recombinant cells since at least one component of the polypeptide's natural environment will not be present. Ordinarily, however, an isolated antibody will be prepared by a least one purification step.

As used herein, the term "treatment" refers to both therapeutic treatment and prophylactic or preventative measures. Those in need of treatment include those already with a disorder as well as those in which a disorder is to be prevented (e.g., those suspected to have or be at risk for a certain disease or disorder).

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The term "substantially identical" with respect to an antibody chain polypeptide sequence may be construed as an antibody chain exhibiting at least 70%, or 80%, or 90%, or 95% sequence identity to the reference polypeptide sequence. The term with respect to a nucleic acid sequence may be construed as a sequence of nucleotides exhibiting at least about 85%, or 90%, or 95%, or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

"Transformation" of a cellular organism, cell, or cell line with DNA means introducing DNA into the target cell so that the DNA is replicable, either as an extrachromosomal element or by chromosomal integration. "Transfection" of a cell or organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases include those formed partially or entirely of glass (e.g., controlled pore glass), polysaccharides (e.g., agarose), polyacrylamides, polystyrene, polyvinyl alcohol, and silicones. In certain embodiments, depending on the context, the solid phase can comprise the well of an assay plate; in others it is a purification column (e.g., an affinity chromatography column).

As used herein, the term "solid tumor" includes, for example, sarcoma, melanoma, carcinoma, prostate carcinoma, lung carcinoma, colon carcinoma, or other solid tumor cancer.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), chronic lymphocytic leukemia (CML), and other cancers described herein.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

The terms "overexpression of Nodal protein" and "aberrant expression of Nodal protein" are intended to indicate a reactivation of the embryonic Nodal signaling pathway or an abnormal level of expression of the Nodal protein in a cell (e.g., within a cancer or tumor or other disease process in which Nodal is elevated) within a specific tissue or organ of a patient relative to the level of expression in a normal cell from that tissue or organ. For example, patients having a cancer characterized by overexpression or aberrant expression of Nodal can be determined by standard assays known in the art. Overexpression or aberrant expression can be measured in fixed cells of frozen or paraffin-embedded tissue sections using immunohistochemical (IHC) detection. When coupled with histological staining, localization of the targeted protein can be determined and extent of its expression (e.g., within a tumor) can be measured both qualitatively and semi-quantitatively.

The term "Nodal positive cancer" refers to a cancer disease such as breast cancer, melanoma or other type of cancer described herein which is characterized by an overexpression or aberrant expression of Nodal.

The term "relapsed cancer" refers to the uncontrolled growth of abnormal cells in tumor patients who initially responded to previous therapy, but in whom the therapeutic response was not maintained. The term "relapsed Nodal positive cancer" refers to the uncontrolled growth of abnormal cells characterized by Nodal protein overexpression or aberrant expression in tumor patients who initially responded to previous therapy with an anti-Nodal antibody, but in whom the therapeutic response was not maintained during treatment with the anti-Nodal antibody.

A therapeutic response (RE) can be established based on the medical judgment of a practitioner ascertained by the results from clinical and laboratory data that are generally known in the art to assess patient treatment. Such data may be obtained, by way of example, from clinical examination, cytological and histological techniques, endoscopy and laparoscopy, ultrasound, CT and MRI scans, chest X-ray and mammography, and measuring the concentration of tumor markers, such as Nodal. Preferably RECIST criteria may be used to determine tumor response (RE). (Therasse et al., J. Nat. Cancer Institute. 92 (2000) 205-216).

According to these RECIST criteria tumor response for solid tumors (Therasse, et al. J. Nat. Cancer Institute. 92 (2000) 205-216) is categorized in dependency of the volume progression or regression of the tumors (e.g. measured via CT) into four levels: complete response (CR) or partial response (PR), stable disease (SD) and progressive disease (PD). Furthermore the European Organization for Research and Treatment of Cancer (EORTC) proposed a categorization into four levels in dependency of the metabolism of tumors measured via 2-[18F]-Fluoro-2-deoxyglucose positron emission tomography (FDG-PET) (Young H., et al., Eur J Canc 35 (1999) 1773-1782 and Kellof, G. J., et al, Clin Canc Res 11 (2005) 2785-2808): complete metabolic response (CMR) or partial metabolic response (PMR), stable metabolic disease (SMD) and progressive metabolic disease (PMD)

"Response (RE)" and "Non-Response (NR)" may be established based on data acquired by the combination of computer tomography (CT) and 2-(18F)-Fluoro-2-deoxyglucose positron emission tomography (FDG-PET) (Kellof, G. J., et al, Clin Canc Res 11 (2005) 2785-2808 and Young H., et al., Eur J Canc 35 (1999) 1773-82) using both the RECIST and FUG-PET criteria described above.

The term "method for manufacturing a medicament" refers to the manufacturing of a medicament for use in an indication as specified herein and in particular for use in the treatment of tumors, tumor metastases, or cancer in general.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed an overall beneficial course of action.

As used herein, the term "metastasis" refers to the transmission of cancerous cells from the primary tumor to one or more sites elsewhere in a patient. Means to determine if a cancer has metastasized are known in the art and include bone scan, chest X-ray, CAT scan, MRI scan, and tumor marker tests.

The terms "medicament for preventing metastasis" or "medicament for reducing metastasis" as used herein refer to use of a medicament as a prophylactic agent against metastasis in patient (e.g., with cancer (e.g., to inhibit or reduce a further transmission of cancerous cells from the primary tumor to one or more sites elsewhere in a patient). Thus, in one embodiment, metastasis of the primary, metastatic tumor or cancer is prevented, delayed, or inhibited.

DETAILED DESCRIPTION

The present invention relates to anti-Nodal antibodies and use of the anti-Nodal antibodies for diagnosing, preventing, and treating a Nodal-related disorder or disease.

Therapeutic Uses of Anti-Nodal Antibodies

An antibody of the invention may be administered alone or in combination with one or more other agents for use as a therapeutic. In some embodiments, the present invention is directed to antibody-based therapies which involve administering antibodies of the invention to a patient (e.g., preferably a human patient) for the treatment of Nodal-related and/or mediated disease, disorder or condition. In one embodiment, a therapeutic of the invention (e.g., comprising anti-Nodal antibody) is administered to a patient to reverse, alleviate, inhibit the progression of, prevent (e.g., partially or completely) the growth of tumors, tumor metastases, or other cancer causing or neoplastic cells in the patient.

The amount of anti-Nodal antibody administration and the timing of administration will depend on the type (e.g., species, gender, age, weight, etc.) and condition of the patient being treated and the severity of the disease or condition being treated. Usually typical dosages of anti-Nodal antibody are used. For example, the dosages for administration of an antibody according to the invention can be about 1 µg/kg to 50 mg/kg (e.g. 0.1-20 mg/kg) of antibody by one or more separate administrations, or by continuous infusion. A typical daily dosage might range from about 1 µg/kg to about 100 mg/kg. In a preferred aspect, the antibodies are administered every two to three weeks, at a dose ranged from about 1 mg/kg to about 15 mg/kg. An exemplary dose is a loading dose of 4 mg/kg administered as continuous infusion and subsequent 3-weekly infusions of 2 mg/kg to 6 mg/kg, preferably 2 mg/kg, administered as continuous infusion until disease progression is detected. Another exemplary dose is 5 mg/kg to 15 mg/kg, preferably 5 mg/kg to 10 mg/kg, and more preferred 5 mg/kg, once every 14 days as an IV infusion.

In a preferred embodiment, therapeutic compositions of the invention are used in methods of treating subjects with cancer. For example, in one embodiment, the invention provides methods for preventing or reducing metastasis in a patient suffering from cancer, increasing the duration of survival of such a patient, increasing the progression free survival of such a patient, and increasing the duration of response, resulting in a statistically significant and clinically meaningful improvement of the treated patient as measured by the duration of survival, progression free survival, response rate or duration of response. In a preferred embodiment, the medicament is useful for increasing the response rate in a group of patients.

A subject receiving a therapeutic composition of the invention may be a mammal in need of a particular treatment, such as a mammal having been diagnosed with a particular disorder, e.g., one relating to Nodal. Methods of administering a therapeutically acceptable dose of an anti-Nodal antibody, or antibodies, of the present invention, or a cocktail of the present antibodies, or in combination with other antibodies of varying sources, alone or in combination with one or more other therapeutic agents described herein (e.g., Lefty) may be used to ameliorate or prevent disease symptoms in the treated mammal (e.g., humans).

Antibodies of the present invention may be used to treat a mammal. The antibody may be administered to a nonhuman mammal for the purposes of obtaining preclinical data. Exemplary nonhuman mammals to be treated include non-human primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

Therapeutic compounds of the invention include, but are not limited to, antibodies of the invention (including fragments, analogs and derivatives thereof as described herein) and nucleic acids encoding antibodies of the invention as described herein (including fragments, analogs and derivatives thereof and anti-idiotypic antibodies as described herein). The antibodies of the invention can be used to treat, inhibit, or prevent diseases, disorders, or conditions associated with aberrant expression and/or activity of Nodal, including, but not limited to, any one or more of the diseases, disorders, or conditions described herein. The treatment and/or prevention of diseases, disorders, or conditions associated with overexpression of, or aberrant expression and/or activity of Nodal includes, but is not limited to, alleviating at least one symptom associated with the diseases, disorders, or conditions. Antibodies of the invention may be provided in pharmaceutically acceptable compositions as known in the art or as described herein.

Anti-Nodal antibodies of the invention may be used therapeutically in a variety of diseases. In one embodiment, the present invention provides a method for preventing or treating Nodal-mediated diseases in a mammal. The method comprises administering a disease preventing or treating amount of anti-Nodal antibodies to the mammal. In one embodiment, the anti-Nodal antibodies bind to Nodal and inhibit its function. In another embodiment, anti-Nodal antibodies are used to inhibit cancer metastasis. In one embodiment, a composition comprising anti-Nodal antibodies is used in a method or prophylactically and/or therapeutically treating a patient suffering from cancer via inhibiting or reducing a transmission of cancerous cells from the primary tumor to one or more sites elsewhere in a patient (e.g., metastasis of the primary, metastatic tumor or cancer is prevented, delayed, or inhibited using methods and compositions of the invention).

The invention is not limited by the type of cancer treated. Indeed, a variety of cancers may be treated including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

The invention is not limited by the type of composition or agent co-administered with an antibody composition of the invention. For example, in the context of the invention, one or more cytotoxic, chemotherapeutic and/or anti-cancer agents, or compounds that enhance the effects of such agents, may be used and/or administered with anti-Nodal antibodies of the invention. Exemplary agents include, but are not limited to, alkylating agents or agents with an alkylating action, such as cyclophosphamide (CTX; e.g. CYTOXAN), chlorambucil (CHL; e.g. LEUKERAN), cisplatin (CisP; e.g. PLATINOL busulfan (e.g. MYLERAN), melphalan, carmustine (BCNU), streptozotocin, triethylenemelamine (TEM), mitomycin C, and the like; anti-metabolites, such as methotrexate (MTX), etoposide (VP16; e.g. VEPESID), 6-mercaptopurine (6 MP), 6-thioguanine (6TG), cytarabine (Ara-C), 5-fluorouracil (5-FU), capecitabine (e.g. XELODA), dacarbazine (DTIC), and the like; antibiotics, such as actinomycin D, doxorubicin (DXR; e.g. ADRIAMYCIN), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL) and paclitaxel derivatives, the cytostatic agents, glucocorticoids such as dexamethasone (DEX; e.g. DECADRON) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL), dactinomycin, mechlorethamine (nitrogen mustard), streptozocin, cyclophosphamide, lomustine (CCNU), doxorubicin lipo (e.g. DOXIL), gemcitabine (e.g. GEMZAR), daunorubicin lipo (e.g. DAUNOXOME), procarbazine, mitomycin, docetaxel (e.g. TAXOTERE), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

In one embodiment, anti-hormonal agents are used with or co-administered with an anti-Nodal antibody of the invention.

The use of the cytotoxic and other anticancer agents described herein in chemotherapeutic regimens is generally well characterized in the cancer therapy arts, and their use herein falls under the same considerations for monitoring tolerance and effectiveness and for controlling administration routes and dosages. Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In another embodiment, an effective amount of ionizing radiation may be carried out and/or a radiopharmaceutical may be used. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. In one embodiment, anti-Nodal antibody may be labeled with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination or single therapy of the invention is enhanced when combined with radiation, optionally with additional chemotherapeutic or anticancer agents.

The amount of antibody which will be effective in the treatment, inhibition, and prevention of a disease or disorder associated with aberrant expression and/or activity of Nodal can be determined by standard clinical techniques. The dosage will depend on the type of disease to be treated, the severity and course of the disease, whether the antibody is administered for preventive or therapeutic purposes, previous therapy, the patient's clinical history and response to the antibody, and the discretion of the attending physician. The antibodies can be administered in treatment regimes consistent with the disease, e.g., a single or a few doses over one to several days to ameliorate a disease state or periodic doses over an extended time to inhibit disease progression and prevent disease recurrence. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

An additional exemplary embodiment for the dosage of an anti-Nodal antibody of the invention administered to a patient is typically 0.1 mg/kg to 150 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing stability, uptake and tissue penetration of the antibodies by modifications such as, for example, lipidation or pegylation. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Anti-Nodal antibodies of the invention may be administered alone or in combination with other types of treatments. In a preferred embodiment, the antibodies are substantially purified (e.g., substantially free from substances that limit its effect or produce undesired side-effects).

Various delivery systems are known and can be used to administer an antibody of the present invention, including injection, e.g., encapsulation in liposomes, microparticles, microcapsules, recombinant cells (genetically modified) capable of expressing the compound, receptor-mediated endocytosis, construction of a nucleic acid as part of a retroviral, lentiviral, adenoviral, or other vector, etc.

Anti-Nodal antibodies can be administered to the mammal in any acceptable manner. Methods of introduction include but are not limited to parenteral, subcutaneous, intraperitoneal, intrapulmonary, intranasal, epidural, inhalation, and oral routes, and if desired for immunosuppressive treatment, intralesional administration. Parenteral infusions include intramuscular, intradermal, intravenous, intraarterial, or intraperitoneal administration. Anti-Nodal antibodies or compositions comprising same may be administered by any convenient route, for example by infusion or bolus injection, by absorption through epithelial or mucocutaneous linings (e.g., oral mucosa, rectal and intestinal mucosa, etc.) and may be administered together with other biologically active agents (e.g., those described herein). Administration can be systemic or local. In addition, it may be desirable to introduce the therapeutic antibodies or compositions of the invention into the central nervous system by any suitable route, including intraventricular and intrathecal injection. In addition, antibodies are suitably administered by pulse infusion, particularly with declining doses of the antibody. Preferably the dosing is given by injections, most preferably intravenous or subcutaneous injections, depending in part on whether the administration is brief or chronic.

In one embodiment, pulmonary administration is employed, e.g., by use of an inhaler or nebulizer, and formulation with an aerosolizing agent. The antibody may also be administered into the lungs of a patient in the form of a dry powder composition.

In a specific embodiment, it may be desirable to administer the therapeutic antibodies or compositions of the invention locally to the area in need of treatment; this may be achieved by, for example, local infusion, topical application, by injection, by means of a catheter, by means of a suppository, or by means of an implant, said implant being of a porous, non-porous, or gelatinous material, including membranes or fibers. In another embodiment, antibodies are delivered in a controlled release system.

The present invention also provides pharmaceutical compositions. Such compositions comprise a therapeutically effective amount of anti-Nodal antibodies and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. Thus, a pharmaceutically acceptable carrier is any carrier known in the art for the delivery of an agent to a subject. The term "carrier" refers to a diluent, adjuvant, excipient, or vehicle with which the therapeutic is administered. Such physiological carriers can be sterile liquids, such as water and oils, including those of petroleum, animal, vegetable, or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. In one embodiment, a composition comprising a therapeutically effective amount of anti-Nodal antibodies and a physiologically acceptable carrier is specifically formulated for the particular mode of administration.

For example, in one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In one embodiment, the container includes a package insert. As used herein, "package insert" refers to instructions customarily included in commercial packages of a therapeutic product, which may include information about the indications, usage, dosage, administration, contraindications and/or warnings concerning the use of such therapeutic products.

The invention also provides therapeutic formulations that are prepared for storage as lyophilized formulations or aqueous solutions by mixing anti-Nodal antibodies having the desired degree of purity with optional "pharmaceutically-acceptable" carriers, excipients or stabilizers typically employed in the art (all of which are termed "excipients"), i.e., buffering agents, stabilizing agents, preservatives, isotonifiers, non-ionic detergents, antioxidants, and other miscellaneous additives. See Remington's Pharmaceutical Sciences, 16th edition, Osol, Ed. (1980). Such additives must be nontoxic to the recipients at the dosages and concentrations employed.

Exemplary buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris may be used. In one embodiment, buffers are utilized to maintain the pH in the range which approximates physiological conditions. Buffers may be present at concentration ranging from about 2 mM to about 50 mM.

Preservatives may be added to retard microbial growth, and may be added in amounts ranging from 0.2%4% (w/v). Exemplary preservatives include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, and alkyl parabens such as methyl or propyl paraben, catechol, resorcinol, cyclohexanol, and 3-pentanol.

Similarly, a variety of stabilizers may be used, for example, polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, alpha.-monothioglycerol and sodium thiosulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers may be present in the range from 0.1 to 10,000 weights per part of weight active protein.

Non-ionic surfactants or detergents may be used, such as, polysorbates (20, 40, 60, 80, etc.), polyoxamers (184, 188 etc.), PLURONIC, polyols, etc. Non-ionic surfactants may be present in a range of about 0.05 mg/ml to about 1.0 mg/ml, although less (e.g., below 0.05 mg/mi) or more (e.g., 1.0 mg/ml) may be used.

Additional miscellaneous excipients include bulking agents, (e.g., starch), chelating agents (e.g., EDTA), anti-oxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be encapsulated in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, Osal, Ed. (1980).

Sustained-release preparations may be used. Suitable examples of sustained-release preparations include semipermeable matrices of solid hydrophobic polymers containing the antibody variant, which matrices are in the form of shaped articles, e.g., films, or microcapsules. Examples of sustained-release matrices include polyesters, hydrogels (for example, poly(2-hydroxyethyl-methacrylate), poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(-)-3-hydroxybutyric acid.

Nodal Immunogen

As described in the Examples, the invention provides Nodal immunogen and methods of generating antibodies using the same. Nodal immunogen may be produced recombinantly or made using synthetic methods. Nodal immunogen may also be isolated and/or purified from a natural source (e.g., endogenous, cellular Nodal protein). Multiple forms of the Nodal immunogen useful for preparing antibodies will be readily apparent to those in the art.

For example, Nodal protein (e.g., full length human Nodal or portions thereof) may be used as the immunogen. In other embodiments, cells expressing Nodal are used as immunogen. Such cells can be derived from a natural source (e.g., cancer cell lines) or may be cells which have been transformed by recombinant techniques to over-express Nodal. In one embodiment, a gene or a cDNA encoding human Nodal is cloned into a plasmid or other expression vector and expressed in any of a number of expression systems according to methods well known to those of skill in the art. A variety of nucleotide sequences encoding Nodal protein or polypeptides may be used based upon the known degeneracy of the genetic code. For example, the nucleotide sequence may be varied by selecting combinations based different codon choices in accordance with the standard triplet genetic code as applied to the nucleotide sequence that codes for naturally occurring Nodal (e.g., thereby enabling one to make any desired altered Nodal sequence). Any one of these polypeptides may be used in the immunization of an animal to generate antibodies that bind Nodal. As described herein, the invention provides both wild type as well as mutant Nodal protein (e.g., fragments) and generation of antibodies using the same in order to identify antibodies that specifically bind to full length, wild type Nodal.

Non-human Nodal proteins (e.g., recombinant and/or endogenous) may also be used as immunogen. Nodal protein may be fused and/or conjugated to other proteins/fragments and/or immunogenic substances (e.g., key hole limpet hemocyanin (KLH)). Conjugation and/or fusion may be used to assist in protein purification, e.g., by permitting the fusion protein to be isolated and purified by affinity chromatography, but can also be used to increase immunogenicity. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

As shown in the Examples, both wild type and mutant Nodal protein were used to immunize mice in order to generate hybridomas that produce monoclonal antibodies of the present invention. As further described, methods are provided for identifying monoclonal antibodies that bind with specificity to the wild type human Nodal, and not to mutant human Nodal. In one embodiment, the invention provides exemplary polypeptides that comprise all or a portion of SEQ ID NO. 13, 15, 17, or variants thereof.

In a preferred embodiment, an anti-Nodal antibody of the invention binds to full length, human Nodal protein. In a further preferred embodiment, an anti-Nodal antibody of the invention binds to wild type Nodal protein, but does not bind to mutant Nodal protein (e.g., mutated at the pre-helix loop region (e.g., hNodal E49A, E50A mutant protein). Thus, in another preferred embodiment, an anti-Nodal antibody of the invention binds with specificity to full length, human Nodal protein at the pre-helix loop region. Accordingly, in one embodiment, an anti-Nodal antibody of the invention, when administered to a patient (e.g. with a Nodal related disease or disorder), provides a prophylactic and/or therapeutic benefit in the patient.

Generation of Anti-Nodal Antibodies

The Nodal specific antibodies of the present invention may be generated by any suitable method known in the art. The antibodies of the present invention may comprise polyclonal antibodies. Methods of preparing polyclonal antibodies are known to the skilled artisan (Harlow, et al., Antibodies; a Laboratory Manual, Cold spring Harbor Laboratory Press, 2nd ed. (1988)), which is hereby incorporated herein by reference in its entirety). Antibodies of the invention include, but are not limited to, polyclonal, monoclonal, monovalent, bispecific, heteroconjugate, multispecific, human, humanized or chimeric antibodies, single chain antibodies, single-domain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The invention provides isolated nucleic acid sequences encoding an antibody or antibody variant as disclosed herein, vector constructs comprising a nucleotide sequence encoding the antibodies of the present invention, host cells comprising such a vector, and recombinant techniques for the production of the antibody.

An immunogenic composition comprising a Nodal immunogen can be used to immunize a mammal, such as a mouse, rat, rabbit, guinea pig, monkey, or human, to produce polyclonal antibodies. If desired, a Nodal immunogen can be conjugated to a carrier protein, such as bovine serum albumin, thyroglobulin, keyhole limpet hemocyanin or other carrier described herein. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, nanoemulsions described herein, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a Nodal immunogen can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984). Such antibodies may be of any immunoglobulin class including IgG, IgM, IgE, IgA, IgD and any subclass thereof. The hybridoma producing monoclonal antibody of the invention may be cultivated in vitro or in vivo. Accordingly, in one embodiment, the invention also provides various cell lines (e.g., immortalized B cell lines) that produce anti-Nodal antibody of the invention.

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grafting of entire complementarity determining regions.

Alternatively, humanized antibodies can be produced using recombinant methods. Antibodies which specifically bind to a particular antigen can contain antigen binding sites which are either partially or fully humanized, as disclosed in U.S. Pat. No. 5,565,332. In another embodiment, completely human antibodies are used and are particularly desirable for therapeutic treatment of human patients. Human antibodies can be made by a variety of methods known in the art including phage display methods using antibody libraries derived from human immunoglobulin sequences.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies which specifically bind to a particular antigen also can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound. The bound antibodies can then be eluted from the column using a buffer with a high salt concentration.

In another embodiment, the invention provides antibody fragments which recognize a specific epitopes (e.g., human Nodal (e.g., pre-helix loop region)) generated by any known technique. Traditionally, antibody fragments were derived via proteolytic digestion of intact antibodies (see, e.g., Morimoto, et al., J Biochem Biophys Methods 24:107 (1992); Brennan, et al., Science 229:81 (1985)). For example, Fab and F(ab').sub.2 fragments of the invention may be produced by proteolytic cleavage of immunoglobulin molecules, using enzymes such as papain (to produce Fab fragments) or pepsin (to produce $F(ab')_2$ fragments). F(ab') 2 fragments contain the variable region, the light chain constant region and the CH1 domain of the heavy chain. However, these fragments can now be produced directly by recombinant host cells. For example, the antibody fragments can be isolated from an antibody phage library. Alternatively, $F(ab')_2$-SH fragments can be directly recovered from *E. coli* and chemically coupled to form F(ab') 2 fragments (Carter, et al., Bio/Technology 10:163 (1992). According to another approach, $F(ab')_2$ fragments can be isolated directly from recombinant host cell culture. Other techniques for the production of antibody fragments will be apparent to the skilled practitioner.

In another embodiment, heteroconjugate antibodies can be utilized in the present invention. Heteroconjugate antibodies are composed of two covalently joined antibodies. Such antibodies have, for example, been proposed to target immune system cells to unwanted cells (U.S. Pat. No. 4,676,980).

Anti-Nodal Antibodies

As described herein, the invention provides monoclonal antibodies that bind Nodal and inhibit Nodal activity (e.g., inhibit Nodal binding to Cripto-1 and/or to Alk4/7/ActRIIB receptor complex, inhibit signaling downstream of Nodal or its complexes, downregulate Nodal expression, etc.). The invention also provides monoclonal antibodies that bind Nodal and inhibit Nodal mediated cellular signaling. The antibodies of the invention include the antibodies designated 1B4, 9B9, 2D12, 10B12, 3D1 and 5F10. In particularly preferred embodiment, the antibody designated 3D1 is used. The present invention also includes antibodies that bind to the same epitope as 3D1. The anti-Nodal antibodies were identified and characterized as described in the examples. Antibodies of the present invention may be described or specified in terms of the epitope(s) or portion(s) of Nodal which they recognize or specifically bind. The epitope(s) or polypeptide portion(s) may be specified as described herein, e.g., by N-terminal and C-terminal positions, by size in contiguous amino acid residues, or listed in the Tables and Figures.

Antibodies of the present invention may also be described or specified in terms of their cross-reactivity. Antibodies that bind Nodal polypeptide, which have at least 95%, at least 90%, at least 85%, at least 80%, at least 75%, at least 70%, at least 65%, at least 60%, at least 55%, and at least 50% identity (as calculated using methods known in the art and described herein) to Nodal polypeptide are also included in the present invention. As described herein, anti-Nodal antibodies may also bind with a $K_D$ of less than about $10^{-7}$ M, less than about $10^{-6}$ M, or less than about $10^{-5}$ M to other proteins.

The invention also provides anti-Nodal antibodies which bind polypeptides encoded by polynucleotides which hybridize to a polynucleotide encoding Nodal protein under stringent hybridization conditions. Antibodies of the present invention may also be described or specified in terms of their binding affinity to a polypeptide of the invention. Preferred binding affinities include those with an equilibrium dissociation constant or $K_D$ from $10^{-8}$ M to $10^{-15}$ M, $10^{-8}$ M to $10^{-12}$ M, $10^{-8}$ M to $10^{-10}$ M, or $10^{-10}$ M to $10^{-12}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

In one embodiment, the invention provides isolated nucleic acid sequences encoding an antibody or antibody variant as disclosed herein, vector constructs comprising a nucleotide sequence encoding the antibodies of the present invention, host cells comprising such a vector, and recombinant techniques for the production of the antibody.

For recombinant production of antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody variant). Standard techniques for cloning and transformation may be used in the preparation of cell lines expressing the antibodies of the present invention.

The invention also provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention. The polynucleotides may be obtained, and the nucleotide sequence of the polynucleotides determined, by any method known in the art.

As described herein, antibodies of the invention can be produced by any method known in the art for the synthesis of antibodies, in particular, by chemical synthesis or preferably, by recombinant expression techniques. For example, recombinant expression of an antibody of the invention, or fragment, derivative, or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination. The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as CHO, in conjunction with a vector such as the major intermediate early gene promoter element from human cytomegalovirus, are an effective expression system for antibodies (Foecking, et al., Gene 45:101 (1986); Cockett, et al., Bio/Technology 8:2 (1990)).

The identification and use of suitable host cells is well known in the art. For example, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, HEK293, NIH3T3, or myeloma cells.

An antibody of the invention (e.g., produced by an animal, chemically synthesized, or recombinantly expressed), may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. In addition, antibodies or fragments thereof of the present invention can be fused to marker sequences, such as a peptide to facilitate purification. In one embodiment, the marker amino acid sequence is a hexa-histidine peptide, HA tag (e.g., derived from the influenza hemagglutinin protein), or FLAG tag.

Embodiments herein encompass conjugates of antibodies or antibody fragments with one or more additional functional agents. For example, in some embodiments, antibody-drug-conjugates or fragment-drug-conjugates are provided (e.g., wherein the functional agent is a drug). In some embodiments, binding of the antibody to its target epitope localizes the functional agent (e.g., drug) to target cells, thereby increasing the efficacy of the functional agent. In some embodiments, the efficacy of the functional agent and antibody is additive. In other embodiments, synergy(ies) between the mode of action of the functional agent and antibody result in greater than additive increase in efficacy of the conjugate over the individual components. In some embodiments, any suitable drugs or classes of drugs described herein for any purpose (e.g., coadministration) may also find use in the preparation and use of antibody-drug-conjugates or fragment-drug-conjugates. In particular embodiments, chemotherapeutics of other agents useful in the treatment of cancer are conjugated (e.g., directly or via a suitable linker) to an antibody or antibody fragment with the scope described herein.

The art knows well various materials and methods that are useful in the purification of antibody of the invention. When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter, et al., Bio/Technology 10:163 (1992) describe a procedure for isolating antibodies which are secreted to the periplasmic space of *E. coli*. Where the antibody variant is secreted into the medium, supernatants from such expression systems are generally first concentrated using a commercially available protein concentration filter, for example, an AMICON or MILLIPORE ultrafiltration unit. Antibody generated and/or isolated from the cells can be purified using, for example, hydroxylapatite chromatography, gel elecrophoresis, dialysis, and affinity chromatography. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark, et al., J Immunol Meth 62:1 (1983)). Protein G is recommended for all mouse isotypes and for human IgG3 (Guss, et al., EMBO J. 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE chromatography on an anion or cation exchange resin (such as a polyaspartic acid column), chromatofocusing, SDS-PAGE, and ammonium sulfate precipitation are well known in the art and can be chose based upon the particular type of antibody. Following any purification step(s), a mixture comprising antibody and contaminants may be further subjected to low pH hydrophobic interaction chromatography using an elution buffer (e.g., at a pH between about 2.5-4.5, preferably performed at low salt concentrations (e.g., from about 0-0.25 M salt)).

Diagnostic Uses for Anti-Nodal Antibody

An antibody of the invention may be used to detect Nodal in both in vitro and in vivo diagnostic methods. For example, an antibody of the invention may be used in immunoassays (e.g., ELISA (e.g., sandwich ELISA, direct ELISA, indirect ELISA, competitive ELISA, etc.), Western blot, immunohistochemistry, protein array, immuno-PCR, etc.) for qualitatively and quantitatively measuring levels of Nodal in a biological sample (e.g., See, e.g., Harlow, et al., Antibodies: A Laboratory Manual, Cold Spring Harbor Laboratory Press, 2nd ed. (1988)). The invention is not limited to any particular type of biological sample. Indeed, a variety of samples may be characterized using the diagnostic methods of the invention, including, but not limited to, any sample in which Nodal protein is found. In some embodiments, the sample is tissue, a bodily fluid, blood, serum, urine, saliva, sputum, or a lung effusion. In some embodiments, a sample comprises cells expressing or suspected of expressing Nodal, Cripto-1, or both Nodal and Cripto-1. In some embodiments, a sample comprises cells that don't express Nodal, but test positive for Nodal due to paracrine signaling. An antibody of the invention may be recombinantly fused or conjugated to molecules useful as labels in detection assays. In some embodiments, any suitable antibodies, antibody fragments, bispecific antibodies, conjugated antibodies, etc. described herein (e.g., for therapeutic uses) may also find use in diagnostic applications. In some embodiments, detection of Nodal in a sample provides diagnostic and/or prognostic information for a clinician. In some embodiments, detection of Nodal in a sample is indicative of, or diagnostic for, an aggressive form of cancer. In some embodiments, Nodal diagnostics described herein are performed with one or more additional diagnostic assays to determine the type of cancer a subject suffers from, and/or to determine an appropriate treatemtn course of action for the subject (e.g., treatment with anti-Nodal antibodies, other cancer treatments, etc.).

An antibody of the invention may be modified (e.g., via covalent attachment of a moiety to the antibody). In a preferred embodiment, an antibody of the invention is modified in such a way that the attachment of a moiety thereto does not interfere with the antibody binding to Nodal. An antibody of the invention may be modified via biotinylation, attachment to an enzyme, or any other type of moiety binding that allows detection of the antibody.

For example, in one embodiment, an antibody or fragments thereof is conjugated to a diagnostic agent. The antibodies can be used diagnostically, for example, to detect expression of a target of interest in specific cells, tissues, plasma, blood or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances are known in the art an include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. In some embodiments, a label is indirectly conjugated to the antibody (e.g., biotin-avidin conjugation). In one embodiment, an immunoassay (e.g., an enzyme linked immunosorbent assay or radioimmunoassay) is used for detection. An antibody of the invention may be used in any known detection assay in the art including, but not limited to competitive binding assays, direct and indirect sandwich assays, and immunoprecipitation assays. In one embodiment, detection of Nodal can be achieved also using label-free techniques employing anti-Nodal antibodies of the invention immobilized on the surface of suitable biochips or biosurfaces as those used for SPR, Bio-Layer Interferometry (BLI), Long Period Gratings (LPG).

In another embodiment, detection of an anti-Nodal antibody is via use of an antibody that detects the anti-Nodal antibody (e.g., a secondary antibody). For example, an antibody, and derivatives and analogs thereof, which specifically bind to Nodal can be used for diagnostic purposes to detect, diagnose, or monitor diseases, disorders, and/or conditions associated with the aberrant expression, overexpression and/or activity of Nodal. In one embodiment, the invention provides detection of Nodal (e.g., overexpression or aberrant expression of Nodal) comprising characterizing the expression and/or activity of Nodal in a biological sample from a subjection or patient (e.g., a subject or patient having or suspected of having cancer) using one or more Nodal specific antibodies of the invention and comparing the level of expression with standard (e.g., non-cancerous control) expression level, whereby an increase or decrease in Nodal expression and/or activity compared to the standard expression level is indicative of aberrant expression and/or activity Anti-Nodal antibody can be used to detect Nodal in any sample. Detecting may comprise contacting the sample with anti-Nodal antibody and determining the amount of antibody that is bound to the sample. For immunohistochemistry, the sample may be fresh or frozen or may be embedded in paraffin and fixed with a preservative such as formalin, for example. Various labels known in the art may be used in the detection methods described herein including, but not limited to, enzyme labels; radioisotopes, luminescent labels, fluorescent labels, rhodamine, and biotin. For label-free detection of Nodal, detection may comprise contacting the biosensors or biosurfaces with immobilized anti-Nodal antibodies of the invention and determining the amount of free protein using suitable devices for any specific biosensor or biosurface.

In another embodiment, the invention provides a diagnostic assay for diagnosing a disease or disorder, comprising characterizing the expression of Nodal in biological sample of a subject/patient using one or more antibodies of the present invention and comparing the level of Nodal expression with a standard protein expression level, whereby an increase or decrease in the assayed expression level compared to the standard expression level is indicative of a particular disorder or disease. In another embodiment, a method of detecting Nodal in a biological sample or a prepared biological sample comprises contacting an antibody of invention with the sample and observing anti-Nodal antibody bound to Nodal in the sample or determining the amount of the anti-Nodal antibody bound to Nodal in the sample. The invention also provides a method of detecting Nodal in a subject comprising administering an antibody of the invention to the subject and observing and/or determining the amount and/or location of anti-Nodal antibody bound to Nodal in the subject. Accordingly, the invention provides compositions and methods of the detection and/or diagnosis for a Nodal related disease or disorder (e.g., a disease or disorder related to aberrant expression and/or overexpression of Nodal in a subject).

For example, in one embodiment, a method of characterizing or diagnosis a subject is provided comprising administering to a subject/patient (e.g., a subject having or suspected of having cancer) an amount of anti-Nodal antibody effective to bind Nodal and monitoring the subject following the administering after a particular time (e.g., minutes, hours, days) sufficient to permit the anti-Nodal antibody to bind sites within the subject that express Nodal. In one embodiment, the time permits unbound Nodal to be cleared from the subject (e.g., so as to reduce and/or eliminate background signal). In another embodiment, the anti-Nodal antibody is labeled. In a further embodiment, the background anti-Nodal antibody level is determined. In a preferred embodiment, detecting labeled anti-Nodal antibody in the subject that is above background level is indicative of a subject/patient with a Nodal related disorder or disease. The art knows well various methods for determining background levels. In a further embodiment, detection of Nodal using the methods described herein are repeated at time intervals (e.g., one, two, three, six, nine, twelve months) such that Nodal levels detected at a later date can be compared to the level of Nodal detected at an earlier date (e.g., so as to provide information regarding disease/disorder progression and/or response to therapy).

In one embodiment, an antibody of the invention is provided in a kit (e.g., for the detection of Nodal (e.g., for in vivo or in vitro diagnostic use). In addition to the information described herein, the art knows well that the kit may include various other reagents useful for the detection of Nodal in a sample.

EXPERIMENTAL

The following examples are provided in order to demonstrate and further illustrate certain preferred embodiments and aspects of the present invention and are not to be construed as limiting the scope thereof.

Example 1

Figure 1:
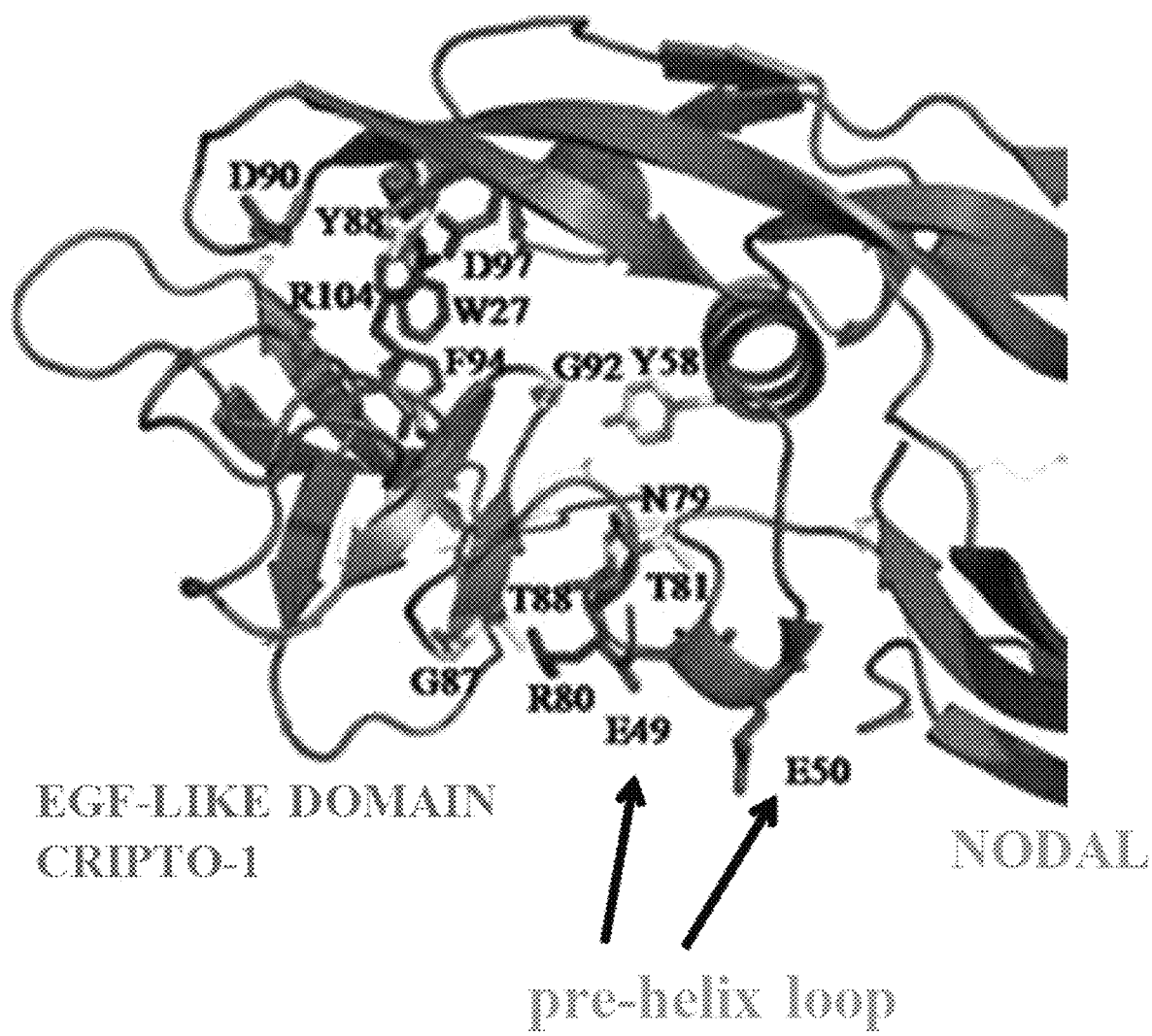
FIG. 1 depicts a molecular model of the interaction interface between Nodal and Cripto-1.

The interaction interface between Nodal and Cripto-1 were studied in order to determine if the interaction could be targeted for generation of Nodal-specific antibodies that could inhibit and/or neutralize Cripto-1-mediated Nodal signaling. Various regions of Cripto-1 and Nodal, and the interactions between the same, are shown in FIG. 1. As discerned from FIG. 1, the pre-helix loop and helix3 region of Nodal are involved in the Nodal recognition of Cripto-1 Amino acids E49 and E50 are important residues for binding to the Cripto-1 EGF-like domain (See, e.g., Calvanese L. et al Biopolymers, 2010).

Various Nodal immunogens were utilized in an effort to generate anti-Nodal antibodies. In particular, a strategy was developed whereby Nodal a peptide immunogen was generated and used to immunize mice. Antibodies generated were then screened to identify antibodies that bound with specificity to the peptide used as immunogen and full length wild-type Nodal, but that did not bind with specificity to mutant Nodal protein fragments.

Nodal human peptide (43-69) containing the residues involved in the interaction of Nodal with the EGF-like domain of Cripto-1-1 was created (See FIG. 2). The following synthetic immunogen was used to immunize mice in order to generate anti-Nodal antibodies:
a) hNODAL (44-69) wild-type
Ac—PNPVGEEFHPTNHAYIQSLLKRYQPH—NH2
(SEQ ID NO: 13)

The Nodal (44-69) peptide and the mutated variant Nodal (44-69) E49A-E50A were synthesized as both acetylated and amidated derivatives or as only amidated derivatives. The immunogen was prepared by conjugating via the N-terminus only the amidated derivative to KLH and used to immunize Balb/c mice. Peptides a and b, reported below
a) hNODAL (44-69) wild-type
Ac—PNPVGEEFHPTNHAYIQSLLKRYQPH—NH2
(SEQ ID NO: 13)
b) hNODAL (44-69) E49A-E50A
Ac—PNPVGAAFHPTNHAYIQSLLKRYQPH—NH2
(SEQ ID NO: 14)
were used for ELISA based screening assays—performed as described below—in order to identify and characterize neutralizing antibodies.

Figure 3:
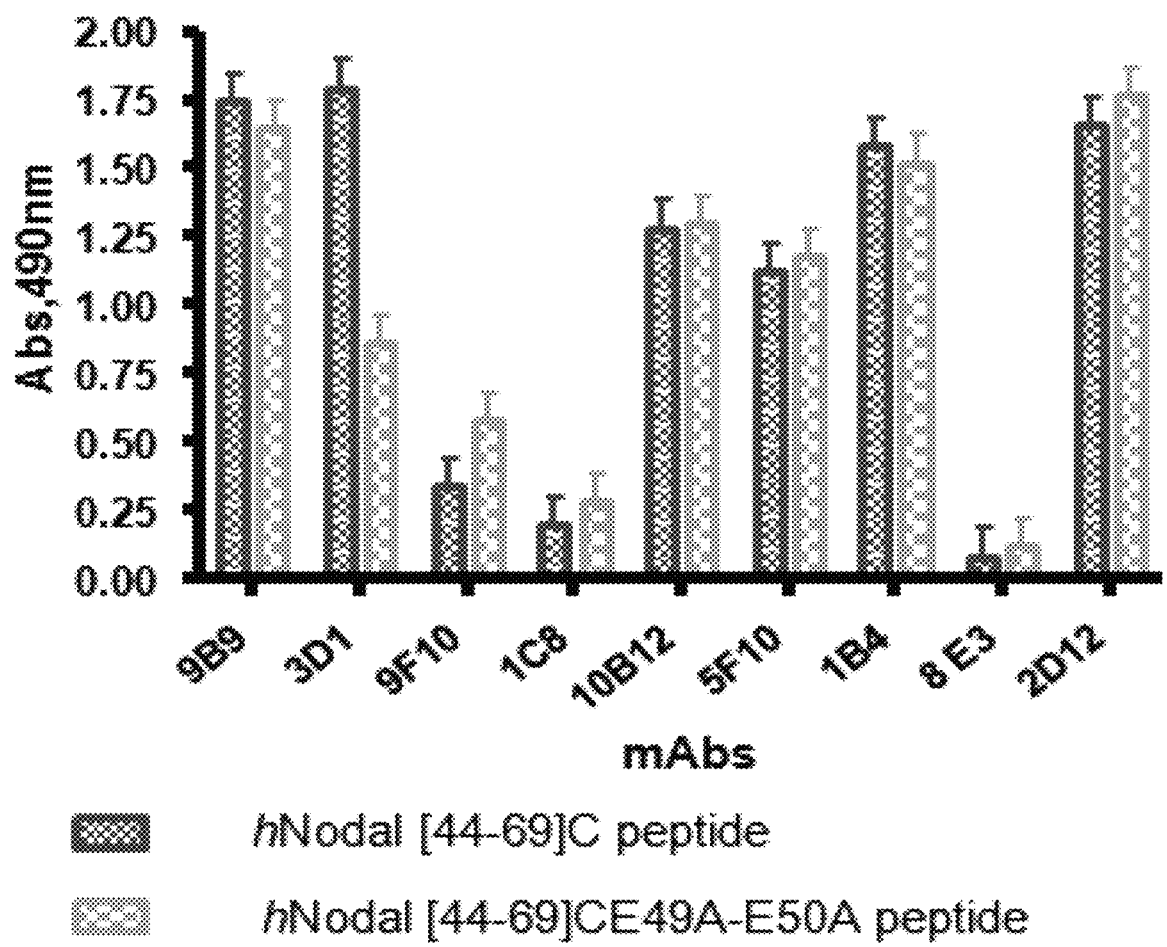
FIG. 3 shows hybridoma clones comparatively screened by ELISA to identify those secreting monoclonal antibodies (mAbs) selectively recognizing Nodal E49E50 residues.

After immunization, multiple clone supernatants were collected and screened by ELISA by immobilizing both the wild type and mutated peptide a and b. FIG. 3 shows hybridoma clones comparatively screened by ELISA to identify those secreting monoclonal antibodies (mAbs) selectively recognizing E49E50 residues of the Nodal prehelix loop region. Monoclonal antibodies (mAbs) selectively recognizing the wild type peptide were selected for further investigation.

Antibodies (mAbs) that selectively recognized wild type human Nodal (E49E50) were further screened in order to identify mAbs that bound full length Nodal. Surface plasmon resonance (SPR) biosensor direct binding assay was used. Recombinant human Nodal protein (rhNodal, *E. coli* derived His238 Leu347, with an N-terminal Met Accession # Q96S42, cat. num 3218ND, R&D System) was immobilized on a CM5 sensor chip. Of all of the various antibodies generated, only two of the antibody clones were able to bind the full length protein: 3D1 and 5F10 (See FIG. 4). Of the antibodies capable of binding full length human Nodal, only clone 3D1 displayed selectivity for wild type Nodal peptide (See FIG. 3).

Figure 5A:
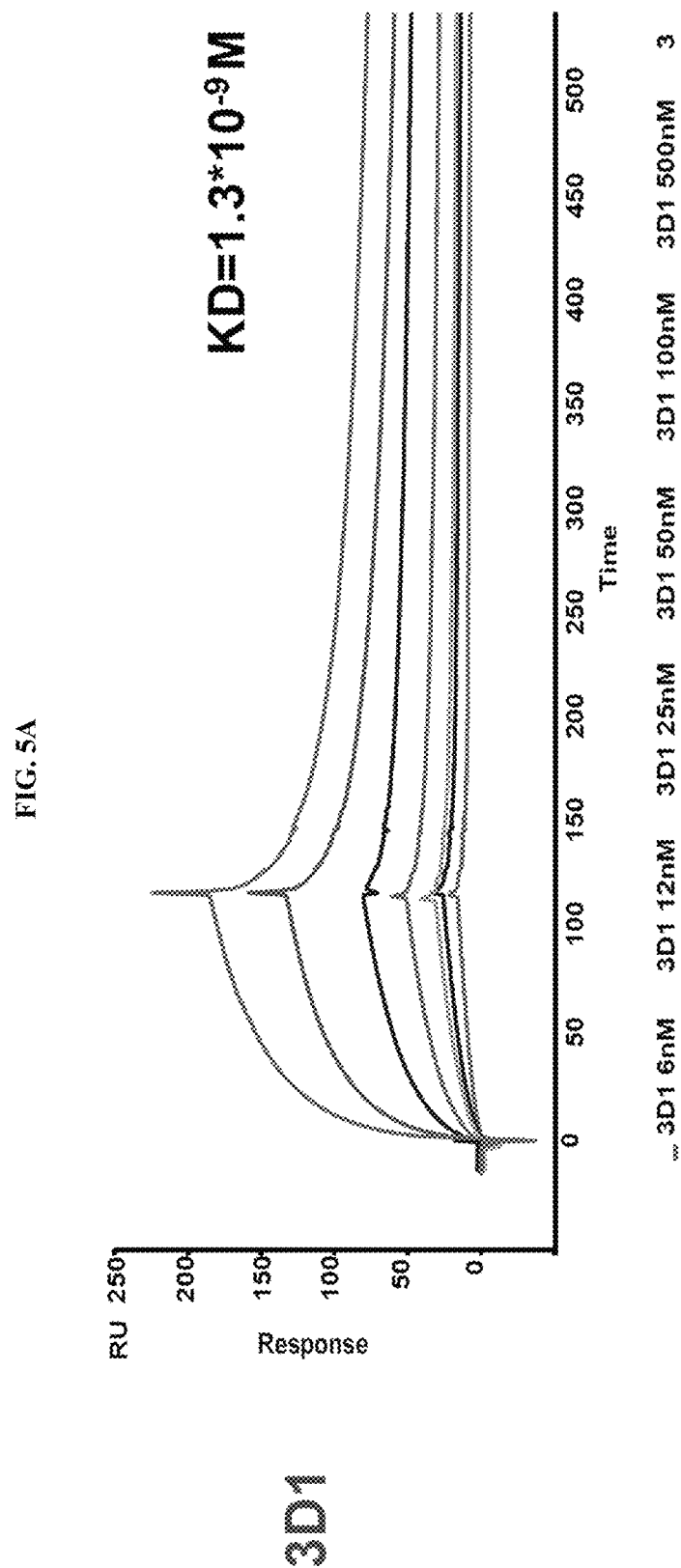
FIGS. 5A-B show SPR dose-dependent binding assays of (a) antibody 3D1 and (b) 5F10 to Nodal.
Figure 5B:
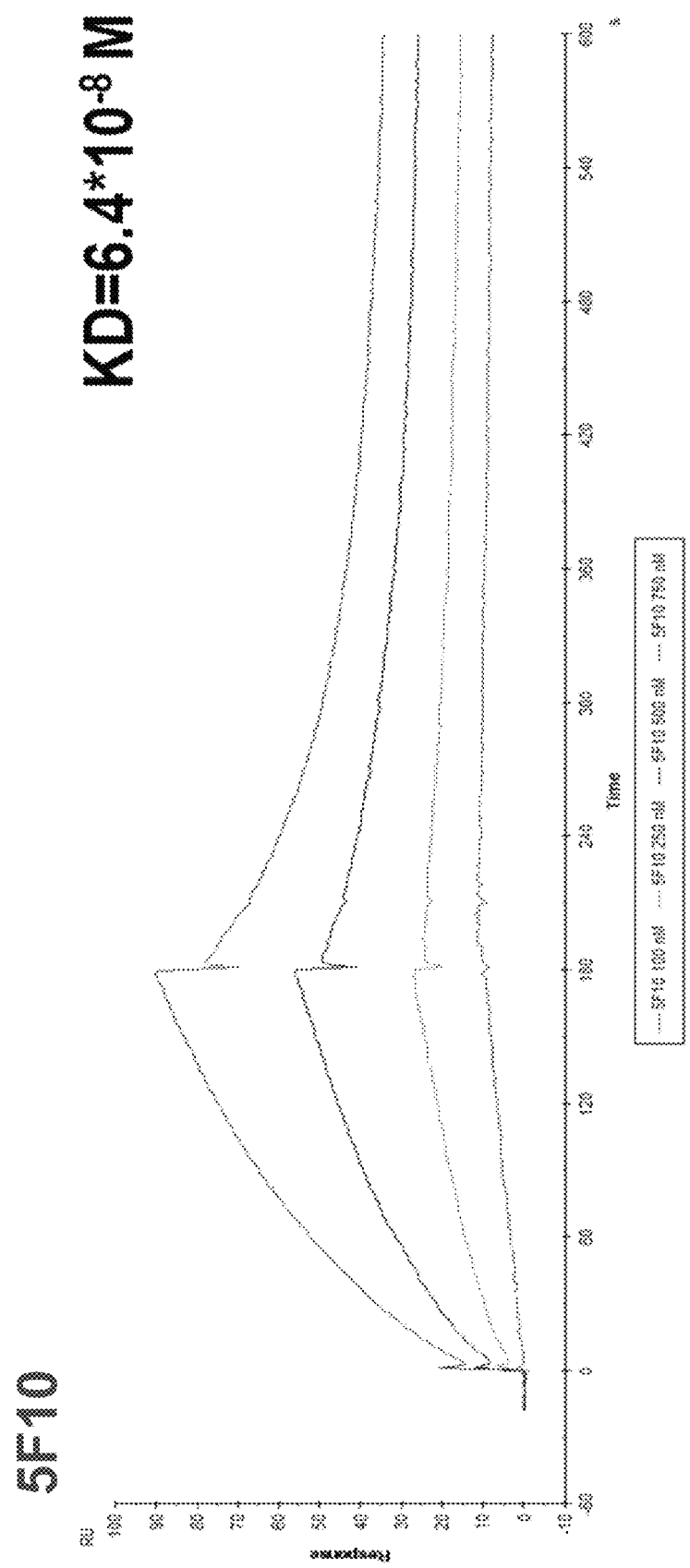

FIGS. 5A-B show SPR dose-dependent binding assays to Nodal for antibody 3D1 and antibody 5F10.

Data were generated immobilizing hNodal on a CM5 sensor chip and injecting 3D1 at the indicated concentrations. 3D1 binds with high affinity to hNodal. The KD was about 1.3 nM.

Data have been generated immobilizing hNodal on a CM5 sensor chip and injecting the 5F10 at the indicated concentrations. 5F10 binds less strongly than 3D1 to hNodal. The KD was about 64 nM.

Figure 6:
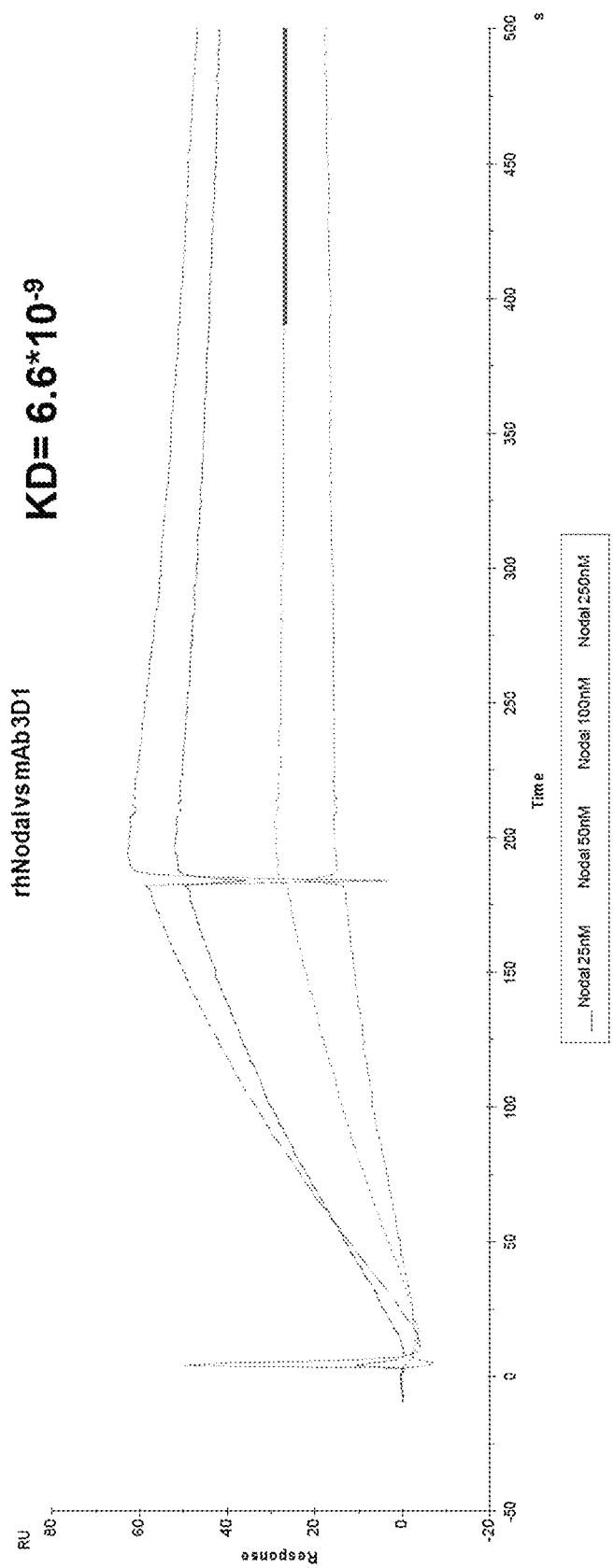
FIG. 6 depicts SPR dose-dependent binding assay of Nodal to antibody 3D1.

Dose-dependent binding of human recombinant Nodal to 3D1 antibody immobilized on the CM5 sensor chip was characterized. The estimated KD was 6.6 nM (See FIG. 6).

Figure 7A:
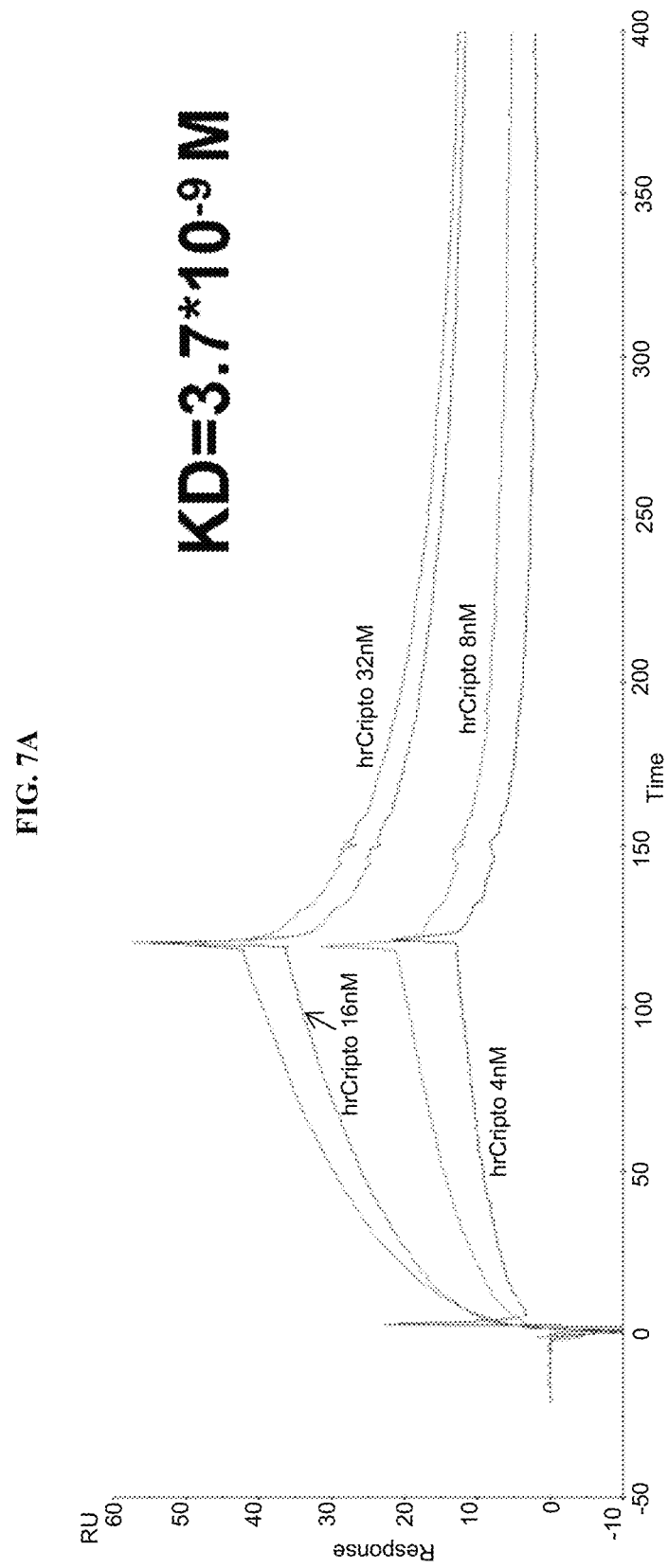
FIGS. 7A-B show two separate binding assays performed to characterize the interaction between Cripto-1 and Nodal. The interaction strength displayed a KD of about 4 nM (average of the two KDs determined, A and B; in A the binding of Nodal to Cripto is reported; in B the binding of Cripto to Nodal is reported).
Figure 7B:
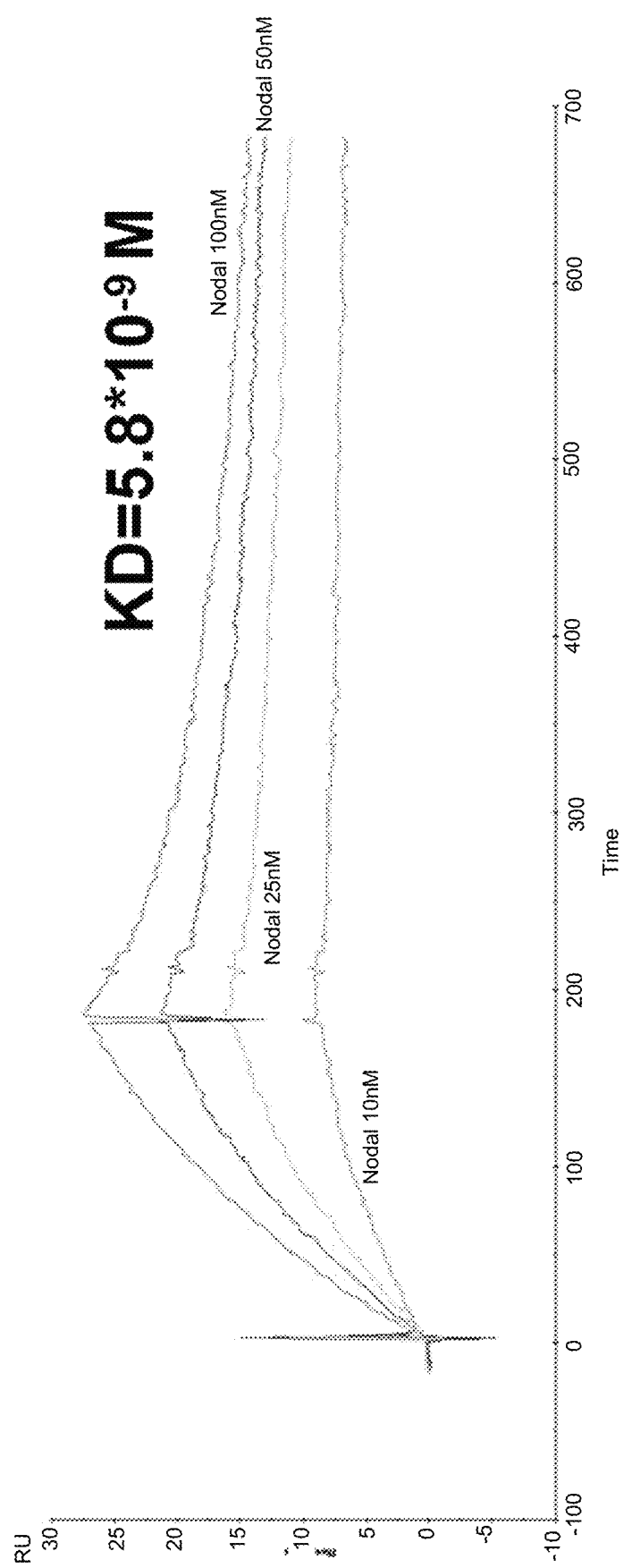

Next, experiments were conducted to assess the ability of 3D1 antibodies to inhibit binding between Nodal and Cripto-1 through SPR experiments. Experiments were performed on CM5 sensor chips with immobilized Cripto-1. As shown in FIG. 7, the interaction between Cripto-1 and Nodal was assessed and determined to have a KD of about 4 nM (average of the two KDs determined).

Figure 8:
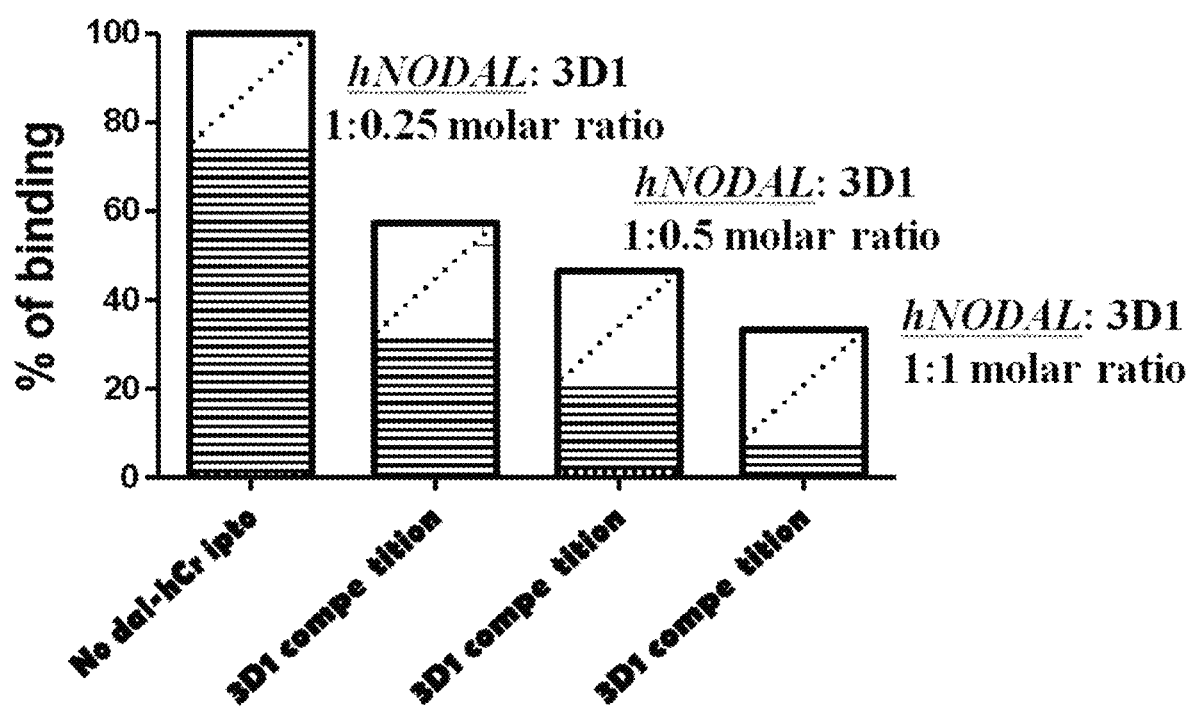
FIG. 8 shows that 3D1 prevents binding of soluble Cripto-1 to the immobilized Nodal.

As shown in FIG. 8, 3D1 prevents the binding of soluble Cripto-1 to the immobilized Nodal. Increasing amounts of 3D1 were incubated with 5 nM Nodal and injected over the Cripto-1-derivatized chip which resulted in the reduction of binding between Cripto-1 and Nodal. The antibody at 1:1 molar ratio prevents the binding of hNodal to hCripto-1-1 by about 70%. Accordingly, the invention provides that, in one embodiment, 3D1 can be used to prevent binding between Cripto-1 and Nodal (e.g., for therapeutic uses described herein (e.g., to inhibit and/or neutralize Cripto-1-mediated Nodal signaling)).

Figure 9:
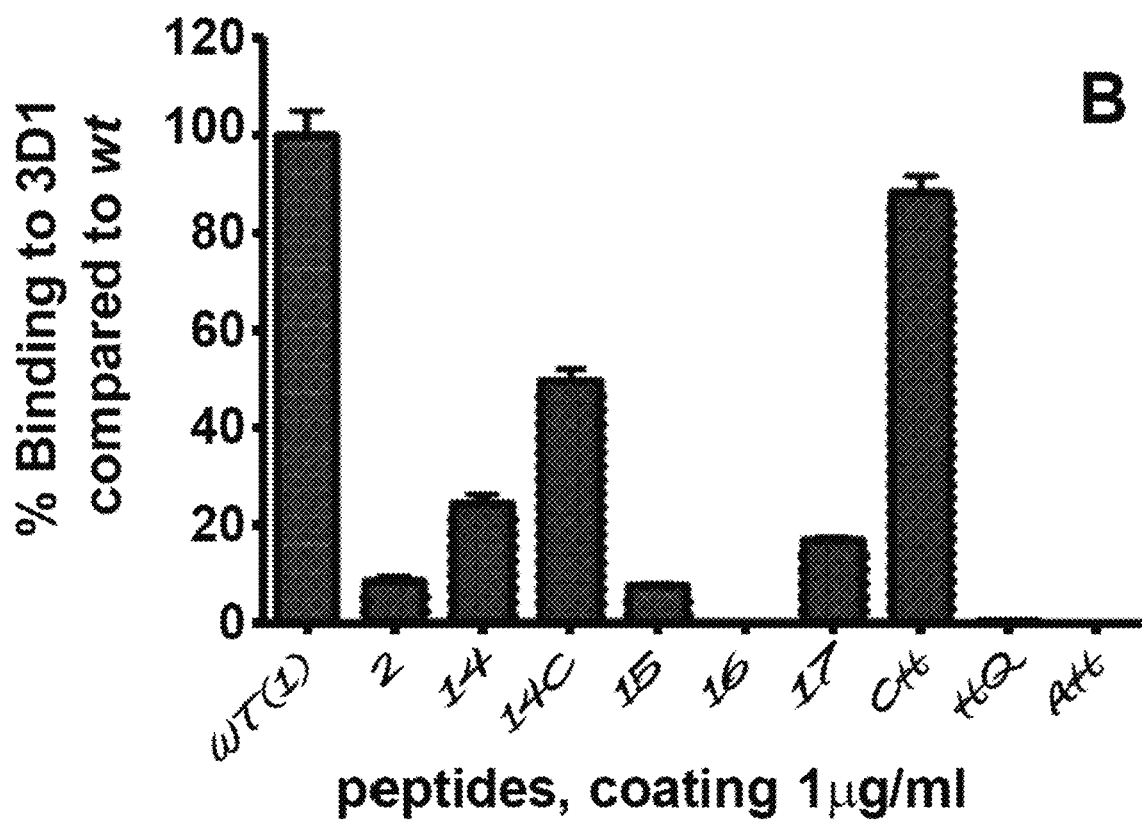
FIG. 9 depicts (A) a set of Nodal synthetic peptides utilized for epitope mapping of the residues underlying the binding between 3D1 and Nodal; (B) percent binding to 3D1 compared to wild type Nodal; and (C) dose-dependent binding of 3D1 to the immobilized immunogen and to the Nodal E49A-E50A doubly mutated variant.
Figure 9:
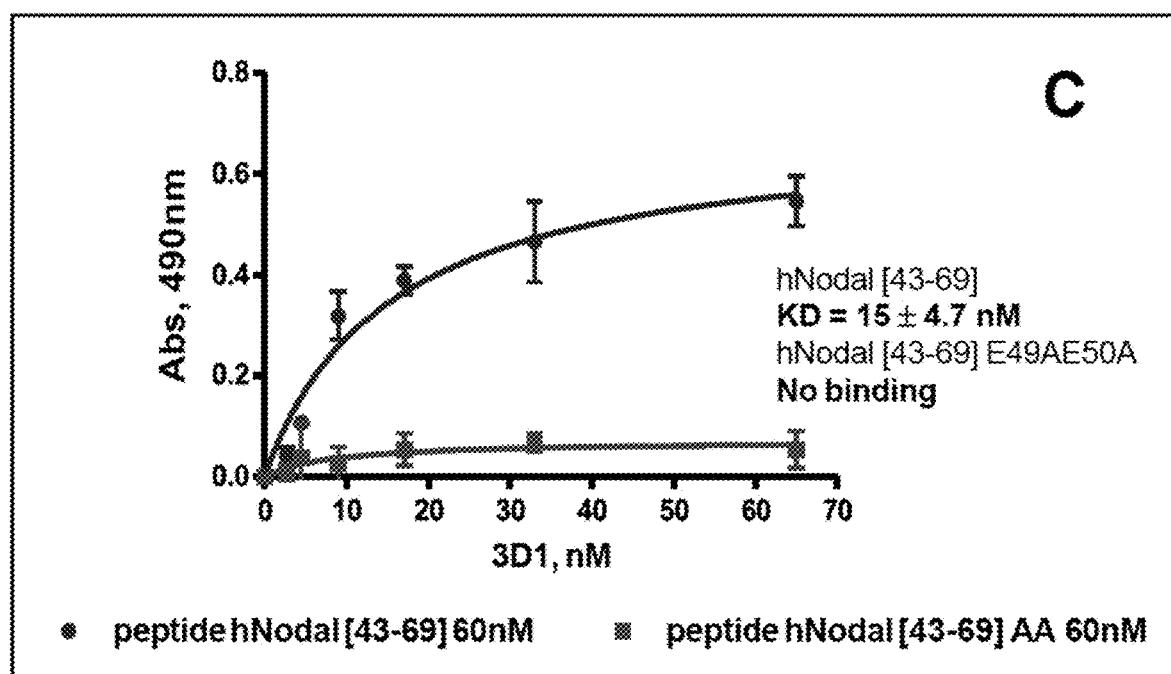

Residues underlying the binding between 3D1 and Nodal were investigated by epitope mapping using a set of Nodal synthetic peptides (See FIG. 9). FIG. 9A shows the set of synthetic peptides used to map residues involved in 3D1 recognition. FIG. 9B: shows binding of peptides reported in FIG. 9A to 3D1. Peptides were immobilized at 1 µg/mL and probed with 3D1 at 5 µg/mL. Data were normalized to the binding of the peptide hNODAL (44-69) wild-type (WT). FIG. 9C shows dose-dependent binding of 3D1 to the immobilized hNODAL (44-69) WT and to the E49A-E50A doubly mutated variant. The data indicates that 3D1 interacts with residues encompassing the 43-56 region. Most interactions were established with C43, P46, V47, E49, ESC). The effect of Y58 can be on the conformation of the peptide.

Figure 10:
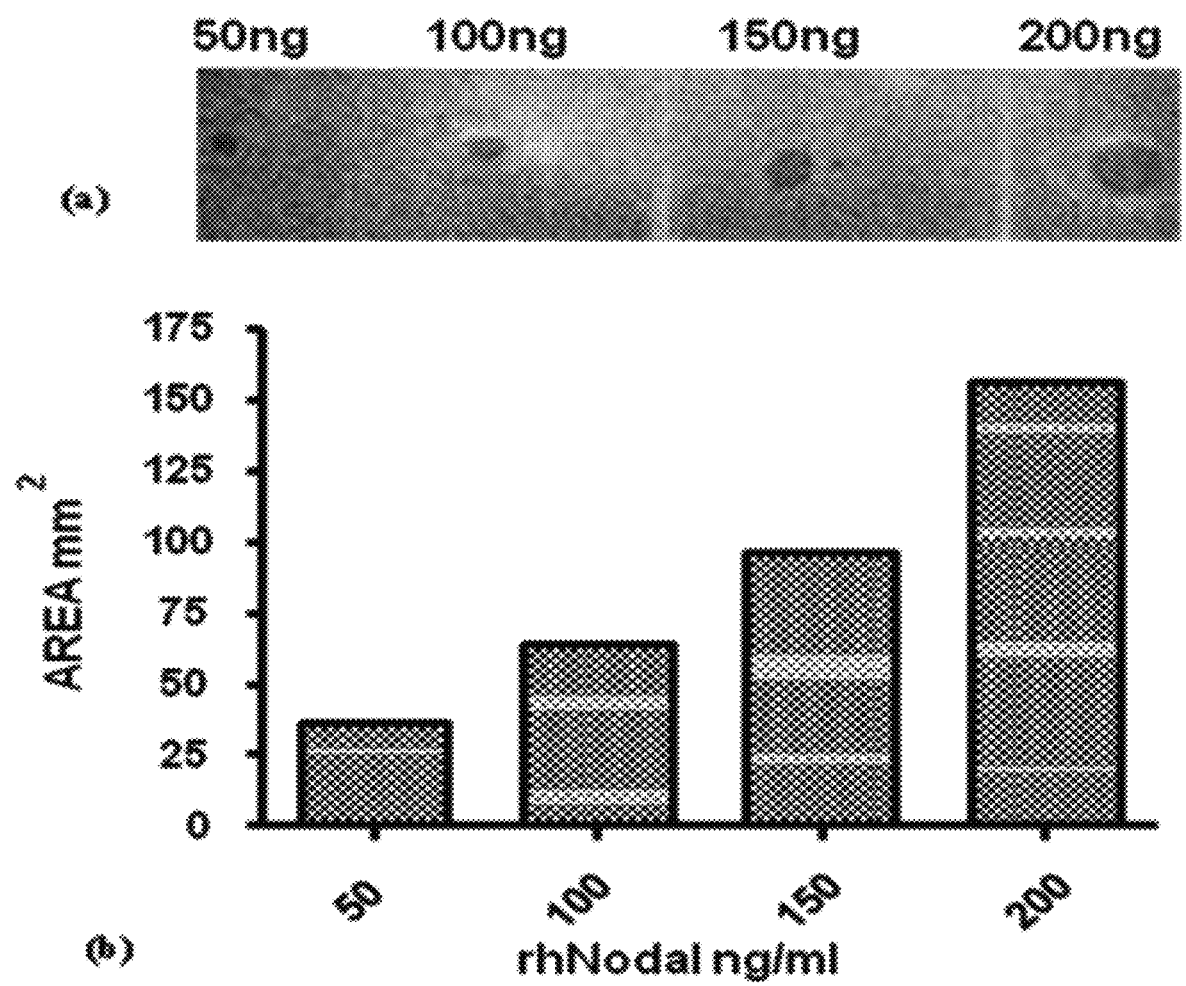
FIG. 10 depicts immune-assays with 3D1. (a) Dot-blot: the rhNodal protein spotted on nitrocellulose membrane at increasing concentrations between 50-200 ng; (b) is the quantification of the dot blot shown in (a); and (c) Western blotting analysis: Nodal protein under reducing condition has been loaded on 15% SDS-Page. GAM-HRP antibody and ECL substrate were used for detection.
Figure 10:
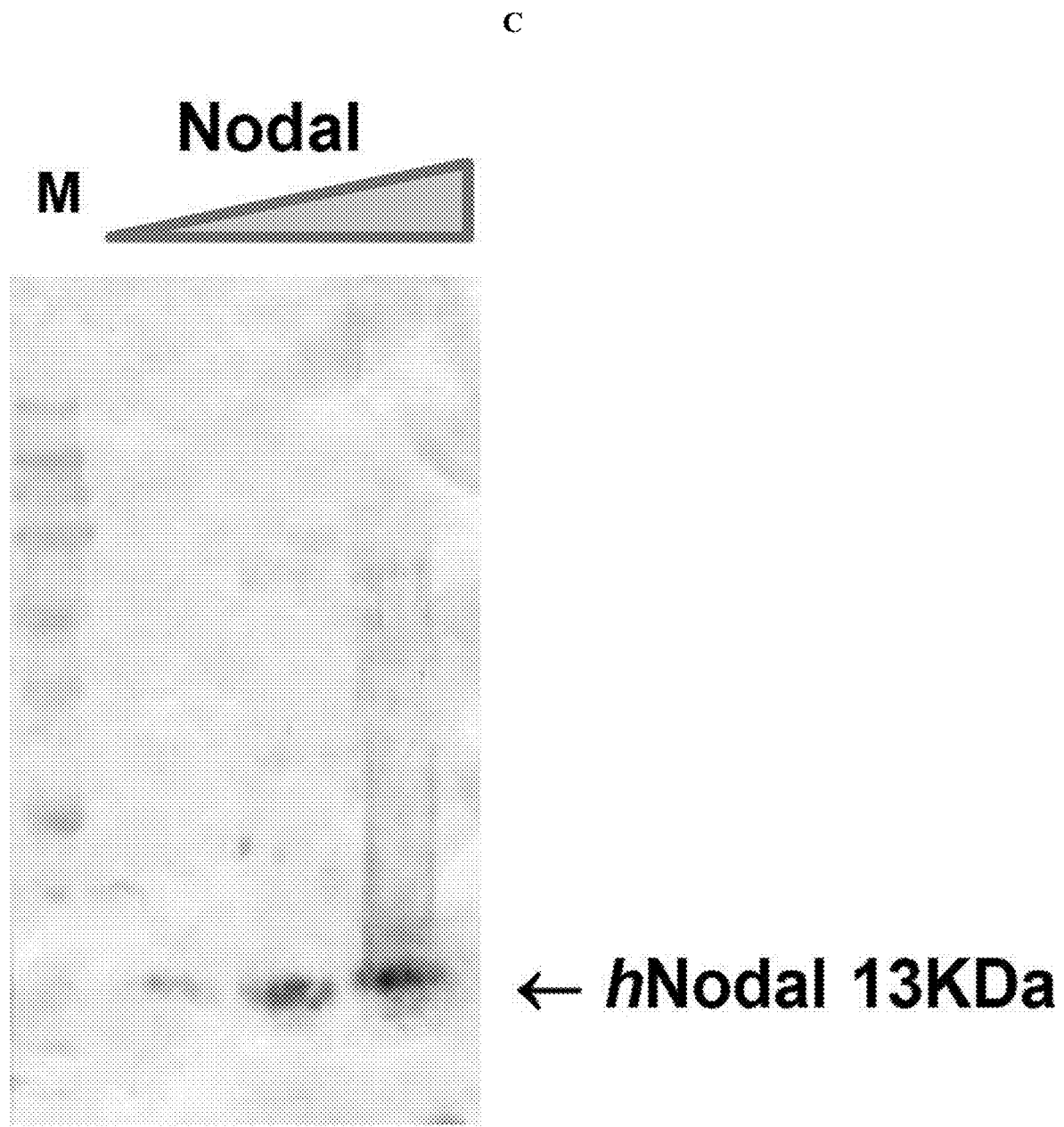

Various immune assays were performed using 3D1. FIG. 10 shows the following:
a) Dot-blot: the rhNodal protein spotted on nitrocellulose membrane at increasing concentrations between 50-200 ng;
b) quantification of the dot blot shown in (a);
c) Western blotting analysis: Nodal protein under reducing condition has been loaded on 15% SDS-Page. GAM-HRP antibody and ECL substrate were used for detection.

Figure 11:
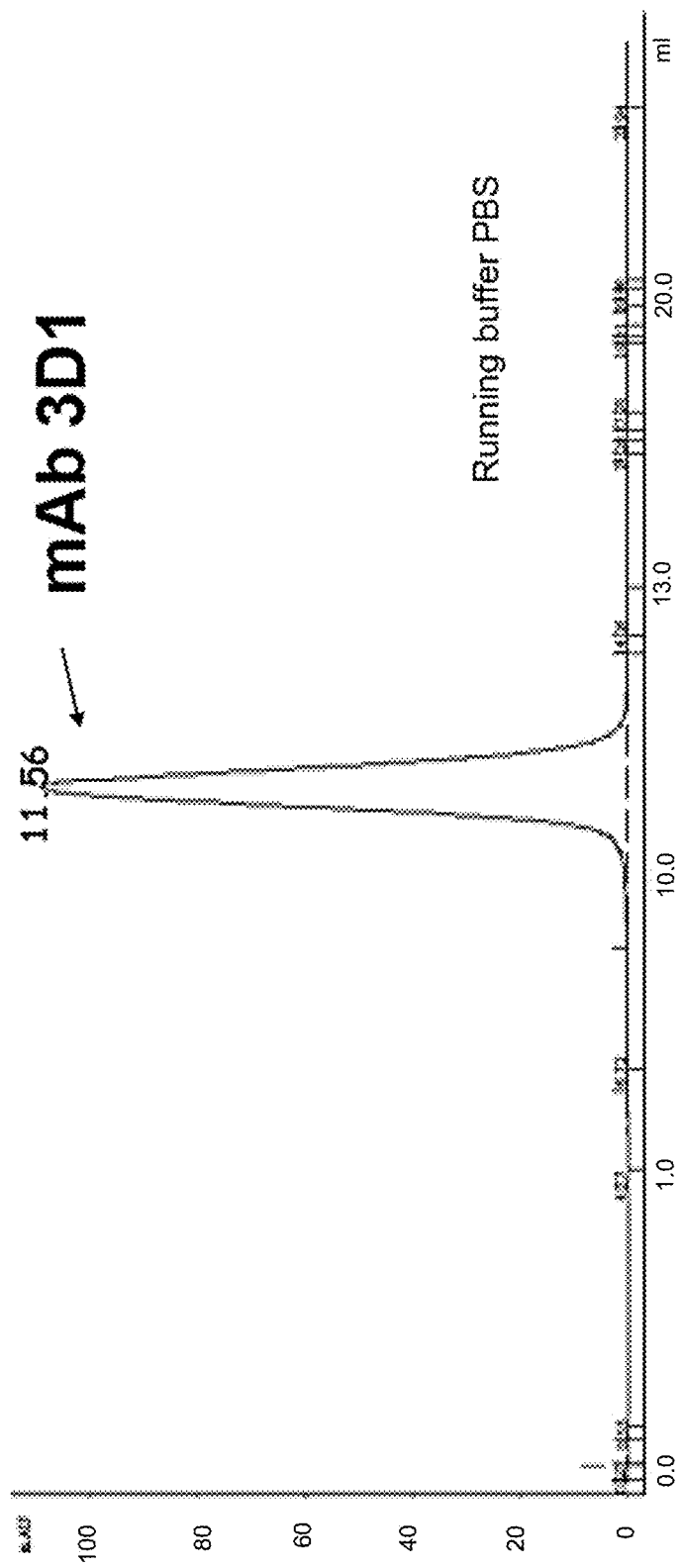
FIG. 11 depicts size exclusion analysis of 3D1 by a Sepharose S200 column.

Size exclusion analysis of 3D1 by a Sepharose S200 column is shown in FIG. 11. One single peak at the elution volume expected for an IgG is observed. No presence of aggregates was observed.

The nucleic acid sequences of the Heavy and Light Chains of 3D1 were determined. 3D1 sequences of the Heavy and Light chains were sequenced using primers that amplify the variable regions of both chains containing the complementary determining regions (CDR or ABR, Antigen Binding Regions).

One distinct sequence was obtained for the antibody light chain, whereas two independent heavy chains were obtained by amplifying the heavy chain CDRs with different primers. The heavy chain obtained with primer n° 10 is likely coding a non-functional protein, because of an extra base located at the 3'-end of the CDR3 mRNA. This extra base, originating during the recombination process, changes the reading frame of the RNA, likely originating a premature stop codon down-stream. Indeed, in this sequence it was possible to detect the CDR1, CDR2 and the N-terminus of the CDR3, but not the C-terminus of the CDR3 and the N-terminus of the FRAME 4.

3D1 sequences were as follows:

>Light_Chain_A_3D1_CHAIN_SEQUENCE (light chain)
(SEQ ID NO: 1)
DIKMTQSPASLSASVGETVTITCRASGNIHNYLAWYQQKQGKSPQLL
VYNAKTLADGVPSRFSGSGSGTQYSLKINSLQPEDFGSYYCQHFWST
PHVRCWDQAGTETEAW

```
ABR1(CDRL1):
                                                (SEQ ID NO: 4)
GNIHNYLA (27-34)

ABR2(CDRL2):
                                                (SEQ ID NO: 5)
LLVYNAKTLAD (46-56)

ABR3(CDRL3):
                                                (SEQ ID NO: 6)
QHFWSTPHVRCWDQA (89-103)

>Heavy_Chain_B_3D1_CHAIN_SEQUENCE (heavy chain)
                                                (SEQ ID NO: 2)
VKLVESGGGLVKPGGSLKLSCAASGFTFSSYAMSWVRQTPEKRLEWV
ASISSGGCTYYPDSVKGRFTISRDNARNILYLQMSSLRSEDTAMYYC
ARGSMITADGNSLLLCYGLLGSRNLXHR ABR1(CDRH1):
                                                (SEQ ID NO: 7)
FTFSSYAMS (26-34)

ABR2(CDRH2):
                                                (SEQ ID NO: 8)
WVASISSGGCTYY (46-58)

ABR3(CDRH3):
                                                (SEQ ID NO: 9)
ARGSMITADGN (95-105)

>Heavy_Chain_C_3D1_CHAIN_SEQUENCE (heavy chain)
                                                (SEQ ID NO: 3)
VKLVESGGGLVQPGGSMKLSCVASGFTFRNYWMSWVRQSPEKGLEWV
AEIRLKSDNYAARYAESVKGKFTISRDDSKSRLYLQMNSLRAEDTGI
YYCTGIRRFAYWGQGTL ABR1(CDRH1):
                                                (SEQ ID NO: 10)
FTFRNYWMS (26-34)

ABR2(CDRH2):
                                                (SEQ ID NO: 11)
WVAEIRLKSDNYAARY (46-61)

ABR3(CDRH3):
                                                (SEQ ID NO: 12)
GIRRFAY (99-105)
```

Targeting Nodal Signaling in Tumor Cells with Stem Cell Properties to Suppress Aggressive Cancer.

Figure 12:
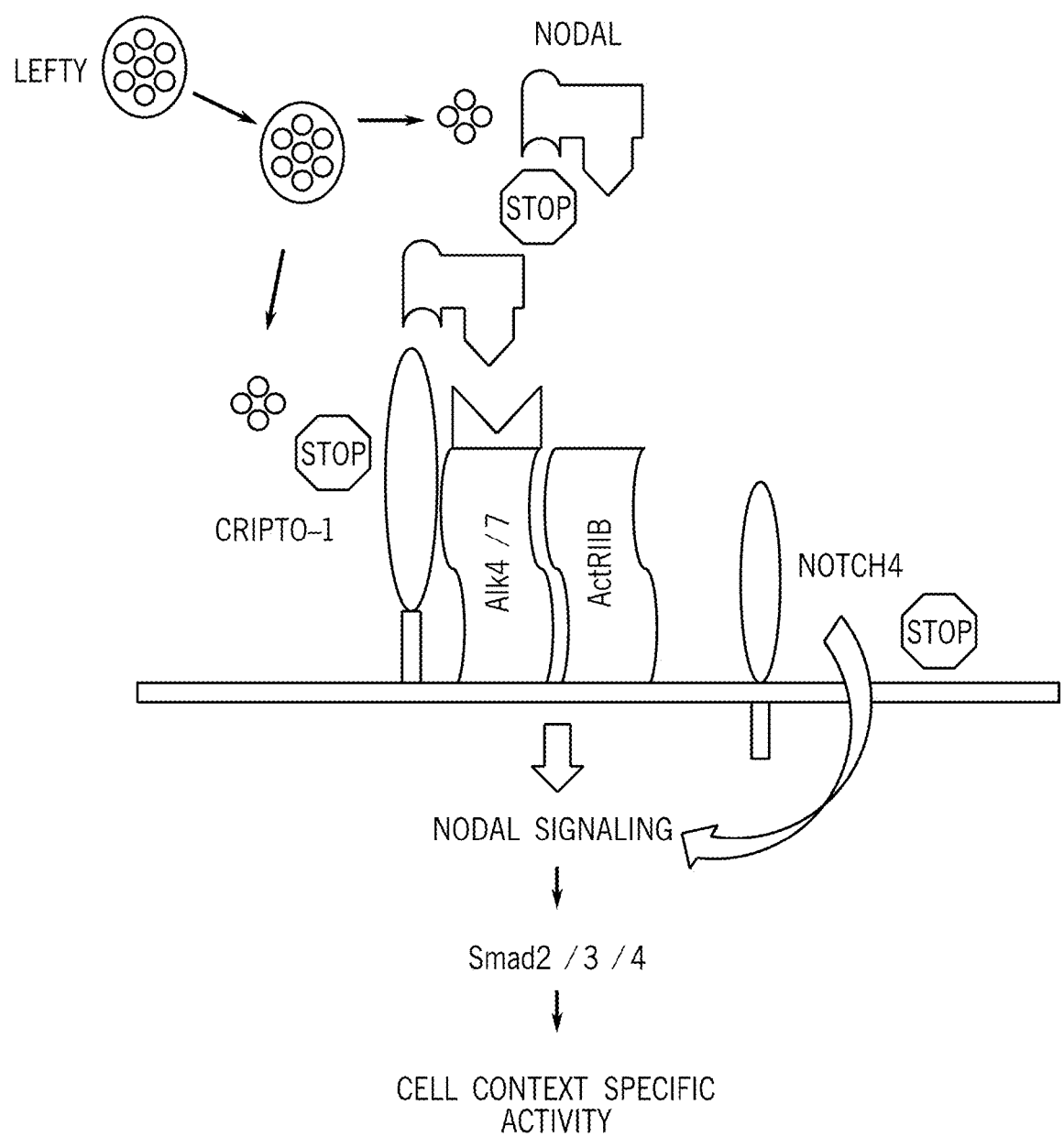
FIG. 12 depicts a schematic of the Nodal signaling pathway and the molecular crosstalk with Notch4.
Figure 13:
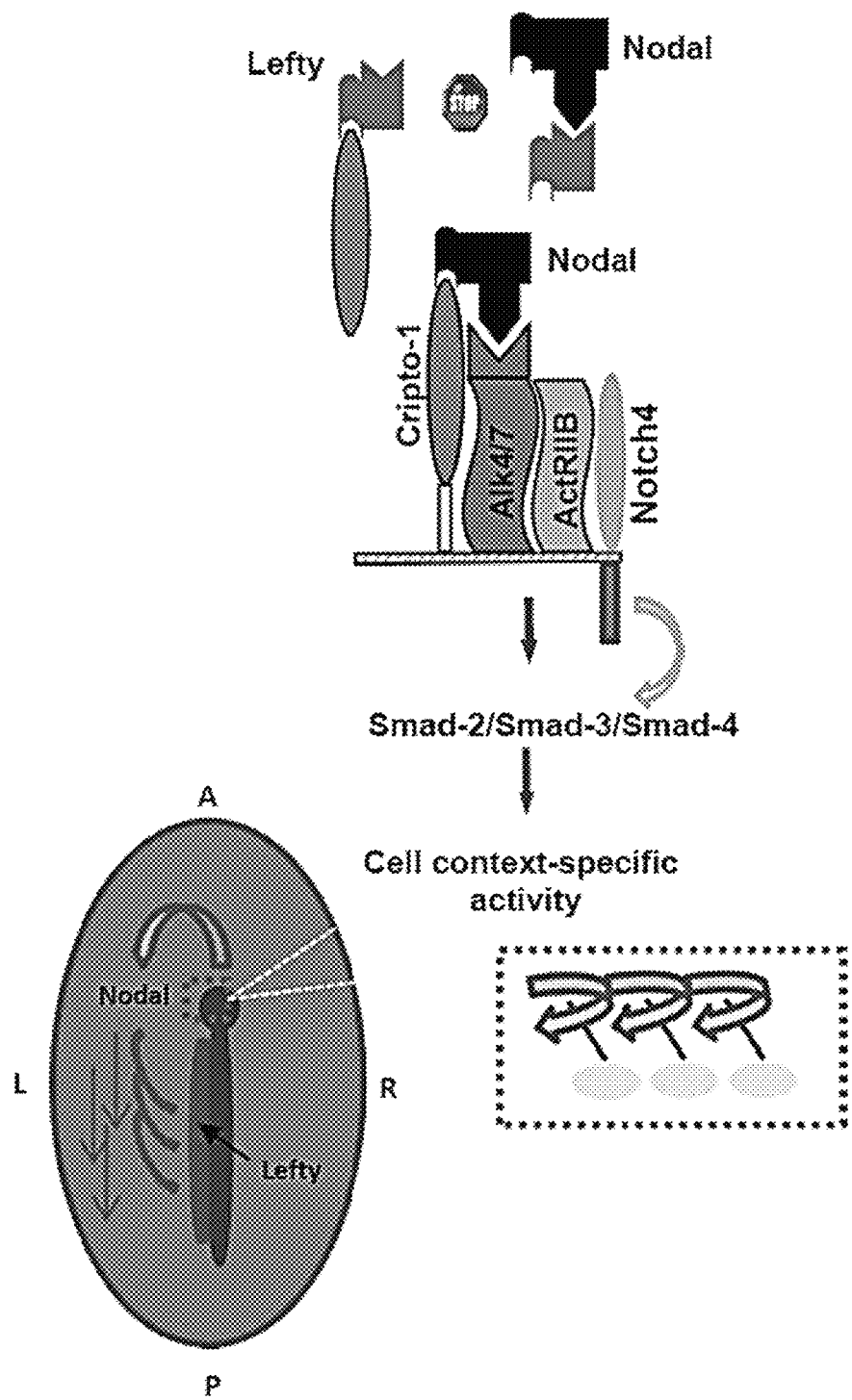
FIG. 13 depicts cell context specific activity of Nodal.

The Nodal signaling pathway (See FIG. 12) underlies multiple aspects of aberrant cellular growth including: The cancer stem cell phenotype; Upregulated tumor growth and metastasis; Acquisition of drug resistance; and Molecular cross-talk with Notch4 stem cell signaling. Heretofore, it has been difficult to study Nodal because it is a secreted protein, making it challenging to isolate and quantify tumor cells expressing Nodal.

Normal adult tissues do not generally express Nodal and Notch4. Nodal is an embryonic morphogen critical in early development and re-expressed in aggressive tumor cells. Nodal is an embryonic growth factor belonging to the TGF-beta superfamily Nodal signals via binding to Cripto-1-1/Alk4/7/ActRIIB receptor complex. Nodal maintains hESC pluripotency and is involved in axis formation and L-R patterning. Lefty, also member of the TGF-beta superfamily, is the natural inhibitor of Nodal. Nodal is capable of inducing its own expression. In humans, Nodal expression is largely restricted to embryonic tissues, and is lost in most normal adult tissues. Nodal is reactivated in aggressive tumor cells, while Lefty is silenced. As in development, Notch expression can upregulate Nodal in tumor cells.

Figure 14:
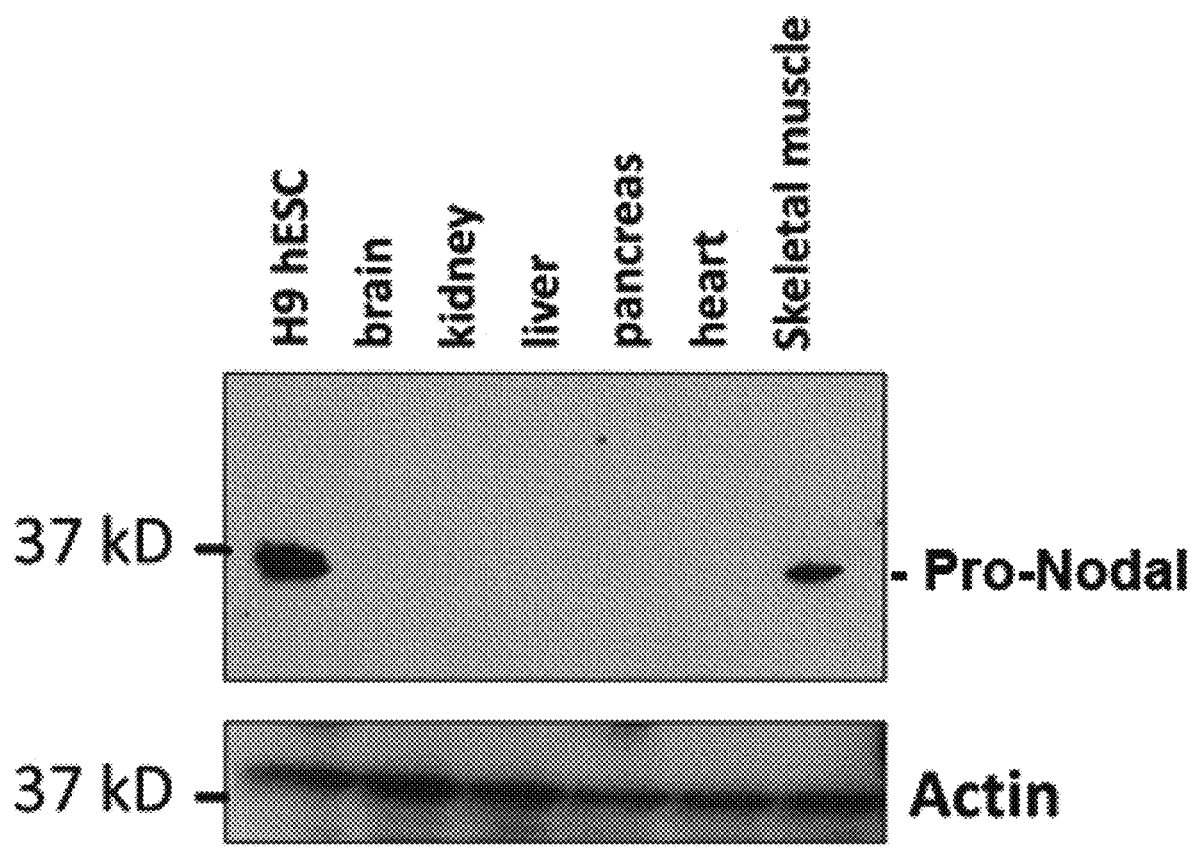
FIG. 14 depicts Nodal expression in normal human tissue lysates.

Nodal expression in normal human tissue lysates was examined (See FIG. 14; see also FIG. 56). A polyclonal anti-Nodal antibody from Santa Cruz (H-110; 1:1000) was used with WB grade normal human tissue lysates purchased from ABCAM. 30 µg of total protein was loaded for each sample. Membrane was incubated with rabbit anti-Nodal for 1 hr at RT. Bands were detected with West Pico reagent. Lysates from H9 hESCs was used as positive control in the first lane.

Figure 15:
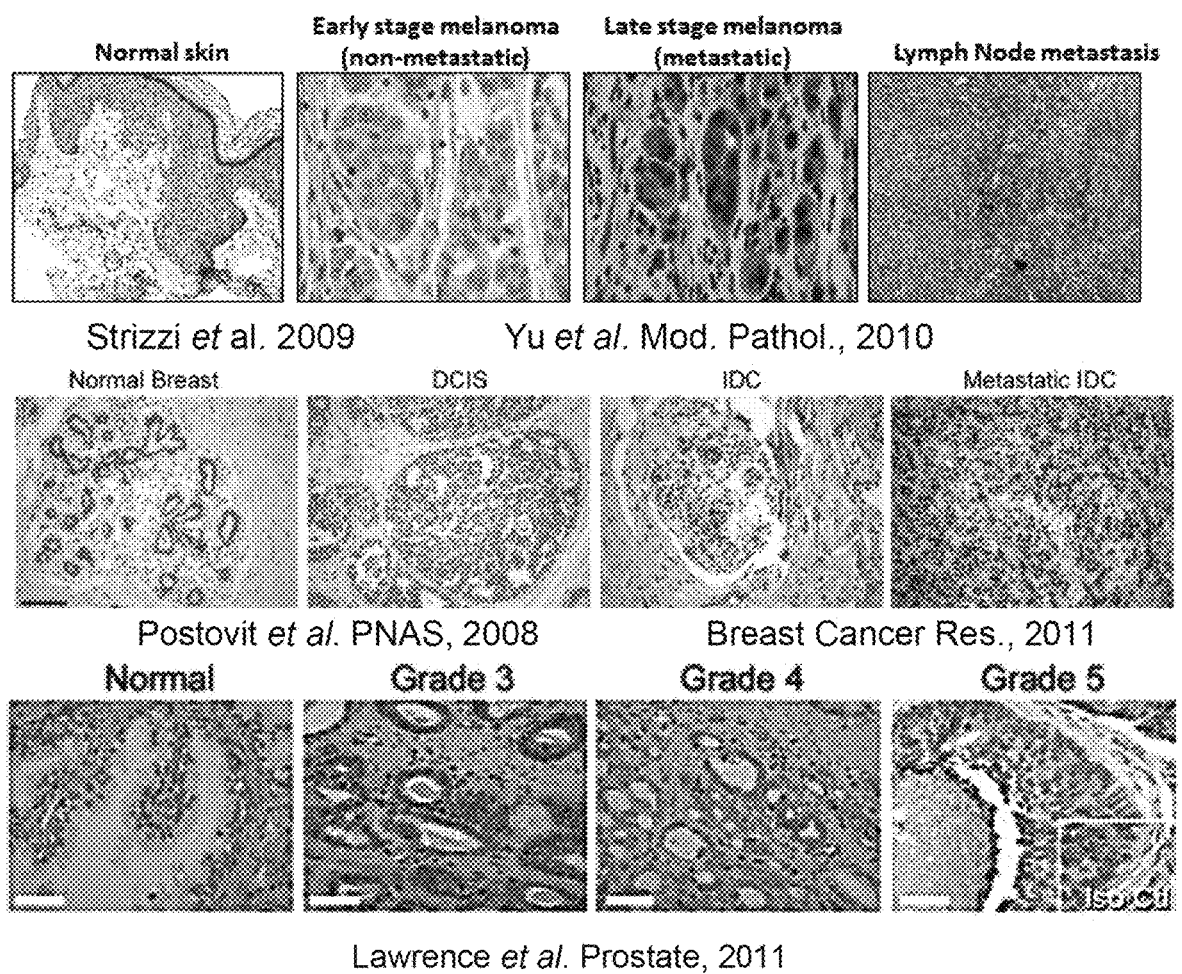
FIG. 15 depicts differences in Nodal expression in various healthy as well as cancerous tissues.
Figure 16:
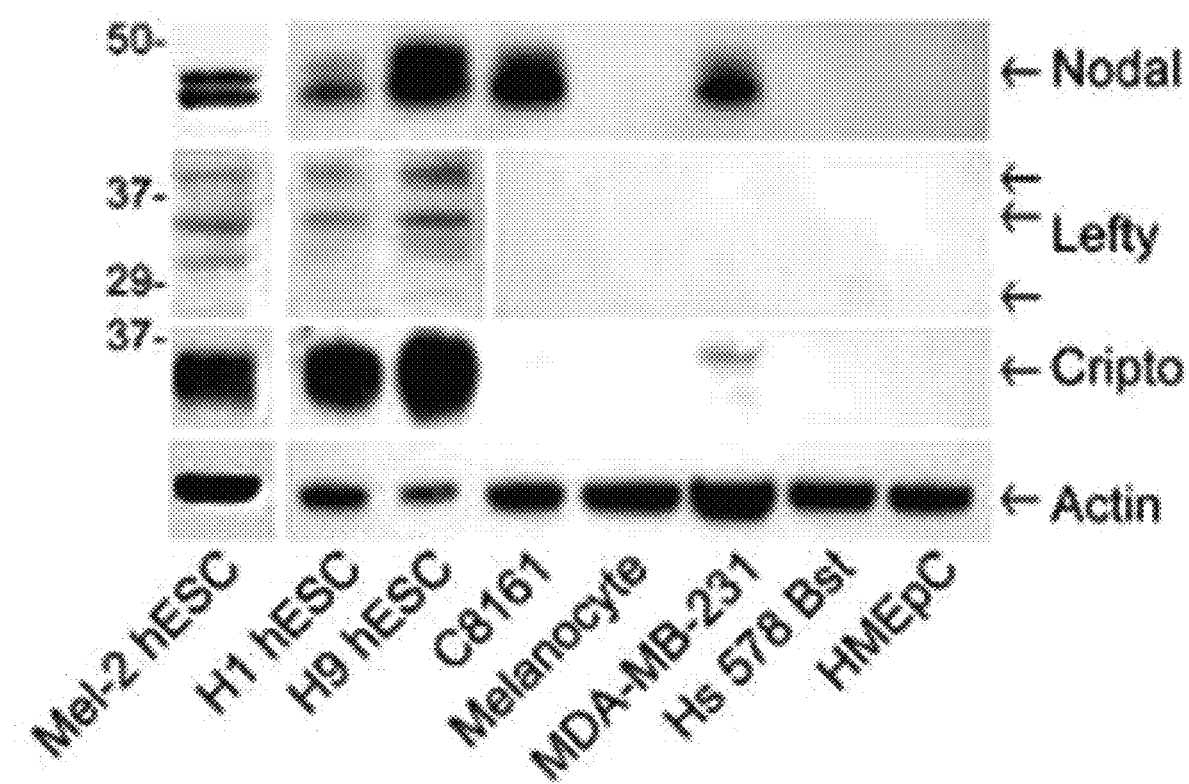
FIG. 16 depicts the expression of Nodal, Lefty, and Cripto-1 in various cells.

As shown in FIG. 15, Nodal is a valuable prognostic biomarker: Immunohistochemistry analyses (red/brown stain) in patient tissues. Nodal is also detected in Dysplastic nevi; Glioblastoma; Neuroblastoma; Pancreatic cancer; Leukemia; Ovarian cancer; Bladder cancer; and Colon cancer. Nodal protein has been observed to be highly expressed by hESCs and metastatic tumor cells; Lefty (Nodal's inhibitor) is not expressed by tumor cells (See FIG. 16).

Mel-2: Human embryonic stem cell line; H1: Human embryonic stem cell line; H9: Human embryonic stem cell line; C8161: Aggressive human melanoma cell line; Melanocyte: Normal human pigmented cell line; MDA-MB-231: Aggressive human breast carcinoma cell line; Hs578 Bst: Normal human breast cell line; HMEpC: Normal human breast epithelial cell line.

No point mutations have been found in hESC vs. C8161 Nodal gene.

Lefty is methylated and silenced in C8161 cells.

Figure 17:
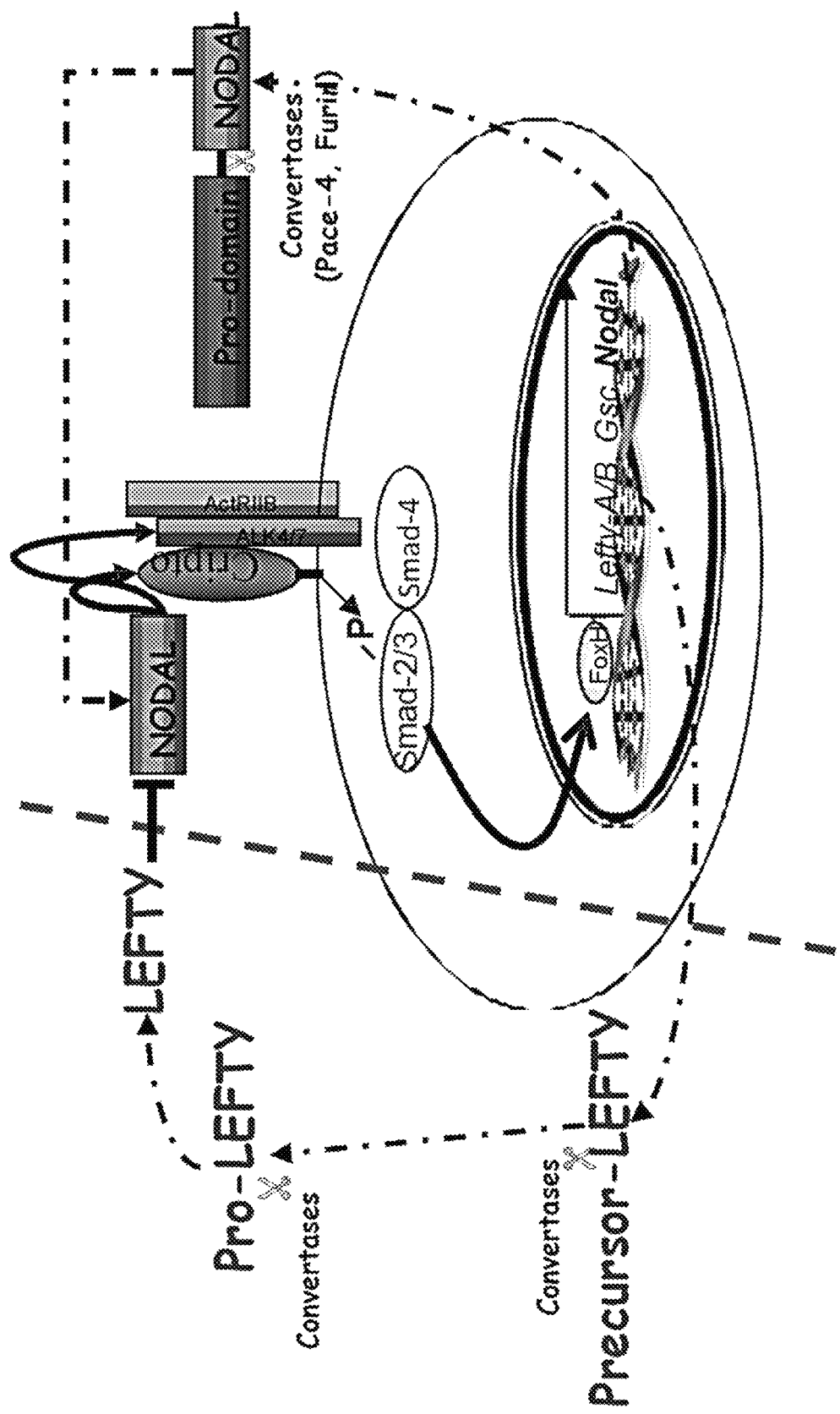
FIG. 17 depicts Nodal signaling.

Nodal signaling is unregulated in tumor cells (PNAS, 2008) (See FIG. 17).

Figure 18:
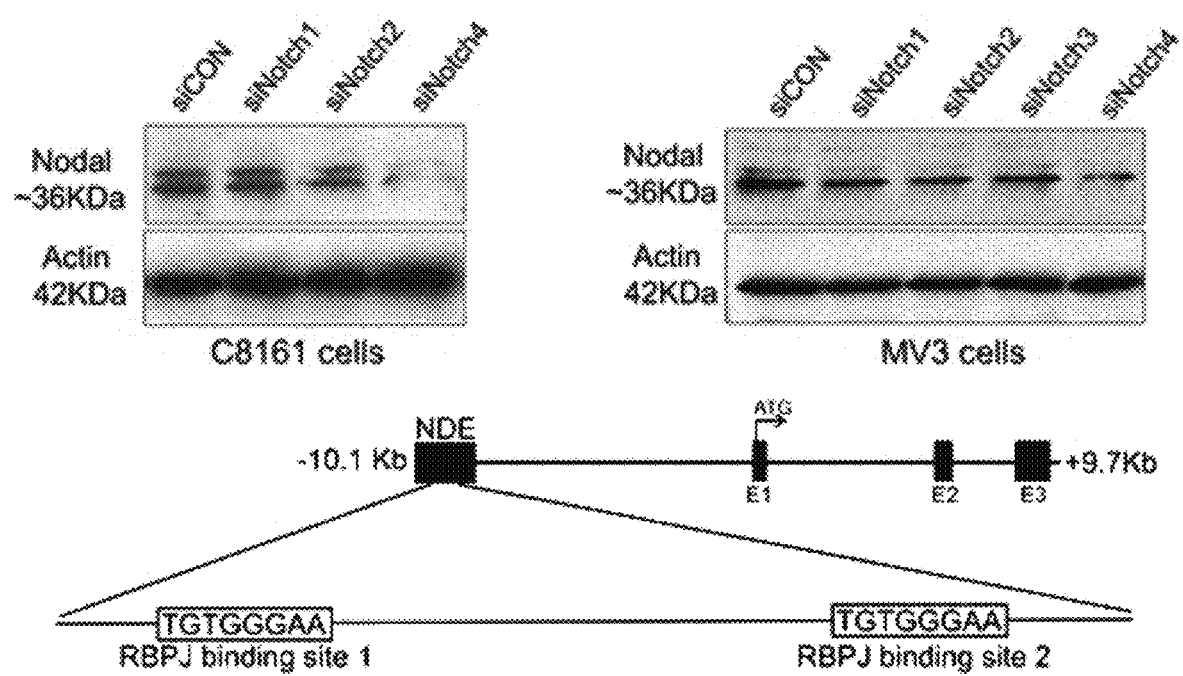
FIG. 18 depicts Notch4 signaling directly regulating Nodal expression, where knockdown of Notch4 expression (by siRNA) in C8161 and MV3 melanoma cells results in Nodal down-regulation.
Figure 19:
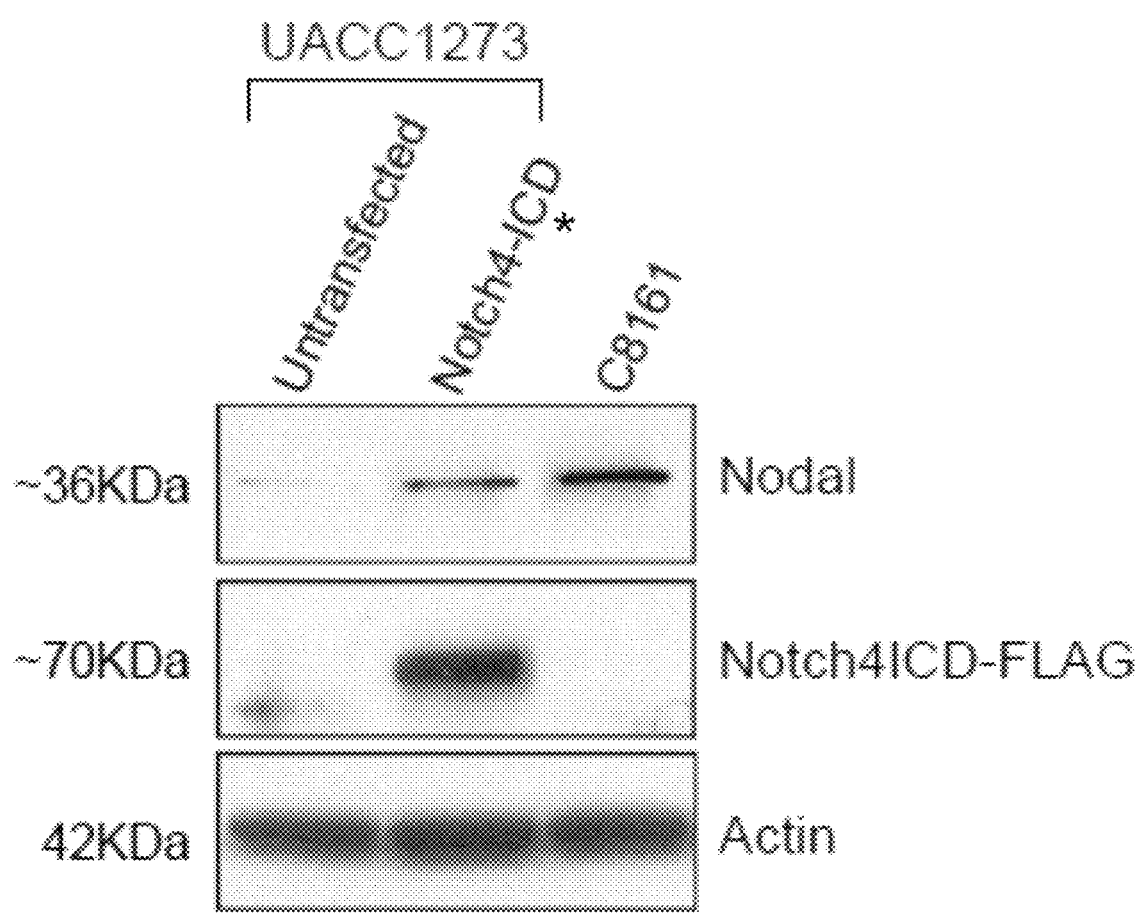
FIG. 19 shows that nonaggressive human melanoma cells (UACC1273) are Nodal-negative, until they received Notch4 ICD-FLAG—which resulted in Nodal upregulation FIG. 20 demonstrates a Nodal Enhancer Element (NDE) located 10 Kb upstream of the Nodal gene contains 2 putative RBPJ binding sites for Notch. ChIP confirms Notch4 ICD directly binding to RBPJ-1 binding sites in the NDE.

FIG. 18 depicts Notch4 signaling directly regulating Nodal expression. Knockdown of Notch expression (by siRNA) in C8161 and MV3 melanoma cells results in Nodal down-regulation. Experimental upregulation of Notch4 in Nodal-negative, non-aggressive UACC1273 melanoma cells results in the upregulation of Nodal (See FIG. 19).

Figure 20:
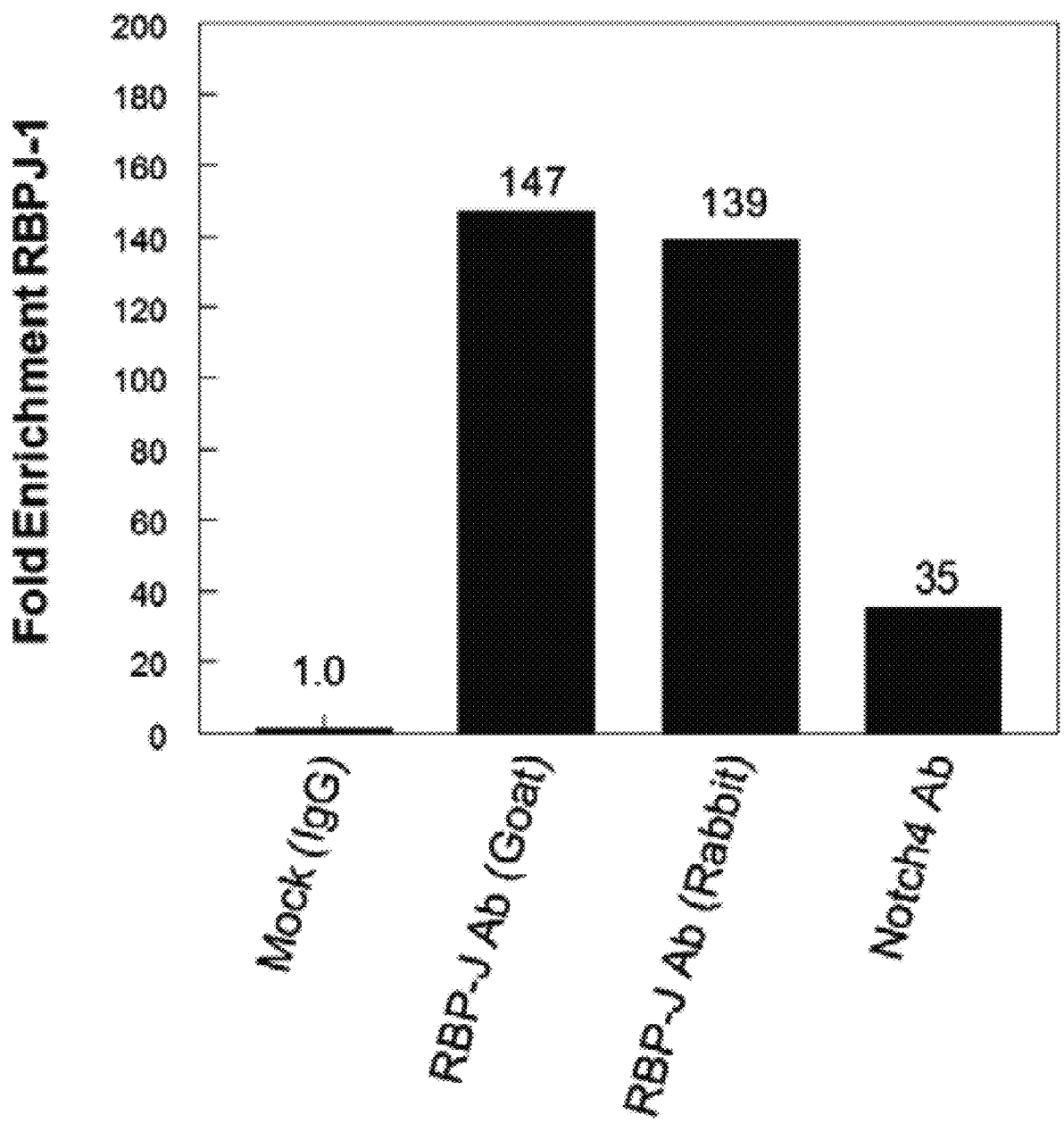

Nodal Enhancer Element (NDE) is located 10 Kb upstream of the Nodal gene and contains 2 putative RBPJ binding sites for Notch. ChIP confirms Notch4 ICD directly binding to RBPJ-1 binding sites in the NDE (See FIG. 20).

Figure 21:
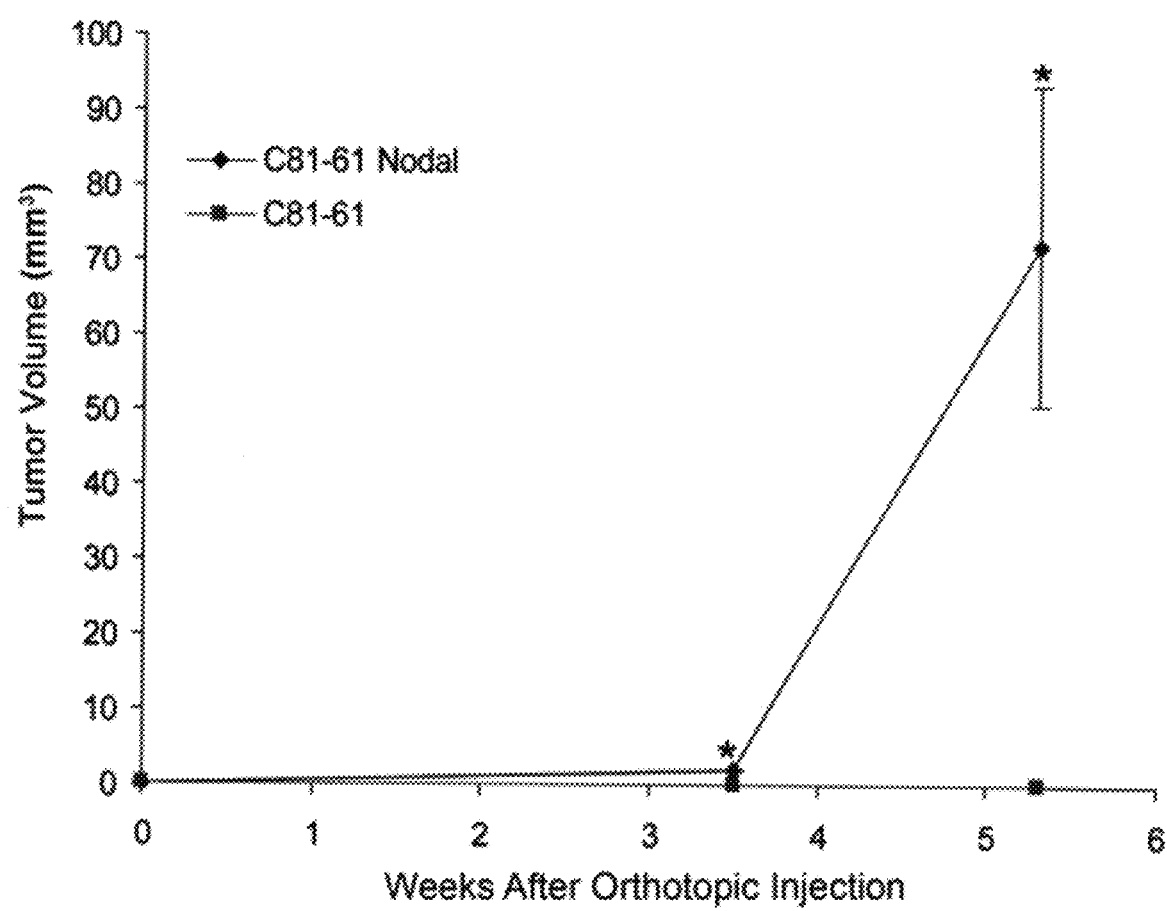
FIG. 21 shows that nonaggressive, Nodal-negative C81-61 melanoma cells are tumorigenic after transfection with Nodal cDNA
Figure 22:
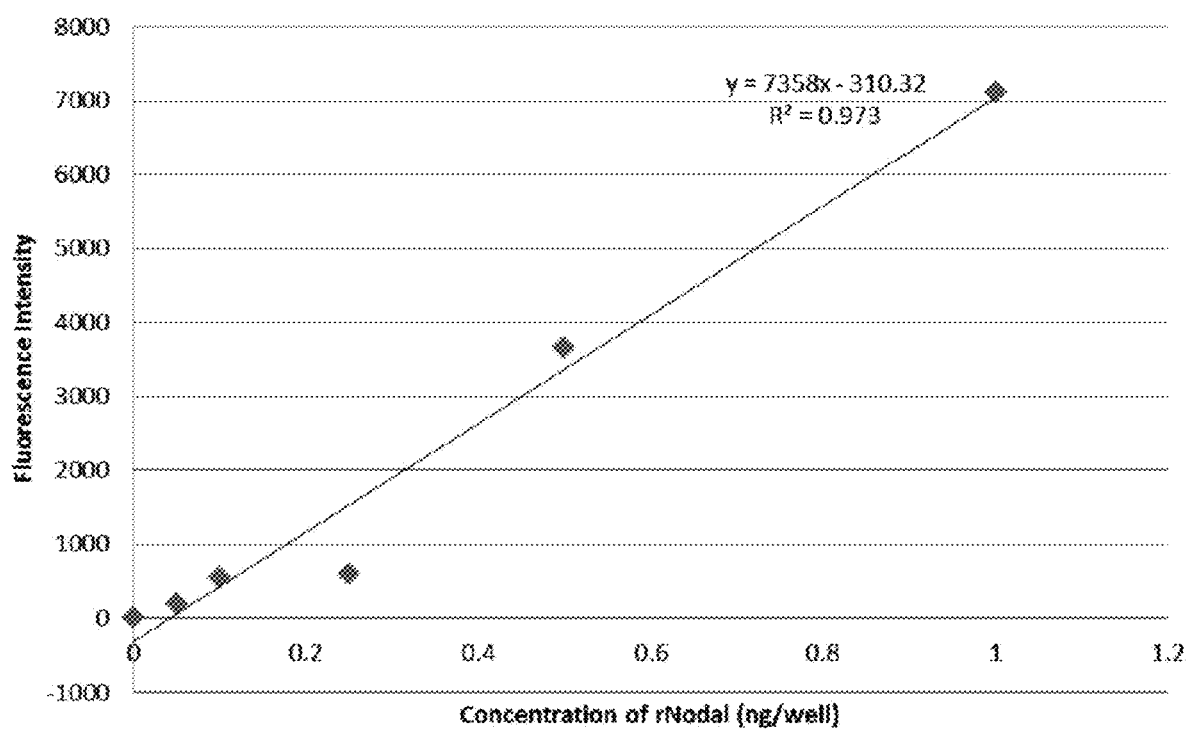
FIG. 22 depicts a sandwich ELISA assay developed to detect Nodal (detection limit 50 pg/well) using monoclonal antibody 3D1 as the capture antibody.

FIG. 21 shows that nonaggressive, Nodal-negative C81-61 melanoma cells are tumorigenic after transfection with Nodal cDNA A typical calibration curve was obtained using a sandwich ELISA assay developed to detect Nodal (detection limit 50 pg/well) (See FIG. 22). The assay used monoclonal anti-Nodal antibody (designated 3D1) to coat an ELISA dish to capture rNodal (recombinant Nodal) from solutions with different concentrations of rNodal and a second, rabbit monoclonal anti-Nodal antibody to detect the captured rNodal. The resulting captured rNodal-antibody complex was then detected with an anti-rabbit antibody conjugated to horseradish peroxidase and a QuantaRed enhanced chemifluorescent horseradish peroxidase substrate.

Figure 23:
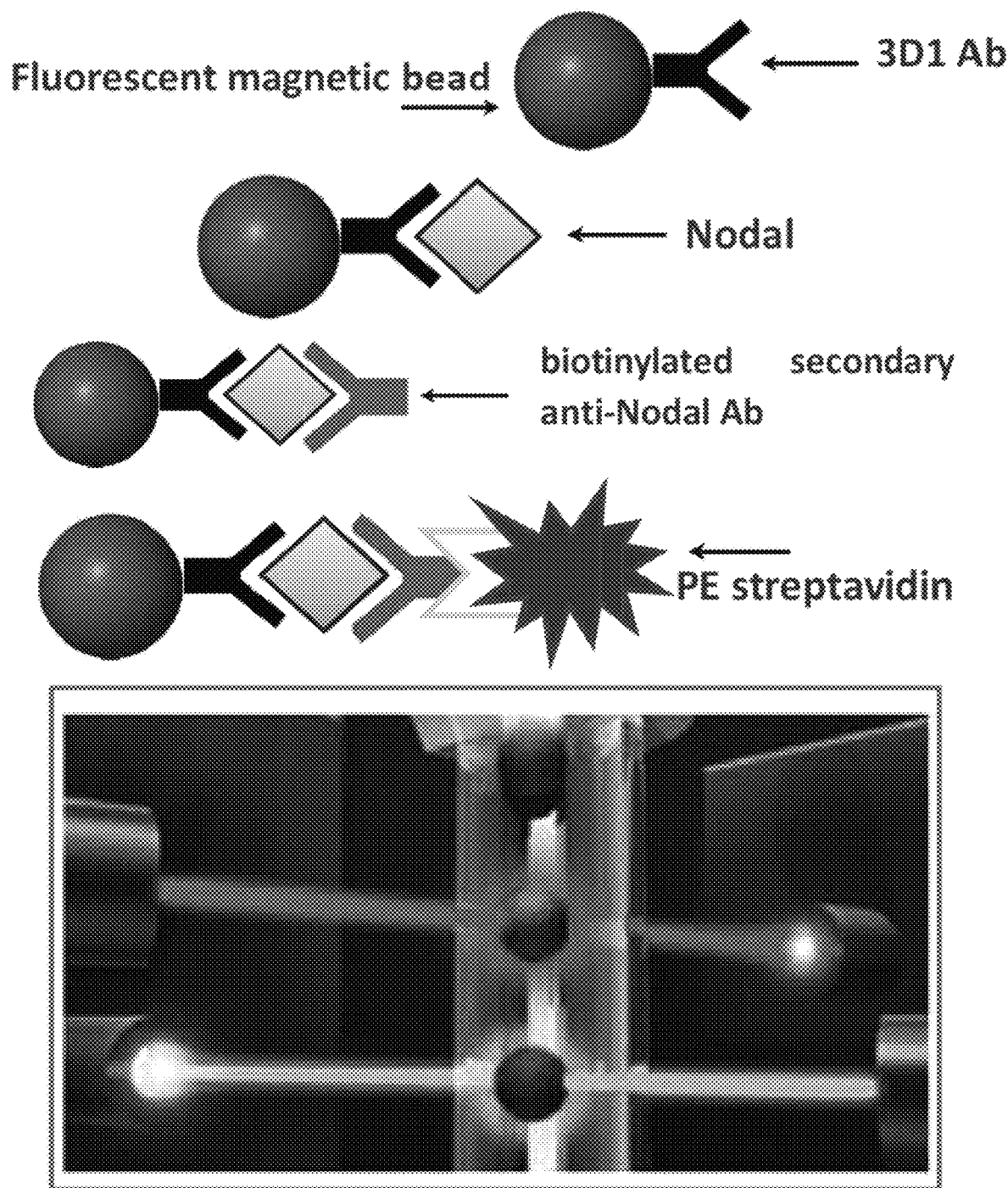
FIG. 23 depicts a specific and sensitive assay developed in one embodiment of the invention using 3D1 and based on xMAP technology for the detection of Nodal in plasma/serum.

A specific and sensitive assay utilizing 3D1 antibody of the invention was developed based on xMAP technology for the detection of Nodal in plasma/serum samples and is shown in FIG. 23.

Figure 24:
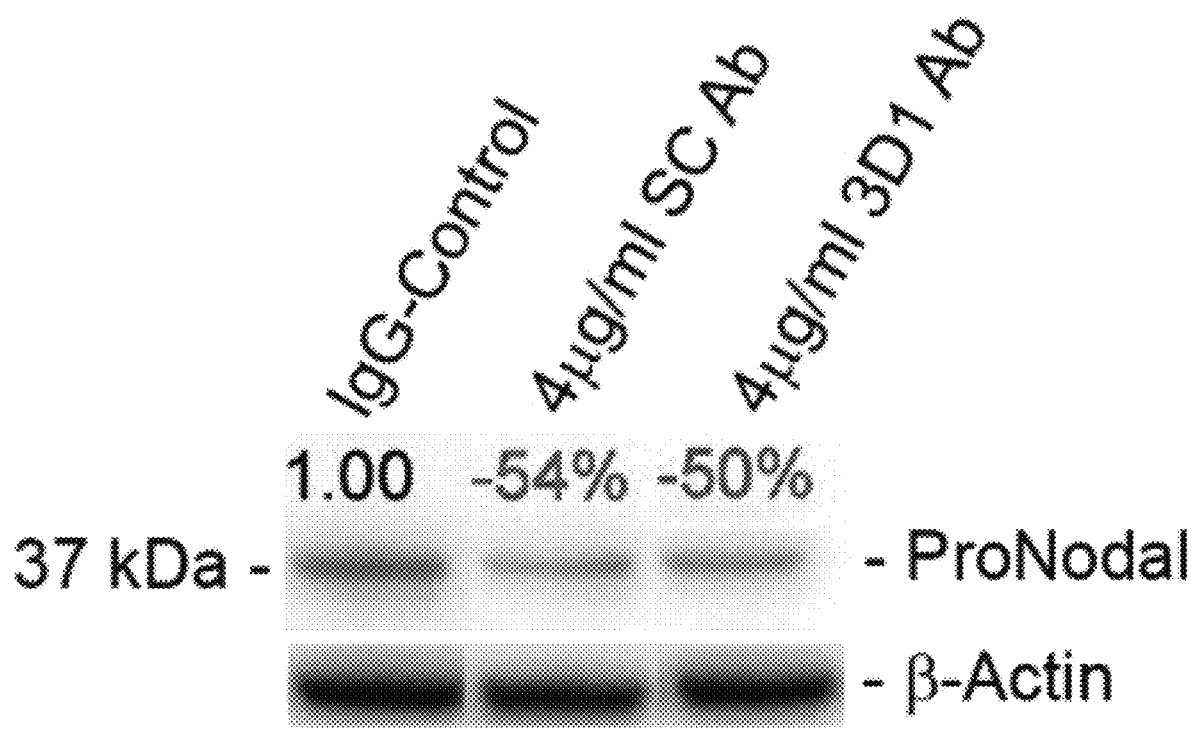
FIG. 24 shows that 3D1 anti-Nodal antibody reduced Nodal expression, clonogenicity, and vasculogenic mimicry in metastatic melanoma cells.
Figure 24:
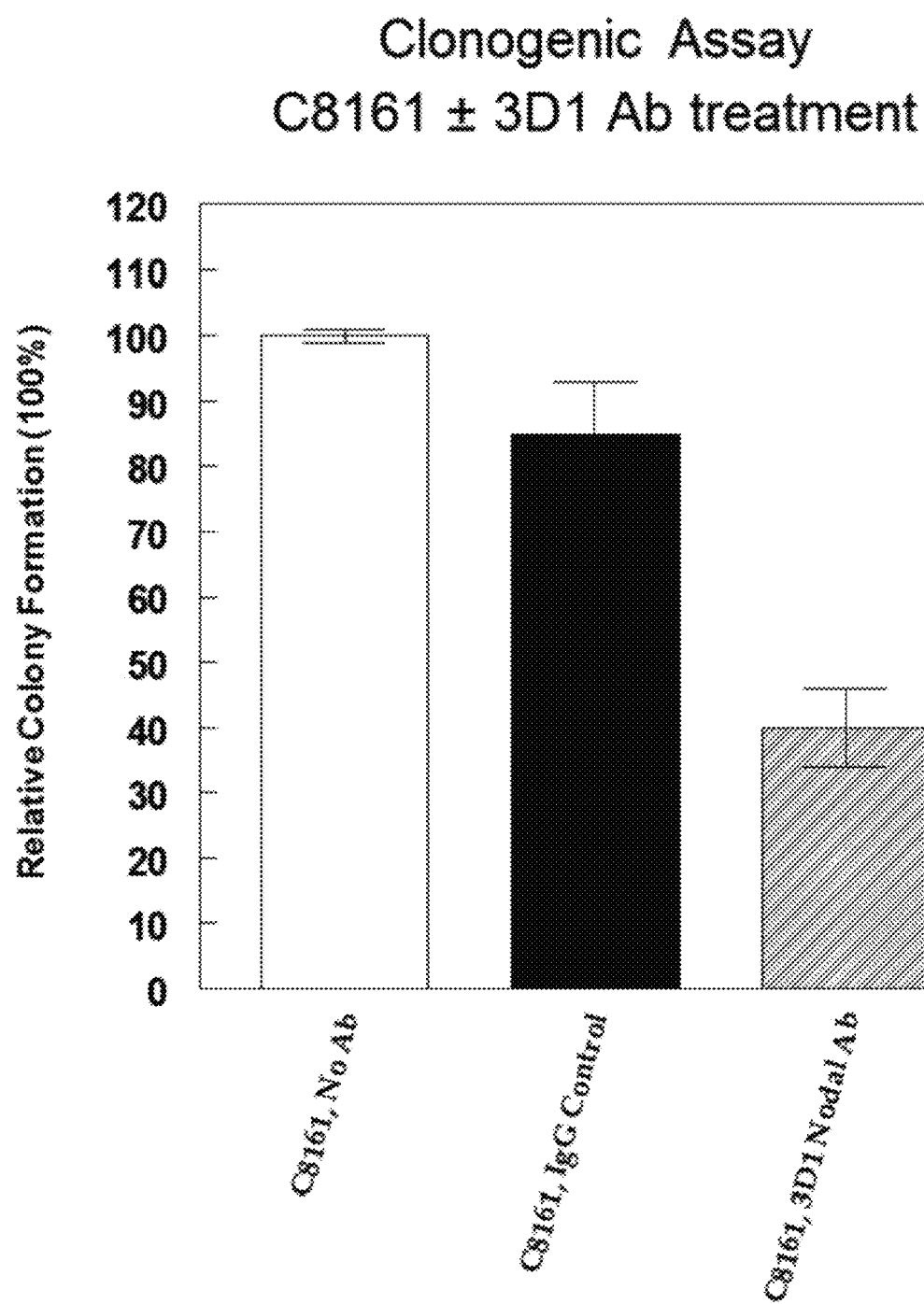
Figure 24:
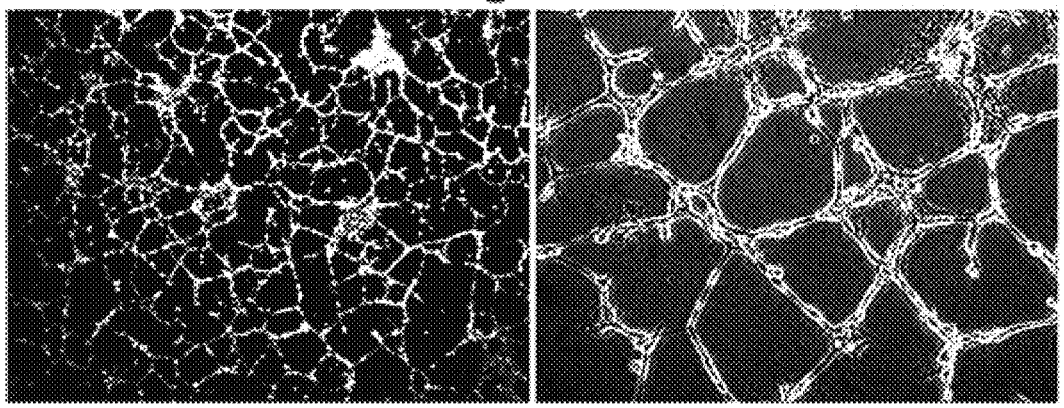
Figure 24:
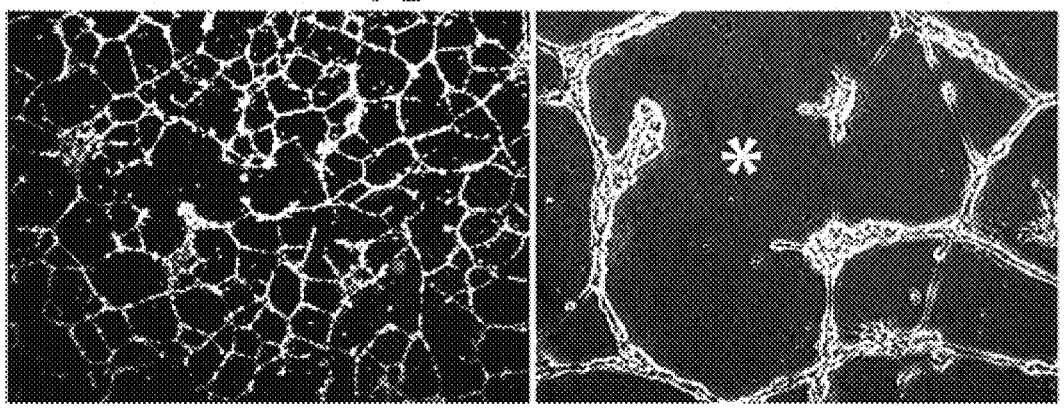
Figure 24:
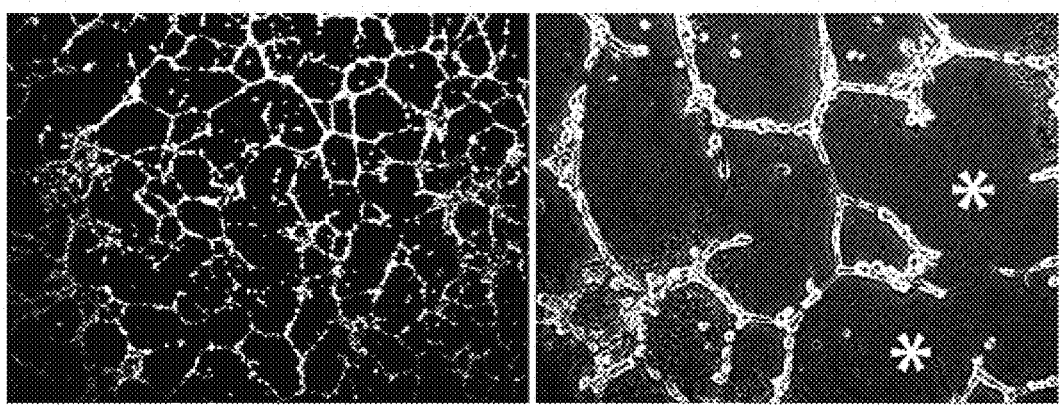

Experiments were conducted in order to assess and characterize the ability of the 3D1 antibody to inhibit Nodal activity. 3D1 reduced Nodal expression, clonogenicity, and vasculogenic mimicry in metastatic melanoma cells (See FIG. 24). C8161 melanoma cells treated with an IgG-Control (negative control) or 4 µg/ml of either Santa Cruz (SC) (used as positive control) or 3D1 function blocking anti-Nodal antibodies for 72 hours. Western blot analysis demonstrates a 54% (SC) and 50% (3D1) inhibition of Nodal protein expression.

Untreated cells, or cells treated with either IgG Control or 3D1 anti-Nodal antibody for 72 hours were cultured in soft agar for three weeks (soft agar clonogenic assay). Cell treated with 3D1 demonstrated a decrease in their ability to form non-adherent spheroidal clusters (a decrease in clonogenicity) compared to untreated cells and cells treated with IgG control antibody. C8161 cells were treated with either 4 µg/ml of either Santa Cruz (SC), or 3D1 function blocking anti-Nodal antibodies, or IgG Control and cultured in three dimensional cultures for 24 hours to measure their ability to engage in vasculogenic mimicry (VM). Cells treated with either the SC or 3D1 antibodies did not complete the formation of networks (*) characteristic of VM seen in the control cells.

Figure 25:
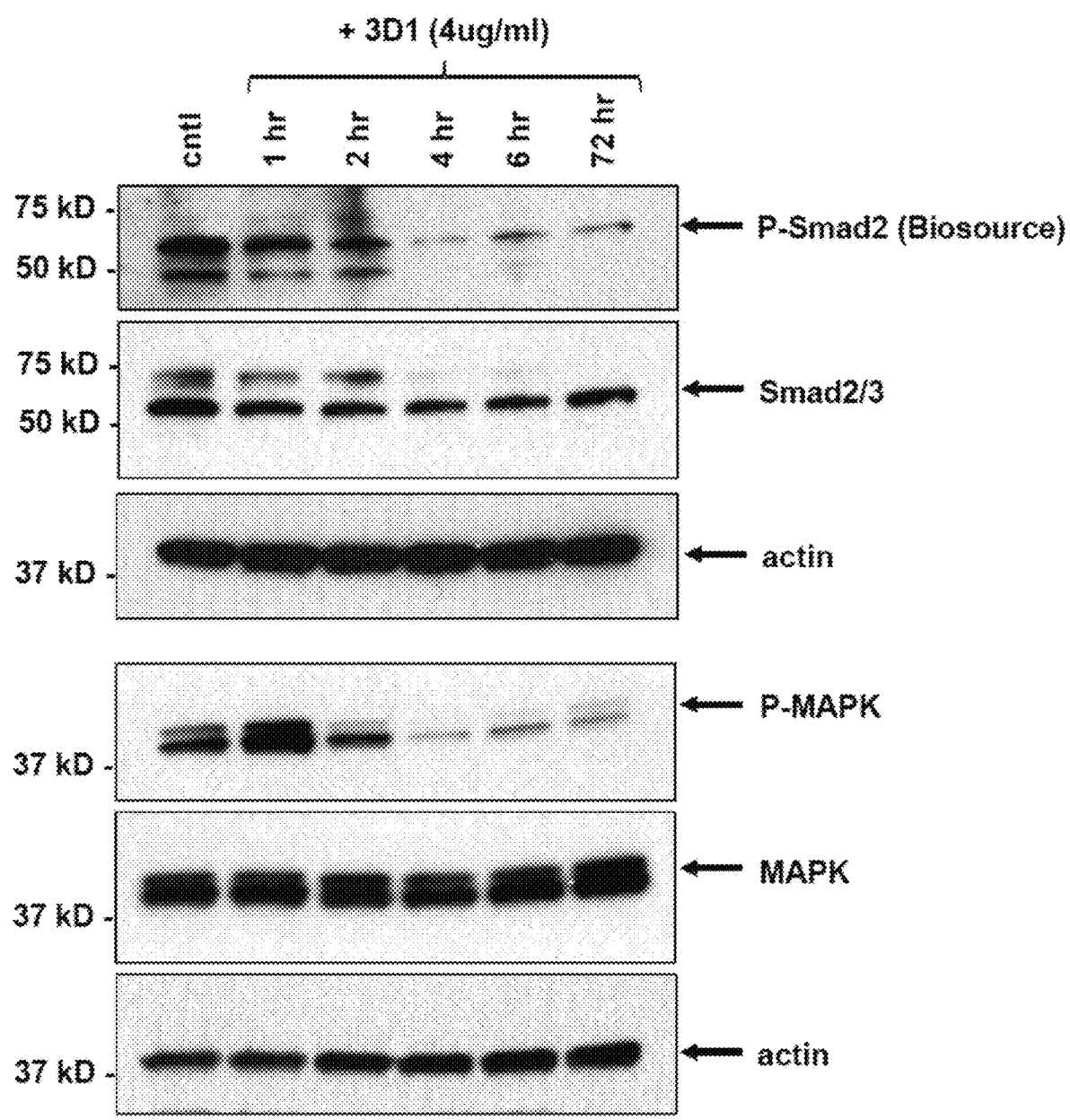
FIG. 25 shows 3D1 anti-Nodal antibody reduced phosphorylation of Smad2 and MAPK.

Additional studies were performed in order to determine if 3D1 antibody could alter phosphorylation of Smad2 or MAPK. 3D1 anti-Nodal antibody reduced phosphorylation of Smad2 and MAPK. Western blot analysis of C8161 melanoma cells treated with 3D1 (4 µg/ml) vs. untreated control for 1 hr, 2 hr, 4 hr, 6 hr or 72 hr (See FIG. 25).

Figure 26:
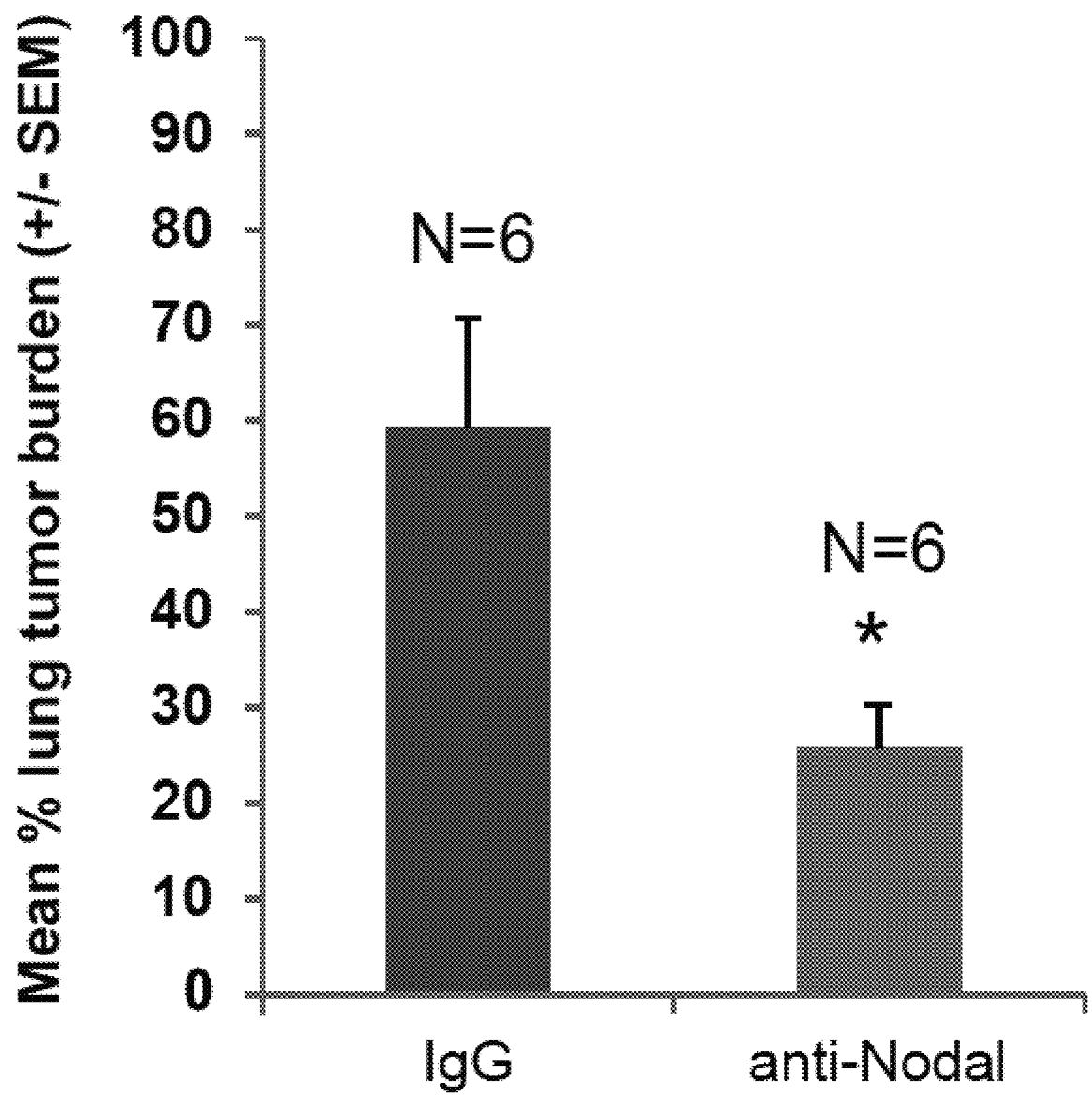
FIG. 26 shows3D1 anti-Nodal antibody reduced lung colonization of metastatic melanoma cells in mice.

3D1 anti-Nodal antibody also reduced lung colonization of metastatic melanoma cells in mice. Lung tumor burden was determined as the mean percentage of lung occupied by C8161 melanoma cell colonies calculated from at least 5 different lung sections per individual mouse (See FIG. 26). Experimental Protocol: 250,000 C8161 metastatic melanoma cells were injected i.v. in Nude mice and lung colonization established. Following colonization, animals received by i.p. delivery either 3D1 monoclonal anti-Nodal antibody (100 µg/injection) or control IgG over the next 10 days, every other day (5 total injections).

Figure 27:
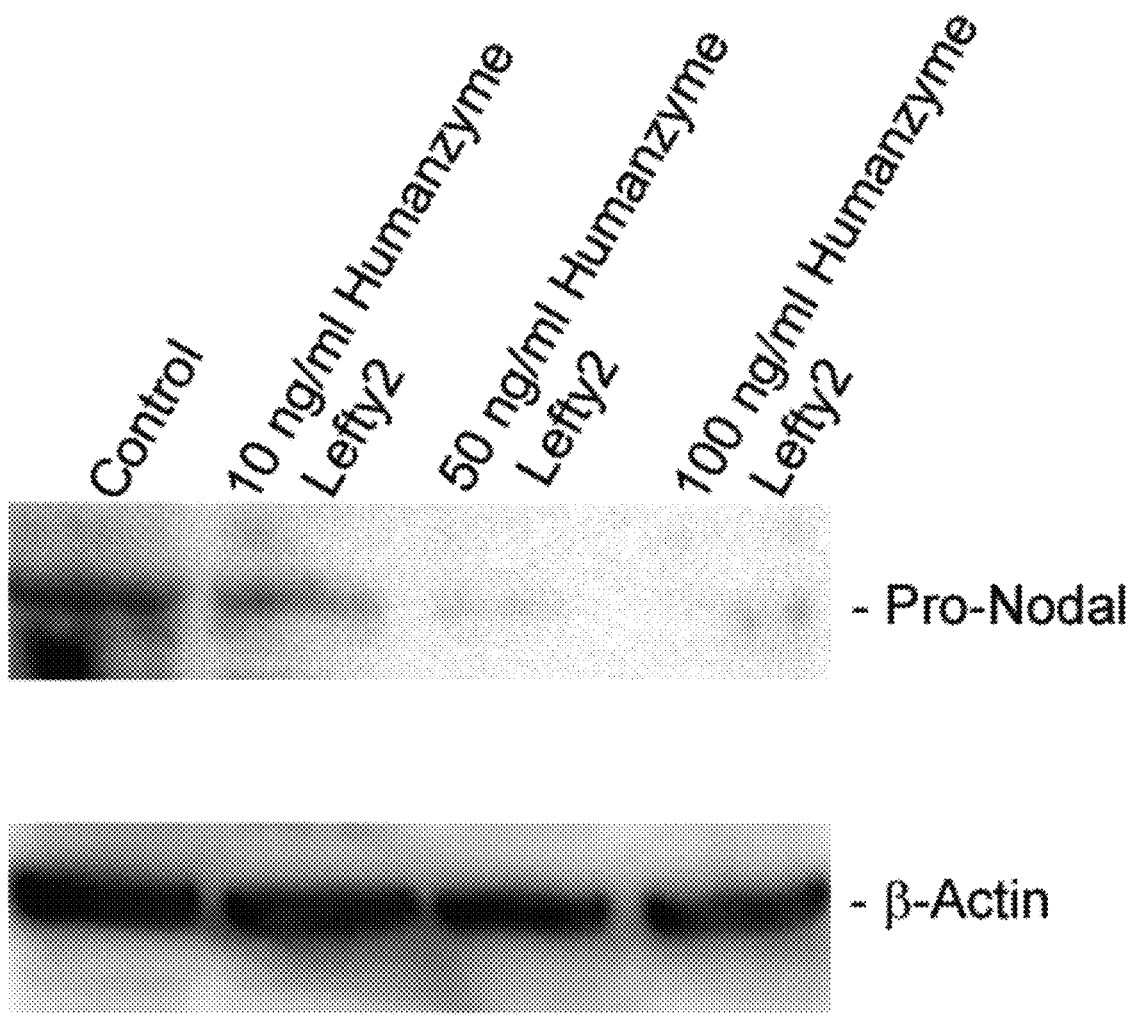
FIG. 27 shows that hLefty is effective in inhibiting Nodal protein expression in metastatic melanoma cells at 10, 50 and 100 ng/ml.
Figure 28:
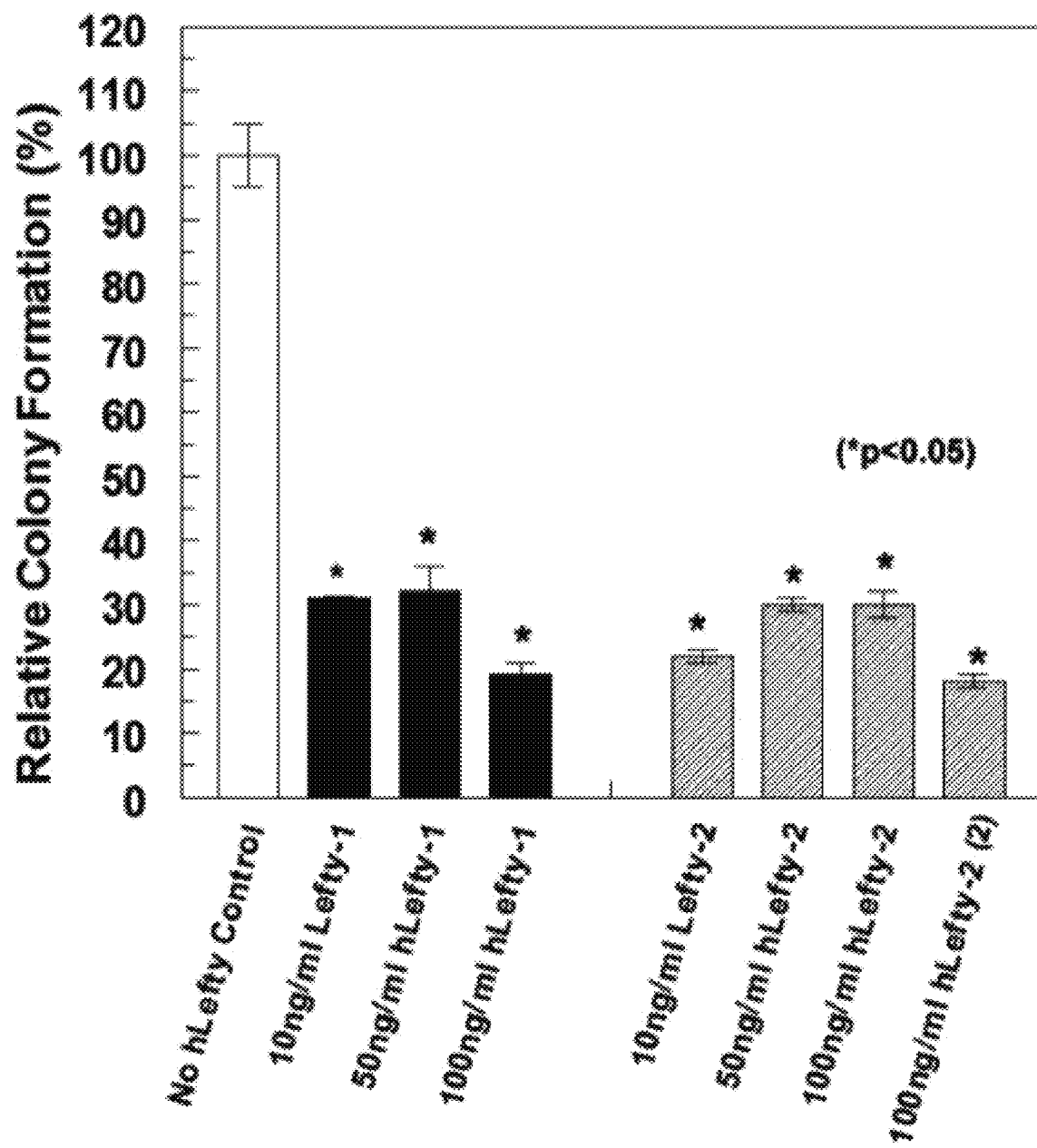
FIG. 28 shows that three week clonogenic assay +/−hLefty demonstrates that hLefty is effective in inhibiting clonogenicity of metastatic melanoma cells.

It has previously been shown that Nodal inhibition in melanoma tumor cells via treatment with human-derived Lefty (hLefty) induces apoptosis and reduces clonogenicity. Intratumoral delivery of 50 ng/ml hLefty (Nodal's natural inhibitor) to animals bearing melanoma tumors induces apoptosis (TUNEL assay showing red fluorescing tumor cells) and diminishes cell proliferation (Ki-67 brown staining marker) in Nodal-positive tumor cells vs. tumors receiving Hank's Basic Salt Solution (HBSS, Control; Strizzi et al., 2009). Direct delivery of hLefty (50 ng/ml) to melanoma tumors in vivo induces apoptosis of Nodal-positive tumor cells; while treatment of metastatic melanoma cells in vitro with hLefty at 10, 50 and 100 ng/ml down-regulates Nodal expression and diminishes clonogenicity in soft agar. FIG. 27 shows that hLefty is effective in inhibiting Nodal protein expression in metastatic melanoma cells at 10, 50 and 100 ng/ml. FIG. 28 shows that three week clonogenic assay +/− hLefty demonstrates that hLefty is effective in inhibiting clonogenicity of metastatic melanoma cells.

Targeting metastatic melanoma with a combinatorial approach is more effective than mono-therapy. Dacarbazine (DTIC) is FDA was approved for treatment of metastatic melanoma in 1970's. It is still first-line therapy today, despite failing for most (80+%) patients. A working hypothesis developed during development of embodiments of the invention was that DTIC therapy is ineffective because this agent would not target Nodal-expressing subpopulations of tumor cells. Accordingly, it was tested whether treating with DTIC and targeting Nodal-expressing cells would have an enhanced killing effect over DTIC alone.

Figure 29:
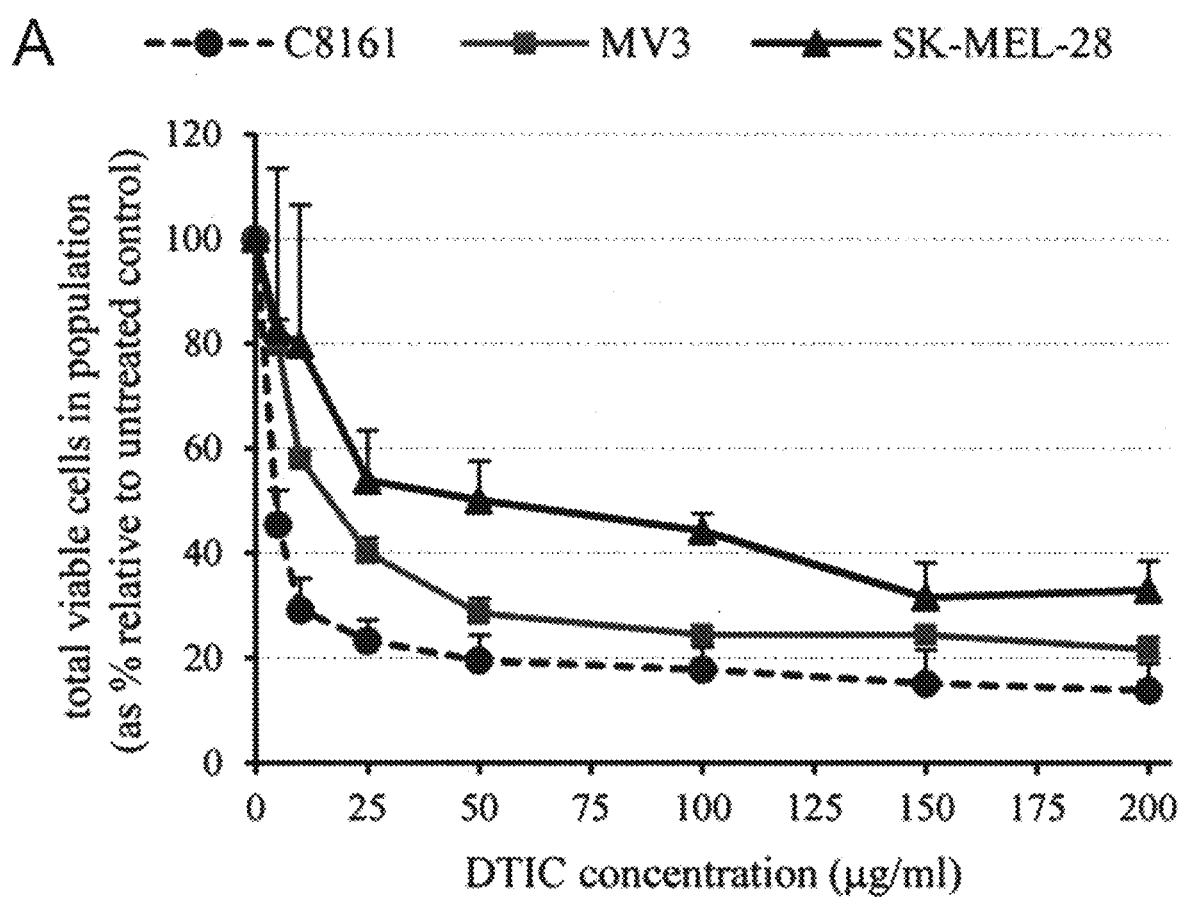
FIG. 29 shows that conventional Dacarbazine (DTIC) treatment leaves a residual melanoma cell population that continues to express Nodal.
Figure 29:
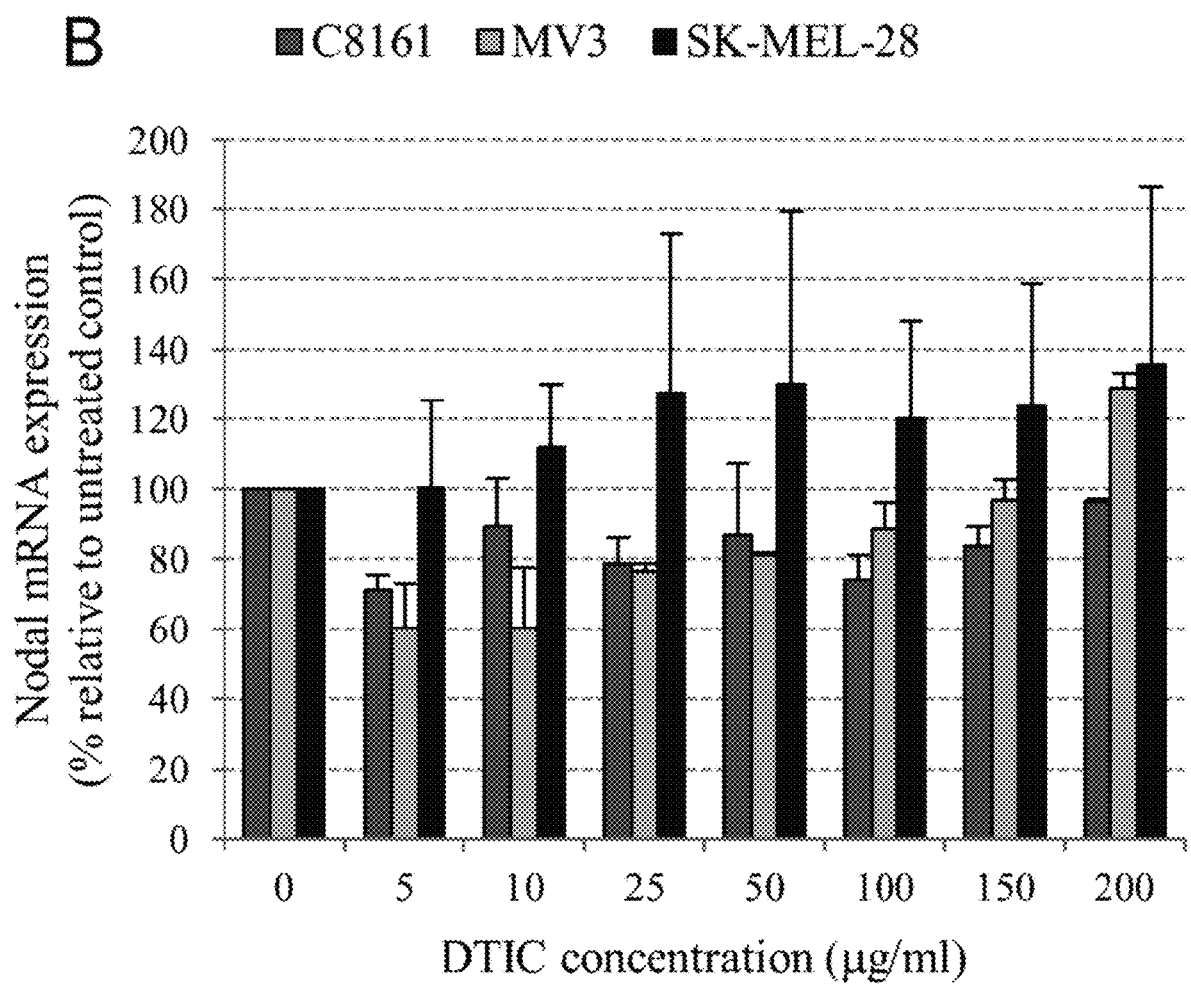
Figure 30:
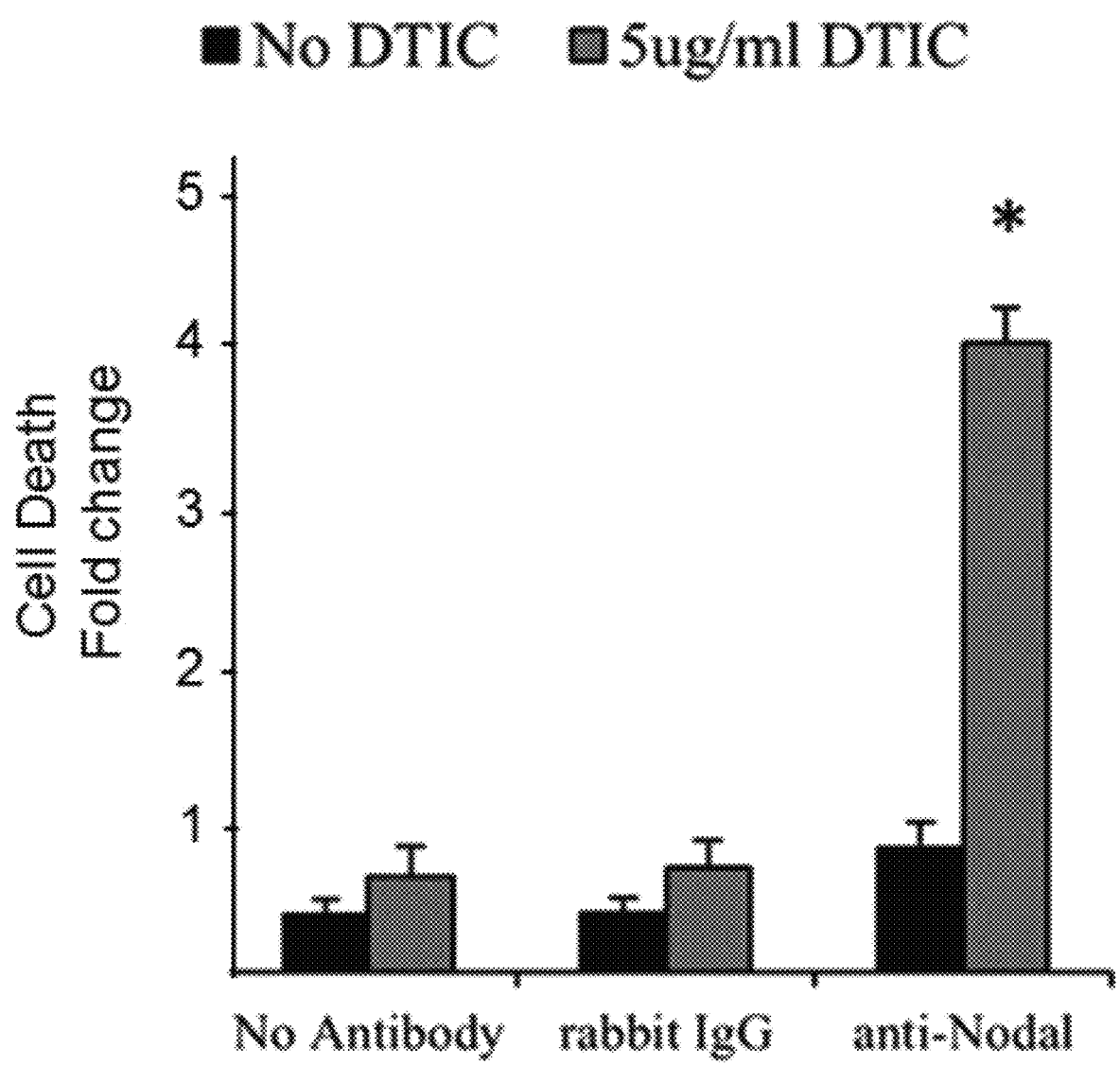
FIG. 30 shows that combining DTIC and anti-Nodal antibody treatment induced cell death.

It was observed that DTIC treatment leaves a residual cell population that continues to express Nodal (See FIGS. 29A and 29B). However, combining DTIC and anti-Nodal antibody treatment induced cell death (See FIG. 30). C8161 metastatic melanoma cells were either untreated or treated with 5 µg/ml DTIC for 72 hours, allowed to recover for 72 hours, then incubated for an additional 72 hours with 3 µg/ml rabbit IgG, or left untreated. End point changes in percent cell death vs. controls (FIG. 30) were evaluated by flow cytometry ($p<0.05$).

Figure 31:
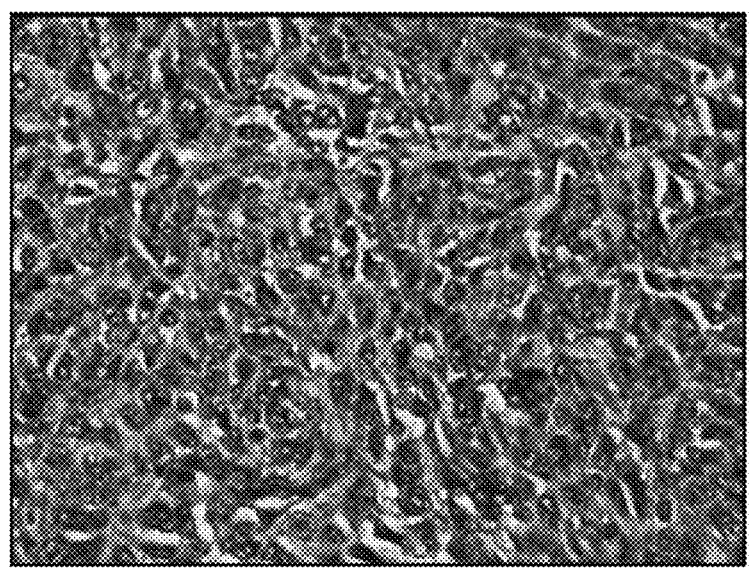
FIG. 31 shows Nodal expression (dark red/brown stain) in human melanoma patient tissue pre- and post-DTIC therapy.
Figure 31:
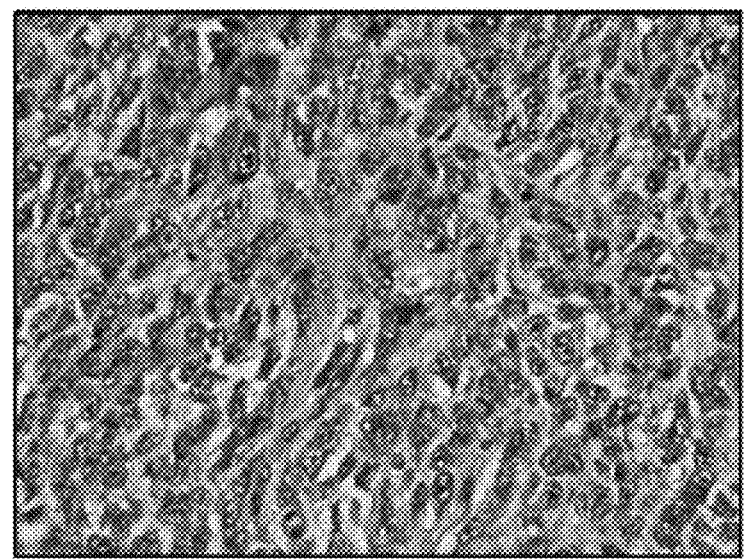
Figure 31:
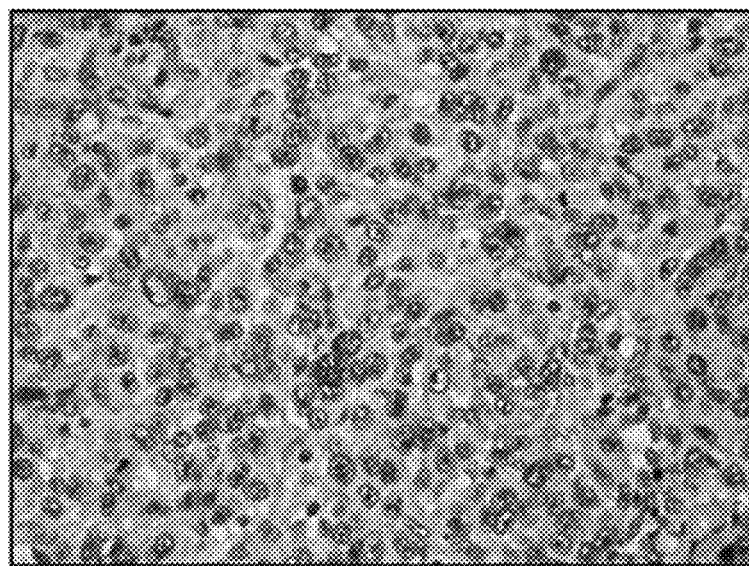

Immunohistochemistry of Nodal localization in patient melanoma tissues before DTIC treatment vs. after DTIC treatment vs. IgG control was analyzed (See FIG. 31). Nodal-positive subpopulations exist pre-and-post-DTIC treatment.

Figure 32:
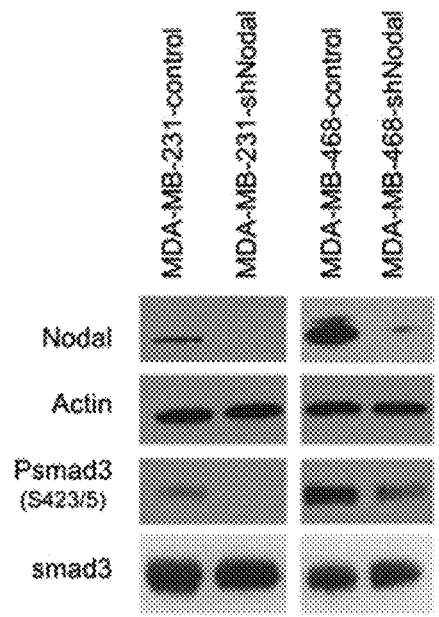
FIG. 32 shows Nodal knockdown impairs growth and aggressive behavior in human breast cancer cell lines.
Figure 32:
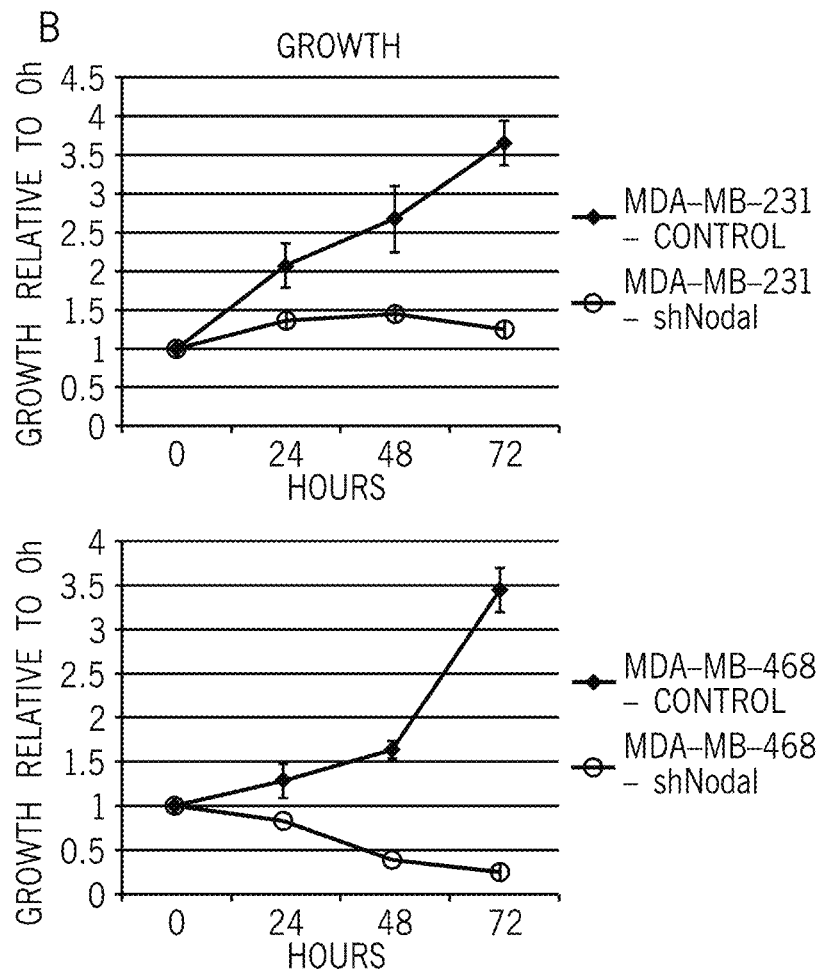
Figure 32:
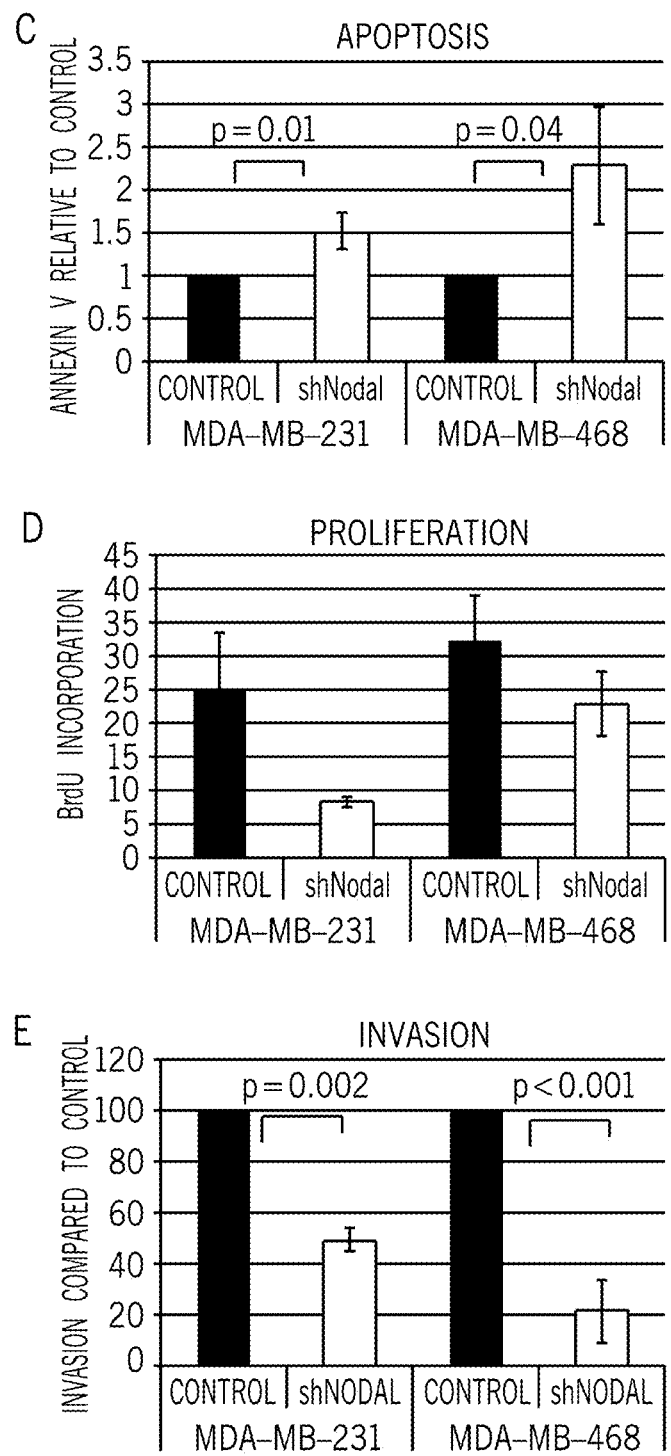
Figure 32:
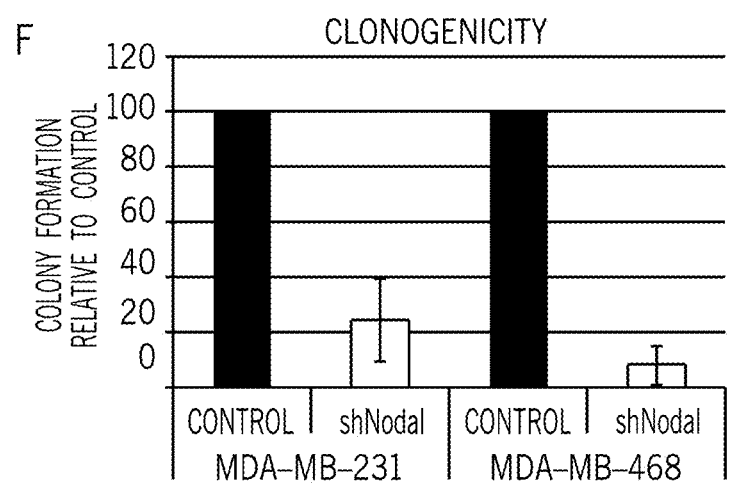

As shown in FIG. 32, Nodal knockdown impairs growth and aggressive behavior in human breast cancer cell lines.

Figure 33:
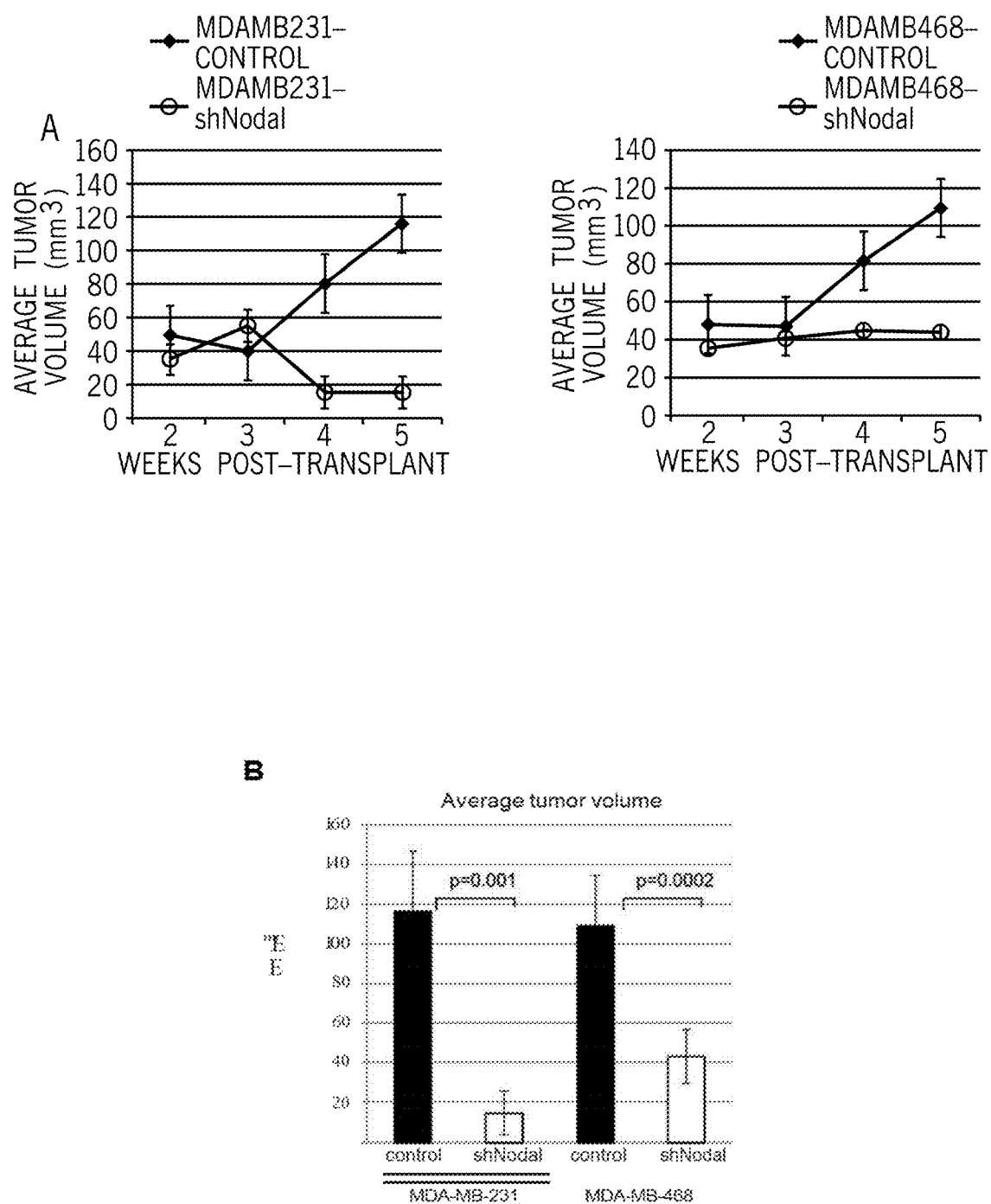
FIG. 33 shows Nodal knockdown impairs breast tumor growth in vivo.
Figure 33:
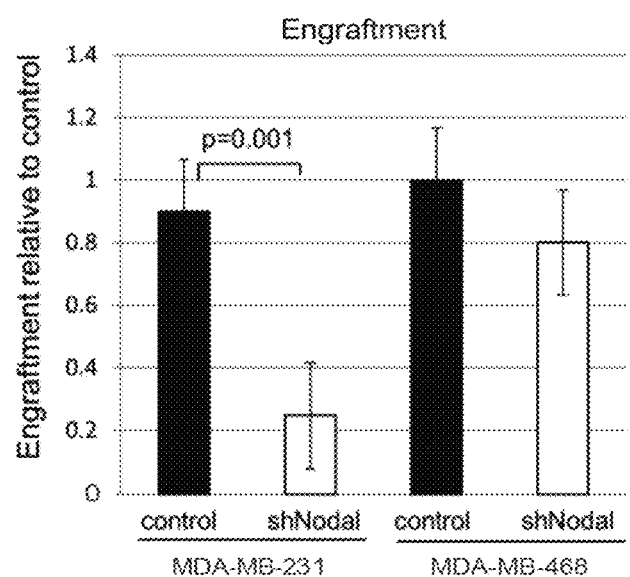
Figure 33:
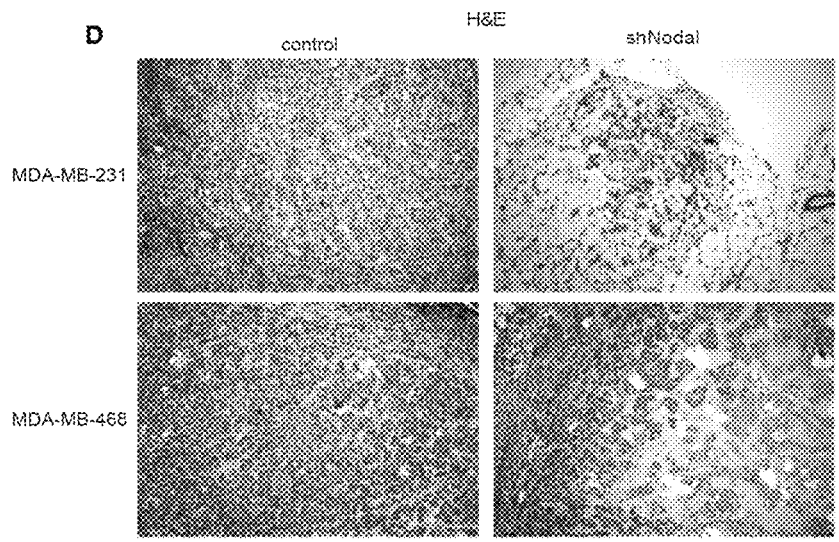

As shown in FIG. 33, Nodal knockdown impairs breast tumor growth in vivo.

Figure 34:
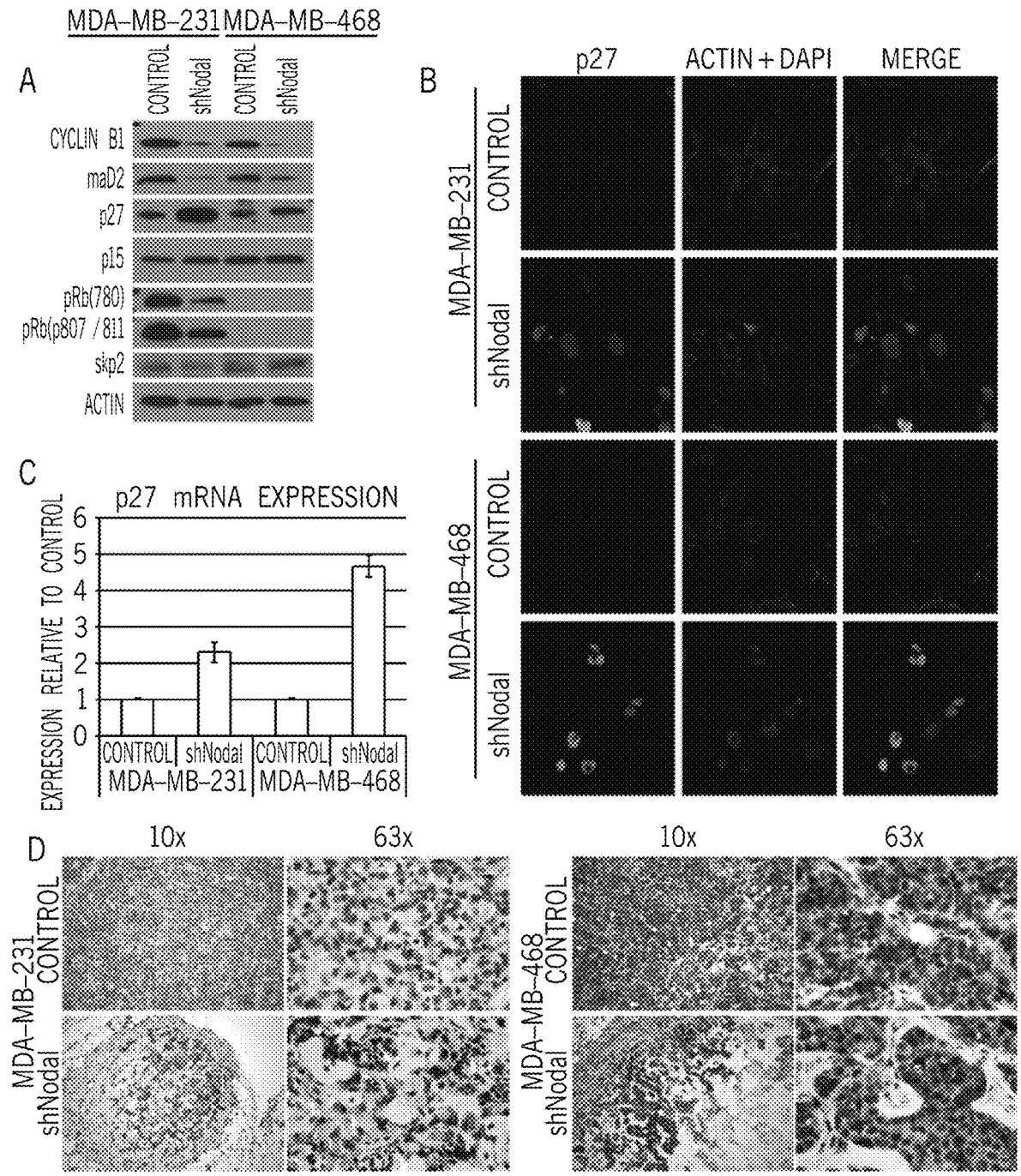
FIG. 34 shows that Nodal knockdown cells are arrested in G1 with increased p27 expression.

FIG. 34 shows that Nodal knockdown cells are arrested in G1 with increased p27 expression.

Figure 35:
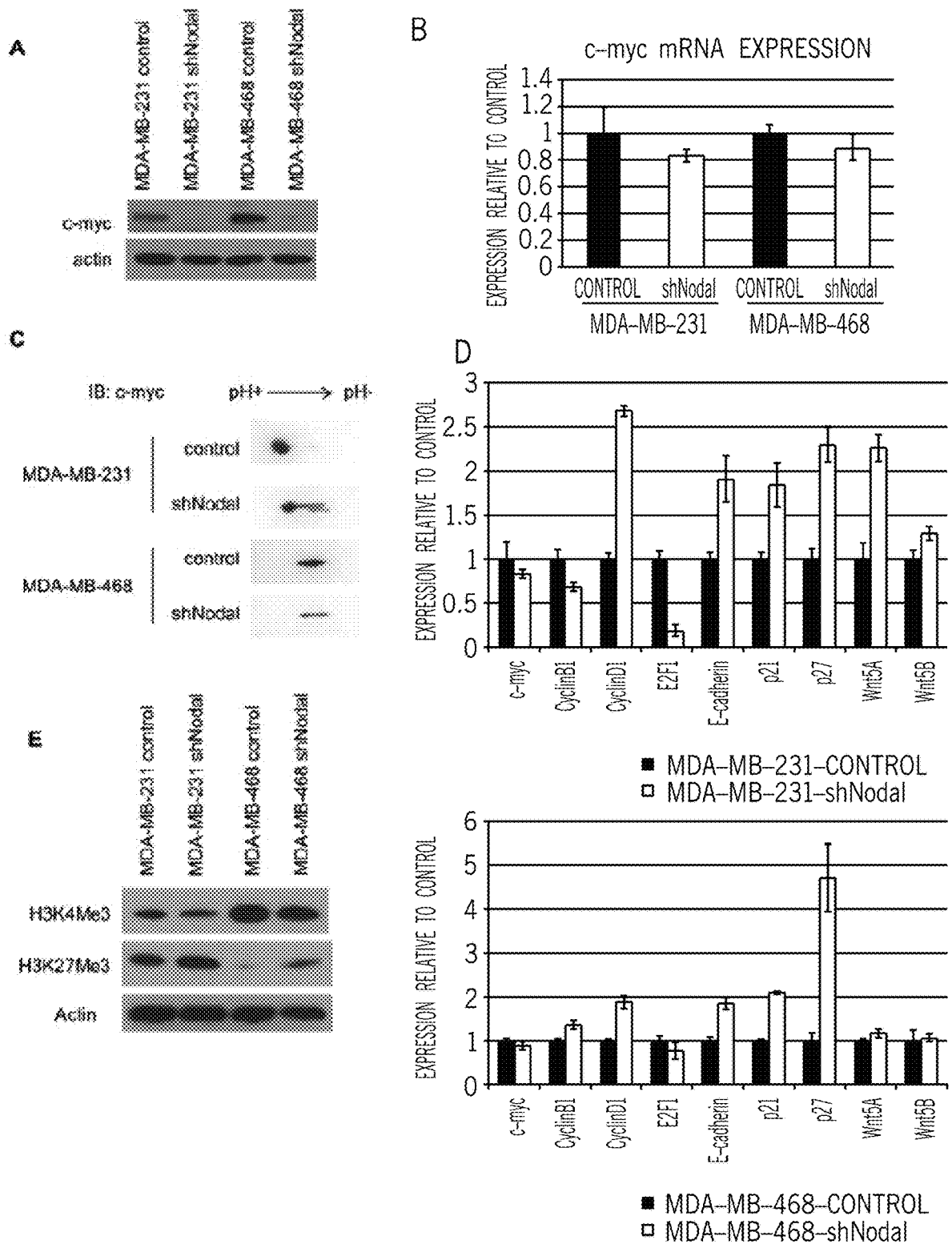
FIG. 35 shows that Nodal signaling regulates C-myc expression.

FIG. 35 shows that Nodal signaling regulates C-myc expression.

Figure 36:
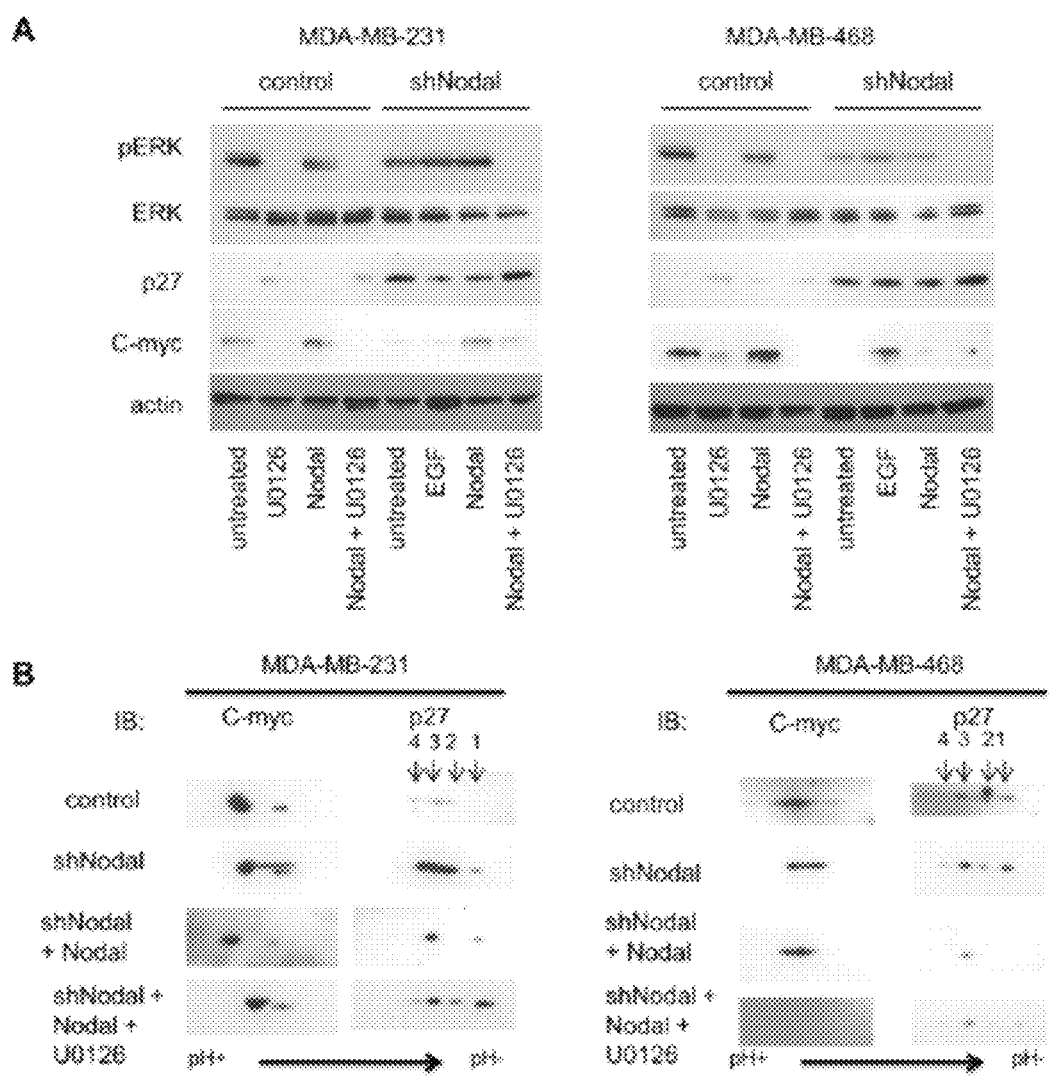
FIG. 36 shows that Nodal regulates p27 and c-myc protein levels and post-translational modifications through ERK activation in breast cancer cells.
Figure 36:
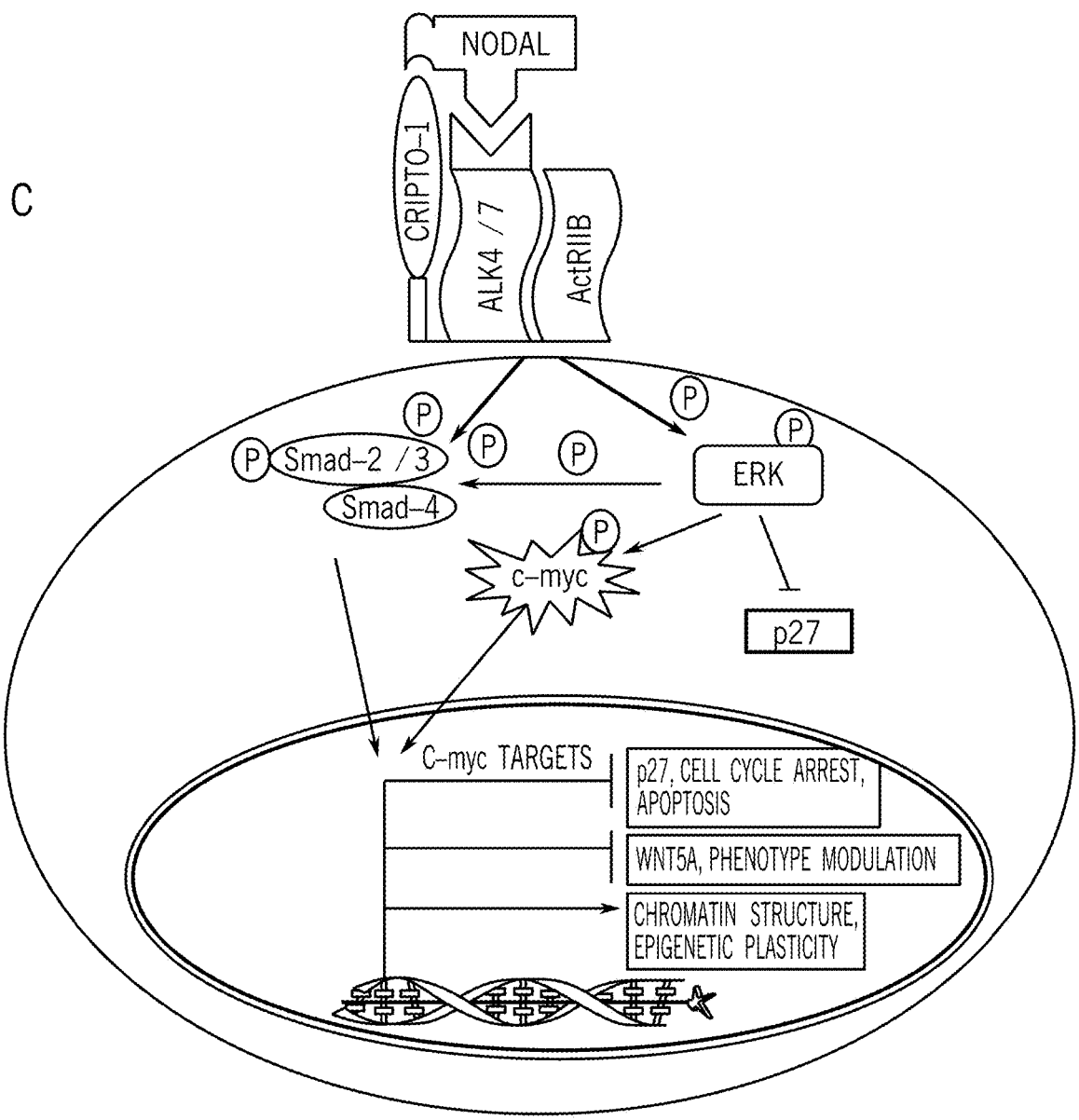

FIG. 36 shows that Nodal regulates p27 and c-myc protein levels and post-translational modifications through ERK activation in breast cancer cells.

Figure 37:
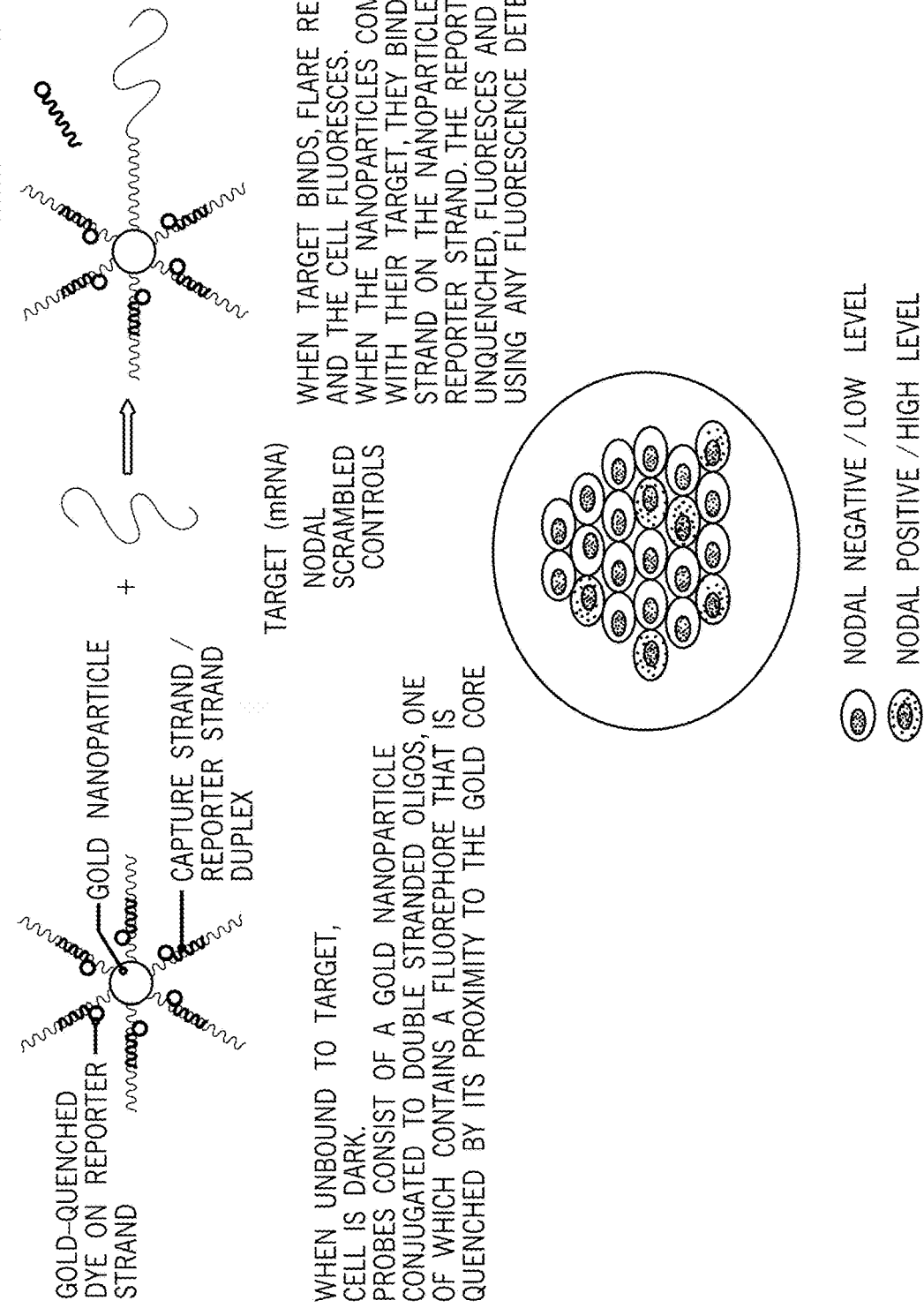
FIG. 37 shows use of SMARTFLARES to separate tumor cell subpopulations expressing stem cell markers, such as Nodal.

Use of SMARTFLARES to separate tumor cell subpopulations expressing stem cell markers, such as Nodal, is shown in FIG. 37. When unbound to target, cell is dark. Probes contain a gold nanoparticle conjugated to double stranded oligos, one of which contains a fluorephore that is quenched by its proximity to the gold core. Target (mRNA) is Nodal and use of scrambled oligos serve as controls. When the target binds, the flare releases and the cell fluoresces. When the nanoparticles come into contact with their target, they bind to the capture strand on the nanoparticle and replace the reporter strand. The reporter strand, now unquenched, fluoresces and can be detected using any fluorescence detection platform. This method can be used for live cell sorting using FACS; Sorted tumor cells analyzed by RT-PCR for gene expression; Western blot for protein expression; for clonogenic potential in soft agar; and for tumorigenic potential in vivo. Confocal microscopy can be performed for image analysis of Nodal mRNA together with CD133, another stem cell marker.

Figure 38:
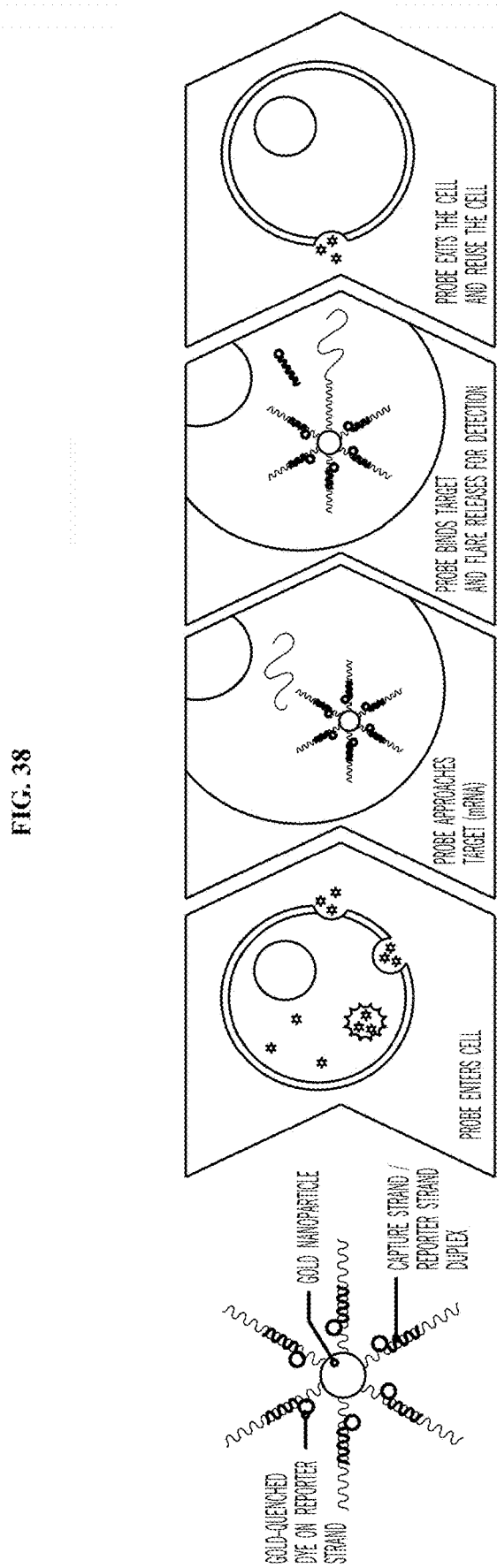
FIG. 38 shows the mechanism(s) of action of SMART-FLARES in detecting target mRNAs.

Thus, with a single incubation and a single reagent, detection can occur overnight. Using a cell's own machinery SMARTFLARE enters the cell; detects the mRNA of interest; exits the cell allowing further experimentation (See FIG. 38).

SMARTFLARES were utilized to measure Nodal expression in both metastatic as well as non-aggressive melanoma cells.

Figure 39:
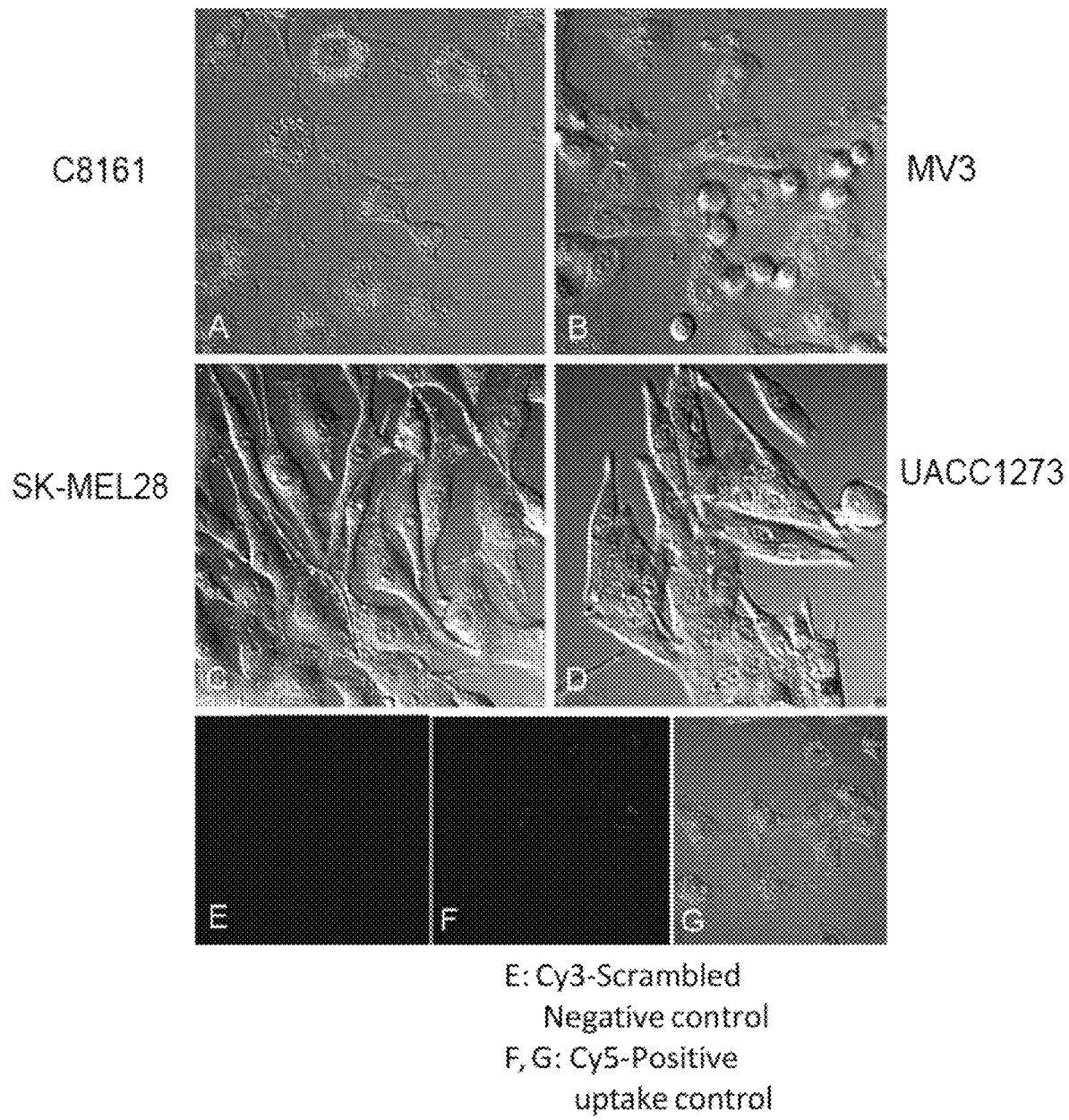
FIG. 39 shows the use of SMARTFLARES to detect Nodal mRNA expression in aggressive metastatic melanoma cells C8161 (A), MV3 (B), SK-MEL28 (C) and no expression of Nodal mRNA in the non-aggressive melanoma cells UACC1273 (D).

As shown in FIG. 39, aggressive metastatic melanoma cells C8161 (A), MV3 (B), SK-MEL28 (C) and non-aggressive melanoma cells UACC1273 (D) were treated with 100 µM Cy3-labeled SMARTFLARES prepared to detect Nodal mRNA for 16 hours in culture, then the live cells were imaged using a Zeiss LSM 700 confocal microscope equipped with a LSM 700 XL S1 incubation system for live cell imaging. The detection of Nodal mRNA as a Cy3 fluorescent green signal is seen in the aggressive melanoma cells (A, B, C), while no signal is seen in the non-aggressive UACC1273 cells (D). A Cy3-labeled scrambled sequence SMARTFLARE representing a negative control shows no green signal in C8161 cells (E), while a positive uptake control demonstrating that SMARTFLARES are taken up by the C8161 cells (Cy5-labeled, red fluorescent) is shown by the red fluorescent signal in these same cells (F) and with red fluorescence and differential interference contrast (DIC) imaging (G). (All magnifications=40×).

Figure 40:
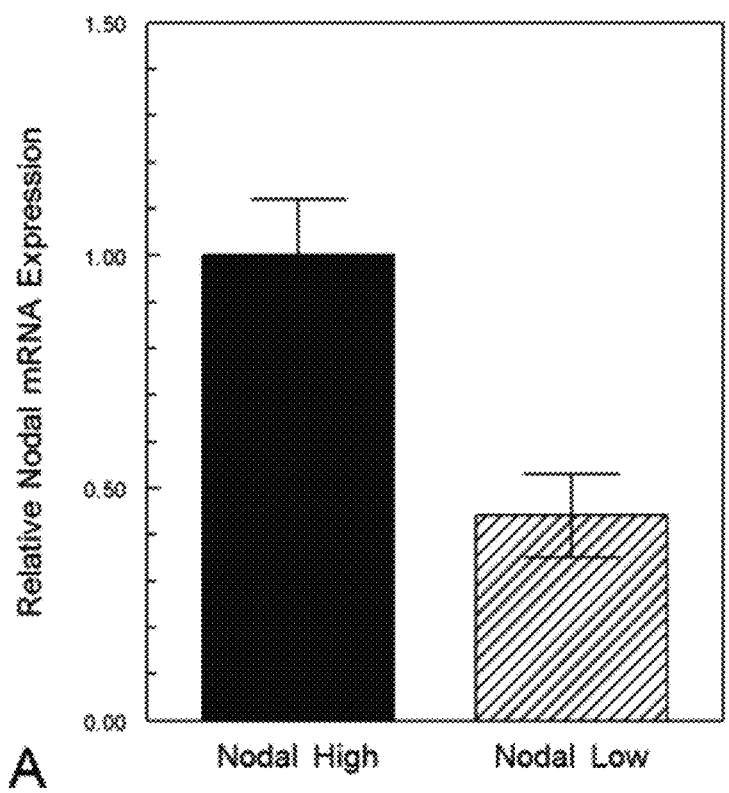
FIG. 40 shows that melanoma subpopulations can be sorted based on high vs. low Nodal mRNA expression.
Figure 40:
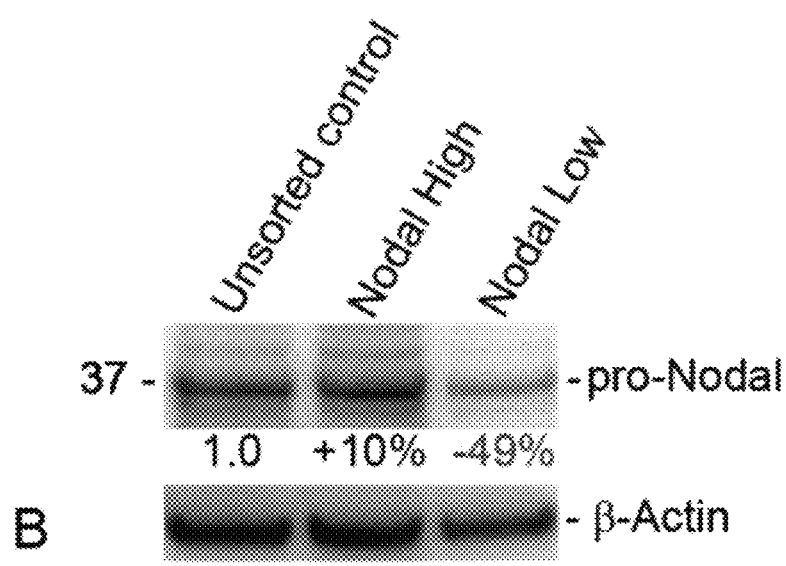

Melanoma subpopulations can be sorted based on high vs. low Nodal expression (See FIG. 40). C8161 cells were treated with Nodal mRNA SMARTFLARES for 16 hours, then sorted into subpopulations based on a high or low fluorescent signal representing Nodal expressing (Nodal High) and Nodal deficient (Nodal Low) subpopulations using a BD Bioscience FACSAria II Cell Sorter. The relative expression of Nodal mRNA in the two subpopulations was determined by real-time polymerase chain reaction (RT-PCR) assay (A) and the relative expression of Nodal protein (detected at 39 kilodaltons as pro-Nodal) determined by Western blot analysis (Epitomics rabbit monoclonal anti-Nodal antibody; B). The differences in pro-Nodal Protein in the High and Low Nodal sorted cells was measured densitometrically relative to the unsorted cells after correction for protein loaded in each lane using β-Actin protein as a control.

Figure 41:
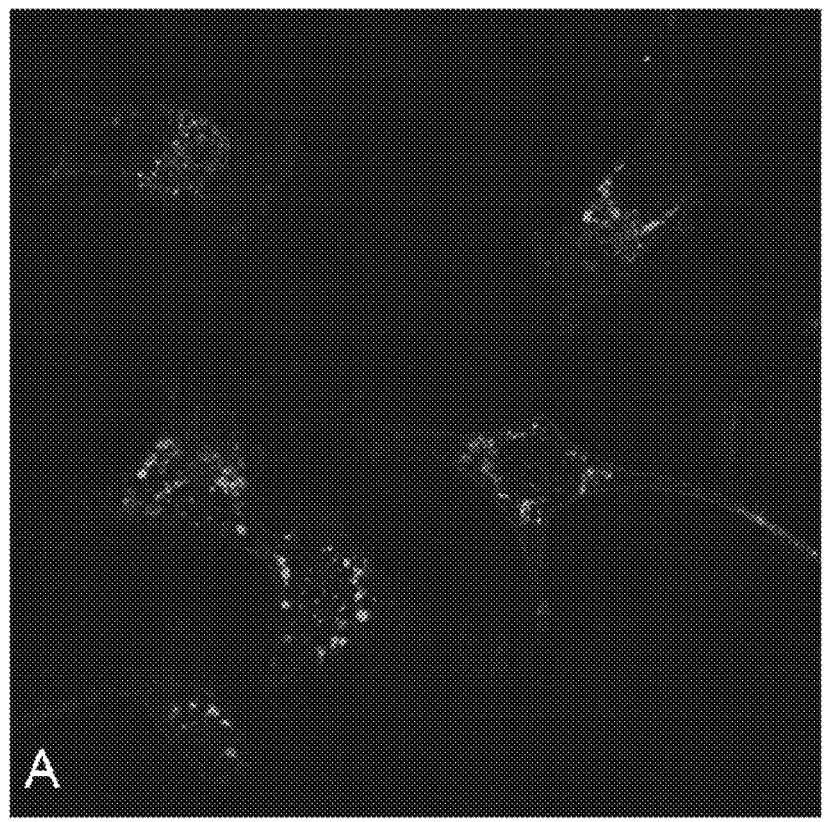
FIG. 41 shows that Nodal mRNA-high-expressing melanoma subpopulations concurrently express the CD133 cancer stem cell marker.
Figure 41:
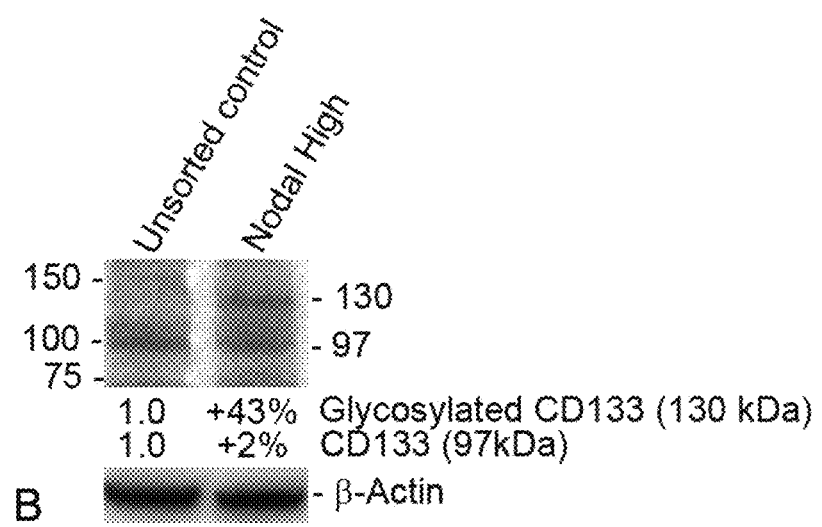

Nodal-high-expressing melanoma subpopulations concurrently express the CD133 cancer stem cell marker (See FIG. 41). A Nodal High population of C8161 cells sorted using Nodal mRNA SMARTFLARES was plated on glass coverslips and fixed and permeabilized with methanol. The cells were then treated with a rabbit primary antibody to Nodal (Santa Cruz; H-110) and a mouse primary antibody to CD133 (Millipore; 17A6.1), followed by an Alexa dye 488-conjugated secondary antibody against the rabbit antibody (green; Nodal) and Alexa dye 594-conjugated secondary antibody against the mouse antibody (red; CD133). CD133 expression appears enriched in the Nodal High sorted subpopulation (A) and Western blot analysis of the Unsorted vs. the Nodal High subpopulations for CD133 protein expression shows an increase in the amount of CD133 glycosylated CD133 (130 kilodalton) protein in the Nodal High selected subpopulation vs. the Unsorted subpopulation (B; corrected for the amount of protein loaded per lane using (3-Actin protein as a control).

Example 2

Figure 42:
FIG. 42 shows an amino acid sequence and secondary structure of the Nodal monomer. A Nodal antigen used to generate the monoclonal antibodies is in bold and boxed by a dashed line.

On the basis of previous docking and binding studies, the region of human Nodal (Uniprot Q96S42) including the H3-wrist helix and the pre-helix loop was chosen as hNodal antigen (FIG. 42). The hNodal(44-67) peptide, referred to the 1-110 residues numbering and corresponding to the mature form of the endogenous protein (238-347 a.a.), is involved in the binding to the co-receptor Cripto-1-1 and contains two glutamic acid residues, E49 and E50, that stabilize the interaction. To select anti-Nodal antibodies able to recognize these two hot-spot residues, a strategy of screening was used in which after immunization and hybridoma generation, cell supernatants were screened using in parallel a mutated peptide named hNodal(44-67) E49A-E50A, in which E49 and E50 were replaced with two alanines.

hNodal(44-67) and the mutated variants were synthesized with either a free amino group at the N-terminus (used for conjugation with KLH and immunogen preparation), or acetylated and amidated to better mimic the peptide within the protein structure A set of mutated variants of hNodal(44-67), see Table 1 below, was designed to define the epitope and to investigate the contribution of specific residues to the recognition with antibodies. Peptides from 1 to 6 (Table 1) included variants of hNodal(44-67) bearing doubly mutated residues at the N-terminus; shorter peptides (entries from 4 to 6, Table 1) were used to confirm the epitope on the N-terminal region. Peptides reported in entries 7-9 of Table 1, Nodal(1-38), Nodal(39-75), and Nodal(76-110), were prepared and used to confirm the specificity of antibodies for the Nodal internal fragment.

Peptides 10 and 11 in Table 1, reproducing the region 433-445 of human GDF5 (Uniprot, P43026), region 386-398 of human GDF 6 (Uniprot, Q6KF10) and region 382-394 of human GDF 7 (Uniprot, Q7Z4P5), belonging to Growth Differentiation Factors (GDF family), which are close structural homologs of Nodal, were tested to explore the selectivity of antibodies among TGF-β family ligands. Sequences were chosen on the basis of multiple alignment of hNodal(44-67) versus all TGF-β ligands performed by using the BLAST server.

TABLE 1

| SEQ ID NO. | peptide # | hNodal peptide | Sequence | MW Theor.* (amu) | MW Exp.** (amu) |
|---|---|---|---|---|---|
| 17 | 1 | (44-67) | PNPVGEEFHPTNHA YIQSLLKRYQ | 2878.44 | 2879.3 |
| 19 | 2 | (44-67) E49A-E50A | PNPVGAAFHPTNHA YIQSLLKRYQ | 2762.43 | 2763.5 |
| 20 | 3 | (44-67) P46A-V47A | PNAAGEEFHPTNHA YIQSLLKRYQ | 2824.39 | 2825.5 |
| 25 | 4 | (44-56) | PNPVGEEFHPTNH | 1617.68 | 1617.8 |
| 23 | 5 | (52-60) | HPTNHAYIQ | 1120.53 | 1121.2 |
| 26 | 6 | (56-67) | AYIQSLLKRYQ | 1422.78 | 1423.5 |
| 27 | 7 | (1-38) | HHLPDRSQLCRKVK FQVDENLIGWGSWI IYPKQYNAYR | 4716.43 | 4718.4 |
| 28 | 8 | (39-75) | CEGECPNPVGEEFH PTNHAYIQSLLKRY QPHRVPSTC | 4276.98 | 4278.7 |
| 29 | 9 | (76-100) | CAPVKTKPLSMLYV DNGRVLLDHHKDMI VEECGCL | 3966.95 | 3968.6 |
| 30 | 10 | hGDF5*** | CEFPLRSHLEPTNH | 1719.8 | 1719.8 |
| 31 | 11 | hGDF6/7 | CDFPLRSHLEPTNH | 1705.78 | 1705.7 |

Screening of hybridoma supernatants was carried out by ELISA coating the hNodal(44-67) BSA-conjugated peptide. Nine clones were positive. The pre-selected hybridoma supernatants were screened using in parallel hNodal(44-67) and its mutated variant hNodal(44-67)E49A-E50A. The assay was performed coating the unconjugated peptides at 330 nM and testing the hybridoma supernatants at a total protein concentration of 5.0 µg/mL (33 nM). Supernatants from six clones, indicated as 9B9, 3D1, 10B12, 5F10, 1B4, and 2D12, although to a different extent, recognized the immobilized antigen (FIG. 43). Clones 9F10, 1C8, and 8E3 showed a very weak signal and were therefore not further considered. 3D1 recognized the wild-type hNodal(44-67) peptide much better than the mutated variant, indicating that binding occurs close to the region encompassing the two glutamic residues crucial for the binding of Nodal to the co-receptor Cripto-1-1.

After selection, the ability of the purified monoclonal antibodies to bind the full-length recombinant human Nodal was evaluated. The screening was carried out by SPR direct binding. MAbs were initially tested at 100 nM; at this concentration only two antibodies, 3D1 and 5F10, were able to bind the full-length rhNodal protein (FIG. 44). To estimate affinity constants, dose-dependent binding experiments were carried out. Analyses were performed injecting increasing doses of antibodies determining for each run association and dissociation rate constants. 3D1 bound Nodal with a KD value of 1.42 nM, whereas 5F10 was characterized by a weaker affinity (83 nM; Table 2). The 3D1 displayed rapid association (average $k_a$=6.95×105 M$^{-1}$ s$^{-1}$) and slow dissociation rates constants (average $k_d$=6.55×10$^{-4}$ s$^{-1}$), resulting in a high binding affinity to the protein. 5F10 exhibited a lower affinity as result of a slower association (average $k_a$=1.91×104 M$^{-1}$ s$^{-1}$) and quicker dissociation rate (average $k_d$=1.08×10$^{-1}$ s$^{-1}$). Binding curves for the two mAbs are reported in FIG. 44b,c. Kinetics parameters are reported in Table 3a,b.

TABLE 2

Anti-Nodal mAbs screened and $K_D$ values determined for the binding to rhNodal functionalized sensor chip.

| mAbs | Binding to rhNodal |
| --- | --- |
| 3D1 | $K_D$ = 1.4 nM |
| 5F10 | $K_D$ = 84 nM |
| 1B4 | NB |
| 9B9 | NB |
| 10B12 | NB |
| 2D12 | NB |

NB: No Binding.

TABLE 2

Association and dissociation rate constants. (a) $K_D$ values determined for the binding of the 3D1 mAb to rhNodal functionalized sensor chip; (b) $K_D$ values determined for the binding of the 5F10 mAb to rhNodal-functionalized sensor chip; (c) $K_D$ values determined for the binding of the 3D1 F(ab')$_2$ to rhNodal functionalized sensor chip; (d) $K_D$ values determined for the binding of the 3D1 Fab' to rhNodal functionalized sensor chip.

(a)

| 3D1 mAb | $k_a$ (1/Ms) | $k_d$ (1/s) | $K_D$ (M) | SD* |
| --- | --- | --- | --- | --- |
| 6 nM | 1.28 × 10$^6$ | 6.29 × 10$^{-4}$ | 4.91 × 10$^{-10}$ | 0.0129 |
| 12 nM | 9.79 × 10$^5$ | 6.83 × 10$^{-4}$ | 6.98 × 10$^{-10}$ | 0.0504 |
| 25 nM | 6.42 × 10$^5$ | 6.22 × 10$^{-4}$ | 9.68 × 10$^{-10}$ | 0.1650 |
| 50 nM | 3.61 × 10$^5$ | 6.97 × 10$^{-4}$ | 1.93 × 10$^{-9}$ | 0.3310 |
| 100 nM | 2.12 × 10$^5$ | 6.44 × 10$^{-4}$ | 3.03 × 10$^{-9}$ | 1.0700 |
| Average | 6.95 × 10$^5$ | 6.55 × 10$^{-4}$ | 1.42 × 10$^{-9}$ | 0.3260 |

(b)

| 5F10 mAb | $k_a$ (1/Ms) | $k_d$ (1/s) | $K_D$ (M) | SD* |
| --- | --- | --- | --- | --- |
| 100 nM | 2.60 × 10$^4$ | 8.16 × 10$^{-4}$ | 3.14 × 10$^{-8}$ | 0.0246 |
| 250 nM | 1.81 × 10$^4$ | 1.08 × 10$^{-3}$ | 5.97 × 10$^{-8}$ | 0.0818 |
| 500 nM | 1.31 × 10$^4$ | 1.33 × 10$^{-3}$ | 1.02 × 10$^{-7}$ | 0.1480 |
| 750 nM | 9.40 × 10$^3$ | 1.30 × 10$^{-3}$ | 1.38 × 10$^{-7}$ | 0.0286 |
| Average | 1.91 × 10$^4$ | 1.08 × 10$^{-3}$ | 8.28 × 10$^{-8}$ | 0.0708 |

(c)

| F (ab')$_2$ | $k_a$ (1/Ms) | $k_d$ (1/s) | $K_D$ (M) | SD* |
| --- | --- | --- | --- | --- |
| 25 nM | 4.40 × 10$^5$ | 1.13 × 10$^{-3}$ | 2.57 × 10$^{-9}$ | 0.0214 |
| 50 nM | 2.77 × 10$^5$ | 1.35 × 10$^{-3}$ | 4.87 × 10$^{-9}$ | 0.0578 |
| 100 nM | 1.87 × 10$^5$ | 1.63 × 10$^{-3}$ | 8.71 × 10$^{-9}$ | 0.323 |
| 250 nM | 8.21 × 10$^4$ | 1.67 × 10$^{-3}$ | 2.03 × 10$^{-8}$ | 0.446 |
| 500 nM | 4.58 × 10$^4$ | 1.84 × 10$^{-3}$ | 4.02 × 10$^{-8}$ | 1.63 |
| Average | 2.06 × 10$^5$ | 1.52 × 10$^{-3}$ | 1.53 × 10$^{-8}$ | 0.496 |

(d)

| Fab' | $k_a$ (1/Ms) | $k_d$ (1/s) | $K_D$ (M) | SD* |
| --- | --- | --- | --- | --- |
| 25 nM | 3.42 × 10$^5$ | 2.02 × 10$^{-3}$ | 5.91 × 10$^{-9}$ | 0.0347 |
| 50 nM | 1.59 × 10$^5$ | 2.62 × 10$^{-3}$ | 1.65 × 10$^{-3}$ | 0.0245 |
| 75 nM | 1.50 × 10$^5$ | 1.92 × 10$^{-3}$ | 1.28 × 10$^{-3}$ | 0.0949 |
| 100 nM | 1.18 × 10$^5$ | 1.56 × 10$^{-3}$ | 1.32 × 10$^{-8}$ | 0.0909 |
| 200 nM | 7.59 × 10$^4$ | 2.31 × 10$^{-3}$ | 3.04 × 10$^{-6}$ | 0.145 |
| average | 1.69 × 10$^5$ | 2.09 × 10$^{-3}$ | 1.58 × 10$^{-6}$ | 0.0780 |

*SD: Standard Deviation.

In the attempt to produce smaller antibody fragments useful for crystallization studies or as additional reagents for Nodal detection, experiments were conducted to develop 3D1-derived Fab fragments by enzymatic digestion. 3D1 was deglycosylated with PNGase F to remove a single N-linked glycan at Asn$^{297}$ on each CH2 domain of the two heavy chains. After deglycosylation, the whole antibody was digested with pepsin. Digestion was completed after four hours of incubation. Pepsin converted 3D1 into F(ab')$_2$, with a MW of about 110 kDa, without formation of other fragments (FIG. 45). F(ab')$_2$ fragment was next isolated from the digestion mixture by a two-step purification procedure that included Protein G affinity and size-exclusion chromatography (FIG. 46a). SEC chromatographic profile showed absence of aggregates and the presence of a highly homogenous product; moreover, its elution volume was in agreement with the expected molecular weight (~110 kDa, FIG. 46c). Integrity and purity of the products were confirmed after each step by SDS-PAGE analysis under reducing and non-reducing conditions (FIG. 46b,d). Fab' fragment was obtained by selective reduction of the hinge-region disulfide bonds of F(ab')$_2$ using mercaptoethylamine Reduction was successfully achieved after three hours, as shown by SDS-PAGE analysis under non-reducing conditions (FIG. 47a). To carry out further analyses, the Fab' was alkylated with IAM, then it was purified by size-exclusion chromatography to confirm its identity and to evaluate the presence of potential aggregates. As indicated by the single peak eluted at 13.65 mL (FIG. 47b), no aggregates were detected. 3D1 Fab' was also characterized by LC-ESI-TOF MS after selective reduction of the disulfide bridge connecting the light and the heavy chain. LC-MS analysis performed on the separated chains (FIG. 48a-c) shows a single mass peak for the light chain and four prevailing peaks for the heavy chain accounting for incomplete IAM derivatization (mass difference of 57 Da) and a double splitting at level of the hinge region. The mass difference of 186 Da observed between the two main peaks and the highly conserved sequences of mouse IgG1 within the hinge region (FIG. 48d), indicates that pepsin operates two cleavages just before and after the S$^{116}$V$^{117}$ residues (UniProtKB, P01868), as indicated by the arrows.

SPR Comparative Binding Analyses of 3D1 F(ab')2/Fab' Fragments

The ability of the F(ab')$_2$ and Fab' fragments to bind to rhNodal protein was assessed by a comparative binding assay carried out by SPR. The 3D1 F(ab')$_2$ and Fab' fragments bound the immobilized rhNodal with similar association and dissociation rate constants, thus also the same affinity ($K_D$=15 nM, FIG. 49a,b). This $K_D$ value is 10-fold higher compared to that exhibited by the whole antibody ($K_D$=1.4 nM), thereby the affinity is 10-fold lower (Table 3c-d).

Epitope Mapping

To finely delineate the epitope recognize by the 3D1 antibody, a mapping of the original antigen was carried out by ELISA and SPR analyses. For this purpose, the peptide antigen and its mutated variants (Table 1) were tested by ELISA and SPR for binding to 3D1 and to functional fragments. ELISA assays carried out by coating the different peptides at the same concentration showed that the strongest signal was detected with the short (44-56) peptide (FIG. 50a), whereas weaker signals were obtained with variants bearing the mutated E49 and E5C). In addition, no binding was observed with variants in which P46 and V47 were mutated to alanines, as well as with other N-terminally truncated shorter peptides. These data demonstrate the high specificity of 3D1 for the N-terminal residues, specifically P46, V47, E49, and E5C).

SPR dose-response binding assays were performed with peptides (44-67) and (44-56) to extrapolate $K_D$ values (FIG. 51a,b; FIG. 52a,b; and Table 4). The data confirms that region (44-56) contains the epitope recognize by 3D1 mAb and that residues from 46 to 50 are improtant for binding. Notably, the region falls within the pre-helix loop, encompassing the two glutamic acid residues crucial for the binding of Nodal to Cripto-1-1. The data indicates that 3D1 does not recognize a conformational epitope but rather a linear epitope.

TABLE 4

Nomenclature and amino acid sequence of hNodal peptides screened in the epitope mapping study and KDvalues determined for the binding of the positive peptides to 3D1 mAb/Fab' functionalized sensor chip. No fitting means that fitting of binding association curve did not converge to any value.

| hNodal Peptide 0.5-20 µM | Sequence | $K_D$ vs. 3D1 mAb | $K_D$ vs. 3D1 Fab' |
|---|---|---|---|
| (44-67) | PNPVGEEFHPTNHAY IQSLLKRYQ (SEQ ID NO: 17) | 613 nM | 590 nM |
| (44-67) E49A-E50A | PNPVGAAFHPTNHAY IQSLLKRYQ (SEQ ID NO: 19) | NO BINDING | NO BINDING |
| (44-67) P46A-V47A | PNAAGEEFHPTNHAY IQSLLKRYQ (SEQ ID NO: 20) | NO BINDING | NO BINDING |
| (44-56) | PNPVGEEFHPTNH (SEQ ID NO: 25) | 413 nM | 371 nM |
| (52-60) | HPTNHAYIQ (SEQ ID NO: 23) | NO BINDING | NO BINDING |
| (56-67) | AYIQSLLKRYQ (SEQ ID NO: 26) | NO BINDING | NO BINDING |

Specificity Assay

ELISA assays were performed to further assess the specificity of the 3D1 mAb for the region of Nodal(44-56) involved in the binding with the co-receptor Cripto-1-1. New Nodal peptides were therefore screened for binding to 3D1. These peptides were: hNodal(1-38) (SEQ ID NO:27), mimicking the protein N-terminal portion; hNodal(39-75) (SEQ ID NO:28), mimicking the central region; and hNodal (76-110) (SEQ ID NO: 29) mimicking the C-terminal portion of the mature form of human Nodal. Other peptides mimicking the region of the TGF-r3 ligand GDF and matching the 44-67 region of Nodal (GDF5 and GDF6/7, see Table 1) were also used for this purpose. Only Nodal(39-75) of Nodal, containing the region 44-67 used to generate the antibody, bound with similar efficiency, whereas the other peptides were essentially unreactive (FIG. 50b).

To further confirm the specificity of 3D1 binding to its antigen and to the full length protein, hNodal(44-56) (SEQ ID NO:25) was used to block the staining of endogenous Nodal expressed in human embryonic stem cells. The experiment was performed by probing the blots with either 3D1 alone and after pre-incubation with the peptide. Both forms of endogenous Nodal were no longer detectable when the mAb was pre-incubated with the peptide (FIG. 53), indicating that 3D1 recognizes the same epitope also on the native protein.

Detection of Endogenous Nodal Protein

Figure 54A:
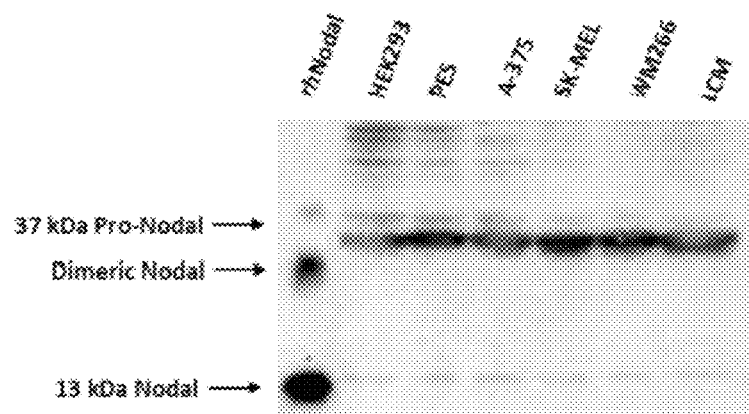
Figure 54B:
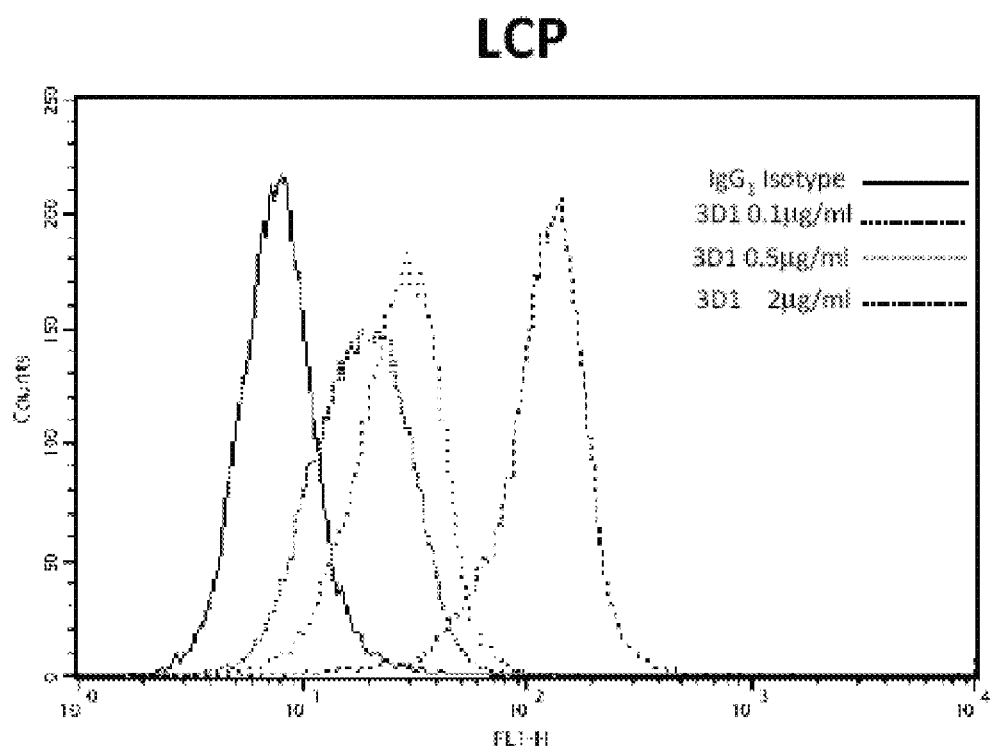
Figure 54C:
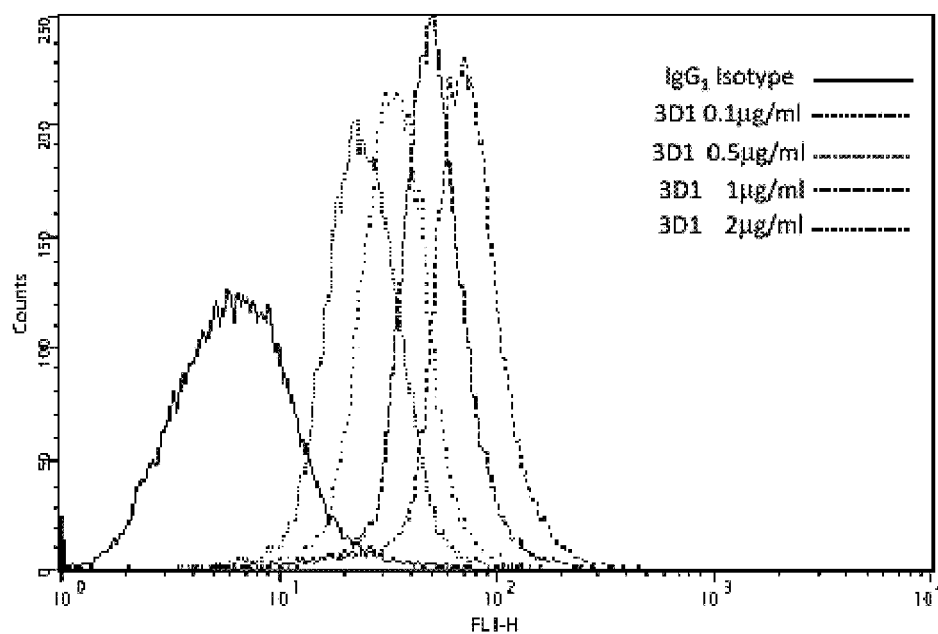
Figure 54D:
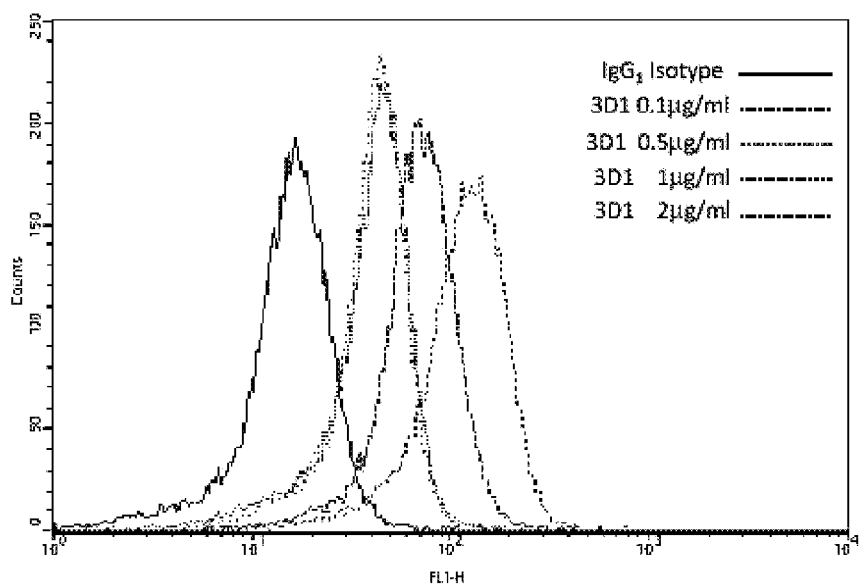

Western blotting analyses were conducted to explore the ability of the mAb to recognize the endogenous forms of Nodal protein in human melanoma cells. 3D1 was able to stain the immature form pro-Nodal (approximately 37 kDa) in a panel of human melanoma cell lines and in non-melanoma HEK-293 cells, used as positive control (FIG. 54a). The smaller mature form of Nodal, approximately 13 kDa, was only barely detected, indicating it is likely highly unstable or that this form is mostly secreted. The capability of 3D1 to recognize endogenous Nodal in melanoma cell lines was also confirmed by cytometric analyses. FACS analyses (FIG. 54b-d) showed that 3D1 bound native Nodal protein also in intact cells at very low concentrations (0.1 µg/mL) and in a dose-dependent manner, as demonstrated by the increase of signal intensity with increasing antibody concentration. Both mature and pro-Nodal are detected by 3D1 in western blot analyses (FIG. 54a).

Example 3

Described below are materials and methods used in conducting the experiments described in Example 2 above.

Peptide Synthesis, Purification, and Identification

The wild-type hNodal(44-67) peptide, its mutated variants, and human GDF peptides 5, and 6/7, were prepared by step-wise solid phase synthesis as C-terminally amidated variants following standard Fmoc chemistry using an automatic SYRO system. A Rink-amide MBHA resin with a substitution grade of 0.57 mmol/g and amino acid derivatives with standard protections were used in all syntheses. Polypeptides were assembled under canonical conditions of peptide synthesis, using for each coupling reaction HATU/DIEA pre-activation and a five-fold excess of Fmoc-protected amino acids. Coupling and deprotection times were kept at 30 and 20 minutes, respectively. Standard side-chain protection groups for Fmoc chemistry were used for all residues. N-terminal acetylation was performed on the resin using acetic anhydride at 0.5 M in DMF with 5% DIEA, 20 min at room temperature. The cleavage of peptides from the solid support was performed by treatment with a trifluoroacetic acid (TFA)/tri-isopropylsilane (TIS)/water (90/5/5, v/v/v) mixture for 90 min at room temperature. Crude peptides were precipitated in cold di-ethyl-ether, dissolved in a water/acetonitrile (1/1, v/v) mixture and lyophilized After lyophilisation, peptides were dissolved in a solution of $H_2O/CH_3CN$ 95/5 v/v, containing 0.1% TFA. They were then purified by reverse-phase HPLC (RP-HPLC) on a WATERS Prep 150 LC preparative system using a semi-preparative 10×1 cm ID C18 monolythic Onyx column, applying a linear gradient of 0.05% TFA in $CH_3CN$ from 5% to 70% over 10 min at a flow rate of 15 mL/min, and monitoring the absorbance at 214 nm. The collected fractions were lyophilized Peptide purity and identity were confirmed by liquid chromatography-mass spectrometry analysis (LC-MS); analyses were carried out on a LCQ DECA XP ion Trap mass spectrometer equipped with an OPTON ESI source and with a complete Surveyor HPLC system. Typical gradients applied to elute the peptides were as follows: flow rate 0.2 mL/min; gradients from 5% solvent B (ACN, 0.05% TFA) to 60% solvent B in 10 mM Solvent A was $H_2O$, 0.08% TFA. Biobasic C18 50×2 mm ID columns were used to separate peptides during LC-MS analyses.

Immunogen Preparation

Non-acetylated hNodal(44-67) peptide was conjugated with 3.0 mg carrier proteins (KLH and BSA) in 2.0 mL of 20 mM phosphate buffer pH 7.0 containing 0.2% v/v glutaraldehyde (stock solution 25%), by stirring the mixture for 3 h at room temperature. The reaction was blocked by adding 1.0 mL of 1.0 M glycine in water, then solutions were extensively dialyzed against PBS buffer pH 7.4 before being lyophilized. The amount of peptide-protein conjugate was determined using the Bradford assay.

Antibody Generation

BALB/c mice were housed and handled according to the institutional guidelines. Five-week old female BALBalb/c mice (Jackson Lab) were immunized by sub cutaneous injection with 300 µL of suspension containing 100 µg of KLH-conjugated hNodal(44-67) peptide mixture emulsified with Complete Freund's Adjuvant. Before immunization, 250 µL blood samples were taken from each mouse from the caudal vein and used as the pre-immune control ($T_0$ samples). Mice were boosted with the same amount of immunogen in incomplete Freund's adjuvant at day 18 and at day 30; blood samples were taken from the caudal vein (250 µL) before every subsequent immunization and tested by ELISA to monitor antibody titer. A final antigen boost was administered sub-cut is in to the mice showing the highest antibody titer seven days before being sacrificed and splenectomised as described below. Cells harvested from spleens of sacrificed animals were fused with myeloma SP2/0 (ATCC) cells at a ratio of 5:1 in RPMI-GM containing polyethylene glycol (PEG) 1300-1600 and 7.5% DMSO.

The fused hybridoma cells were re-suspended in 30 mL of selection medium containing of RPMI-GM medium containing 10% FBS, 100 U/mL penicillin, 100 µg/mL streptomycin, 100 µM hypoxanthine, 16 µM thymidine and 400 nM aminopterin (RPMI-HAT Sigma-Aldrich, Milano, Italy). The cell suspension (200 µL) was dispensed into 96-well plates and incubated at 37° C. in a 5% CO2 atmosphere. Between day 12 and 14, supernatants were screened by ELISA for binding to hNodal(44-67) peptide and its mutated variant hNodal(44-67)E49A-E50A, in which the glutamic acids 49 and 50 were substituted with two alanine residues.

The hybridoma clone named 3D1, with strong reactivity with hNodal(44-67) peptide (but not with the mutated variant) was re-cloned twice by limited dilution and its reactivity was re-confirmed by ELISA. Sub-cloned hybridoma cells were cultured in RPMI-HAT containing 10% FBS and slowly adopted to serum-free medium. The OPTI-MEM medium containing 10% FBS. Adapted cells were cultured in Optimem medium and then transferred to the Bioreactor (Bio Cell Line, Becton Dickinson) for large scale production.

Isotype of the anti-Nodal antibodies produced by the selected clones was determined by using the commercial kit specific for murine antibodies, in accordance to the manufacturer's instructions (Pierce Rapid Mouse antibody Isotyping kit, Thermo Scientific).

ELISA: Antibody Titration in Mouse Sera

To determine the antibody titer in mouse sera, 96-well ELISA plates were coated with 50 µL of the BSA-conjugated hNodal(44-67), 1 µg/mL in PBS, overnight at 4° C. The plate was then washed three times with PBS containing 0.05% Tween 20 (PBS-T). Non-specific sites of the plate were blocked with 5% BSA and incubated at R.T. for 120 min Wells were then washed three times with PBS-T and serum was (50 µL) added to the wells in three-fold serial dilutions starting from 1:100 to 1:100,000. The plate was incubated at 37° C. for 1 h and washed again with PBS-T. Then, 50 µL of a 1:1000 dilution of HRP-conjugated rabbit anti-mouse Ig (1.0 mg/mL) were added to the wells and incubation was carried out for 1 h at 37° C. After washing, 100 µL of 2,2-Azino-bis(3-ethylbenzothiazoline-6-sulfonic acid) (ABTS) substrate solution was added to each well. After 15 min, the reaction was stopped by adding 50 µL of 1% SDS solution in water to each well. The Optical Density (OD) was measured at 415 nm by a microplate reader. Antibody titers were evaluated sufficiently high when the average absorbance values from triplicate wells incubated with immune sera dilutions at 1:10,000 were at least thrice those determined on wells incubated with the pre-immune serum.

ELISA: Screening of Hybridoma Supernatants

For hybridoma supernatants screening, hNodal(44-67) and hNodal(44-67)E49A-E50A were coated at 330 nM diluted in PBS on polystyrene conical flat bottom 96-well plates at 4° C. overnight (100 µL/well). After incubation, the coated wells were washed three times with PBS containing 0.005% Tween-20 (PBS-T) and non-specific binding sites were blocked by incubating with 1% BSA in PBS (300 µL/well) for 1 h at 37° C. After washing three times with PBS-T, supernatants of hybridomas diluted in PBS at 33 nM were incubated for 1 h at 37° C. (100 µL/well). After incubation, plates were triple washed with PBS-T and goat anti-mouse HRP-conjugated antibody (1 mg/mL, Blotting Grade Affinity Purified Goat Anti-Mouse IgG (H+L)) diluted 1:1000 in PBS was added as secondary antibody (100 µL/well) and incubated for 1 h at 37° C. After incubation and three washes with PBS-T, bound antibodies were detected by adding 100 µL/well of freshly prepared O-phenylenediamine (0.4 mg/mL) containing $H_2O_2$ (0.4 mg/mL) in 0.1 M citrate buffer (pH 5.2) (SIGMAFAST™ OPD tablet Sigma-Aldrich). The peroxidase reaction was stopped after 5 mM with 50 µL/well of 2.5 M $H_2SO_4$ and the optical density was measured at 490 nm, using a microplate reader. The dose-dependent binding of 3D1 to immobilized hNodal(44-67) and hNodal(44-67)E49A-E50A was performed by coating the peptides at 60 nM and using 3D1 at concentrations between 0.1 and 66 nM.

ELISA: Epitope Mapping and Specificity Assay

Peptides used for the epitope mapping and for the specificity assay of the 3D1 mAb were coated at 1.0 µg/mL diluted in PBS; 3D1 mAb, dissolved in PBS, was used as primary antibody at 1.0 µg/mL.

Purification of Monoclonal Antibodies and F(ab')2/Fab' Fragments

Antibodies and F(ab')2/Fab' fragments were purified by standard procedures. After centrifugation at 4000 rpm for 20 mM at 4° C., hybridoma cell-culture supernatants, containing monoclonal IgGs, were filtered on a 0.22 µm filter and loaded onto a HiTrap™ Protein G HP column (GE Healthcare). Purifications were performed on an AKTA FPLC™ instrument (GE Healthcare) at a flow rate of 0.6 mL/min, monitoring the absorbance at 280 nm. After washing away the unbound material using PBS (pH 7.4) as loading buffer, bound antibodies were recovered by changing drastically the pH conditions using 100 mM Glycine pH 2.7 as elution buffer. Eluted antibodies were quickly neutralized by adding 1/10 volume 2 M TRIS pH 9.0. To ensure the stability of purified mAbs and of related fragments they were buffer-exchanged into PBS (pH 7.4) and concentrated using an appropriate centrifugal filter (Millipore, city Darmstadt, state, USAGermany). The concentration was estimated by using the Bradford assay. Purity of concentrated proteins was evaluated by SDS-PAGE and Coomassie blue staining.

Size-exclusion chromatography purifications were performed on a Superdex™ 200 HR 10/300 (GE Healthcare, Piscataway, N.J., USA) gel filtration column, using PBS pH 7.4 as running buffer, at a constant flow rate of 0.5 mL/min, with an elution volume of 25 mL and monitoring the absorbance at 280 nm.

SPR Analyses

SPR analyses were performed on a Biacore 3000 instrument from GE Healthcare, using CH5 sensor chips and certified HBS buffer (20 mM HEPES, 0.15 M NaCl, pH 7.4, P20, 0.005%). Protein immobilization was carried out following the canonical amine coupling chemistry using the surface immobilization wizard procedure, operating at 5 µL/min Channels were activated with EDC/NHS for 7 mM; for the binding assays of purified mAbs to Nodal protein, rhNodal, opportunely diluted in the pre-selected sodium acetate buffer pH 4.5, was coupled until a 4000 RU level was achieved. Residual reactive groups on the sensor chip surface were deactivated by addition of 1.0 M ethanolamine hydrochloride, pH 8.5. Antibody binding was tested at 20 µL/min injecting solutions of 3D1 (60 µL) in HBS-EP at increasing concentrations (6-100 nM). A 10 mM NaOH solution was used to regenerate the chip surface.

After the single-dose screening, dose-dependent binding analyses were carried out with the two antibodies, 3D1 and 5F10, able to bind the full-length protein. Binding of 3D1 was carried out at concentrations ranging between 6 and 100 nM. For 5F10 higher concentrations were required (100, 250, 500 and 750 nM). Dissociations were monitored for at least 500 s. To carry out the mapping of the 3D1 epitope, the whole antibody was immobilized at 5 µg/mL in 10 mM NaAc buffer pH 5 at a flow rate of 5 µL/min by standard amine coupling chemistry on a CH5 sensor chip. The immobilization level reached with the mAb was about 5350 RU. On another channel of the same sensor chip, the 3D1 Fab' was immobilized at 10 µg/mL in 10 mM NaAc buffer pH 4.5 at a flow rate of 5 µL/min, following the standard amine coupling chemistry. The amount of immobilized Fab' was about 2570 RU. Residual reactive groups were deactivated by 1M ethanolamine hydrochloride, pH 8.5. The blank channel was prepared as already described. Real-time binding analyses were performed at a flow rate of 20 µL/min, using HBS-EP buffer, injecting a constant sample volume of 60 µL. Peptides opportunely diluted in HBS-EP buffer were injected at the following concentrations: 0.5, 1, 2.5, 5, 10, and 20 µM. Dissociations were monitored for at least 500 s; the regeneration solution was 5 mM NaOH.

For each analysis, experimental sensorgrams were aligned, subtracted of blank signals and overlapped. All mathematical manipulations and fitting were performed using the BiaEvaluation software, vers. 4.1 from GE Healthcare. All experimental data gave optimal fittings when processed assuming a 1:1 Langmuir binding interaction.

Antibody Deglycosylation and Pepsinolysis

To improve the splitting of the antibody by pepsin to get functional fragments, 3D1 was first subjected to a deglycosylation reaction with the Peptide-N-glycosidase F (PNGase F), supplied by New England Biolabs (Beverly, city, Mass., USA). Following a first preliminary small-scale attempt, the large-scale deglycosylation reaction was performed incubating 1.5 mg of the mAb, diluted in PBS (pH 7.4), with 11 units of PNGase F at 37° C. The time for optimal deglycosylation was identified as being 48 h. Pepsinolysis reaction, monitored by SDS-PAGE, was optimized in 20 mM sodium acetate buffer, pH 4.0, using a final w/w ratio of pepsin to antibody 1:25 and incubating the mixture in a 37° C. water bath for 4 h.

Preparation of Fab' Fragments

Fab' fragments were produced by reducing selectively the hinge-region disulfide bonds of F(ab')2 using 5 mM 2-Mercaptoethylamine 20 mM sodium acetate buffer pH 4.0 was added to the F(ab')2 fragments in PBS pH 7.4 to adjust the pH at 6.0 and 2 mM EDTA was also added. The mixture was incubated for 3 h at 37° C. After incubation, PBS was added to the mixture to adjust the pH to neutrality. Reduction of F(ab')2 to Fab' fragments was checked and confirmed by 12% SDS-PAGE gel under non-reducing conditions. After reduction, Fab' fragments were incubated with 25 mM IAM (Iodoacetamide) for 30 mM at room temperature in the dark to block reactive thiols.

LC-ESI-TOFMS Analysis of 3D1 Fab'

The sample analyzed by mass spectrometry was reduced using 20 mM DTT for 1 h at 37° C. Mass spectrometry analyses were performed on an Agilent 1290 Infinity LC System coupled to an Agilent 6230 time-of-flight (TOF) LC/MS System. The liquid chromatography Agilent 1290 LC module was coupled with a photodiode array (PDA) detector and a 6230 time-of-flight MS detector, along with a binary solvent pump degasser, column heater, and autosampler. Based on manufacturer recommendations, the pump was connected to a gradient binary solvent system: solvent A, 0.01% TFA in $H_2O$ (v/v) and solvent B, 0.01% TFA in CH3CN (v/v). Chromatographic analyses were performed using a Phenomenex AERIS WIDEPORE reverse phase C4 3.6 mm (50×2.1 mm) applying a linear gradient from 25% to 65% solvent B in 15 min. The column flow rate was kept at 0.2 mL/min with the heater at a constant 20° C. UV spectra were monitored in the range 200-400 nm. Injection volume was 1 µL followed by needle wash. The mass analyzer Agilent 6230 TOF MS was set to operate in positive ion scan mode with mass scanning from 100 to 3200 m/z. The ion source was upgraded from the original Agilent Jet Stream (AJS) source to the dual-sprayer version for improved reference mass delivery. Nitrogen was used as the drying and nebulizer gas. The instrument acquired data using the following parameters: drying gas temperature, 325° C.; drying gas flow, 10 L/min; nebulizer, 20 psi; sheath gas temperature, 400° C.; sheath gas flow, 11 L/min; VCap. 3.500 V; nozzle, 0 V; fragmentor, 200 V; skimmer, 65 V and octapole RF Vpp was 750. The instrument state was set to extended dynamic range mode (2 GHz). Tuning and calibration were performed before sample runs. Data collection and integration were performed using MassHunter workstation software (version B.05.00). Data were stored in both centroid and profile formats during acquisition. A constant flow of Agilent TOF reference solution through the reference nebulizer allowed the system to continuously correct for any mass drift by using two independent reference lock-mass ions, purine (m/z 119.03632) and HP-922 (m/z 922.000725), to ensure mass accuracy and reproducibility. Target compounds were detected and reported from accurate-mass scan data using Agilent MassHunter Qualitative software.

Competition Between 3D1 Antigen Peptide and Endogenous Nodal Protein

Thirty micrograms of H9 and H14 human embryonic stem cell total protein lysates, obtained as previously described, were separated on a 15% SDS-PAGE gel under reducing conditions and the resolved proteins were transferred onto a PVDF membrane. 50 ng of rhNodal protein were used as positive control. A Western blotting procedure was conducted: membranes were blocked, then probed with the 3D1 alone at 4.0 µg/mL in 2.5% NFDM in TBS-T and with the 3D1 mAb at 4.0 µg/mL pre-incubated with its antigen, the hNodal(44-56) peptide at 10 µg/mL. Detection was achieved with GAM-HRP (Bio-Rad) 1:1000 (1.0 µg/mL). Blots were developed with Enhanced Chemiluminescence Western Blot Substrate (Pierce, Rockford, Ill., USA) following the manufacturer's instructions and were acquired by using a Chemidoc XRS video densitometer (Bio-Rad, Hercules, Calif., USA).

Detection of Endogenous Human Nodal in Melanoma Cells

Western blot analyses for the detection of endogenous Nodal protein were performed using the following human skin malignant melanoma cell lines: PES, A-375, SK-MEL, WM 266 and LCM. HEK-293 (human embryonic kidney) cells and 100 ng of rhNodal protein were used as positive controls. Cells were lysed performing three freeze/thaw cycles in 50 mM Tris-HCl pH 7.5, 500 mM NaCl, 1% NP-40, 10 mM EDTA, 1 mM $MgCl_2$, 1 mM $CaCl_2$, 10% Glycerol, with an added cocktail of protease inhibitors and PMSF (phenyl-methanesulfonylfluoride). Cell lysates were cleared by centrifugation at 12,000 rpm for 20 min at 4° C. and the supernatants were quantified by Bradford assay. 50 µg of cell lysate from each sample were applied to a 15% SDS-PAGE gel under reducing conditions and electrophoresed for 3 h at 80 V. Separated proteins were transferred onto a polyvinylidene difluoride (PVDF) membrane (Millipore), previously soaked in methanol 100% for 5 min. The blot was blocked with 5% milk (NFDM) in Tris-buffered saline containing 0.1% Tween-20 (TBS-T) for 1 h at room temperature under shaking; next, the membrane was probed overnight at 4° C. with 3D1 mAb as primary antibody at 2 µg/mL in 2.5% NFDM in TBS-T under shaking. The membrane was then triple-washed with TBS-T and incubated with GAM-HRP as secondary antibody diluted 1:1000 in TBS-T for 1 h at room temperature under agitation. The target protein was detected using the enhanced chemiluminescent substrate method with the SuperSignal West Pico kit provided by Pierce Chemical Co. following the manufacturer's instructions. Signals were acquired with the ChemiDoc XRS video densitometer using the Quantity One software.

FACS Analyses

LCP, A375 and WM266 melanoma cells were collected by centrifugation. After aspiration of supernatant, the cells were resuspended in 500 µL of PBS and formaldehyde was added to obtain a final concentration of 4%. Cells were fixed for 10 mM at room temperature. After fixation, cells were permeabilized by adding 500 µL of PBS-Tween 20. $1 \times 10^6$ cells were aliquoted into each vial; 1 mL of PBS (incubation buffer) was added to each vial and cells were washed by centrifugation at 4000 rpm for 5 mM at 4° C. Cells were resuspended in 100 µL of solution of 3D1 anti-Nodal antibody (primary antibody), diluted in PBS at the following concentrations: 0.1, 0.5, 1.0 and 2.0 µg/mL. A standard IgG1 isotype was used as negative control. Cells were incubated with the primary antibody for 1 h at 4° C. under shaking. After incubation, cells were washed by centrifugation in 1 mL of PBS, resuspended and incubated with a FITC-conjugated anti-mouse antibody (secondary antibody), diluted 1:1000 (1.0 µg/mL) in PBS, for 40 min at 4° C. in the dark under stirring. Cells were washed by centrifugation with 1 mL of incubation buffer, re-suspended in 500 µL of PBS and analyzed on flow cytometer. Fluorescence was evaluated using the BD FACScalibur System.

Example 4

Expression of Nodal in Various Human Tissues

Experiments were conducted during development of embodiments herein to test a series of normal human tissue extracts for Nodal expression by WB analysis. Compared to Nodal detected in lysates from the H9 human embryonic stem cell line (H9) used as control, which is known to show robust expression of Nodal, no appreciable Nodal protein expression was observed in the major organs of brain, kidney, liver, pancreas or heart (FIG. 55). A band with a similar molecular weight as that detected in H9 and C8161 cell lysates but with appreciably lower intensity was observed, however, in lysates from one of two skeletal muscle samples tested.

Generation and Characterization of Anti-Nodal mAbs

Production and selection of anti-Nodal mAbs. 3D1 binds antigen hNodal144-671, whereas it recognizes less robustly the mutated peptide variant hNodal144-671E49A-E50A (FIG. 56a), indicating that it preferentially interacts with the two glutamic residues involved in the binding with Cripto-1-1 and potentially has a neutralization activity for the Nodal/Cripto-1-1 receptor complex interaction.

Binding of anti-Nodal mAb to rhNodal. The ability of 3D1 to bind rhNodal was assessed by SPR by immobilizing the protein on Biacore sensor chips and injecting the purified antibody at increasing concentrations (FIG. 57b). Association and dissociation rate constants together with thermodynamic dissociation constants ($K_D$) were determined for each run and averaged. A $K_D$ value of 1.42 nM was estimated in this way for the interaction between the 3D1 mAb and the protein.

Competition assays. Competition assays were performed using Biacore sensor chips derivatized with rhCripto-1-1. The binding between immobilized rhCripto-1-1 and rhNodal was assessed by injecting solutions of the Nodal protein at increasing concentrations. rhNodal was incubated at 5 nM with 3D1 mAb at concentrations matching 1:0.5, 1:1 and 1:2 molar ratios (protein:mAb). The 3D1 mAb at 5 nM (1:2 molar ratio) inhibited the binding of Nodal to Cripto-1-1 by approximately 70% (FIG. 56c), demonstrating the capacity of 3D1 to block the interaction between Nodal and Cripto-1-1 co-receptor.

Function-Blocking Effects of 3D1 mAb In Vitro

To determine whether the 3D1 mAb had the potential to affect C8161 melanoma tumor colony forming ability, untreated cells, or cells treated with either IgG control or 3D1 mAb for 72 hours were cultured in soft agar for three weeks (measuring anchorage independent growth). Cells treated with 3D1 mAb demonstrated a reduced ability to form non-adherent spheroidal clusters (signifying a decrease in anchorage independent growth) compared to untreated cells and cells treated with IgG control (FIG. 57a). Nodal has been shown to underlie tumor cell plasticity associated with a cancer stem cell phenotype. In particular, Nodal induces phenotypic switching whereby melanoma cells are capable of assuming an endothelial-like phenotype via formation of capillary-like structures in a process known as vasculogenic mimicry (VM), which can be recapitulated in a three-dimensional (3D) culture system for in vitro studies. When C8161 cells were treated with 4 mg/ml of either 3D1 mAb or IgG control, and then grown in 3D cultures for 24 hours to measure their ability to engage in VM, the 3D1 mAb treated tumor cells were unable to form complete networks characteristic of VM, as measured by the reduced number of junctions and tubules using the AngioSys software package, compared to control (FIG. 57b).

3D1 mAb Effects on Nodal Signaling and Cell Cycle Regulators

Melanoma cells: Treatment of C8161 cells with 4 µg/ml of 3D1 mAb caused a reduction in phosphorylation of the Nodal related signaling molecules, Smad2 and ERK1/2, that was evident after 4 hrs and maintained through 72 hrs duration of the experiment (FIG. 58a). Also, after 72 hrs of 3D1 mAb treatment, there was an associated reduction in Nodal expression (FIG. 58b). Cyclin B 1, a regulatory protein involved in mitosis and highly expressed in actively proliferating cells, was also reduced in C8161 cells treated with 3D1 mAb for 72 hrs (FIG. 58b). Concomitantly, increases in p27, a cell cycle inhibitor protein that causes cell cycle arrest in G1 phase and the mitosis specific proliferation marker phospho-Histone H3 (P-H3) were observed in the same 3D1 treated C8161 cells versus control (FIG. 58b).

Breast cancer cells: Analysis was extended to include the treatment of MDA-MB-231 human breast cancer cells with 3D1 mAb for the same time period. These results show a noteworthy reduction in Nodal expression as well as P-H3 by WB (FIG. 60).

These results indicate that 3D1 mAb treatment diminishes Nodal expression, as well as downstream phosphorylation of Smad2 and ERK1/2, and reduces Cyclin B1 while increasing p27 in melanoma cells and that similar effects can be observed in breast cancer cells.

Effect of 3D1 mAb In Vivo

Several different xenograft models were established in Nude mice. First, an orthotopic model of cutaneous melanoma was established by injecting C8161 cells subcutaneously. Once appreciable tumors were detected in the mice, treatment was initiated with 3D1 mAb or control IgG via direct intratumoral injection. From days 8 to 14 of the experiment tumor volumes were significantly smaller in the 3D1 mAb treated mice compared to the IgG treated controls (FIG. 60a). Sections of representative tumors formed by C8161 cells in these mice were analyzed to determine the effects of 3D1 mAb on Nodal signaling. IHC staining for P-Smad2 in these sections showed a significant reduction in the mean percentage (±SEM) of cells with strong positive nuclear P-Smad2 staining in the 3D1 mAb treated animals compared to the IgG treated control [IgG=83%±8.2% (N=4) versus 51.3%±3.3% (N=4); P<0.05] (FIG. 61b). Since metastatic melanoma represents the most aggressive and clinically challenging form of the disease, a relevant metastatic model was established in Nude mice via systemic injection of C8161 cells. In this model, it has been shown that C8161 cells readily colonize the lung within 7-10 days post-injection and that these cells are targetable using a commercially available polyclonal antibody against Nodal. In experiments conducted during development of embodiments herein it has been demonstrated that when Nude mice treated with IgG control are compared to those treated with 3D1 mAb, a significant reduction in the mean percentage (±SEM) of lung tissue occupied by the C8161 colonies (lung tumor burden) was observed (FIG. 61c) [3D1 mAb=25.8%±4.6% (N=8) versus IgG control=59.3%±11.4% (N=8); P<0.05] (FIG. 60d). Sections representative of C8161 lung colonies from 3D1 mAb and IgG treated mice were processed for IHC staining to determine the effects on Nodal related signaling. As with the subcutaneous tumors, the sections of lung from 3D1 mAb treated Nude mice showed significantly lower mean percentage (±SEM) of cells with nuclear localization of P-Smad2 compared to lung colonies in sections of the IgG control treated mice l3D1 mAb=39±8.9 (N=6) versus IgG control=59.4±9.9 (N=6); P<0.011 (FIG. 60e). Additional staining in these lung colony sections showed a significant decrease in the 3D1 mAb treated Nude mice of the percentage (+/−SEM) of cells staining for Cyclin B1 l3D1 mAb=25.9%±9.4% (N=6) versus IgG control=38.8%±10.5% (N=6); P<0.0011, along with a significant increase in 3D1 treated Nude mice of the mean percentage (±SEM) of cells staining for p27 [3D1 mAb=39.5%±17% (N=6) versus IgG control=21%±15.3% (N=6); P<0.001] (FIG. 61).

Experiments conducted during development of embodiments herein demonstrate that when the human melanoma cell line A375SM (containing the active BRAF mutation) is treated with the BRAFi dabrafenib, P-ERK1/2 is significantly reduced, as expected, but Nodal expression is relatively unaffected (FIG. 62a). However, Nodal expression is significantly reduced in A375SM cells when treated with 3D1 mAb (FIG. 62b). Furthermore, tumor volumes of A375SM orthotopic xenografts formed in Nude mice are significantly reduced in 3D1 mAb treated mice compared to BRAFi treated or IgG control treated mice (FIG. 63a). IHC staining of P-Smad2 in representative tissue sections from these treated animals (FIG. 63b) show a significant reduction of the mean percentage (±SEM) of nuclear P-Smad2 in 3D1 treated mice compared to mice treated with either the BRAFi or IgG control [3D1=28.1%±2.6% (N=4); BRAFi=68.7%±6.3% (N=4); IgG=50.2%±7.3 (N=4); P<0.05]. These data demonstrate the Nodal function-blocking activity and tumor diminishing effect(s) of 3D1 mAb treatment in vivo.

ELISA Detection of Soluble Nodal

Nodal ELISA was developed to determine whether Nodal can be detected in serum samples from breast cancer patients. A calibration curve using a sandwich ELISA for detecting soluble recombinant Nodal is depicted in FIG. 64a. Initially, conditioned medium from Nodal secreting H9 cells was employed to test the validity of the assay in evaluating secreted Nodal by ELISA. These findings supported a viable approach that led to the testing of biological fluids (e.g., serum) to identify secreted Nodal as a potential biomarker. Using this ELISA, Nodal was detected in 15/23 (65%) serum samples. When the serum samples were categorized based on the aggressiveness of the disease (FIG. 64b), a trend for higher Nodal levels was noted in the invasive compared to noninvasive breast cancer patient sera [median for invasive breast cancer=6807 (range: 0-23467; N=12) versus median for noninvasive breast cancer=3509 (range: 0-11541; N=11)]. Thus, these results show that Nodal can be detected in sera from cancer patients with our novel 3D1 mAb based ELISA.

Experiments were conducted during development of embodiments of the present invention to produce and demonstrate the function of 3D1, a mAb capable of targeting and functionally blocking human Nodal. The data demonstrate that 3D1 mAb is capable of robust binding of Nodal and that it binds in proximity to the Cripto-1-1 co-receptor interacting region encompassing Glu49 and Glu50. The 3D1 antibody also efficiently blocks the in vitro binding of Nodal to Cripto-1-1, thus indicating it can prevent the Cripto-1-1 co-receptor complex-dependent Nodal downstream signaling. Melanoma cells treated in vitro showed significant reduction of Nodal protein expression levels and reduction of the activated (phosphorylated) forms of SMAD2 and ERK1/2. This treatment was also accompanied by reductions in anchorage independent growth and vasculogenic mimicry, and decreased levels of the cell proliferation-associated molecules Cyclin B1 and P-H3, complemented by an increase of the cell cycle inhibitor p27. Nude mice xenograft models, both subcutaneous orthotopic and lung colonization models, treated with 3D1 mAb showed antitumor effects in terms of reduced tumor volume and lung tumor burden, respectively. Analysis of IHC staining for P-Smad2, p27 and Cyclin B1 in tumor sections confirmed the in vitro results. The effect of 3D1 treatment of breast cancer cells showing the down-regulation of Nodal expression and the accompanying decrease in P-H3.

Example 5

Described below are materials and methods used in conducting the experiments described in Example 4 above.
Reagents TRIzol and restriction endonuclease enzymes were purchased from Invitrogen (Carlsbad, Calif., USA). The protein G column was purchased from GE Healthcare. SPR analyses were performed on a Biacore 3000 instrument from GE Healthcare, using CM5 sensor chips and certified HBS buffer (20 mM HEPES, 0.15 M NaCl, pH 7.2, P20, 0.005%). Recombinant human Nodal (rhNodal) and human Cripto-1-1 (rhCripto-1-1) were from R&D Systems (Minneapolis, Minn., USA). The following antibodies were used for WB: rabbit anti-Nodal (H-110; Santa Cruz Biotechnology, Dallas Tex.); rabbit anti-P-Smad2 (44-244G; Life Technologies, Grand Island, N.Y.); rabbit anti-Smad2/3 (07-408; Millipore, Lake Placid, N.Y.); rabbit anti-P-p44/42 MAPK (P-ERK1/2) (9101S; Cell Signaling, Beverley, Mass.); rabbit anti-p44/24 MAPK (ERK1/2) (44-654-G; Life Technologies); mouse anti-actin (MAB1501; Millipore, Temecula, Calif.). The following antibodies were used for immunohistochemistry: goat anti-human Nodal antibody (LS-B3955; LifeSpan Biosciences, Seattle, Wash.) 1:150; rabbit anti-P-Smad2 (AB3849; Millipore) 1:100-1:250; anti-p27 (2552; Cell Signaling) 1:400; rabbit anti-CyclinB1 (ab32053; Abcam, Cambridge, Mass.) 1:200.
Generation and Analytical Characterization of 3D1

3D1 antibody was generated against region 44-67 of human Nodal. The antigen contains two glutamic residues, E49 and E50, involved in the binding with the co-receptor Cripto-1-1. To select anti-Nodal antibodies able to recognize these two hot-spot residues, clones were screened using both hNodal144-671 and a mutated peptide, hNodal144-671E49A-E50A, in which E49 and E50 were replaced with two alanines. In typical ELISA assays, peptides were coated at 0.18 µg/mL (60 nM) and binding was probed using the antibody at increasing concentrations between 1.0 and 67 nM. Only antibodies binding the wild type peptide were further developed and tested for binding against the full length recombinant Nodal by both ELISA and Surface Plasmon Resonance (SPR). The 3D1 antibody was purified to homogeneity by two chromatographic steps including protein G affinity chromatography and gel filtration of bound fractions.
Surface Plasmon Resonance (SPR) Analyses SPR analyses were performed at 25° C. using HBS as running buffer. Protein immobilization was carried out following the canonical amine coupling chemistry using the surface immobilization wizard procedure, operating at 5 µL/min Channels were activated with EDC/NHS [N-(3-dimethylaminopropyl)-N'-ethylcarbodiimide hydrochloride (EDC)/N-hydroxysulfosuccinimide(NHS) for 7 mM; for the binding assays, rhNodal, appropriately diluted in the pre-selected sodium acetate buffer pH 4.5, was coupled until a 4000 RU level was achieved. Residual reactive groups on the sensor chip surface were deactivated by addition of 1.0 M ethanolamine hydrochloride, pH 8.5. Antibody binding was tested at 20 µL/min injecting solutions of 3D1 (60 µL) in HBS at increasing concentrations (6.0 nM-100 nM). A 10 mM NaOH solution was used to regenerate the chip surface. For competition assays, rhCripto-1-1 was covalently immobilized at 5 µg/mL in 10 mM Sodium Acetate buffer pH 4.5 at a flow rate of 5 µL/min onto a CH5 sensor chip, reaching an immobilization level of 600 RU. rhNodal at 5 nM in HBS was incubated with 3D1 at increasing concentrations. To achieve Nodal:antibody final molar ratios of 1.0:0.5, 1:1 and 1.0:2.0. Each mixture was incubated for 30 mM at room temperature before passing on the sensor chip. 60 µL of each solution was injected at a flow rate of 20 µL/min. On each biochip, an underivatized surface was prepared and used as control blank. Analyses were carried out at a flow rate of 20 µL/min, injecting a constant volume of 60 µL of antibody or competition solutions opportunely diluted in the HBS running buffer at various concentrations. The contact time was 3 minutes for the binding. Dissociations were monitored for at least 3 additional minutes. For each analysis, experimental sensorgrams were aligned, subtracted of blank signals and overlapped. Mathematical manipulations and fitting were performed using the BiaEvaluation software, vers. 4.1 from GE Healthcare. Experimental data gave optimal fittings when processed assuming a 1:1 Langmuir binding interaction.
Cell Lines Cell lines were authenticated by short tandem repeat genotyping, routinely tested for mycoplasma contamination with a PCR ELISA kit (Roche Applied Science), and maintained according to standard procedures.
Anchorage Independent Growth Assay C8161 melanoma cells (5,000 cells/well) were suspended in 0.35% agarose, RPMI 1640; 10% serum with of either 4 µg/ml mouse IgG control (Jackson ImmunoResearch, West Groove, Pa.) or 3D1 mAb (2.8 µg/ml) and were then overlayed onto a solidified layer of 0.5% agar; RPMI 1640; 10% serum in 6-well dishes. Cell clusters were allowed to form and were scored (50 cells or larger clusters) after 3 weeks in culture. Triplicate wells were averaged from separate experiments and presented as a percentage (mean±SEM) of IgG control.
Vasculogenic Network Formation Assay Three-dimensional matrices were prepared by spreading 75 µl of ice-cold Matrigel (average 12-15 mg/ml; Corning, Bedford, Mass.) into 12-well culture dishes and polymerized for one hour at 37° C. C8161 human melanoma cells ($1\times10^5$ cells/well) were then plated onto the prepared Matrigel matrices in the presence of either 4 µg/ml mouse IgG control or 3D1 mAb (2.8 µg/ml). No additional antibody was added. Tubular network formation was then observed after 24 hr and images captured digitally using a Zeiss model 25 inverted microscope (Carl Zeiss, Inc, Thornwood, N.Y.) and Hitachi HV-C20 CCD camera (Hitachi Denshi Ltd., Woodbury, N.Y.). Mean values were calculated from images of at least four different fields of both the IgG control and 3D1 mAb treated cultures, and then analyzed using the AngioSys software package (TCS CellWorks, Ltd., Buckingham, UK)

with the mean number (±SEM) of junctions and tubules calculated from the analyzed fields.

Western Blot Analysis

To determine the level of Nodal expression in brain, kidney, liver, pancreas, heart and skeletal muscle ready to use adult tissue extracts for Western blotting (WB) were purchased from Santa Cruz Biotechnology. For WB experiments of cell lines, whole cell lysates were prepared and quantified. SDS-PAGE gel electrophoresis and WB were performed using standard techniques. PVDF membranes were blocked in 5% non-fat milk or 5% BSA and antibodies diluted in either 5% non-fat milk or 5% bovine serum albumin overnight at 4° C., depending on the manufacturer's recommendations. Signal was detected using West Pico chemiluminescence reagent (Thermo Fisher) and exposure to x-ray film.

In Vivo Experiments

To evaluate the in vivo effects of 3D1 mAb, a metastatic melanoma lung metastasis model was established by injecting 250,000 C8161 cells intravenously in Nude mice. After 4 days during which cells were allowed to colonize the lungs, mice were separated into treatment and control groups. The treatment group received a total of 500 µg of 3D1 mAb versus 500 µg of irrelevant isotype IgG in the control group administered over 10 days (alternate day intraperitoneal injection (IP) of 100 µg of either 3D1 mAb or IgG). At the end of the treatment period, mice were sacrificed and lungs harvested and processed for histologic evaluation of lung tumor burden and immunohistochemistry. Lung tumor burden was determined by evaluating the mean percentage of lung tissue occupied by C8161 in at least 4 separate fields at low power (10× objective) in lungs from at least 4 separate mice for each group and performed by 2 different observers. A final mean±SEM was calculated from the separate means determined by the individual observers.

Experiments were carried out to determine the in vivo effects of 3D1 mAb on primary melanoma. To this end, 500,000 C8161 cells were injected subcutaneously in Nude mice. Palpable tumors were then injected directly with either 700 µg of total 3D1 mAb or IgG control antibody (alternate day intratumoral injection of 100 µg over 14 days). Mice were then sacrificed and subcutaneous tumors harvested and processed as previously described. To evaluate the effect of 3D1 mAb in the presence of the BRAF(V600E) mutation, a third orthotopic xenograft model was established in Nude mice via subcutaneous injection of approximately 150,000 A375SM human metastatic melanoma cells. Mice were treated IP with 3D1 mAb or IgG control, as described above, or 3 mg/kg of dabrafenib.

Immunohistochemistry

Four micron thick, formalin fixed, paraffin embedded tissue sections were prepared and immunohistochemistry was carried out on a Dako Plus autostainer (DAKO, Inc, Carpenteria, Calif.). Following antigen retrieval and blocking steps, sections were incubated in primary antibody for 60 mins, followed by appropriate biotinylated secondary antibody (Biocare Medical, Conrad, Calif.), and then streptavidin-horseradish peroxidase (Thermo Scientific Lab Vision). Color was developed with 3,3'-diaminobenzidine substrate (Thermo Scientific Lab Vision) and sections were counterstained with hematoxylin (Biocare Medical, LLC). As a negative control, adjacent serial sections were incubated with species appropriate irrelevant IgG (Jackson ImmunoResearch Labs) at the same concentration as primary antibodies. Similar to the lung tumor burden evaluation described above, mean percentage of positive staining±SEM was determined by 2 different observers, each calculating the ratio of positive cells/total number of cells×100 for 4 separate high power fields (63× objective) from at least 2 different mice per group.

Sandwich ELISA

By epitope mapping of commercially available Nodal antibodies and 3D1 mAb, the latter was chosen as the capture antibody for coating ELISA dishes, while a rabbit monoclonal anti-Nodal (Abcam) served for detecting the bound Nodal. The immune complex was subsequently quantified using a horseradish peroxidase-conjugated anti-rabbit antibody in conjunction with QuantaRed enhanced chemifluorescent horseradish peroxidase substrate (ThermoFisher). The established sandwich ELISA assay detects Nodal as a recombinant protein in conditioned media from human embryonic stem cells and in biological fluids with a detection limit (calculated using recombinant Nodal) of 75 pg/well. Human serum samples from breast cancer patients were purchased from BioOptions (Brea, Calif.).

REFERENCES

The following publications are herein incorporated by reference in their entireties.

Schier, A. F. Nodal signaling in vertebrate development. Ann. Rev. Cell Dev. Biol. 2003, 19, 589-621.

Shen, M. M. Nodal signaling: developmental roles and regulation. Development 2007, 134, 1023-1034.

Schier, A. F. Nodal morphogens. Cold Spring Harb. Perspect. Biol. 2009, 1, a003459.

Strizzi, L.; Hardy, K. M.; Kirschmann, D. A.; Ahrlund-Richter, L.; Hendrix, M. J. Nodal expression and detection in cancer: Experience and challenges. Cancer Res. 2012, 72, 1915-1920.

Strizzi, L.; Postovit, L. M.; Margaryan, N. V.; Lipaysky, A.; Gadiot, J.; Blank, C.; Seftor, R. E.; Seftor, E. A.; Hendrix, M. J. Nodal as a biomarker for melanoma progression and a new therapeutic target for clinical intervention. Expert. Rev. Dermatol. 2009, 4, 67-78.

Strizzi, L.; Hardy, K. M.; Margaryan, N. V.; Hillman, D. W.; Seftor, E. A.; Chen, B.; Geiger, X. J.; Thompson, E. A.; Lingle, W. L.; Andorfer, C. A.; et al. Potential for the embryonic morphogen Nodal as a prognostic and predictive biomarker in breast cancer. Breast Cancer Res. 2012, 11, R75.

Lawrence, M. G.; Margaryan, N. V.; Loessner, D.; Collins, A.; Kerr, K. M.; Turner, M.; Seftor, E. A.; Stephens, C. R.; Lai, J.; Postovit, L. M.; et al. Reactivation of embryonic nodal signaling is associated with tumor progression and promotes the growth of prostate cancer cells. The Prostate 2011, 71, 1198-1209.

Quail, D. F.; Siegers, G. M.; Jewer, M.; Postovit, L. M. Nodal signalling in embryogenesis and tumorigenesis. Int. J. Biochem. Cell Biol. 2013, 45, 885-898.

Topczewska, J. M.; Postovit, L. M.; Margaryan, N. V.; Sam, A.; Hess, A. R.; Wheaton, W. W.; Nickoloff, B. J.; Topczewski, J.; Hendrix, M. J. Embryonic and tumorigenic pathways converge via Nodal signaling: role in melanoma aggressiveness. Nat. Med. 2006, 12, 925-932.

Postovit, L. M.; Margaryan, N. V.; Seftor, E. A.; Hendrix, M. J. Role of nodal signaling and the microenvironment underlying melanoma plasticity. Pigment Cell Melanoma Res. 2008, 21, 348-357.

Strizzi, L.; Hardy, K. M.; Kirsammer, G. T.; Gerami, P.; Hendrix, M. J. Embryonic signaling in melanoma: Potential for diagnosis and therapy. Lab Investig. 2011, 91, 819-824.

Seftor, E. A.; Seftor, R. E.; Weldon, D. S.; Kirsammer, G. T.; Margaryan, N. V.; Gilgur, A.; Hendrix, M. J. Melanoma tumor cell heterogeneity: a molecular approach to study subpopulations expressing the embryonic morphogen nodal. Semin Oncol. 2014, 41, 259-266.

Hardy, K. M.; Strizzi, L.; Margaryan, N. V.; Gupta, K.; Murphy, G. F.; Scolyer, R. A.; Hendrix, M. J. Targeting nodal in conjunction with dacarbazine induces synergistic anticancer effects in metastatic melanoma. Mol. Cancer Res. 2015, 13, 670-680.

Postovit, L. M.; Margaryan, N. V.; Seftor, E. A.; Kirschmann, D. A.; Lipaysky, A.; Wheaton, W. W.; Abbott, D. E.; Seftor, R. E.; Hendrix, M. J. Human embryonic stem cell microenvironment suppresses the tumorigenic phenotype of aggressive cancer cells. Proc. Natl. Acad. Sci. USA 2008, 105, 4329-4334.

Costa, F. F.; Seftor, E. A.; Bischof, J. M.; Kirschmann, D. A.; Strizzi, L.; Arndt, K.; Bonaldo Mde, F.; Soares, M. B.; Hendrix, M. J. Epigenetically reprogramming metastatic tumor cells with an embryonic microenvironment. Epigenomics 2009, 1, 387-398.

Strizzi, L.; Hardy, K. M.; Seftor, E. A.; Costa, F. F.; Kirschmann, D. A.; Seftor, R. E. B.; Postovit, L.-M.; Hendrix, M. J. Development and cancer: at the crossroads of Nodal and Notch signaling. Cancer Res. 2009, 69, 7131-7134.

Hardy, K. M.; Kirschmann, D. A.; Seftor, E. A.; Margaryan, N. V.; Postovit, L. M.; Strizzi, L.; Hendrix, M. J. Regulation of the embryonic morphogen Nodal by Notch4 facilitates manifestation of the aggressive melanoma phenotype. Cancer Res. 2010, 70, 10340-10350.

Bianco, C.; Adkins, H. B.; Wechselberger, C.; Seno, M.; Normanno, N.; De Luca, A.; Sun, Y.; Khan, N.; Kenney, N.; Ebert, A.; at al. Cripto-1 activates nodal- and ALK4-dependent and -independent signaling pathways in mammary epithelial Cells. Mol. Cell Biol. 2002, 22, 2586-2597.

Reissmann, E.; Jörnvall, H.; Blokzijl, A.; Andersson, O.; Chang, C.; Minchiotti, G.; Persico, M. G.; Ibáñez, C. F.; Brivanlou, A. H. The orphan receptor ALK7 and the Activin receptor ALK4 mediate signaling by Nodal proteins during vertebrate development. Genes Dev. 2001, 15, 2010-2022.

Calvanese, L.; Sandomenico, A.; Caporale, A.; Focà, A.; Focà, G.; D'Auria, G.; Falcigno, L.; Ruvo, M. Conformational features and binding affinities to Cripto, ALK7 and ALK4 of Nodal synthetic fragments. J. Pept. Sci. 2015, 21, 283-293.

De Luca, A.; Lamura, L.; Strizzi, L.; Roma, C.; D'Antonio, A.; Margaryan, N.; Pirozzi, G.; Hsu, M. Y.; Botti, G.; Mari E.; et al. Normanno N. Expression and functional role of CRIPTO-1 in cutaneous melanoma. Br. J. Cancer 2011, 105, 1030-1038.

Strizzi, L.; Margaryan, N. V.; Gilgur, A.; Hardy, K. M.; Normanno, N.; Salomon, D. S.; Hendrix, M. J. The significance of a Cripto-1 positive subpopulation of human melanoma cells exhibiting stem cell-like characteristics. Cell Cycle. 2013, 12, 1450-1456.

Quail, D. F.; Zhang, G.; Findlay, S. D.; Hess, D. A.; Postovit, L. M. Nodal promotes invasive phenotypes via a mitogen-activated protein kinase-dependent pathway. Oncogene 2014, 33, 461-473.

Kirsammer, G.; Strizzi, L.; Margaryan, N. V.; Gilgur, A.; Hyser, M.; Atkinson, J.; Kirschmann, D. A.; Seftor, E. A.; Hendrix, M. J. Nodal signaling promotes a tumorigenic phenotype in human breast cancer. Semin. Cancer Biol. 2014, 29, 40-50.

Karimkhani, C.; Gonzalez, R.; Dellavalle, R. P. A review of novel therapies for melanoma. Am. J. Clin. Dermatol. 2014, 15, 323-337.

Hao, M.; Song, F.; Du, X.; Wang, G.; Yang, Y.; Chen, K.; Yang, J. Advances in targeted therapy for unresectable melanoma: New drugs and combinations. Cancer Lett. 2015, 359, 1-8.

Spagnolo, F.; Ghiorzo, P.; Orgiano, L.; Pastorino, L.; Picasso, V.; Tornari, E.; Ottaviano, V.; Queirolo, P. BRAF-mutant melanoma: treatment approaches, resistance mechanisms, and diagnostic strategies. Onco Targets Ther. 2015, 8, 157-168.

Eggermont, A. M.; Kirkwood, J. M. Re-evaluating the role of dacarbazine in metastatic melanoma: What have we learned in 30 years? Eur. J. Cancer 2004, 12, 1825-1836.

Sullivan, R. J.; Flaherty, K. T. Resistance to BRAF-targeted therapy in melanoma. Eur. J. Cancer 2013, 49, 1297-1304.

Calvanese, L.; Marasco, D.; Doti, N.; Saporito, A.; D'Auria, G.; Paolillo, L.; Ruvo, M.; Falcigno, L. Structural investigations on the Nodal-Cripto binding: A theoretical and experimental approach. Biopolymers 2010, 93, 1011-1021.

Saporito, A. Chemical synthesis of proteins for biotechnology applications. PhD Thesis, Univerisity of Naples "Federico II", 2005.

de Caestecker, M. The transforming growth factor-beta superfamily of receptors. Cytokine Growth Factor Rev. 2004, 15, 1-11.

Wilson, D. S.; Wu, J.; Peluso, P.; Nock, S. Improved method for pepsinolysis of mouse IgG(1) molecules to F(ab')(2) fragments. J. Immunol. Methods 2002, 260, 29-36.

Yamaguchi, Y.; Kim, H.; Kato, K.; Masuda, K.; Shimada, I.; Arata, Y. Proteolytic fragmentation with high specificity of mouse immunoglobulin G. Mapping of proteolytic cleavage sites in the hinge region. J. Immunol. Methods 1995, 181, 259-267.

Sondermann, P.; Huber, R.; Oosthuizen, V.; Jacob, U. The 3.2-A crystal structure of the human IgG1 Fc fragment-Fc gamma RIII complex. Nature 2000, 406, 267-273.

Fields, G. B.; Noble, R. L. Solid phase peptide synthesis utilizing 9 fluorenylmethoxycarbonyl amino acids. Int. J. Pept. Protein Res. 1990, 35, 161-214.

Carter, J. M. Techniques for conjugation of synthetic peptides to carrier molecules. Methods Mol. Biol. 1994, 36, 155-191.

Bradford, M. M. Rapid and sensitive method for the quantitation of microgram quantities of protein utilizing the principle of protein-dye binding. Anal. Biochem. 1976, 72, 248-254.

Kohler, G.; Milstein, C. Derivation of specific antibody-producing tissue culture and tumor lines by cell fusion. Eur. J. Immunol. 1976, 6, 511-519.

Johnsson, B.; Lofas, S.; Lindquist, G Immobilization of proteins to a carboxymethyldextran-modified gold surface for biospecific interaction analysis in surface plasmon resonance sensors. Anal. Biochem. 1991, 198, 268-277.

Malchenko, S.; Galat, V.; Seftor, E. A.; Vanin, E. F.; Costa, F. F.; Seftor, R. E.; Soares, M. B.; Hendrix, M. J. Cancer hallmarks in induced pluripotent cells: New insights. J. Cell Physiol. 2010, 225, 390-393.

Aykul, S.; Ni, W.; Mutatu, W.; Martinez-Hackert, E. Human Cerberus prevents nodal-receptor binding, inhibits nodal signaling, and suppresses nodal-mediated phenotypes. PLoS ONE 2015, 10, e0114954.

Song X, Zhao Z, Barber B, Farr A M, Ivanov B and Novich M. Overall survival in patients with metastatic melanoma. Curr Med Res Opin. 2015; 31(5):987-991.

Gogas H J, Kirkwood J M and Sondak V K. Chemotherapy for metastatic melanoma: time for a change? Cancer. 2007; 109(3):455-464.

Han S F, Liu P, Zhang W, Bu L, Shen M, Li H, Fan Y H, Cheng K, Cheng H X, Li C X and Jia G L. The opposite-direction modulation of CD4+CD25+Tregs and T helper 1 cells in acute coronary syndromes. Clin Immunol. 2007; 124(1):90-97.

Coit D G, Thompson J A, Andtbacka R, Anker C J, Bichakjian C K, Carson W E, 3rd, Daniels G A, Daud A, Dimaio D, Fleming M D, Gonzalez R, Guild V, Halpern A C, et al. Melanoma, version 4.2014. J Natl Compr Canc Netw. 2014; 12(5):621-629.

Hodi F S, O'Day S J, McDermott D F, Weber R W, Sosman J A, Haanen J B, Gonzalez R, Robert C, Schadendorf D, Hassel J C, Akerley W, van den Eertwegh A J, Lutzky J, et al. Improved survival with ipilimumab in patients with metastatic melanoma. N Engl J Med. 2010; 363(8):711-723.

Chapman P B, Hauschild A, Robert C, Haanen J B, Ascierto P, Larkin J, Dummer R, Garbe C, Testori A, Maio M, Hogg D, Lorigan P, Lebbe C, et al. Improved survival with vemurafenib in melanoma with BRAF V600E mutation. N Engl J Med. 2011; 364(26):2507-2516.

Ascierto P A, Minor D, Ribas A, Lebbe C, O'Hagan A, Arya N, Guckert M, Schadendorf D, Kefford R F, Grob J J, Hamid O, Amaravadi R, Simeone E, et al. Phase II trial (BREAK-2) of the BRAF inhibitor dabrafenib (GSK2118436) in patients with metastatic melanoma. J Clin Oncol. 2013; 31(26):3205-3211.

Flaherty K T, Robert C, Hersey P, Nathan P, Garbe C, Milhem M, Demidov L V, Hassel J C, Rutkowski P, Mohr P, Dummer R, Trefzer U, Larkin J M, et al. Improved survival with MEK inhibition in BRAF-mutated melanoma. N Engl J Med. 2012; 367(2):107-114.

Topalian S L, Hodi F S, Brahmer J R, Gettinger S N, Smith D C, McDermott D F, Powderly J D, Carvajal R D, Sosman J A, Atkins M B, Leming P D, Spigel D R, Antonia S J, et al. Safety, activity, and immune correlates of anti-PD-1 antibody in cancer. N Engl J Med. 2012; 366(26):2443-2454.

Robert C, Karaszewska B, Schachter J, Rutkowski P, Mackiewicz A, Stroiakovski D, Lichinitser M, Dummer R, Grange F, Mortier L, Chiarion-Sileni V, Drucis K, Krajsoya I, et al. Improved overall survival in melanoma with combined dabrafenib and trametinib. N Engl J Med. 2015; 372(1):30-39.

Long G V, Fung C, Menzies A M, Pupo G M, Carlino M S, Hyman J, Shahheydari H, Tembe V, Thompson J F, Saw R P, Howle J, Hayward N K, Johansson P, et al. Increased MAPK reactivation in early resistance to dabrafenib/trametinib combination therapy of BRAF-mutant metastatic melanoma. Nat Commun. 2014; 5:5694.

Larkin J, Chiarion-Sileni V, Gonzalez R, Grob J J, Cowey C L, Lao C D, Schadendorf D, Dummer R, Smylie M, Rutkowski P, Ferrucci P F, Hill A, Wagstaff J, et al. Combined Nivolumab and Ipilimumab or Monotherapy in Untreated Melanoma. N Engl J Med. 2015.

Klinac D, Gray E S, Millward M and Ziman M. Advances in personalized targeted treatment of metastatic melanoma and non-invasive tumor monitoring. Front Oncol. 2013; 3:54.

Roesch A. Tumor heterogeneity and plasticity as elusive drivers for resistance to MAPK pathway inhibition in melanoma. Oncogene. 2015; 34(23):2951-2957.

Ascierto P A. Immunotherapies and novel combinations: the focus of advances in the treatment of melanoma. Cancer Immunol Immunother. 2015; 64(3):271-274.

Smalley K S, Haass N K, Brafford P A, Lioni M, Flaherty K T and Herlyn M. Multiple signaling pathways must be targeted to overcome drug resistance in cell lines derived from melanoma metastases. Mol Cancer Ther. 2006; 5(5):1136-1144.

Strizzi L, Hardy K, Seftor E, Costa F, Kirschmann D, Seftor R, Postovit L and Hendrix M. Development and cancer: at the crossroads of Nodal and Notch signaling. Cancer Res. 2009; 69:7131-7134.

Shen M M. Nodal signaling: developmental roles and regulation. Development. 2007; 134(6):1023-1034.

Costa F F, Seftor E A, Bischof J M, Kirschmann D A, Strizzi L, Arndt K, Bonaldo Mde F, Soares M B, Hendrix M J. Epigenetically reprogramming metastatic tumor cells with an embryonic microenvironment. Epigenomics. 2009; 1(2):387-98.

Strizzi L, Hardy K M, Kirsammer G T, Gerami P and Hendrix M J. Embryonic signaling in melanoma: potential for diagnosis and therapy. Lab Invest. 2011; 91(6): 819-824.

Strizzi L, Hardy K, Margaryan N, Hillman D, Seftor E, Chen B, Geiger X, Thompson E, Lingle W, Andorfer C, Perez E and Hendrix M. Potential for the embryonic morphogen Nodal as a prognostic and predictive biomarker in breast cancer. Breast Cancer Research. 2012; 14(3):R75.

Lawrence M, Margaryan N, Loessner D, Collins A, Kerr K, Turner M, Seftor E, Stephens C, Lai J, BioResource A, Postovit L, Clements J and Hendrix M. Reactivation of embryonic nodal signaling is associated with tumor progression and promotes the growth of prostate cancer cells. Prostate. 2011; 71:1198-1209.

Postovit L M, Margaryan N V, Seftor E A, Kirschmann D A, Lipaysky A, Wheaton W W, Abbott D E, Seftor R E and Hendrix M J. Human embryonic stem cell microenvironment suppresses the tumorigenic phenotype of aggressive cancer cells. Proc Natl Acad Sci USA. 2008; 105(11): 4329-4334.

Strizzi L, Postovit L M, Margaryan N V, Lipaysky A, Gadiot J, Blank C, Seftor R E, Seftor E A and Hendrix M J. Nodal as a biomarker for melanoma progression and a new therapeutic target for clinical intervention. Expert Rev Dermatol. 2009; 4(1):67-78.

Kirsammer G, Strizzi L, Margaryan N V, Gilgur A, Hyser M, Atkinson J, Kirschmann D A, Seftor E A and Hendrix M J. Nodal signaling promotes a tumorigenic phenotype in human breast cancer. Semin Cancer Biol. 2014; 29:40-50.

Hardy K M, Strizzi L, Margaryan N V, Gupta K, Murphy G F, Scolyer R A and Hendrix M J. Targeting nodal in conjunction with dacarbazine induces synergistic anticancer effects in metastatic melanoma. Mol Cancer Res. 2015; 13(4):670-680.

Focà A, Sanguigno L, Focà G, Strizzi L, Iannitti R, Palumbo R, Hendrix M J C, Leonardi A, Ruvo M, Sandomenico A. New anti-Nodal monoclonal antibodies targeting the Nodal pre-helix loop involved in Cripto-1 binding. Int J Mol Sci 2015; 16(9): 21342-21362.

Calvanese L, Sandomenico A, Caporale A, Foca A, Foca G, D'Auria G, Falcigno L and Ruvo M. Conformational features and binding affinities to Cripto, ALK7 and ALK4 of Nodal synthetic fragments. J Pept Sci. 2015; 21(4): 283-293.

Topczewska J M, Postovit L M, Margaryan N V, Sam A, Hess A R, Wheaton W W, Nickoloff B J, Topczewski J and Hendrix M J. Embryonic and tumorigenic pathways converge via Nodal signaling: role in melanoma aggressiveness. Nature Med. 2006; 12(8):925-932.

Maniotis A J, Folberg R, Hess A, Seftor E A, Gardner L M, Pe'er J, Trent J M, Meltzer P S and Hendrix M J. Vascular channel formation by human melanoma cells in vivo and in vitro: vasculogenic mimicry. Am J Pathol. 1999; 155 (3):739-752.

Lo J A and Fisher D E. The melanoma revolution: from UV carcinogenesis to a new era in therapeutics. Science. 2014; 346(6212):945-949.

Hodis E, Watson I R, Kryukov G V, Arold S T, Imielinski M, Theurillat J P, Nickerson E, Auclair D, Li L, Place C, Dicara D, Ramos A H, Lawrence M S, et al. A landscape of driver mutations in melanoma. Cell. 2012; 150(2):251-263.

Murphy G F, Wilson B J, Girouard S D, Frank N Y and Frank M H. Stem cells and targeted approaches to melanoma cure. Mol Aspects Med. 2014; 39:33-49.

Vallier L, Reynolds D and Pedersen R A. Nodal inhibits differentiation of human embryonic stem cells along the neuroectodermal default pathway. Dev Biol. 2004; 275 (2):403-421.

Li F Z, Dhillon A S, Anderson R L, McArthur G and Ferrao P T. Phenotype switching in melanoma: implications for progression and therapy. Front Oncol. 2015; 5:31.

Quail D F, Zhang G, Findlay S D, Hess D A and Postovit L M. Nodal promotes invasive phenotypes via a mitogen-activated protein kinase-dependent pathway. Oncogene. 2014; 33(4):461-473.

Huang S, Holzel M, Knijnenburg T, Schlicker A, Roepman P, McDermott U, Garnett M, Grernrum W, Sun C, Prahallad A, Groenendijk F H, Mittempergher L, Nijkamp W, et al. MED12 controls the response to multiple cancer drugs through regulation of TGF-beta receptor signaling. Cell. 2012; 151(5):937-950.

Khalkhali-Ellis Z, Kirschmann D A, Seftor E A, Gilgur A, Bodenstine T M, Hinck A P and Hendrix M J. Divergence (s) in nodal signaling between aggressive melanoma and embryonic stem cells. Int. 1 Cancer. 2015; 136(5):E242-251.

Calvanese L, Marasco D, Doti N, Saporito A, D'Auria G, Paolillo L, Ruvo M and Falcigno L. Structural investigations on the Nodal-Cripto binding: a theoretical and experimental approach. Biopolymers. 2010; 93(11):1011-1021.

Calvanese L, Falcigno L and D'Auria G. Essential dynamics analysis captures the concerted motion of the integrin-binding site in jerdostatin, an RTS disintegrin. Biopolymers. 2015; 103(3):158-166.

Delyon J, Mateus C, Lefeuvre D, Lanoy E, Zitvogel L, Chaput N, Roy S, Eggermont A M, Routier E and Robert C. Experience in daily practice with ipilimumab for the treatment of patients with metastatic melanoma: an early increase in lymphocyte and eosinophil counts is associated with improved survival. Ann Oncol. 2013; 24(6): 1697-1703.

Johnsson B, Lofas S and Lindquist G Immobilization of proteins to a carboxymethyldextran-modified gold surface for biospecific interaction analysis in surface plasmon resonance sensors. Anal Biochem. 1991; 198(2):268-277.

Gaddameedhi S, Kemp M G, Reardon J T, Shields J M, Smith-Roe S L, Kaufmann W K and Sancar A. Similar nucleotide excision repair capacity in melanocytes and melanoma cells. Cancer research. 2010; 70(12):4922-4930.

Hardy K M, Kirschmann D A, Seftor E A, Margaryan N V, Postovit L M, Strizzi L and Hendrix M J. Regulation of the embryonic morphogen Nodal by Notch4 facilitates manifestation of the aggressive melanoma phenotype. Cancer Res. 2010; 70(24):10340-10350.

Kozlowski J M, Hart I R, Fidler I J and Hanna N. A human melanoma line heterogeneous with respect to metastatic capacity in athymic nude mice. J Natl Cancer Inst. 1984; 72(4):913-917.

Bodenstine T M, Seftor R E, Seftor E A, Khalkhali-Ellis Z, Samii N A, Monarrez J C, Chandler G S, Pemberton P A and Hendrix M J. Internalization by multiple endocytic pathways and lysosomal processing impact maspin-based therapeutics. Mol Cancer Res. 2014; 12(10):1480-1491.

Adkins H B, Bianco C, Schiffer S G, Rayhorn P, Zafari M, Cheung A E, Orozco O, Olson D, De Luca A, Chen L L, Miatkowski K, Benjamin C, Normanno N, et al. Antibody blockade of the Cripto CFC domain suppresses tumor cell growth in vivo. J Clin Invest. 2003; 112(4):575-87.

Yu L, Harms P W, Pouryazdanparast P, Kim D S, Ma L, Fullen D R. Expression of the embryonic morphogen Nodal in cutaneous melanocytic lesions. Mod Pathol. 2010; 23(9):1209-14.

Lee C C, Jan H J, Lai J H, Ma H I, Hueng D Y, Lee Y C, Cheng Y Y, Liu L W, Wei H W, Lee H M. Nodal promotes growth and invasion in human gliomas. Oncogene. 2010; 29(21):3110-23.

Fu G, Peng C. Nodal enhances the activity of FoxO3a and its synergistic interaction with Smads to regulate cyclin G2 transcription in ovarian cancer cells. Oncogene. 2011; 30(37):3953-66.

Jamil S, Cedervall J, Hultman I, Ali R, Margaryan N V, Rasmuson A, Johnsen J I

Sveinbjornsson B, Dalianis T, Kanter L, Orrego A, Strizzi L, Hendrix M J, et al. Neuroblastoma cells injected into experimental mature teratoma reveal a tropism for embryonic loose mesenchyme. Int J Oncol. 2013; 43(3):831-8.

Duan W, Li R, Ma J, Lei J, Xu Q, Jiang Z, Nan L, Li X, Wang Z, Huo X, Han L, Wu Z, Wu E, et al. Overexpression of Nodal induces a metastatic phenotype in pancreatic cancer cells via the Smad2/3 pathway. Oncotarget. 2015; 6(3):1490-506.

Kong B, Wang W, Esposito I, Friess H, Michalski C W, Kleeff J. Increased expression of Nodal correlates with reduced patient survival in pancreatic cancer. Pancreatology. 2015; 15(2):156-61.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claims is:

1. An anti-Nodal antibody, wherein the antibody comprises:
    (a) a hypervariable region (HVR)-H1 comprising the amino acid sequence of SEQ ID NO: 10;
    (b) an HVR-H2 comprising the amino acid sequence of SEQ ID NO: 11;
    (c) an HVR-H3 comprising the amino acid sequence of SEQ ID NO: 12;
    (d) an HVR-L1 comprising the amino acid sequence of SEQ ID NO: 4;
    (e) an HVR-L2 comprising the amino acid sequence of SEQ ID NO: 5; and
    (f) an HVR-L3 comprising the amino acid sequence of SEQ ID NO: 6.

2. The antibody of claim 1, wherein the antibody comprises a heavy chain variable domain (VH) having at least 90% sequence identity to the amino acid sequence of SEQ ID NO: 3 and a light chain variable domain (VL) having at least 90% sequence identity to the amino acid sequence of SEQ ID NO: 1.

3. The antibody of claim 1, further comprising at least one framework selected from a human VH Acceptor 2 framework and a human VL kappa subgroup I consensus framework.

4. The antibody of claim 1, wherein the antibody binds to an epitope in SEQ ID NO:13.

5. The antibody of claim 1, wherein the antibody is an antibody fragment.

6. The antibody of claim 5, wherein the antibody fragment is a Fab, Fab'-SH, Fv, scFv, or (Fab')$_2$ fragment.

7. The antibody of claim 1, which is a human, humanized, or chimeric antibody.

8. A method of inhibiting Nodal activity, the method comprising exposing a cell that expresses Nodal to an antibody of claim 1.

9. A method of inhibiting Nodal activity in a subject with a disorder associated with increased expression or activity of Nodal, the method comprising administering to the subject an effective amount of an antibody of claim 1.

10. The method of claim 9, wherein the disorder is cancer.

11. The method of claim 10, wherein the cancer is selected from the group consisting of glioblastoma, neuroblastoma, melanoma, breast cancer, pancreatic cancer, ovarian cancer, bladder cancer, colon cancer, prostate cancer, hepatoma, and leukemia.

12. A method of detecting Nodal in a sample, comprising contacting the sample with an antibody of claim 1.

13. The method of claim 12, wherein the sample is a biological sample.

14. The method of claim 13, wherein the biological sample is selected from the group consisting of blood, serum, bodily fluid, biopsied cells, intestinal scraping, sputum, lung effusion, urine, and tissue sample.

15. The method of claim 13, wherein the biological sample comprises cancer cells or tumor cells.

16. The method of claim 15, wherein the cancer is selected from the group consisting of glioblastoma, neuroblastoma, melanoma, breast cancer, pancreatic cancer, ovarian cancer, bladder cancer, colon cancer, prostate cancer, hepatoma, and leukemia.

17. The method of claim 12, wherein Nodal is detected by an immunoassay.

18. The method of claim 17, wherein binding of the antibody to Nodal is detected by a label selected from an enzymatic label, a fluorescent label, a chemiluminescent label, a radioactive label, and a dye label.

19. The method of claim 12, wherein the antibody is attached to a solid support.

20. The method of claim 12, comprising quantifying the level of Nodal in the sample.

* * * * *